US012552804B2

(12) United States Patent
McCammant et al.

(10) Patent No.: US 12,552,804 B2
(45) Date of Patent: Feb. 17, 2026

(54) TRICYCLIC HETEROCYCLES AS FGFR INHIBITORS

(71) Applicant: Incyte Corporation, Wilmington, DE (US)

(72) Inventors: Matthew S. McCammant, Newark, DE (US); Evan Styduhar, Media, PA (US); Oleg Vechorkin, Wilmington, DE (US); Robert Swyka, Wilmington, DE (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 18/545,487

(22) Filed: Dec. 19, 2023

(65) Prior Publication Data

US 2024/0287086 A1 Aug. 29, 2024

Related U.S. Application Data

(63) Continuation of application No. 17/110,740, filed on Dec. 3, 2020, now Pat. No. 11,897,891.

(60) Provisional application No. 62/943,540, filed on Dec. 4, 2019.

(51) Int. Cl.
*C07D 471/14* (2006.01)
*A61P 35/00* (2006.01)
*C07D 487/14* (2006.01)

(52) U.S. Cl.
CPC ............ *C07D 487/14* (2013.01); *A61P 35/00* (2018.01); *C07D 471/14* (2013.01)

(58) Field of Classification Search
CPC ............................ C07D 487/14; C07D 471/14
See application file for complete search history.

(56) References Cited

U.S. PATENT DOCUMENTS

| | | | |
|---|---|---|---|
| 850,370 | A | 4/1907 | Hynes |
| 3,894,021 | A | 7/1975 | Denzel et al. |
| 4,271,074 | A | 6/1981 | Lohmann et al. |
| 4,339,267 | A | 7/1982 | Levitt |
| 4,347,348 | A | 8/1982 | Chernikhov et al. |
| 4,402,878 | A | 9/1983 | D'Alelio et al. |
| 4,405,519 | A | 9/1983 | D'Alelio et al. |
| 4,405,520 | A | 9/1983 | D'Alelio et al. |
| 4,405,786 | A | 9/1983 | D'Alelio et al. |
| 4,460,773 | A | 7/1984 | Suzuki et al. |
| 4,874,803 | A | 10/1989 | Baron et al. |
| 4,940,705 | A | 7/1990 | Boshagen et al. |
| 5,159,054 | A | 10/1992 | Keller |
| 5,240,941 | A | 8/1993 | Bruneau |
| 5,480,887 | A | 1/1996 | Hornback et al. |
| 5,521,184 | A | 5/1996 | Zimmermann et al. |
| 5,536,725 | A | 7/1996 | Cullen et al. |
| 5,541,324 | A | 7/1996 | TenBrink et al. |
| 5,760,068 | A | 6/1998 | Talley et al. |
| 5,783,577 | A | 7/1998 | Houghten et al. |
| 5,845,025 | A | 12/1998 | Garito et al. |
| 5,994,364 | A | 11/1999 | Njoroge et al. |
| 6,465,484 | B1 | 10/2002 | Bilodeau et al. |
| 6,998,408 | B2 | 2/2006 | Pinto |
| 7,074,801 | B1 | 7/2006 | Yoshida et al. |
| 7,125,880 | B1 | 10/2006 | Chen |
| 7,488,802 | B2 | 2/2009 | Collins et al. |
| 7,618,975 | B2 | 11/2009 | Cai et al. |
| 7,642,255 | B2 | 1/2010 | Sim |
| 7,648,973 | B2 | 1/2010 | DeLuca et al. |
| 7,943,743 | B2 | 5/2011 | Korman et al. |
| 8,008,449 | B2 | 8/2011 | Korman et al. |
| 8,168,757 | B2 | 5/2012 | Finnefrock et al. |
| 8,217,149 | B2 | 7/2012 | Irving et al. |
| 8,754,114 | B2 | 6/2014 | Yao et al. |
| 8,759,398 | B2 | 6/2014 | Nelson |
| 8,889,711 | B2 | 11/2014 | Bedjeguelal |
| 9,266,892 | B2 | 2/2016 | Zhuo et al. |
| 9,388,185 | B2 | 7/2016 | Lu et al. |
| 9,533,954 | B2 | 1/2017 | Yao et al. |

(Continued)

FOREIGN PATENT DOCUMENTS

| | | |
|---|---|---|
| CL | 2014003355 | 6/2015 |
| CL | 2015002628 | 8/2016 |

(Continued)

OTHER PUBLICATIONS

Fun et al. (Acta Crystallographica, Section E: Structure Reports, (2008), 64(9), o1741-o1742 and sup1-sup8).*
"Substance Record for SID 240993001," Feb. 13, 2015, pp. 1-8.
Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.
Adib et al., "FGFR2/3 genomic alterations and response to Enfortumab Vedotin in metastatic urothelial carcinoma," BJUI Compass., 2022, 3:169-172.
Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.

(Continued)

*Primary Examiner* — Susanna Moore

(74) *Attorney, Agent, or Firm* — Fish & Richardson P.C.

(57) ABSTRACT

The present disclosure relates to tricyclic heterocycles, and pharmaceutical compositions of the same, that are inhibitors of the FGFR enzyme and are useful in the treatment of FGFR-associated diseases such as cancer.

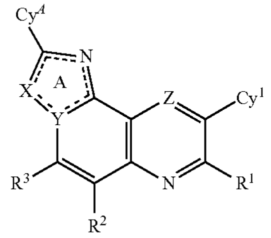

34 Claims, No Drawings

Specification includes a Sequence Listing.

(56) References Cited

U.S. PATENT DOCUMENTS 9,533,984 B2 1/2017 Sun et al.
9,580,423 B2 2/2017 Lu et al.
9,611,267 B2 4/2017 Wu et al.
9,708,318 B2 7/2017 Lu et al.
9,745,311 B2 8/2017 Lu et al.
9,801,889 B2 10/2017 Lu et al.
9,890,156 B2 2/2018 Lu et al.
10,016,348 B2 7/2018 Lu et al.
10,040,790 B2 8/2018 Sun et al.
10,131,667 B2 11/2018 Wu et al.
10,208,024 B2 2/2019 Andrews et al.
10,213,427 B2 2/2019 Yao et al.
10,214,528 B2 2/2019 Lu et al.
10,251,892 B2 4/2019 Sokolsky et al.
10,308,644 B2 6/2019 Wu et al.
10,350,240 B2 7/2019 Gore et al.
10,357,431 B2 7/2019 Staric et al.
10,450,313 B2 10/2019 Lu et al.
10,611,762 B2 4/2020 Jia et al.
10,632,126 B2 4/2020 Lu et al.
10,669,271 B2 6/2020 Wu et al.
10,738,048 B2 8/2020 Lu et al.
10,813,930 B2 10/2020 Yao et al.
10,851,105 B2 12/2020 Wu et al.
10,947,230 B2 3/2021 Sun et al.
11,014,923 B2 5/2021 Lu et al.
11,053,246 B2 7/2021 Wu et al.
11,173,162 B2 11/2021 Sokolsky et al.
11,174,257 B2 11/2021 Jia et al.
11,407,750 B2 8/2022 Tao et al.
11,466,004 B2 10/2022 Burn
11,607,416 B2 3/2023 Vechorkin et al.
11,897,891 B2 2/2024 McCammant et al.
11,939,331 B2 3/2024 Li et al.
12,012,409 B2 6/2024 Roach et al.
2003/0078255 A1 4/2003 Pinto
2003/0078277 A1 4/2003 Hibi et al.
2003/0181622 A1 9/2003 Chiu et al.
2004/0044012 A1 3/2004 Dobrusin et al.
2004/0067948 A1 4/2004 Hallett
2004/0097493 A1 5/2004 Chen et al.
2004/0122029 A1 6/2004 Liu et al.
2004/0127536 A1 7/2004 Bhagwat et al.
2004/0127538 A1 7/2004 Oinuma et al.
2004/0204427 A1 10/2004 Chen et al.
2005/0009876 A1 1/2005 Bhagwat et al.
2005/0070542 A1 3/2005 Hodgetts et al.
2005/0148603 A1 7/2005 Jimenez et al.
2005/0197340 A1 9/2005 Arora et al.
2005/0222171 A1 10/2005 Bold et al.
2006/0222637 A1 10/2006 Bamdad
2006/0270849 A1 11/2006 Nishino et al.
2007/0116984 A1 5/2007 Park et al.
2007/0197510 A1 8/2007 Ohmoto et al.
2007/0225286 A1 9/2007 Ren et al.
2007/0280943 A1 12/2007 Friedman et al.
2008/0249301 A1 10/2008 Hornberger et al.
2009/0098086 A1 4/2009 Zask et al.
2009/0099165 A1 4/2009 Hurley et al.
2009/0099190 A1 4/2009 Flynn et al.
2009/0105233 A1 4/2009 Chua et al.
2009/0131467 A1 5/2009 Kanazawa et al.
2009/0163545 A1 6/2009 Goldfarb
2009/0246198 A1 10/2009 Dong et al.
2010/0032626 A1 2/2010 Akino
2010/0099684 A1 4/2010 Cook, II et al.
2010/0105661 A1 4/2010 Shirakami et al.
2010/0143547 A1 6/2010 Kriegel et al.
2010/0204235 A1 8/2010 Lizos
2010/0210636 A1 8/2010 Ishikawa et al.
2010/0216798 A1 8/2010 Nakai et al.
2010/0239496 A1 9/2010 Gangadharmath et al.
2011/0045511 A1 2/2011 Graus Porta et al.
2011/0159604 A1 6/2011 Fan et al.
2011/0160203 A1 6/2011 Liu et al.
2011/0195968 A1 8/2011 Greul et al.
2011/0212077 A1 9/2011 Noronha et al.
2011/0224155 A1 9/2011 Tachdjian et al.
2011/0262525 A1 10/2011 Wang et al.
2011/0313003 A1 12/2011 Shi et al.
2012/0035153 A1 2/2012 Saxty et al.
2012/0135997 A1 5/2012 Kato et al.
2012/0165305 A1 6/2012 Yao et al.
2012/0295881 A1 11/2012 Lange et al.
2012/0319095 A1 12/2012 Tada et al.
2013/0078731 A1 3/2013 George et al.
2013/0200356 A1 8/2013 Jung et al.
2013/0210825 A1 8/2013 Rehwinkel et al.
2013/0338134 A1 12/2013 Wu et al.
2014/0045814 A1 2/2014 Lu et al.
2014/0054564 A1 2/2014 Kim et al.
2014/0080892 A1 3/2014 Bhanot et al.
2014/0088100 A1 3/2014 Bifulco, Jr. et al.
2014/0103325 A1 4/2014 Shin et al.
2014/0117318 A1 5/2014 Choi et al.
2014/0148548 A1 5/2014 Yamanaka et al.
2014/0171405 A1 6/2014 Zhuo et al.
2014/0187559 A1 7/2014 Miduturu
2014/0194430 A1 7/2014 Eis et al.
2014/0228370 A1 8/2014 Eis et al.
2014/0243308 A1 8/2014 Yao et al.
2014/0288069 A1 9/2014 Eis et al.
2014/0296233 A1 10/2014 D'Agostino et al.
2014/0315902 A1 10/2014 Sun et al.
2014/0374722 A1 12/2014 Kim et al.
2014/0378468 A1 12/2014 Aichholz et al.
2014/0378481 A1 12/2014 Bifulco, Jr. et al.
2014/0378483 A1 12/2014 Benazet et al.
2015/0011548 A1 1/2015 Linnanen et al.
2015/0011560 A1 1/2015 Legeai-Mallet
2015/0011579 A1 1/2015 Clary-Ceccato et al.
2015/0038485 A1 2/2015 Eis et al.
2015/0197519 A1 7/2015 Bifulco
2016/0115164 A1 4/2016 Wu et al.
2016/0244448 A1 8/2016 Lu et al.
2016/0244449 A1 8/2016 Lu et al.
2016/0244450 A1 8/2016 Lu et al.
2016/0280713 A1 9/2016 Lu et al.
2017/0107216 A1 4/2017 Wu et al.
2017/0119782 A1 5/2017 Lu et al.
2017/0137424 A1 5/2017 Wu et al.
2017/0145025 A1 5/2017 Li et al.
2017/0165263 A1 6/2017 Yao et al.
2017/0166564 A1 6/2017 Sun et al.
2017/0174671 A1 6/2017 Wu et al.
2017/0174679 A1 6/2017 Lajkiewicz et al.
2017/0260168 A1 9/2017 Andrews et al.
2017/0267685 A1 9/2017 D'Agostino et al.
2017/0275291 A1 9/2017 Geng et al.
2017/0290839 A1 10/2017 Lu et al.
2017/0320875 A1 11/2017 Li et al.
2017/0320877 A1 11/2017 Wu et al.
2017/0342060 A1 11/2017 Lu et al.
2017/0362253 A1 12/2017 Xiao et al.
2018/0008610 A1 1/2018 Lu et al.
2018/0016260 A1 1/2018 Yu et al.
2018/0057486 A1 3/2018 Wu et al.
2018/0072718 A1 3/2018 Liu et al.
2018/0177784 A1 6/2018 Wu et al.
2018/0177870 A1 6/2018 Liu et al.
2018/0179179 A1 6/2018 Wu et al.
2018/0179197 A1 6/2018 Wu et al.
2018/0179201 A1 6/2018 Wu et al.
2018/0179202 A1 6/2018 Wu et al.
2018/0244672 A1 8/2018 Lu et al.
2018/0273519 A1 9/2018 Wu et al.
2019/0040082 A1 2/2019 Xiao et al.
2019/0055237 A1 2/2019 Pan et al.
2019/0062327 A1 2/2019 Sun et al.
2019/0062345 A1 2/2019 Xiao et al.
2019/0071439 A1 3/2019 Li et al.
2019/0092767 A1 3/2019 Li et al.
2019/0127376 A1 5/2019 Wu et al.
2019/0127467 A1 5/2019 Shah et al.

(56) References Cited

U.S. PATENT DOCUMENTS

| | | | |
|---|---|---|---|
| 2019/0144439 A1 | 5/2019 | Wu et al. |
| 2019/0152973 A1 | 5/2019 | Lee et al. |
| 2019/0202824 A1 | 7/2019 | Wu et al. |
| 2019/0225601 A1 | 7/2019 | Wu et al. |
| 2019/0240220 A1 | 8/2019 | Yao et al. |
| 2019/0241560 A1 | 8/2019 | Lu et al. |
| 2019/0269693 A1 | 9/2019 | Lu et al. |
| 2019/0284187 A1 | 9/2019 | Wu et al. |
| 2019/0300524 A1 | 10/2019 | Wu et al. |
| 2019/0337948 A1 | 11/2019 | Frietze et al. |
| 2019/0345170 A1 | 11/2019 | Wu et al. |
| 2020/0002338 A1 | 1/2020 | Jia et al. |
| 2020/0055853 A1 | 2/2020 | Ellies et al. |
| 2020/0095244 A1 | 3/2020 | Sun et al. |
| 2020/0255424 A1 | 8/2020 | Wu et al. |
| 2020/0270245 A1 | 8/2020 | Pan et al. |
| 2020/0277309 A1 | 9/2020 | Wu et al. |
| 2020/0306256 A1 | 10/2020 | Lu et al. |
| 2020/0377504 A1 | 12/2020 | Wu et al. |
| 2020/0399267 A1 | 12/2020 | Lu et al. |
| 2021/0009582 A1 | 1/2021 | Vechorkin et al. |
| 2021/0094935 A1 | 4/2021 | Vechorkin |
| 2021/0106588 A1 | 4/2021 | Vechorkin et al. |
| 2021/0115053 A1 | 4/2021 | Shvartsbart et al. |
| 2021/0171522 A1 | 6/2021 | Tao et al. |
| 2021/0171535 A1 | 6/2021 | McCammant et al. |
| 2021/0214366 A1 | 7/2021 | Roach et al. |
| 2021/0380587 A1 | 12/2021 | Wu et al. |
| 2021/0395246 A1 | 12/2021 | Sun et al. |
| 2022/0009921 A1 | 1/2022 | Lu et al. |
| 2022/0153740 A1 | 5/2022 | Jia et al. |
| 2023/0002384 A1 | 1/2023 | Swyka et al. |
| 2023/0002385 A1 | 1/2023 | Li et al. |
| 2023/0192722 A1 | 6/2023 | Liu et al. |
| 2023/0338389 A1 | 10/2023 | Vechorkin et al. |
| 2025/0057852 A1 | 2/2025 | Vechorkin et al. |

FOREIGN PATENT DOCUMENTS

| | | |
|---|---|---|
| CL | 2017000654 | 12/2017 |
| CL | 2017001984 | 3/2018 |
| CL | 2018000089 | 5/2018 |
| CL | 2018000124 | 5/2018 |
| CL | 2017002117 | 6/2018 |
| CL | 2018000036 | 6/2018 |
| CL | 2018000128 | 6/2018 |
| CL | 2018003322 | 1/2019 |
| CN | 1863774 | 11/2006 |
| CN | 101007778 | 8/2007 |
| CN | 101679408 | 3/2010 |
| CN | 101715451 | 5/2010 |
| CN | 102399220 | 4/2012 |
| CN | 102399233 | 4/2012 |
| CN | 102666536 | 9/2012 |
| CN | 103571502 | 2/2014 |
| CN | 103588771 | 2/2014 |
| CN | 104262330 | 1/2015 |
| DE | 2156720 | 5/1973 |
| DE | 2934578 | 3/1981 |
| DE | 3432983 | 4/1985 |
| DE | 280853 | 7/1990 |
| DE | 3937633 | 5/1991 |
| DE | 4119767 | 12/1992 |
| DE | 19912638 | 9/2000 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| EP | 3184521 | 6/2017 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S 6310630 | 1/1988 |
| JP | 02009895 | 1/1990 |
| JP | H 03275669 | 12/1991 |
| JP | 04179576 | 6/1992 |
| JP | H 04158084 | 6/1992 |
| JP | H 04328121 | 11/1992 |
| JP | H 05320173 | 12/1993 |
| JP | H 05320515 | 12/1993 |
| JP | H 09188812 | 7/1997 |
| JP | H 1060426 | 3/1998 |
| JP | H 0348656 | 3/1999 |
| JP | H 11171865 | 6/1999 |
| JP | 2000123973 | 4/2000 |
| JP | 2001035664 | 2/2001 |
| JP | 2001265031 | 9/2001 |
| JP | 2002516327 | 6/2002 |
| JP | 2002296731 | 10/2002 |
| JP | 2003335788 | 11/2003 |
| JP | 2004203749 | 7/2004 |
| JP | 2004346145 | 12/2004 |
| JP | 2005015395 | 1/2005 |
| JP | 2005320288 | 11/2005 |
| JP | 2006028027 | 2/2006 |
| JP | 2006514624 | 5/2006 |
| JP | 2006284843 | 10/2006 |
| JP | 2006522756 | 10/2006 |
| JP | 2006316054 | 11/2006 |
| JP | 2007500725 | 1/2007 |
| JP | 2007511618 | 5/2007 |
| JP | 2007522098 | 8/2007 |
| JP | 2008198769 | 8/2008 |
| JP | 2009537520 | 10/2009 |
| JP | 2010180147 | 8/2010 |
| JP | 2010248429 | 11/2010 |
| JP | 2010267847 | 11/2010 |
| JP | 2010270245 | 12/2010 |
| JP | 2010272618 | 12/2010 |
| JP | 2010272727 | 12/2010 |
| JP | 2010278114 | 12/2010 |
| JP | 2011009348 | 1/2011 |
| JP | 2011044637 | 3/2011 |
| JP | 2011116840 | 6/2011 |
| JP | 2011222650 | 11/2011 |
| JP | 2012116825 | 6/2012 |
| JP | 2012136476 | 7/2012 |
| JP | 5120580 | 1/2013 |
| JP | 2013049251 | 3/2013 |
| JP | 2013179181 | 9/2013 |
| JP | 2015517376 | 6/2015 |
| JP | 2018507214 | 3/2018 |
| JP | 2018511573 | 4/2018 |
| JP | 6336665 | 6/2018 |
| KR | 20010043829 | 5/2001 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 20140099105 | 8/2014 |
| WO | WO 1988/03025 | 5/1988 |
| WO | WO 1991/09835 | 7/1991 |
| WO | WO 1991/10172 | 7/1991 |
| WO | WO 1992/06078 | 4/1992 |
| WO | WO 1992/22552 | 12/1992 |
| WO | WO 1993/24488 | 12/1993 |
| WO | WO 1994/13669 | 6/1994 |
| WO | WO 1994/15995 | 7/1994 |
| WO | WO 1994/25438 | 11/1994 |
| WO | WO 1995/20965 | 8/1995 |
| WO | WO 1996/15128 | 5/1996 |
| WO | WO 1996/40707 | 12/1996 |
| WO | WO 1997/47601 | 12/1997 |
| WO | WO 1998/05661 | 2/1998 |
| WO | WO 1998/06703 | 2/1998 |

(56) References Cited

FOREIGN PATENT DOCUMENTS

| | | |
|---|---|---|
| WO | WO 1998/11438 | 3/1998 |
| WO | WO 1998/18781 | 5/1998 |
| WO | WO 1998/28281 | 7/1998 |
| WO | WO 1998/33798 | 8/1998 |
| WO | WO 1998/46609 | 10/1998 |
| WO | WO 1998/54156 | 12/1998 |
| WO | WO 1999/06422 | 2/1999 |
| WO | WO 1999/07732 | 2/1999 |
| WO | WO 1999/09030 | 2/1999 |
| WO | WO 1999/42442 | 8/1999 |
| WO | WO 1999/59975 | 11/1999 |
| WO | WO 1999/61444 | 12/1999 |
| WO | WO 1999/64400 | 12/1999 |
| WO | WO 2000/09495 | 2/2000 |
| WO | WO 2002/000196 | 2/2000 |
| WO | WO 2000/24744 | 5/2000 |
| WO | WO 2000/053595 | 9/2000 |
| WO | WO 2000/68186 | 11/2000 |
| WO | WO 2001/02369 | 1/2001 |
| WO | WO 2001/014402 | 3/2001 |
| WO | WO 2001/22938 | 4/2001 |
| WO | WO 2001/23386 | 4/2001 |
| WO | WO 2001/29041 | 4/2001 |
| WO | WO 2001/29042 | 4/2001 |
| WO | WO 2001/42247 | 6/2001 |
| WO | WO 2001/47892 | 7/2001 |
| WO | WO 2001/53273 | 7/2001 |
| WO | WO 2001/55148 | 8/2001 |
| WO | WO 2001/57037 | 8/2001 |
| WO | WO 2001/57038 | 8/2001 |
| WO | WO 2001/58899 | 8/2001 |
| WO | WO 2001/064655 | 9/2001 |
| WO | WO 2001/66099 | 9/2001 |
| WO | WO 2001/68647 | 9/2001 |
| WO | WO 2001/83472 | 11/2001 |
| WO | WO 2001/85722 | 11/2001 |
| WO | WO 2002/00655 | 1/2002 |
| WO | WO 2002/12442 | 2/2002 |
| WO | WO 2002/14315 | 2/2002 |
| WO | WO 2002/20011 | 3/2002 |
| WO | WO 2002/051831 | 7/2002 |
| WO | WO 2002/055082 | 7/2002 |
| WO | WO 2002/066481 | 8/2002 |
| WO | WO 2002/74754 | 9/2002 |
| WO | WO 2002/076953 | 10/2002 |
| WO | WO 2002/083648 | 10/2002 |
| WO | WO 2002/088095 | 11/2002 |
| WO | WO 2002/094825 | 11/2002 |
| WO | WO 2002/096873 | 12/2002 |
| WO | WO 2002/102793 | 12/2002 |
| WO | WO 2003/000187 | 1/2003 |
| WO | WO 2003/000688 | 1/2003 |
| WO | WO 2003/000690 | 1/2003 |
| WO | WO 2003/009852 | 2/2003 |
| WO | WO 2003/014083 | 2/2003 |
| WO | WO 2003/024967 | 3/2003 |
| WO | WO 2003/037347 | 5/2003 |
| WO | WO 2003/037891 | 5/2003 |
| WO | WO 2003/040131 | 5/2003 |
| WO | WO 2003/042402 | 5/2003 |
| WO | WO 2003/049542 | 6/2003 |
| WO | WO 2003/062236 | 7/2003 |
| WO | WO 2003/075836 | 9/2003 |
| WO | WO 2003/082871 | 10/2003 |
| WO | WO 2003/097609 | 11/2003 |
| WO | WO 2003/099771 | 12/2003 |
| WO | WO 2003/099818 | 12/2003 |
| WO | WO 2003/101985 | 12/2003 |
| WO | WO 2004/002986 | 1/2004 |
| WO | WO 2004/005281 | 1/2004 |
| WO | WO 2004/011465 | 2/2004 |
| WO | WO 2004/014382 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/046120 | 6/2004 |
| WO | WO 2004/046152 | 6/2004 |
| WO | WO 2004/048343 | 6/2004 |
| WO | WO 2004/052291 | 6/2004 |
| WO | WO 2004/052862 | 6/2004 |
| WO | WO 2004/056786 | 7/2004 |
| WO | WO 2004/056822 | 7/2004 |
| WO | WO 2004/056830 | 7/2004 |
| WO | WO 2004/065378 | 8/2004 |
| WO | WO 2004/080980 | 9/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/112793 | 12/2004 |
| WO | WO 2004/113307 | 12/2004 |
| WO | WO 2005/007653 | 1/2005 |
| WO | WO 2005/011597 | 2/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/028444 | 5/2005 |
| WO | WO 2005/040119 | 5/2005 |
| WO | WO 2005/046589 | 5/2005 |
| WO | WO 2005/047289 | 5/2005 |
| WO | WO 2005/056524 | 6/2005 |
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/105097 | 11/2005 |
| WO | WO 2005/113536 | 12/2005 |
| WO | WO 2005/116035 | 12/2005 |
| WO | WO 2005/121130 | 12/2005 |
| WO | WO 2005/121142 | 12/2005 |
| WO | WO 2006/000420 | 1/2006 |
| WO | WO 2006/024486 | 3/2006 |
| WO | WO 2006/024487 | 3/2006 |
| WO | WO 2006/024834 | 3/2006 |
| WO | WO 2006/028289 | 3/2006 |
| WO | WO 2006/030031 | 3/2006 |
| WO | WO 2006/038112 | 4/2006 |
| WO | WO 2006/050076 | 5/2006 |
| WO | WO 2006/050162 | 5/2006 |
| WO | WO 2006/052712 | 5/2006 |
| WO | WO 2006/055752 | 5/2006 |
| WO | WO 2006/024524 | 6/2006 |
| WO | WO 2006/056399 | 6/2006 |
| WO | WO 2006/058120 | 6/2006 |
| WO | WO 2006/062465 | 6/2006 |
| WO | WO 2006/065703 | 6/2006 |
| WO | WO 2006/074293 | 7/2006 |
| WO | WO 2006/087230 | 8/2006 |
| WO | WO 2006/092691 | 9/2006 |
| WO | WO 2006/102588 | 9/2006 |
| WO | WO 2006/102610 | 9/2006 |
| WO | WO 2006/105448 | 10/2006 |
| WO | WO 2006/107644 | 10/2006 |
| WO | WO 2006/112666 | 10/2006 |
| WO | WO 2006/119504 | 11/2006 |
| WO | WO 2006/124462 | 11/2006 |
| WO | WO 2006/124731 | 11/2006 |

(56) References Cited

FOREIGN PATENT DOCUMENTS

| | | |
|---|---|---|
| WO | WO 2006/135821 | 12/2006 |
| WO | WO 2006/136442 | 12/2006 |
| WO | WO 2007/013964 | 2/2007 |
| WO | WO 2007/017096 | 2/2007 |
| WO | WO 2007/021795 | 2/2007 |
| WO | WO 2007/022268 | 2/2007 |
| WO | WO 2007/023105 | 3/2007 |
| WO | WO 2007/025949 | 3/2007 |
| WO | WO 2007/030366 | 3/2007 |
| WO | WO 2007/032466 | 3/2007 |
| WO | WO 2007/033780 | 3/2007 |
| WO | WO 2007/038209 | 4/2007 |
| WO | WO 2007/044698 | 4/2007 |
| WO | WO 2007/044729 | 4/2007 |
| WO | WO 2007/048802 | 5/2007 |
| WO | WO 2007/053135 | 5/2007 |
| WO | WO 2007/053452 | 5/2007 |
| WO | WO 2007/053498 | 5/2007 |
| WO | WO 2007/055418 | 5/2007 |
| WO | WO 2007/056023 | 5/2007 |
| WO | WO 2007/056075 | 5/2007 |
| WO | WO 2007/056170 | 5/2007 |
| WO | WO 2007/058392 | 5/2007 |
| WO | WO 2007/058626 | 5/2007 |
| WO | WO 2007/059108 | 5/2007 |
| WO | WO 2007/061554 | 5/2007 |
| WO | WO 2007/064883 | 6/2007 |
| WO | WO 2007/064931 | 6/2007 |
| WO | WO 2007/066189 | 6/2007 |
| WO | WO 2007/067444 | 6/2007 |
| WO | WO 2007/071752 | 6/2007 |
| WO | WO 2007/084314 | 7/2007 |
| WO | WO 2007/088999 | 8/2007 |
| WO | WO 2007/092879 | 8/2007 |
| WO | WO 2007/093901 | 8/2007 |
| WO | WO 2007/109334 | 9/2007 |
| WO | WO 2007/110868 | 10/2007 |
| WO | WO 2007/112347 | 10/2007 |
| WO | WO 2007/120097 | 10/2007 |
| WO | WO 2007/120339 | 10/2007 |
| WO | WO 2007/125351 | 11/2007 |
| WO | WO 2007/125405 | 11/2007 |
| WO | WO 2007/126841 | 11/2007 |
| WO | WO 2007/134259 | 11/2007 |
| WO | WO 2007/136465 | 11/2007 |
| WO | WO 2007/140957 | 12/2007 |
| WO | WO 2007/143600 | 12/2007 |
| WO | WO 2007/147217 | 12/2007 |
| WO | WO 2008/001070 | 1/2008 |
| WO | WO 2008/003766 | 1/2008 |
| WO | WO 2008/005877 | 1/2008 |
| WO | WO 2008/008234 | 1/2008 |
| WO | WO 2008/008747 | 1/2008 |
| WO | WO 2008/012635 | 1/2008 |
| WO | WO 2008/021389 | 2/2008 |
| WO | WO 2008/021851 | 2/2008 |
| WO | WO 2008/025556 | 3/2008 |
| WO | WO 2008/033858 | 3/2008 |
| WO | WO 2008/033999 | 3/2008 |
| WO | WO 2008/034859 | 3/2008 |
| WO | WO 2008/034860 | 3/2008 |
| WO | WO 2008/037459 | 4/2008 |
| WO | WO 2008/042639 | 4/2008 |
| WO | WO 2008/052898 | 5/2008 |
| WO | WO 2008/052934 | 5/2008 |
| WO | WO 2008/060907 | 5/2008 |
| WO | WO 2008/063583 | 5/2008 |
| WO | WO 2008/063609 | 5/2008 |
| WO | WO 2008/071455 | 6/2008 |
| WO | WO 2008/074068 | 6/2008 |
| WO | WO 2008/075068 | 6/2008 |
| WO | WO 2008/076278 | 6/2008 |
| WO | WO 2008/078091 | 7/2008 |
| WO | WO 2008/078100 | 7/2008 |
| WO | WO 2008/079460 | 7/2008 |
| WO | WO 2008/079933 | 7/2008 |
| WO | WO 2008/085942 | 7/2008 |
| WO | WO 2008/089105 | 7/2008 |
| WO | WO 2008/099075 | 8/2008 |
| WO | WO 2008/107436 | 9/2008 |
| WO | WO 2008/107544 | 9/2008 |
| WO | WO 2008/109181 | 9/2008 |
| WO | WO 2008/109943 | 9/2008 |
| WO | WO 2008/115974 | 9/2008 |
| WO | WO 2008/117269 | 10/2008 |
| WO | WO 2008/118454 | 10/2008 |
| WO | WO 2008/123755 | 10/2008 |
| WO | WO 2008/128141 | 10/2008 |
| WO | WO 2008/130584 | 10/2008 |
| WO | WO 2008/131972 | 11/2008 |
| WO | WO 2008/141065 | 11/2008 |
| WO | WO 2008/142720 | 11/2008 |
| WO | WO 2008/144253 | 11/2008 |
| WO | WO 2008/151184 | 12/2008 |
| WO | WO 2008/153207 | 12/2008 |
| WO | WO 2008/153852 | 12/2008 |
| WO | WO 2008/154221 | 12/2008 |
| WO | WO 2008/156712 | 12/2008 |
| WO | WO 2009/013335 | 1/2009 |
| WO | WO 2009/013354 | 1/2009 |
| WO | WO 2009/097446 | 1/2009 |
| WO | WO 2009/016253 | 2/2009 |
| WO | WO 2009/019518 | 2/2009 |
| WO | WO 2009/021083 | 2/2009 |
| WO | WO 2009/029473 | 3/2009 |
| WO | WO 2009/029625 | 3/2009 |
| WO | WO 2009/030871 | 3/2009 |
| WO | WO 2009/032861 | 3/2009 |
| WO | WO 2009/036012 | 3/2009 |
| WO | WO 2009/044788 | 4/2009 |
| WO | WO 2009/046606 | 4/2009 |
| WO | WO 2009/047255 | 4/2009 |
| WO | WO 2009/047506 | 4/2009 |
| WO | WO 2009/047522 | 4/2009 |
| WO | WO 2009/047993 | 4/2009 |
| WO | WO 2009/049018 | 4/2009 |
| WO | WO 2009/050183 | 4/2009 |
| WO | WO 2009/053737 | 4/2009 |
| WO | WO 2009/055828 | 4/2009 |
| WO | WO 2009/056886 | 5/2009 |
| WO | WO 2009/071535 | 6/2009 |
| WO | WO 2009/073153 | 6/2009 |
| WO | WO 2009/085185 | 7/2009 |
| WO | WO 2009/086130 | 7/2009 |
| WO | WO 2009/086509 | 7/2009 |
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO 2009/099982 | 8/2009 |
| WO | WO 2009/103652 | 8/2009 |
| WO | WO 2009/105717 | 8/2009 |
| WO | WO 2009/108332 | 9/2009 |
| WO | WO 2009/108827 | 9/2009 |
| WO | WO 2009/112826 | 9/2009 |
| WO | WO 2009/114870 | 9/2009 |
| WO | WO 2009/114874 | 9/2009 |
| WO | WO 2009/122180 | 10/2009 |
| WO | WO 2009/123967 | 10/2009 |
| WO | WO 2009/124755 | 10/2009 |
| WO | WO 2009/125808 | 10/2009 |
| WO | WO 2009/125809 | 10/2009 |
| WO | WO 2009/126584 | 10/2009 |
| WO | WO 2009/128520 | 10/2009 |
| WO | WO 2009/131687 | 10/2009 |
| WO | WO 2009/131926 | 10/2009 |
| WO | WO 2009/132980 | 11/2009 |
| WO | WO 2009/133127 | 11/2009 |
| WO | WO 2009/141386 | 11/2009 |
| WO | WO 2009/144205 | 12/2009 |
| WO | WO 2009/144302 | 12/2009 |
| WO | WO 2009/146034 | 12/2009 |
| WO | WO 2009/148916 | 12/2009 |

(56) References Cited

FOREIGN PATENT DOCUMENTS

| | | |
|---|---|---|
| WO | WO 2009/150150 | 12/2009 |
| WO | WO 2009/150240 | 12/2009 |
| WO | WO 2009/151997 | 12/2009 |
| WO | WO 2009/153592 | 12/2009 |
| WO | WO 2009/157423 | 12/2009 |
| WO | WO 2010/006947 | 1/2010 |
| WO | WO 2010/007099 | 1/2010 |
| WO | WO 2010/007116 | 1/2010 |
| WO | WO 2010/009155 | 1/2010 |
| WO | WO 2010/009195 | 1/2010 |
| WO | WO 2010/009207 | 1/2010 |
| WO | WO 2010/009735 | 1/2010 |
| WO | WO 2010/015643 | 2/2010 |
| WO | WO 2010/017047 | 2/2010 |
| WO | WO 2010/019210 | 2/2010 |
| WO | WO 2010/019899 | 2/2010 |
| WO | WO 2010/030027 | 3/2010 |
| WO | WO 2010/036959 | 4/2010 |
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/062571 | 6/2010 |
| WO | WO 2010/064621 | 6/2010 |
| WO | WO 2010/064875 | 6/2010 |
| WO | WO 2010/067886 | 6/2010 |
| WO | WO 2010/067888 | 6/2010 |
| WO | WO 2010/075074 | 7/2010 |
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/089411 | 8/2010 |
| WO | WO 2010/092181 | 8/2010 |
| WO | WO 2010/099938 | 9/2010 |
| WO | WO 2010/103306 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/053518 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/066342 | 6/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082400 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101409 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |
| WO | WO 2011/112995 | 9/2011 |
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |
| WO | WO 2011/147198 | 12/2011 |
| WO | WO 2011/147199 | 12/2011 |
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2011/159877 | 12/2011 |
| WO | WO 2011/161699 | 12/2011 |
| WO | WO 2011/163330 | 12/2011 |
| WO | WO 2012/000103 | 1/2012 |
| WO | WO 2012/003544 | 1/2012 |
| WO | WO 2012/004217 | 1/2012 |

(56) References Cited

FOREIGN PATENT DOCUMENTS

| | | |
|---|---|---|
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |
| WO | WO 2012/031004 | 3/2012 |
| WO | WO 2012/032031 | 3/2012 |
| WO | WO 2012/032065 | 3/2012 |
| WO | WO 2012/032067 | 3/2012 |
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061156 | 5/2012 |
| WO | WO 2012/061337 | 5/2012 |
| WO | WO 2012/062462 | 5/2012 |
| WO | WO 2012/063207 | 5/2012 |
| WO | WO 2012/064715 | 5/2012 |
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/078777 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |
| WO | WO 2012/083954 | 6/2012 |
| WO | WO 2012/084704 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/129344 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |
| WO | WO 2013/033981 | 3/2013 |
| WO | WO 2013/039854 | 3/2013 |
| WO | WO 2013/041634 | 3/2013 |
| WO | WO 2013/049352 | 4/2013 |
| WO | WO 2013/053051 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/170063 | 10/2014 |
| WO | WO 2014/171755 | 10/2014 |
| WO | WO 2014/172644 | 10/2014 |
| WO | WO 2014/174307 | 10/2014 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/057938 | 4/2015 |
| WO | WO 2015/057963 | 4/2015 |
| WO | WO 2015/059668 | 4/2015 |
| WO | WO 2015/061572 | 4/2015 |
| WO | WO 2015/066452 | 5/2015 |
| WO | WO 2015/108992 | 7/2015 |
| WO | WO 2016/042084 | 3/2016 |
| WO | WO 2016/064960 | 4/2016 |
| WO | WO 2016/134292 | 8/2016 |
| WO | WO 2016/134314 | 8/2016 |
| WO | WO 2016/192680 | 12/2016 |
| WO | WO 2017/009275 | 1/2017 |
| WO | WO 2017/009400 | 1/2017 |
| WO | WO 2017/011561 | 1/2017 |
| WO | WO 2017/011820 | 1/2017 |
| WO | WO 2017/023972 | 2/2017 |
| WO | WO 2017/023988 | 2/2017 |
| WO | WO 2017/023989 | 2/2017 |
| WO | WO 2017/024003 | 2/2017 |
| WO | WO 2017/024004 | 2/2017 |
| WO | WO 2017/024015 | 2/2017 |
| WO | WO 2017/024025 | 2/2017 |
| WO | WO 2017/028314 | 2/2017 |
| WO | WO 2017/050864 | 3/2017 |
| WO | WO 2017/223414 | 12/2017 |
| WO | WO 2018/041091 | 3/2018 |
| WO | WO 2018/049214 | 3/2018 |
| WO | WO 2018/067512 | 4/2018 |
| WO | WO 2018/093029 | 5/2018 |
| WO | WO 2018/093215 | 5/2018 |
| WO | WO 2018/105972 | 6/2018 |
| WO | WO 2018/105973 | 6/2018 |
| WO | WO 2018/153373 | 8/2018 |
| WO | WO 2018/234354 | 12/2018 |
| WO | WO 2019/037640 | 2/2019 |
| WO | WO 2019/079369 | 4/2019 |
| WO | WO 2019/105886 | 6/2019 |
| WO | WO 2019/213506 | 11/2019 |
| WO | WO 2020/049017 | 3/2020 |
| WO | WO 2020/131627 | 6/2020 |

(56) References Cited

FOREIGN PATENT DOCUMENTS

| | | |
|---|---|---|
| WO | WO 2020/131674 | 6/2020 |
| WO | WO 2020/182062 | 9/2020 |
| WO | WO 2021/113479 | 6/2021 |

OTHER PUBLICATIONS

Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.

Anonymous, "American Society for Clinical Pharmacology and Therapeutics," Clin Pharma and Thera., Feb. 13, 2019, 105(S1):S5-S121.

Anonymous, "In Vitro Metabolism- and Transporter-Mediated Drug-Drug Interaction Studies Guidance for Industry", Clinical Pharmacology, Oct. 2017, 47 pages.

Antonios-McCrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.

Arai et al., "Characterization of the cell or origin and propagation potential of the fibroblast growth factor 9-induced mouse model of lung adenocarcinoma," J. Pathol., Mar. 2015, 235(4): 593-605.

Arai et al., "Fibroblast growth factor receptor 2 tyrosine kinase fusions define a unique molecular subtype of cholangiocarcinoma," Hepatology, 2014, 59(4):1427-1434.

Argentina Office Action in Argentina Application No. 20130102068, dated Jul. 17, 2020, 10 pages.

Argentina Office Action in Argentina Application No. 20140101651, dated Jul. 29, 2021, 9 pages.

Argentina Office Action in Argentina Application No. 20180101392, dated Mar. 8, 2022, 6 pages.

Argentina Office Action in Argentina Application No. 20140101651, dated Nov. 21, 2019, 5 pages.

Atzrodt et al., "The Renaissance of H/D Exchange," Angew Chem Int Ed., 2007, 7744-7765.

Australian Allowance in Australian Application No. 2020250201, dated Jun. 23, 2022, 4 pages.

Australian Office Action in Australian Application No. 2013287176, dated Sep. 12, 2017, 4 pages.

Australian Office Action in Australian Application No. 2014253798, dated Jul. 31, 2017, 4 pages.

Australian Office Action in Australian Application No. 2016219816, dated Aug. 26, 2019, 3 pages.

Australian Office Action in Australian Application No. 2016219822, dated Jul. 8, 2019, 4 pages.

Australian Office Action in Australian Application No. 2018208772, dated Jul. 1, 2018, 5 pages.

Australian Office Action in Australian Application No. 2018272013, dated Sep. 2, 2021, 4 pages.

Australian Office Action in Australian Application No. 2019200066, dated Aug. 27, 2019, 6 pages.

Australian Office Action in Australian Application No. 2020250211, dated Sep. 13, 2021, 4 pages.

Australian Office Action in Australian Application No. 2020270520, dated Dec. 16, 2021, 4 pages.

Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.

Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.

Balek, L., "Arq 087 inhibits FGFR signaling and rescues aberrant cell proliferation and differentiation in experimental models of craniosynostoses and chondrodysplasias caused by activating mutations in FGFR1, FGFR2 and FGFR3," Bone, Dec. 2017, 105:57-66.

Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.

Bauer, "Pharmaceutical Solids—The Amorphous Phase", Journal of Validation Technology, 2009, 15(3):63-68.

Bavin, "Polymorphism in Process Development," Chemistry & Industry, Society of Chemical Industry, Aug. 1989, 527-529.

Bazyl et al., "The selective ortho-methoxylation of pentafluorobenzoic acid—a new way to tetrafluorosalicylic acid and its derivatives," J Flour Chem., Feb. 11, 1999, 94(1):11-13.

Beekman et al., "New Molecular Targets and Novel Agents in the Treatment of Advanced Urothelial Cancer," Semin Oncol, 2007, 34: 154-164.

Bello et al., "E-3810 is a potent dual inhibitor of VEGFR and FGFR that exerts antitumor activity in multiple preclinical models," Cancer Res, 2011.

Bello et al., "E-3810 is a potent dual inhibitor of VEGFR and FGFR that exerts antitumor activity in multiple preclinical models," Cancer Res, 2011, Supplemental figures, 4 pages.

Bello et al., "E-3810 is a potent dual inhibitor of VEGFR and FGFR that exerts antitumor activity in multiple preclinical models," Cancer Res, 2011, Supplemental table, 3 pages.

Bello et al., "E-3810 is a potent dual inhibitor of VEGFR and FGFR that exerts antitumor activity in multiple preclinical models," Cancer Res, 2011, Supplementary data, 4 pages.

Benet-Pages et al., "An FGF23 missense mutation causes familial tumoral calcinosis with hyperphosphatemia, " Human Molecular Genetics, 2005, 14(3):385-390.

Berge et al., "Pharmaceutical Salts", Journal of Pharmaceutical Science, 1977, 66(2):1-19.

Bergwitz and Juppner, "Regulation of Phosphate Homeostasis by PTH, Vitamin D, and FGF23," Annu. Rev. Med., 2010, 61:91-104.

Bhide et al., "Discovery and Preclinical Studies of (R )-1-(4-(4-Fluoro-2-methyl-1H-indol-5-yloxy)-5-methylpyrrolo[2,1-f][1,2,4]triazin-6-yloxy)propan-2-ol (BMS-540215), an In Vivo Active Potent VEGFR-2 Inhibitor," Journal of Medicinal Chemistry, 2006, 49(7): 2143-2146.

Billerey et al., "Frequent FGFR3 Mutations in Papillary Non-Invasive Bladder (pTa) Tumors," American Journal of Pathology, Jun. 2001, 158(6): 1955-1959.

Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.

Biocentury, Week of Nov. 10, 2014, 52 pages.

Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.

Black et al., "Targeted therapies in bladder cancer—an update," Urologic Oncology: Seminars and Original Investigations, 2007, 433-438.

Blom et al., "Optimizing Preparative LC-MS Configurations and Methods for Parallel Synthesis Purification", J Combi Chem., 2003, 5:670.

Blom et al., Preparative LC-MS Purification: Improved Compound Specific Method Optimization, J Combi Chem. 2004, 6(6):874-883.

Blom, K., "Two-Pump at Column Dilution Configuration for Preparative LC-MS", J Combi Chem., 2002, 4:295.

Bonaventure et al., "Common Mutations in the Fibroblast Growth Factor Receptor 3 (FRFR3) Gene Account for Achondroplasia, Hypochondroplasia and Thanatophoric Dwarfism," Clin Pediatr Endocrinol, 1997, 105-113.

Bono et al., "Inhibition of Tumor Angiogenesis and Growth by a Small-Molecule Multi-FGF Receptor Blocker with Allosteric Properties," Cancer Cell, Apr. 2013, 477-488.

Borad et al., "Fibroblast growth factor receptor 2 fusions as a target for treating cholangiocarcinoma," Current opinion in Gastroenterology, May 2015, 31(3):264-268.

Brazilian Office Action in Brazilian Application No. BR112019024769-6, dated Aug. 29, 2022, 7 pages.

(56) References Cited

OTHER PUBLICATIONS

Brennfuhrer et al., "Palladium-Catalyzed Carbonylation Reactions of Aryl Halides and Related Compounds," Angew Chem Int Ed., May 25, 2009, 48(23):4114-4133.
Brooks et al., "Fibroblast growth factor signaling: a new therapeutic opportunity in cancer," Clinical Cancer Research, 2012, 1-23.
Byrn et al., "Pharmacautical Solids: A Strategic Approach to Regulatory Considerations," Pharmaceutical Research., Jul. 1995, 12(7):945-954.
Caira, "Crystalline Polymorphism of Organic Compounds," Topics in Current Chemistry, Jan. 1, 1998, 198:163-208.
Canada Office Action in Canada Application No. 2,976,788, dated Apr. 7, 2022, 4 pages.
Canada Office Action in Canada Application No. 2,976,790, dated Apr. 25, 2022, 4 pages.
Cancer [online], [retrieved on Jul. 6, 2007] Retrieved from the Internet, URL: http://www.nlm.nih.gov/medlineplus/cancer.html.
Capelletti et al., "Identification of Recurrent FGFR3-TACC3 Fusion Oncogenes from Lung Adenocarcinoma," AACR Journals, 2014, 6551-6558.
Cappellen et al., "Frequent activating mutations of FGFR3 in human bladder and cervix carcinomas," Nature Genetics, Sep. 1999, 23: 18-20.
Carmichael et al., "Familial Tumoral Calcinosis: A Forty-Year Follow-up on One Family," The Journal of Bone & Joint Surgery, 2009, 664-671.
Casey et al., "Translating in vivo metabolomic analysis of succinate dehydrogenase deficient tumours into clinical utility," JCO Precis Oncol., Mar. 29, 2018, 2:1-12.
Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.
Chandrani et al., "Drug-sensitive FGFR3 mutations in lung adenocarcinoma," Annals of Oncology, 2017, 28: 597-603.
Charoenngam et al., "Hereditary metabolic bone diseases: A review of pathogenesis, diagnosis and management," Genes, Oct. 2022, 13:1-34.
Chase et al., "Activity of TKI258 against primary cells and cell lines with FGFR1 fusion genes associated with the 8p11 myeloproliferative syndryome," Blood, 2007, 110:3729-3734.
Chefetz and Sprecher, "Familial tumoral calcinosis and the role of O-glycosylation in the maintenance of phosphate homeostasis," Biochimica et Biophysica Acta, 2009, 847-852.
Chefetz et al., "A novel homozygous missense mutation in FGF23 causes Familial Tumoral Calcinosis associated with disseminated visceral calcification," Hum Genet, 2005, 118:261-266.
Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.
Chen et al., "Acenaphtho[1,2-b]pyrrole-Based Selective Fibroblast Growth Factor Receptors 1 (FRGR1) Inhibitors: Design, Synthesis, and Biological Activity," Jounal of Medicinal Chemistry, 2011, 54: 3732-3745.
Chen et al., "FGFR3 as a therapeutic target of the small molecule inhibitor PKC412 in hematopoietic malignancies," Oncogene, 2005, 24: 8259-8267.
Chen et al., "Genome-Wide Loss of Heterozygosity and DNA Copy Number Aberration in HPV-Negative Oral Squamous Cell Carcinoma and Their Associations with Disease-Specific Survival," Plos One, Aug. 2015, 23 pages.
Cherukupalli et al., "An insight on synthetic and medicinal aspects of pyrazolo[1,5-alpyrimidine scaffold," European Journal of Medicinal Chemistry, Nov. 10, 2016, 126:298-352.
Chesi et al., "Activated fibroblast growth factor receptor 3 is an oncogene that contributes to tumor progression in multiple myeloma," Blood, 2001, 97:729-736.
Chesi et al., "Frequent translocation t(4;14)(p16.3;q32.3) in multiple myeloma is associated with increased expression and activating mutations of fibroblast growth factor receptor 3," Nature Genetics, 1997, 260-264.
Chilean Office Action in Chilean Application No. 1984-2017, dated Sep. 12, 2019, 9 pages.
Chilean Office Action in Chilean Application No. 2015-003089, dated Apr. 24, 2017, 17 pages (with English Translation).
Chilean Office Action in Chilean Application No. 2015-003089, dated Jan. 23, 2018, 8 pages.
Chilean Office Action in Chilean Application No. 2122-2017, dated Apr. 22, 2019, 25 pages.
Chilean Office Action in Chilean Application No. 2122-2017, dated Nov. 15, 2019, 15 pages.
Chilean Office Action in Chilean Application No. 2839-2020, dated Jan. 31, 2022, 42 pages (with English translation).
Chilean Office Action in Chilean Application No. 2848-2020, dated Mar. 7, 2022, 23 pages.
Chilean Office Action in Chilean Application No. 3355-2014, dated Jan. 18, 2017, 17 pages (with English translation).
Chilean Office Action in Chilean Application No. 3439-2019, dated Feb. 10, 2021, 26 pages.
Chilean Office Action in Chilean Application No. 3439-2019, dated Jan. 31, 2022, 15 pages.
Chilean Opposition in Chilean Application No. 3355-2014, received Feb. 3, 2017, 3 pages (English translation only).
Chinese Office Action in Chinese Application No. 10874686.0, dated Oct. 8, 2019, 10 pages.
Chinese Office Action in Chinese Application No. 201380041027.9, dated Feb. 13, 2017, 10 pages (with English translation).
Chinese Office Action in Chinese Application No. 201380041027.9, dated Jul. 12, 2016, 11 pages (with English translation).
Chinese Office Action in Chinese Application No. 201380041027.9, dated Oct. 28, 2015, 17 pages (with English translation).
Chinese Office Action in Chinese Application No. 201480028858.7, dated Apr. 4, 2018, 10 pages (English Translation).
Chinese Office Action in Chinese Application No. 201480028858.7, dated Aug. 19, 2016, 18 pages (English Translation).
Chinese Office Action in Chinese Application No. 201480028858.7, dated Jul. 12, 2017, 10 pages (English Translation).
Chinese Office Action in Chinese Application No. 201680011332.7, dated Aug. 5, 2019, 14 pages.
Chinese Office Action in Chinese Application No. 201680011348.8, dated Aug. 2, 2019, 14 pages.
Chinese Office Action in Chinese Application No. 201710395346.X, dated Jan. 22, 2019, 17 pages.
Chinese Office Action in Chinese Application No. 201710395346.X, dated Sep. 9, 2019, 10 pages.
Chinese Office Action in Chinese Application No. 201710874686.0, dated Feb. 25, 2019, 17 pages.
Chinese Office Action in Chinese Application No. 201910023729.3, dated Mar. 23, 2022, 11 pages.
Chinese Office Action in Chinese Application No. 201910023729.3, dated Sep. 8, 2021, 11 pages.
Chinese Office Action in Chinese Application No. 2020800850230, dated Apr. 12, 2024, 12 pages (with English Translation).
Chinese Office Action in Chinese Application No. 201910023729.3, dated Mar. 3, 2021, 15 pages.
Chng et al., "Translocation t(4;14) retains prognostic significance even in the setting of high-risk molecular signature," Leukemia, 2008, 2: 459-461.
Chuaqui et al., "Interaction Profiles of Protein Kinase—Inhibitor Complexes and Their Application to Virtual Screening," J. Med. Chem., 2005, 48: 121-133.
Ciappetti and Geithlen "Molecular Variations Based on Isosteric Replacements," The Practice of Medicinal Chemistry, 2008, Chapter 15, pp. 290-341.
Clinicaltrials.gov, "A Study to Evaluate the Efficacy and Safety of Pemigatinib Versus Cherrotherapy in Unresectable or Metastatic Chol (FIGHT-302)," NCT03656536, Mar. 6, 2019, retrieved from URL <https://www.clinicaltrials.gov/ct2/history/NCT03656536?V_5=View#StudyPageTop,>, 4 pages.

(56) References Cited

OTHER PUBLICATIONS

Cole et al., "Inhibition of FGFR2 and FGFR 1 increases cisplatin sensitivity in ovarian cancer," Cancer Biol. Therapy, Sep. 1, 2010, 10(5):495-504.
Coleman, "Positive and negative regulation of cellular sensitivity to anti-cancer drugs by FGF-2," Drug Resistance Updates, 2003, 85-94.
Colombian Office Action in Colombian Application No. 14-275934-6, dated May 31, 2016, 3 pages (English translation only).
Colombian Office Action in Colombian Application No. 14-275934-6, dated Nov. 17, 2015, 12 pages (English translation only).
Colombian Office Action in Colombian Application No. 16100866, dated Aug. 10, 2017, 9 pages.
Colombian Office Action in Colombian Application No. NC2017/0008795, dated Nov. 29, 2018, 8 pages.
Colombian Office Action in Colombian Application No. NC2017/0008795, dated Aug. 16, 2019, 6 pages.
Colombian Office Action in Colombian Application No. NC2017/0008795, dated Aug. 29, 2017, 2 pages.
Colombian Office Action in Colombian Application No. NC2017/0008824, dated Aug. 31, 2017, 3 pages.
Colombian Office Action in Colombian Application No. NC2017/0008824, dated Nov. 29, 2018, 8 pages.
Colombian Office Action in Colombian Application No. NC2019/0009690, dated Jan. 22, 2020, 20 pages.
Colombian Office Action in Colombian Application No. NC2019/0014699, dated Jun. 6, 2022, 31 pages.
Colombian Opposition in Colombian Application No. NC 2021/0004568, dated Apr. 15, 2021, 21 pages.
Cordovilla et al., "The Stille Reaction, 38 Years Later," ACS Catal., Apr. 17, 2015, 5(5):3040-3053.
Corre et al., "Synthesis and biological evaluation of a triazole-based library of pyrido[2,3-d]pyrimidines as FGFR3 tyrosine kinase inhibitors," Organic & Biomolecular Chemistry, 2010, 8:2164-2173.
Costa Rican Office Action in Costa Rican Application No. 2014-0577, dated Apr. 15, 2020, 18 pages.
Costa Rican Office Action in Costa Rican Application No. 2014-0577, dated Jun. 13, 2019, 17 pages.
Costa Rican Office Action in Costa Rican Application No. 2015-0578, dated Jun. 11, 2020, 15 pages.
Costa Rican Office Action in Costa Rican Application No. 2019-573, dated Jul. 12, 2022, 12 pages.
Costa Rican Opposition in Costa Rican Application No. PCT/US2013/045309, dated Jun. 29, 2015, 14 pages (English Translation).
Covic et al., "Vascular calcification in chronic kidney disease," Clinical Science, 2010, 119: 111-121.
Crose et al., "FGFR4 Blockade Exerts Distinct Antitumorigenic Effects in Human Embryonal versus Alveolar Rhabdomyosarcoma," Clin Cancer Res., 2012, 18:3780-3790.
Dailey et al., "Mechanisms underlying differential responses to FGF signaling," Cytokine & Growth Factor Reviews, 2005, 233-247.
Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.
Desnoyers et al., "Targeting FGF19 inhibits tumor growth in colon cancer xenograft and FGF19 transgenic hepatocellular carcinoma models," Oncogene, 2008, 27:85-97.
Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.
Dieci et al., "Fibroblast Growth Factor Receptor Inhibitors as a Cancer Treatment: From a Biologic Rationale to Medical Perspectives," Cancer Discovery, 2013, 1-16.
Dienstmann et al., "Genomic aberrations in the FGFR pathway: opportunities for targeted therapies in solid tumors," Annals of Oncology, 2013, 1-12.
Diller and Li, "Kinases, Homology Models, and High Throughput Docking," J. Med. Chem., 2003, 46: 4638-4647.
Dimopoulos et al., "Lenalidomide plus Dexamethasone for Relapsed or Refractory Multiple Myeloma," The New England Journal of Medicine, 2007, 357:2123-2132.
Ding et al., "Somatic mutations affect key pathways in lung adenocarcinoma," Nature., Oct. 23, 2008, 455:1069-1075.
Dovedi and Davies, "Emerging targeted therapies for bladder cancer: a disease waiting for a drug," Cancer Metastasis Rev, 2009, 28:355-367.
Dring et al., "A Global Expression-based Analysis of the Consequences of the t(4;14) Translocation in Myeloma," Clinical Cancer Research, Sep. 2004, 10: 5692-5701.
Drueke et al., "Phosphate binders in CKD: bad news or good news?," Journal of the American Society of Nephrology, Aug. 2012, 23(8):1277-1280.
Dutt et al., "Drug-sensitive FGFR2 mutations in endometrial carcinoma," PNAS, Jun. 24, 2008, 105(25):8713-8717.
Dutt et al., "Drug-sensitive FGFR2 mutations in endometrial carcinoma," Supporting Information, Jun. 2008, 8 pages.
Ecuador Office Action in Ecuador Application No. IEPI-2015-1225, dated Dec. 30, 2021, 21 pages.
Ecuador Office Action in Ecuador Application No. IEPI-2015-1225, dated May 11, 2022, 18 pages.
Ecuador Opposition in Ecuador Application No. SENADI-2020-78226, dated Jun. 2022, 19 pages.
Ecuador Opposition in Ecuador Application No. SENADI-2020-78230, dated Jun. 2022, 21 pages.
Edmondson et al., "Aminopiperidine-fused imidazoles as dipeptidyl peptidase-IV inhibitors," Bioorg & Med Chem Lett., 2009, 19(15):4097-4101.
Eissa, "Synthesis and evaluation of some surface active agents from long chain fatty amine," Spanish National Research Council, Jan. 2007, 58(4):379-389.
Elsheikh et al., "FGFR1 amplification in breast carcinomas: a chromogenic in situ hybridisation analysis," Breast Cancer Research, Mar. 2007, 9(2): 1-12.
Erian at al., "2-Aryl-1,1-dicyano-3-phenylsulfonylpropenes in heterocyclic synthesis. A synthetic strategy towards heterocyclic sulfones," Monatshefte fuer Chemie, 1998, 129(10):1049-1056.
Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.
Eswarakumar and Schlessinger, "Cellular signaling by fibroblast growth factor receptors," Cytokine & Growth Factor Reviews, 2005, 139-149.
Eurasian Office Action in Eurasian Application No. 201590005, dated Oct. 21, 2015, 6 pages.
Eurasian Office Action in Eurasian Application No. 201590005, Mar. 28, 2018, 6 pages.
Eurasian Office Action in Eurasian Application No. 201791866, dated Feb. 19, 2018, 10 pages (English Translation).
Eurasian Office Action in Eurasian Application No. 201791867, dated Apr. 4, 2018, 4 pages (English Translation).
Eurasian Office Action in Eurasian Application No. 201992794, dated Sep. 17, 2021, 7 pages.
Eurasian Office Action in Eurasian Application No. 202091923, dated Apr. 5, 2022, 4 pages.
Eurasian Office Action in Eurasian Application No. 202091923, dated Jul. 27, 2021, 6 pages (English Translation).
Eurasian Office Action in Eurasian Application No. 202092648, dated Feb. 8, 2022, 7 pages.
Eurasian Office Action in Eurasian Application No. 202092649/26, dated Apr. 22, 2022, 6 pages.
Eurasian Office Action in Eurasian Application No. 202190877, dated Oct. 6, 2021, 4 pages.
European Communication pursuant to Article 94(3) EPC in European Application No. 13783125.1, dated Jan. 26, 2016, 4 pages.
European Office Action in European Application No. 16715139.8, dated May 18, 2021, 9 pages.
European Office Action in European Application No. 18733045.1, dated Jan. 11, 2021, 5 pages.
European Office Action in European Application No. 19724670, dated Aug. 31, 2022, 3 pages.

(56) References Cited

OTHER PUBLICATIONS

European Office Action in European Application No. 19724670.5, dated Nov. 9, 2021, 4 pages.
European Office Action in European Application No. 19724676.2, dated Aug. 26, 2021, 5 pages.
European Office Action in European Application No. 20192679.7, dated Feb. 11, 2021, 7 pages.
European Office Action in European Application No. 20834013.3, dated Jul. 12, 2022, 3 pages.
European search report in European Application No. 16203866.5, dated Mar. 1, 2017, 7 pages.
European Search Report in European Application No. 17199421.3, dated Jul. 12, 2018, 15 pages.
European Search Report in European Application No. 17199421.3, dated Mar. 12, 2018, 14 pages.
Ezzat et al., "Dual Inhibition of RET and FGFR4 Restrains Medullary Thyroid Cancer Cell Growth," Clinical Cancer Research, 2005, 11:1336-1341.
Faul et al., "FGF23 induces left ventricular hypertrophy," The Journal of Clinical Investigation, 2010, 1-16.
FDA.gov, "FDA grants accelerated approval to pemigatinib for cholangiocarcinoma with an FGFR2 rearrangement or fusion," Apr. 20, 2020, [Retrieved on Apr. 27, 2021], retrieved from URL <https://www.fda.gov/drugs/resources-information-approved-drugs/fda-grants-accelerated-approval-pemigatinib-cholangiocarcinoma-fgfr2-rearrangement-or-fusion>, 2 pages.
Feng et al., "Guidance to rational use of pharmaceuticals in gallbladder sarcomatoid carcinoma using patient-derived cancer cells and whole exome sequencing," Oncotarget, 2017, 8(3): 5349-5360.
Feng et al., "Targeting Fibroblast Growth Factor Receptor Signaling Inhibits Prostate Cancer Progression," Clinical Cancer Research, 2012, 1-9.
Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cell lung cancer cells: therapeutic implications and synergism with epidermal growth factor receptor inhibition," Mol Cancer Therapy, 2008, 3408-3419.
French et al., Targeting FGFR4 inhibits hepatocellular carcinoma in preclinical mouse models, PLoS One 2012;7:e36713.
Fricker, "Metal based drugs: from serendipity to design," Dalton Transactions, 2007, 43:4903-4917.
Fricker, "The therapeutic application of lanthanides," Chemical Society Reviews, 2006, 35(6):524-533.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperostosis-hyperphosphatemia syndrome and familial tumoral calcinosis are allelic disorders," J Mol Med, 2005, 83:33-38.
Fu et al., "Intratumoral inorganic phosphate deprivation: A new anticancer strategy," Medical Hypotheses, Feb. 2020, 135:109497.
Fukumoto and Yamashita, "FGF23 is a hormone-regulating phophate metabolism—Unique biological characteristics of FGF23," Bone, 2007, 1190-1195.
Fun et al., "2-7(7,8-Diphenyl-1H-imidazo[4,5-f]-quinoxalin-2-yl)phenol methanol disolvate," Acta Crystallographica Section E Structure Reports Online, 2008, 64(9):o1741-01742.
Furniss "Acidic/Basic characteristics for purification," Vogel's Textbook of Practical Organic Chemistry, 5th edition, 1989, 131-133, 135-143.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Gallo et al., "Functions of Fibroblast Growth Factor Receptors in cancer defined by novel translocations and mutations," Cytokine & Growth Factor Reviews, 2015, 26(4):425-449.
Garringer et al., "Molecular genetic and biochemical analyses of FGF23 mutations in familial tumoral calcinosis," Am J Physiol Endocrinol Metab, 2008, 929-937.
Gattineni et al., "FGF23 decreases renal NaPi-2a and NaPi-2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gennaro et al., "Pharmaceutical Sciences," Remington's Pharmaceutical Sciences 17th Ed., Jan. 1985, 14-18 and 1409-1423.
Gerby et al., "2-Arylidenedihydroindole-3-ones: Design, synthesis, and biological activity on bladder carcinoma cell lines," Bioorganic & Medicinal Chemistry Letters, 2007, 208-213.
Ghorab et al., "Synthesis of some sulfur containing Tetrahydrobenzoabuthieno[b] Thieno(Pyridines, Quinolines, Oxazines and Pyrimidines) as possible radioprotective and Antineoplastic agents," Phosphorus, Sulfur and Silicon, Jan. 1998, 134/135:57-76.
Gibson, "Pharmaceutical Preformulation and Formulation," CRC Press LLC, 2009, 2nd ed, 559 pages.
Goetz et al., "Isolated C-terminal tail of FGF23 alleviates hypophosphatemia by inhibiting FGF23-FGFR-Klotho complex formation," PNAS, Jan. 2010, 107(1):407-412.
Golub et al., "Molecular Classification of Cancer: Class Discovery and Class Prediction by Gene Expression Monitoring," Science, 1999, 286: 531-537.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11):1045-1089.
Goyal et al,. "Polyclonal Secondary FGFR2 Mutations Drive Acquired Resistance to FGFR Inhibition in Patients with FGFR2 Fusion-Positive Cholangiocarcinoma," Cancer Discov., 2016, 7(3):252-263.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Granberg et al., "Strong FGFR3 staining is a marker for FGFR3 fusions in diffuse gliomas," Neuro-Oncology, 2017, 19(9): 1206-1216.
Grand et al., "Targeting FGFR3 in multiple myeloma: inhibition of t(4;14)-positive cells by SU5402 and PD173074," Leukemia, 2004, 18: 962-966.
Greene, T. W. and Wuts, P. G. M., "Protective Groups in Organic Synthesis", 3rd Ed., Wiley & Sons, Inc., New York (1999), pp. 696-926.
Greulich and Pollock, "Targeting mutant fibroblast growth factor receptors in cancer," Cell Press, May 2011, 17(5): 283-292.
Grose and Dickson, "Fibroblast growth factor signaling in tumorigenesis," Cytokine & Growth Factor Reviews, 2005, 179-186.
Gu et al., "Phosphotyrosine profiling identifies the KG-1 cell line as a model for the study of FGFR1 fusions in acute myeloid leukemia," Blood, Dec. 15, 2006, 108(13):4202-42040.
Guagnano et al., "Discovery of 3-(2,6-Dichloro-3,5-dimethoxy-phenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase," J. Med. Chem., 2011, 54: 7066-7083.
Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.

(56) References Cited

OTHER PUBLICATIONS

Gust et al., "Fibroblast Growth Factor Receptor 3 Is a Rational Therapeutic Target in Bladder Cancer," Molecular Cancer Therapeutics, Jul. 2013, 12(7): 1245-1254.
Haas et al., "Recent Developments in Negishi Cross-Coupling Reactions," ACS Catal., 2016, 6(3): 1540-1552.
Hackam et al. "Translation of Research Evidence From Animals to Humans," JAMA, 296(14), 2006, 296(14):1731-1732.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 2015, 1-14.
Hara and Saito, "CARD9 versus CARMA1 in innate and adaptive immunity," Cell Press, 2009, 234-242.
Heinrich et al., "Fragment-based discovery of new highly substituted 1H-pyrrolo[2,3-b]- and 3H-imidazolo[4,5-b]-pyridines as focal adhesion kinase inhibitors," J of Med Chem., Jan. 8, 2013, 56(3):1160-1170.
Heinzle C, et al., "Differential Effects of Polymorphic Alleles of FGF Receptor 4 on Colon Cancer Growth and Metastasis," Cancer Research, Nov. 2012, 72(22):5767-5777.
Heinzle et al., "Is fibroblast growth factor receptor 4 a suitable target of cancer therapy?," Cur. Pharm. Des., 2014, 20:2881-2898.
Heinzle et al., "Targeting fibroblast-growth-factor-receptor-dependent signaling for cancer therapy," Expert Opinion, 2011, 1-18.
Helsten et al., "The FGFR Landscape in Cancer: Analysis of 4,853 Tumors by Next-Generation Sequencing," Clin. Cancer Res., Jan. 2016, 22:259-267.
Hess et al., "Synergistic effect of combination of pemigatinib with enfortumab vedotin (EV) in human bladder cancer models," Molecular Cancer Therapeutics, Presented at AACR-NCI-EORT Virtual International Conference on Molecular Targets and Cancer Therapeutics, presented Oct. 7-10, 2021, 9 pages.
Hideshima and Anderson, "Preclinical Studies of Novel Targeted Therapies," Hematol Oncol Clin N Am, 2007, 1071-1091.
Ho et al., "Fibroblast growth factor receptor 4 regulates proliferation, anti apoptosis and alpha-fetoprotein secretion during hepatocellular carcinoma progression and represents a potential target for therapeutic intervention," J Hepatol, 2009, 50:118-127.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Hu and Cong, "Fibroblast growth factor 19 is correlated with an unfavorable prognosis and promotes progression by activating fibroblast growth factor receptor 4 in advanced-stage serous ovarian cancer," Oncol Rep., Aug. 20, 2015, 34(5):2683-2691.
Huynh, "Tyrosine kinase inhibitors to treat liver cancer," Expert Opinion, 2010, 13-26.
Hynes and Dey, "Potential for Targeting the Fibroblast Growth Factor Receptors in Breast Cancer," Cancer Res, 2010, 70:5199-5202.
ICH Harmonised Tripartite Guideline, "Specifications: Test Procedures and Acceptance Criteria for New Drug Substances and New Drug Products Chemical Substances," ICHTRRPHU, Oct. 6, 1999, 35 pages.
Ichikawa et al., "A homozygous missense mutation in human KLOTHO causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder Is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
Indian Office Action in Indian Application No. 10665/DELNP/2014, dated Jun. 25, 2018, 8 pages.
Indian Office Action in Indian Application No. 201717030265, dated Dec. 12, 2019, 5 pages.
Indian Office Action in Indian Application No. 201717030267, dated Dec. 3, 2019, 7 pages.
Indian Office Action in Indian Application No. 202017052609, dated May 23, 2022, 7 pages.
Indian Office Action in Indian Application No. 202017052853, dated May 13, 2022, 6 pages.
Indian Office Action in Indian Application No. 9781/DELNP/2015, dated Jan. 18, 2019, 6 pages.
Indian Oral Hearing in Indian Application No. 201717030265, dated Jan. 13, 2022, 2 pages.
Indian Oral Hearing in Indian Application No. 9781/DELNP/2015, dated Sep. 14, 2022, 3 pages.
Indonesian Office Action in Indonesian Application No. P00201507153, dated Apr. 27, 2018, 5 pages (English Translation).
Indonesian Office Action in Indonesian Application No. P00202205354, dated Nov. 30, 2023, 8 pages (with English Translation).
Indonesian Office Action in Indonesian Application No. PID201705977, Jun. 5, 2020, 5 pages.
Inokuchi et al., "Therapeutic targeting of fibroblast growth factor receptors in gastric cancer," Gastroenterol Res Pract., Apr. 27, 2015, 2015:796380, 8 pages.
International Invitation to Pay Fees in International Appln. No. PCT/US2019/030633, dated Aug. 12, 2019, 5 pages.
International Preliminary Report on Patentability and Written Opinion in International Application No. PCT/US2011/066473, issued Jun. 25, 13, 10 pages.
International Preliminary Report on Patentability in International Application No. PCT/US2013/045309, mailed Dec. 24, 2014, 11 pages.
International Preliminary Report on Patentability in International Application No. PCT/US2013/054361, mailed Feb. 19, 2015, 7 pages.
International Preliminary Report on Patentability in International Application No. PCT/US2014/034662, dated Oct. 29, 2015, 12 pages.
International Preliminary Report on Patentability in International Application No. PCT/US2015/056583, dated Apr. 25, 2017, 7 pages.
International Preliminary Report on Patentability in International Application No. PCT/US2016/018737, dated Aug. 31, 2017, 8 pages.
International Preliminary Report on Patentability in International Application No. PCT/US2016/018770, dated Aug. 22, 2017, 10 pages.
International Preliminary Report on Patentability in International Application No. PCT/US2016/018787, dated Aug. 22, 2017, 7 pages.
International Preliminary Report on Patentability in International Application No. PCT/US2018/034559, dated Nov. 26, 2019, 8 pages.
International Preliminary Report on Patentability in International Application No. PCT/US2019/030578, dated Nov. 10, 2020, 14 pages.

(56) References Cited

OTHER PUBLICATIONS

International Preliminary Report on Patentability in International Application No. PCT/US2019/030633, dated Nov. 10, 2020, 10 pages.
International Preliminary Report on Patentability in International Application No. PCT/US2020/021313, dated Aug. 25, 2021, 11 pages.
International Preliminary Report on Patentability in International Application No. PCT/US2020/041104, dated Jan. 11, 2022, 7 pages.
International Preliminary Report on Patentability in International Application No. PCT/US2020/053436, dated Apr. 5, 2022, 8 pages.
International Preliminary Report on Patentability in International Application No. PCT/US2020/055547, dated Apr. 19, 2022, 7 pages.
International Preliminary Report on Patentability in International Application No. PCT/US2020/055735, dated Apr. 19, 2022, 8 pages.
International Preliminary Report on Patentability in International Application No. PCT/US2020/063038, dated Jun. 16, 2022, 8 pages.
International Preliminary Report on Patentability in International Application No. PCT/US2020/063064, dated May 17, 2022, 7 pages.
International Preliminary Report on Patentability in International Application No. PCT/US2021/013438, dated Jul. 28, 2022, 7 pages.
International Preliminary Report on Patentability in International Application No. PCT/US2022/053582, dated Jul. 4, 2024, 11 pages.
International Preliminary Report on Patentability in International Appln. No. PCT/US2022/032603, mailed on Dec. 21, 2023, 7 pages.
International Preliminary Report on Patentability in International Appln. No. PCT/US2022/032604, mailed on Dec. 21, 2023, 8 pages.
International Search Report and Written Opinion for International Application No. PCT/US2015/056583, dated Dec. 15, 2015, 10 pages.
International Search Report and Written Opinion for International Appln. No. PCT/US2022/053582 mailed Jun. 2, 2023, 17 pages.
International Search Report and Written Opinion in International Application No. PCT/US2020/053436, dated Dec. 4, 2020, 15 pages.
International Search Report and Written Opinion in International Application No. PCT/US2013/045309, mailed on Jan. 22, 2014, 19 pages.
International Search Report and Written Opinion in International Application No. PCT/US2013/054361, dated Oct. 16, 2013, 12 pages.
International Search Report and Written Opinion in International Application No. PCT/US2014/034662, mailed Oct. 24, 2014, 18 pages.
International Search Report and Written Opinion in International Application No. PCT/US2016/018737, dated Apr. 20, 2016, 12 pages.
International Search Report and Written Opinion in International Application No. PCT/US2016/018770, dated Jun. 2, 2016, 14 pages.
International Search Report and Written Opinion in International Application No. PCT/US2016/018787, dated Jun. 2, 2016, 12 pages.
International Search Report and Written Opinion in International Application No. PCT/US2018/034559, dated Mar. 8, 2019, 14 pages.
International Search Report and Written Opinion in International Application No. PCT/US2019/030578, dated Jul. 11, 2019, 26 pages.
International Search Report and Written Opinion in International Application No. PCT/US2019/030633, dated Nov. 28, 2019, 21 pages.
International Search Report and Written Opinion in International Application No. PCT/US2020/021313, dated Jun. 26, 2020, 19 pages.
International Search Report and Written Opinion in International Application No. PCT/US2020/041104, dated Sep. 4, 2020, 14 pages.
International Search Report and Written Opinion in International Application No. PCT/US2020/055547, dated Jan. 11, 2021, 13 pages.
International Search Report and Written Opinion in International Application No. PCT/US2020/055735, dated Dec. 15, 2020, 16 pages.
International Search Report and Written Opinion in International Application No. PCT/US2021/013438, dated Apr. 20, 2021, 16 pages.
International Search Report and Written Opinion in International Application No. PCT/US2022/032603, dated Aug. 26, 2022, 14 pages.
International Search Report and Written Opinion in International Application No. PCT/US2022/032604, dated Sep. 6, 2022, 15 pages.
International Search Report and Written Opinion in International Application. No. PCT/US2011/066473, dated Jun. 19, 2012, 15 pages.
International Search Report and Written Opinion in International Appln. No. PCT/US2020/063038, dated Mar. 15, 2021, 16 pages.
International Search Report and Written Opinion in International Appln. No. PCT/US2020/063064, dated Feb. 12, 2021, 13 pages.
Invitation to Pay Additional Fees and, Where Applicable, Protest Fee in International Application No. PCT/US2013/045309, mailed Nov. 25, 2013, 5 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Israeli Office Action in Israeli Application No. 236,078 dated Mar. 21, 2017, 10 pages (English Translation).
Israeli Office Action in Israeli Application No. 289834 dated Jul. 14, 2022, 4 pages.
Jackson et al., "8p11 Myeloproliferative syndrome: a review," Human Pathology, Apr. 1, 2010, 41:461-476.
Jan de Beur, "Tumoral Calcinosis: A Look into the Metabolic Mirror of Phosphate Homeostasis," The Journal of Clinical Endocrinology & Metabolism, 2005, 90: 2469-2471.
Japanese Office Action in Japanese Application No. 2015-517376, dated Feb. 21, 2017, 5 pages (with English translation).
Japanese Office Action in Japanese Application No. 2016-509131, dated Feb. 20, 2018, 5 pages (English Translation).
Japanese Office Action in Japanese Application No. 2017-543981, dated Dec. 3, 2019, 4 pages.
Japanese Office Action in Japanese Application No. 2017-544021, dated Nov. 26, 2019, 5 pages.
Japanese Office Action in Japanese Application No. 2018-228352, dated Aug. 20, 2019, 6 pages.
Japanese Office Action in Japanese Application No. 2019-565177, dated May 13, 2022, 11 pages.
Japanese Office Action in Japanese Application No. 2020-069604, dated Nov. 15, 2021, 7 pages.
Japanese Office Action in Japanese Application No. 2020-093529, dated Mar. 1, 2022, 5 pages.
Javidi-Sharifi et al., "Crosstalk between KIT and FGFR3 Promotes Gastrointestinal Stromal Tumor Cell Growth and Drug Resistance," Cancer Research, Mar. 2015, 75(5): 880-892.
Jebar et al., "FGFR3 and Ras gene mutations are mutually exclusive genetic events in urothelial cell carcinoma," Oncogene, 2005, 24: 5218-5225.
Ji et al., "Embase abstract: Modeling and simulation as gating for clinical pharmacology studies of INCB054828," 119th Annual Meeting of the American Society for Clinical Pharmacology and Therapeutics, Mar. 1, 2018, 2 pages.

(56) References Cited

OTHER PUBLICATIONS

Jiang et al., "miR-99a promotes proliferation targeting FGFR3 in human epithelial ovarian cancer cells," Biomedicine & Pharmacotherapy, 2014, 68: 163-169.
Johnson et al., "Pharmacological and Functional Comparison of the Polo-like Kinase Family: Insight into Inhibitor and Substrate Specificity," Biochemistry, 2007, 46:9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Jordan, "Tamoxifen: A Most Unlikely Pioneering Medicine," Nature Reviews: Drug Discovery, Mar. 2003, 2:205-213.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.
Kassack et al., "Structure-activity relationships of analogues of NF449 confirm NF449 as the most potent and selective known P2X1 receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Khojasteh et al., "Chemical inhibitors of cytochrome P450 isoforms in human liver microsomes: a re-evaluation of P450 isoform selectivity," Eur J Drug Metab Pharmacokinet., Mar. 2011, 36:1-16.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.
Kim et al., "The design, synthesis, and biological evaluation of potent receptor tyrosine kinase inhibitors," Bioorganic & Medicinal Chemistry Letters, 2012, 4979-4985.
Klein et al., "FGFRI Kinase Inhibitors: Close Regioisomers Adopt Divergent Binding Modes and Display Distinct Biophysical Signatures," American Chemical Society, 2014, 166-171.
Knights and Cook, "De-regulated FGF receptors as therapeutic targets in cancer," Pharmacology & Therapeutics, 2010, 125:105-117.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS ONE, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Korean Office Action in Korean Application No. 10-2015-7000701, dated Aug. 26, 2019, 19 pages.
Korean Office Action in Korean Application No. 10-2015-7032502, dated Sep. 9, 2020, 16 pages.
Korean Office Action in Korean Application No. 10-2020-7021884, dated Oct. 25, 2021, 6 pages.
Korean Office Action in Korean Application No. 10-2020-7021884, dated Oct. 28, 2020, 15 pages.
Korean Office Action in Korean Application No. 10-2021-7018897, dated Oct. 1, 2021, 15 pages.
Korean Office Action in Korean Application No. 10-2022-7018808, dated Sep. 16, 2022, 5 pages.
Kotha et al., "Recent applications of the Suzuki-Miyaura cross-coupling reaction in organic synthesis," Tetrahedron, 2002, 58:9633-9695.
Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Koziczak et al., "Blocking of FGFR signaling inhibits breast cancer cell proliferation through downregulation of D-type cyclins," Oncogene, 2004, 23:3501-3508.
Krejci et al., "Molecular pathology of the fibroblast growth factor family," Hum Mutat, Sep. 2009, 30(9): 1245-1255.
Krejci et al., "NF449 Is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kuroso et al., "Immunohistochemical Detection of Fibroblast Growth Factor Receptor 3 in Human Breast Cancer: Correlation with Clinicopathological/Molecular Parameteres and Prognosis," Pathobiology, Mar. 2010, 77: 231-240.
Kurosu et al., "Regulation of Fibroblast Growth Factor-23 Signaling by Klotho," The Journal of Biological Chemistry, Mar. 2006, 281(10): 6120-6123.
Lala et al., "Role of nitric oxide in tumor progression: Lessons from experimental tumors," Cancer and Metastasis Reviews, 1998, 17: 91-106.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Lamont et al., "Small molecule FGF receptor inhibitors block FGFR-dependent urothelial carcinoma growth in vitro and in vivo," Br. J Cancer, 2011, 104:75-82.
Le Corre et al., "Synthesis and biological evaluation of a triazole-based library of pyrido[2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.
L'Hote and Knowles, "Cell responses to FGFR3 signalling: growth, differentiation and apoptosis," Experimental Cell Research, 2005, 417-431.
Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liang et al., "Small molecule inhibition of fibroblast growth factor receptors in cancer," Cytokine & growth factor reviews, Jul. 2013, 24: 467-475.
Liang et al., "Anticancer molecules targeting fibroblast growth factor receptors," Cell Press, 2012, 11 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.

(56) References Cited

OTHER PUBLICATIONS

Liu et al., "Pathogenic role of Fgf23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Luo et al., "Deficiency of metabolic regulator FGFR4 delays breast cancer progression through systemic and microenvironmental metabolic alterations," Cancer & Metabolism, 2013, 20 pages.
Maeda et al., "Transforming property of TEL-FGFR3 mediated through PI3-K in a T-cell lymphoma that subsequently progressed to AML," Blood, Mar. 2005, 105(5):2115-2123.
Malaysian Office Action in Malaysian Application No. 2014003396, dated Dec. 15, 2017, 4 pages.
Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Marfe and Stefano, "in vitro Anti-leukaemia Activity of Pyrrolo[1,2-b][1,2,5]benzothiadiaze-pines (PBTDs)," Recent Patents on Anti-Cancer Drug Discovery, 2010, 58-68.
Marks et al., "Mutational Analysis of EGFR and Related Signaling Pathway Genes in Lung Adenocarcinomas Identifies a Novel Somatic Kinase Domain Mutation in FGFR4," PLoS ONE, May 9, 2007, 2:e426.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
Martino et al., "Mutant fibroblast growth factor receptor 3 induces intracellular signaling and cellular transformation in a cell type- and mutation-specific manner," Oncogene, 2009, 28: 4306-4316.
Matsuda et al., "Fibroblast Growth Factor Receptor 2 IIIc as a Therapeutic Target for Colorectal Cancer Cells," Mol Cancer Ther., 2012, 52 pages.
Mcconkey et al., "Molecular genetics of bladder cancer: Emerging mechanisms of tumor initiation and progression," Urologic Oncology: Seminars and Original Investigations, 2010, 429-440.
Mcmahon, "VEGF Receptor Signaling in Tumor Angiogenesis," Oncologist, 2000, 5(suppl 1):3-10.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5):566-570.
Metzner, "Fibroblast Growth Factor Receptors as Therapeutic Targets in Human Melanoma: Synergism with BRAF Inhibition," J Investigative Dermatol., 2011, 131:2087-2095.
Mexican Office Action in Mexican Application No. MX/a/2014/015192, dated Jan. 24, 2018, 6 pages.
Mexican Office Action in Mexican Application No. MX/a/2019/014097, dated Aug. 11, 2022, 13 pages.
Mexican Office Action in Mexican Application No. MX/a/2019/014097, dated Mar. 15, 2022, 12 pages.
Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and G1/G0 Arrest," The Journal of Pharmacology and Experimental Therapeutics, 2010, 332(3):795-802.
Mohammadi et al., "Crystal structure of an angiogenesis inhibitor bound to the FGF receptor tyrosine kinase domain," The EMBO Journal, 1998, 5896-5904.
Mohammadi et al., "Structures of the Tyrosine Kinase Domain of Fibroblast Growth Factor Receptor in Complex with Inhibitors," Science, May 1997, 276:955-960.
Murphy et al., "Evidence for distinct alterations in the FGF axis in prostate cancer progression to an aggressive clinical phenotype," J Pathol., 2010, 220:452-460.
Naito et al., "Progressive tumoral calcinosis as the presenting feature of sarcoidosis in a patient on haemodialysis treatment," Nephrol Dial Transplant, 1999, 14:2716-2719.
Nakatani et al., "In vivo genetic evidence for klotho-dependent, fibroblast growth factor 23 (Fgf23)-mediated regulation of systemic phosphate homeostasis," The FASEB Journal, Feb. 2009, 23:433-441.
Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.
Neidle et al., "Failure Modes in the Discovery Process," Cancer Drug Design, 2008, pp. 427-431.
New Zealand Examination Report in New Zealand Application No. 743274, dated Jul. 18, 2018, 4 pages.
New Zealand Office Action in New Zealand Application No. 702747, dated Mar. 8, 2019, 2 pages.
New Zealand Office Action in New Zealand Application No. 702747, dated Sep. 16, 2016, 3 pages.
New Zealand Office Action in New Zealand Application No. 713074, dated Feb. 18, 2020, 3 pages.
New Zealand Office Action in New Zealand Application No. 743274, dated Jul. 19, 2018, 5 pages.
New Zealand Office Action in New Zealand Application No. 752422, dated Feb. 18, 2020, 2 pages.
Nitta, "Relationship between Fibroblast Growth Factor-23 and Mineral Metabolism in Chronic Kidney Disease," International Journal of Nephrology, 2010, 1-7.
Nomura et al., "FGF10/FGFR20 signal induces cell migration and invasion in pancreatic cancer," Br. J Cancer, 2008, 99:305-313.
Norman et al., "Protein-Ligand Crystal Structures Can Guide the Design of Selective Inhibitors of the FGFR Tyrosine Kinase," J. Med. Chem., 2012, 55(11):5003-5012.
Novelli, "Fosrenol (TM) reduces damaging high levels of phosphate in end-stage kidney disease patients," EurekAlert!, Nov. 2, 2002 [retrieved on Dec. 1, 2020], retrieved from URL <https://www.eurekalert.org/pub_releases/2002-11/pn-fr110202.php>, 4 pages.
Office Action from the Intellectual Property Office of the Philippines in Application No. 1-2014-502772, dated Mar. 17, 2016, 3 pages.
Office Action in Chilean Appln. No. 2022-000923, dated Aug. 21, 2023, 26 pages (with Machine Translation).
Office Action in Dominican Republic Application No. P2022-0082, dated May 15, 2024, 10 pages (with English Translation).
Office Action in Eurasian Appln. No. 202291162, dated May 19, 2023, 7 pages (with English Translation).
Office Action in Georgian Appln. No. 202015945, dated Aug. 31, 2023, 7 pages (with English Translation).
Ornitz et al., "Receptor Specificity of the Fibroblast Growth Factor Family," The Journal of Biological Chemistry, 1996, 271(25): 15292-15297.
Pai et al., "Antibody-Mediated Inhibition of Fibroblast Growth Factor 19 Results in Increased Bile Acids Synthesis and Ileal Malabsortion of Bile Acides in Cynomolgus Monkeys," Toxicological Sciences, 2012, 126(2): 446-456.
Pan et al., "MK-2461, a Novel Multitargeted Kinase Inhibitor, Preferentially Inhibits the Activated c-Met Receptor," Cancer Res, Feb. 2010, 1524-1533.
Pandith et al., "Oncogenic role of fibroblast growth factor receptor 3 in tumorigenesis of urinary bladder cancer," Urologic Oncology: Seminars and Original Investigations, 2010, 1-9.
Pandith et al., "Oncogenic role of fibroblast growth factor receptor 3 in tumorigenesis of urinary bladder cancer," Urologic Oncology: Seminars and Original Investigations, 2013, 31: 398-406.

(56) References Cited

OTHER PUBLICATIONS

Pardo et al., "The Fibroblast Growth Factor Receptor Inhibitor PD173074 Blocks Small Cell Lung Cancer Growth In vitro and In vivo," Cancer Res, Nov. 2009, 8645-8651.
Paterson et al., "Preclinical studies of fibroblast growth factor receptor 3 as a therapeutic target in multiple myeloma," British Journal of Haematology, 2004, 124:595-603.
Peruvian Office Action in Peruvian Application No. 1424, dated Mar. 12, 2021, 13 pages.
Peruvian Office Action in Peruvian Application No. 1429, dated Mar. 19, 2021, 12 pages.
Peruvian Office Action in Peruvian Application No. 2433, dated Nov. 27, 2018, 13 pages.
Peterson et al., Expanding the Scope of Crystal Form Evaluation in Pharmaceutical Science, J Pharm Pharmaceut Sci., 9(3): 317-326.
Petursson et al., "Protecting Groups in Carbohydrate Chemistry," J. Chem. Education, Nov. 1997, 74(11):1297-1303.
Philippine Allowance in Philippine Application No. 1/2015/502383, dated Jun. 6, 2022, 2 pages.
Philippine Office Action in Philippine Application No. 1/2015/502383, dated Nov. 11, 2021, 4 pages.
Philippine Office Action in Philippine Application No. 1/2017/501483, dated Dec. 12, 2019, 5 pages.
Philippine Office Action in Philippine Application No. 1/2019/502810, dated Dec. 7, 2021, 4 pages.
Philippine Office Action in Philippine Application No. 1-2017-501481, dated Oct. 29, 2019, 4 pages.
Philippine Office Action in Philippine Application No. 1/2015/502383, dated Jul. 8, 2019, 7 pages.
Philippine Office Action in the Philippine Application No. 1/2017/501483, dated Aug. 31, 2020, 4 pages.
Piazza et al., "Towards a new age in the treatment of multiple myeloma," Ann Hematol, 2007, 86:159-172.
Pinedo and Slamon, "Translational Research: The Role of VEGF in Tumor Angiogenesis," Oncologist, 2000, 5(suppl 1):1-2.
Piro et al., "An FGFR3 Autocrine Loop Sustains Acquired Resistance to Trastuzumab in Gastric Cancer Patients," Clinical Cancer Research, Dec. 2016, 22(24): 6164-6175.
Platt et al., "Spectrum of Phosphatidylinositol 3-Kinase Pathway Gene Alterations in Bladder Cancer," Clin Cancer Res, Oct. 2009, 6008-6017.
Pliarchopoulou et al., "Current chemotherapeutic options for the treatment of advanced bladder cancer: A review," Urologic Oncology: Seminars and Original Investigations, 2010, 1-9.
Plowright et al., "Ectopic expression of fibroblast growth factor receptor 3 promotes myeloma cell proliferation and prevents apoptosis," Blood, Feb. 2000, 95(3):992-998.
Podar et al., "Emerging therapies for multiple myeloma," Expert Opin. Emerging Drugs, 2009, 14(1):9-127.
Podar et al., "Targeting signalling pathways for the treatment of multiple myeloma," Expert Opin. Ther. Targets, 2005, 359-381.
Pollett et al., "Overexpression of the myeloma-associated oncogene fibroblast growth factor receptor 3 confers dexamethasone resistance," Blood, Nov. 2002, 100(10): 3819-3821.
Pollock et al., "Frequent activating FGFR2 mutations in endometrial carcinomas parallel germline mutations associated with craniosynostosis and skeletal dysplasia syndromes," Oncogene, 2007, 26:7158-7162.
Porta, "FGFR a promising druggable target in cancer: Molecular biology and new drugs." Critical reviews in oncology hematology, 2017, 113:256-267.
Propper et al., "Phase I and Pharmacokinetic Study of PKC412, an Inhibitor of Protein Kinase C," J Clin Oncol, 2001, 19(5):1485-1492.
Qian et al., "Targeting Tumor Angiogenesis with Histone Deacetylase Inhibitors: the Hydroxamic Acid Derivative LBH589," Clin Cancer Res, Jan. 2006, 634-642.
Qing et al., "Antibody-based targeting of FGFR3 in bladder carcinoma and t(4;14)-positive multiple myeloma in mice," The Journal of Clinical Investigation, May 2009, 119(5): 1216-1229.
Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.
Qiu et al., "Over-expression of fibroblast growth factor receptor 3 in human hepatocellular carcinoma," World J Gastroenterol, 2005, 11(34): 5266-5272.
Raab et al., "Multiple myeloma," Lancet, 2009, 374: 324-339.
Ravindranathan et al., "Discovery of Novel Fibroblast Growth Factor Receptor 1 Kinase Inhibitors by Structure-Based Virtual Screening," J. Med. Chem., 2010, 53:1662-1672.
Razzaque, "FGF23-mediated regulation of systemic phosphate homeostasis: is Klotho an essential player?," Am J Physiol Renal Physiol, 2009, 470-476.
Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.
Reis-Filho et al., "FGFR1 Emerges as a Potential Therapeutic Target for Lobular Breast Carcinomas," Clin Cancer Res, Nov. 2006, 6652-6662.
Reiter et al., "Consistent Fusion of ZNF198 to the Fibroblast Growth Factor Receptor-1 in the t(8;13)(p11;q12) Myeloproliferative Syndrome," Blood, Sep. 1998, 92(5): 1735-1742.
Remington's Pharmaceutical Sciences, 17th ed., Mack Publishing Company, Easton, Pa., 1985, p. 1418*.
Renhowe et al., "Design, Structure—Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.
Ribatti et al., "The discovery of basic fibroblast growth factor/fibroblast growth factor-2 and its role in haematological malignancies," Cytokine & Growth Factor Reviews, 2007, 18: 327-334.
Ribatti, "Tyrosine Kinase Inhibitors as Antiangiogenic Drugs in Multiple Myeloma," Pharmaceuticals, 2010, 3: 1225-1231.
Roidl et al., "Resistance to Chemotherapy Is Associated with Fibroblast Growth Factor Receptor 4 Up-Regulation," Clin Cancer Res, Mar. 2009, 2058-2066.
Ronchetti et al., "Deregulated FGFR3 mutants in multiple myeloma cell lines with t(4;14): comparative analysis of Y373C, K650E and the novel G384D mutations," Oncogene, 2001, 20: 3553-3562.
Roumiantsev et al., "Distinct stem cell myeloproliferative/T lymphoma syndromes induced by ZNF198-FGFR1 and BCR-FGFR1 fusion genes from 8p11 translocations, " Cancer Cell, Mar. 2004, 5: 287-298.
Rowe et al., "Handbook of Pharmaceutical Excipients," The Pharmaceutical Press and the American Pharmaceutical Association, 2009, 6th Edition, 917 pages.
Ryan et al., "Toxicologic Pathology of Unique Biotechnology Agents and Biotherapies," Toxicologic Pathology, 1999, 27(1): 78-86.
Sabiosciences.com [online]. "FGF Pathway," 2000-2012, [retrieved on Jun. 23, 2015]. Retrieved from the Internet: URL <http://www.sabiosciences.com/pathway.php?sn=FGF Signaling>, 3 pages.
Sakurai et al., "A novel angiogenesis inhibitor, Ki23057, is useful for preventing the progression of colon cancer and the spreading of cancer cells to the liver," European Journal of Cancer, 2007, 2612-2620.
Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.
Saudi Arabian Office Action in Saudi Arabian Application No. 522432263, dated Mar. 17, 2024, 6 pages (with English Translation).
Saxty et al., "Fragment-based drug discovery of selective inhibitors of fibroblast growth factor receptor (FGFr)," Cancer Res, Apr. 15, 2010, 70, 5778.
Schenone et al., "Small Molecules ATP-Competitive Inhibitors of FLT3: A Chemical Overview," Current Medicinal Chemistry, 2008, 15(29): 3113-3132.
Schlapbach et al., "A novel Pd-catalyzed cyclization rection of ureas for the synthesis of dihydroquinazolinone p38 kinase inhibitors," Bioorg. Med. Chem. Lett., 2004, 357-360.

(56) References Cited

OTHER PUBLICATIONS

Science IP Order 3032627, Chemical Structure Search , Science IP, Apr. 2012, 78 pages.
Science IP Order 3101926, Chemical Structure Search , Science IP, Jan. 2015, 50 pages.
Science IP Order 3101983, Chemical Structure Search , Science IP, Jan. 2015, 70 pages.
Science IP Order 3104564, Patent Chemical Structure Search , Science IP, Mar. 2015, 90 pages.
Science IP Order 3104565, Patent Chemical Structure Search , Science IP, Mar. 2015, 521 pages.
Segev et al., "Restrained chondrocyte proliferation and maturation with abnormal growth plate vascularization and ossification in human FRFR-3G380R transgenic mice," Human Molecular Genetics, 2000, 9(2): 249-258.
Seitzer et al., "A single nucleotide change in the mouse genome accelerates breast cancer progression," Cancer Res., Jan. 2010, 70(2):802-812.
Shah et al., "The role of fluorine in medicinal chemistry," Journal of Enzyme Inhibition and Medicinal Chemistry, Oct. 2007, 22(5):527-540.
Shariat et al., "Association of Angiogenesis Related Markers With Bladder Cancer Outcomes and Other Molecular Markers," The Journal of Urology, May 2010, 183:1744-1750.
Sharkey et al., "PKC412 demonstrates JNK-dependent activity against human multiple myeloma cells," Blood, Feb. 2007, 109(4): 1712-1719.
Shi et al., "High Expression of FGFR4 Enhances Tumor Growth and Metastasis in Nasopharyngeal Carcinoma," Journal of Cancer, 2015, 6(12): 1245-1254.
Shinya et al., "Fgf signalling through MAPK cascade is required for development of the subpallial telencephalon in zebrafish embryos," Development, 2001, 4153-4164.
sigmaaldrich.com, "4-Chloro-1H-pyrrolo[2,3-b]pyridine-5-carbaldehyde," CAS # 958230-19-8, [retrieved on Feb. 4, 2021] retrieved from URL <https://www.sigmaaldrich.com/catalog/product/aldrich/ade000976?lang=en&region=US>, 2 pages.
Singh et al., "Transforming Fusions of FGFR and TACC Genes in Human Glioblastoma," Science, Sep. 2012, 337:1231-1235.
Slavin et al., "Familial Tumoral Calcinosis," The American Journal of Surgican Pathology, 1993, 17(8): 188-802.
Smith et al., "Circulating aKlotho influences phosphate handling by controlling FGF23 production," The Journal of Clinical Investigation, Dec. 2012, 122(12):4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptor 3-lllc mediates colorectal cancer growth and migration," British Journal of Cancer, 2010, 1-12.
Soria, "FGFR inhibition overview of clinical development programs," Presentation, presented at TAT in Washington DC on Mar. 5-7, 2014, 54 pages.
Soverini et al., "Novel mutation and RNA splice variant of fibroblast growth factor receptor 3 in multiple myeloma patients at diagnosis," Haematologica, 2002, 87:1036-1040.
Specktor et al., "Hyperphosphatemic familial tumoral calcinosis caused by a mutation in GALNT3 in a European kindred," J Hum Genet, 2006, 51:487-490.
Squires et al., "Development of inhibitors of the fibroblast growth factor receptor (FGFR) kinase using a fragment based approach," Cancer Res 70, Apr. 15, 2010, 3626.
Squires et al., "Development of inhibitors of the fibroblast growth factor receptor (FGFR) kinase using a fragment based approach," Cancer Res, 2008, 1 page.
Staerk et al., "Pan-Src Family Kinase Inhibitors Replace Sox2 during the Direct Reprogramming of Somatic Cells," Angewandte Chem., Jun. 14, 2011, 50(25):5734-5736.
STN International Search Report for CAS RN 2380276-25-3, dated Nov. 20, 2019, 11 pages.
STN Search Report dated Jan. 6, 2020, 88 pages.
STN Search Report, dated Sep. 11, 2019, 31 pages.
Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (F1k-1/KDR), FGF-R1, and PDGF-Rβ Tyrosine Kinases," J. Med. Chem., 2000, 43: 2655-2663.
Sun et al., "Synthesis and Biological Evaluations of 3-Substituated Indolin-2-ones: A Novel Class of Tyrosine Kinase Inhibitors That Exhibit Selectivity toward Particular Receptor Tyrosine Kinases," J. Med. Chem., 1998, 41: 2588-2603.
Surry et al., "Dialkylbiaryl Phosphines in Pd-Catalyzed Amination: A User's Guide," Chem Sci., 2011, 2(1):27-50.
Taiwan Office Action in Taiwan Application No. 103114284, dated Apr. 9, 2018, 4 pages (English Search Report).
Taiwan Office Action in Taiwan Application No. 105104993, dated Feb. 11, 2020, 9 pages.
Taiwan Office Action in Taiwan Application No. 105105018, dated Oct. 22, 2019, 7 pages.
Taiwan Office Action in Taiwan Application No. 107146498, dated Dec. 19, 2019, 7 pages.
Taiwan Office Action in Taiwan Application No. 109132389, dated Aug. 23, 2021, 4 pages.
Taiwanese Office Action in Taiwan Application No. 102120946, dated Nov. 9, 2016, 9 pages (with English translation).
Taiwanese Office Action in Taiwanese Application No. 102120946, dated Jul. 13, 2017, 7 pages (English Translation).
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Takii et al., "Serotonin Derivative, N-(p-Coumaroyl)serotonin, Isolated from Safflower (*Carthamus tinctorius* L.) Oil Cake Augments the Proliferation of Normal Human and Mouse Fibroblasts in Synergy with Basic Fibroblast Growth Factor (bFGF) or Epidermal Growth Factor (EGF)", J Biochem., 1995, 125(5):910-915.
Tan et al., "Development of covalent inhibitors that can overcome resistance to first-generation FGFR kinase inhibitors, " PNAS, Oct. 2014, E4869-E4877.
Tang et al., "Role of fibroblast growth factor receptor 4 in cancer," Cancer Science, Oct. 2018, 109(10):3024-3031.
Taylor et al., "Identification of FGFR4-activating mutations in human rhabdomyasarcomas that promote metastasis in xenotransplanted models," J Clin Invest., Nov. 2009, 119(11):3395-3407.
Taylor, "Inhibitor PD-173074 Bound to the Tyrosine Kinase Domain of FGFR 1," Molecular & Behavioral Neuroscience Institute , Feb. 2006, 1 page.
Taylor, "Inhibitor SU-5402 Bound to the Tyrosine Kinase Domain of FGFR 1," Molecular & Behavioral Neuroscience Institute , Apr. 2006, 1 page.
Terai et al., "Vascular calcification and secondary hyperparathyroidism of severe chronic kidney disease and its relation to serum phosphate and calcium levels," British Journal of Pharmacology, 2009, 156: 1267-1278.
Thai Office Action in Thai Application No. 1401007417, dated Jun. 5, 2016, 7 pages (with English translation).
The Cancer Genome Atlas Research Network, "Comprehensive molecular characterization of urothelial bladder carcinoma," Nature, 2014, 507: 315-22.
Thome and Weil, "Post-translational modifications regulate distinct functions of CARMA1 and BCL10," TRENDS in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.
Thompson et al., "Photochemical Preparation of a Pyridone Containing Tetracycle: A Jak Protein Kinase Inhibitor," Bioorganic & Medicinal Chemistry Letters 12:1219-1223, 2002.

(56) References Cited

OTHER PUBLICATIONS

Thompson et al., "Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Thussbas et al., "FGFR4 Arg388 Allele Is Associated With Resistance to Adjuvant Therapy in Primary Breast Cancer," J. Clin. Oncol., Aug. 10, 2006, 23:3747-3755.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.
Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al., "Inhibition of fibroblast growth factor receptor 3 induces differentiation and apoptosis in t(4;14) myeloma," Blood, May 2004, 103(9):3521-3528.
Trudel et al., "The inhibitory anti-FGFR3 antibody, PRO-001, is cytotoxic to t(4;14) multiple myeloma cells," Blood, May 2006, 107(10): 4039-4046.
Trudel, "CHIR-258, a Novel Multi-targeted Tyrosine KinaseInhibitor, for the Treatment of t(4;14) Multiple Myeloma," Presentation, Presented at International Myeloma Foundation, Apr. 2005, 18 pages.
Turkington et al., "Fibroblast growth factor receptor 4 (FGFR4): a targetable regulator of drug resistance in colorectal cancer," Cell Death Dis., Feb. 6, 2014, 5:e1046.
Turner and Grose, "Fibroblast growth factor signalling: from development to cancer," Nature Reviews Cancer, 2010, 10:116-129.
Turner et al., "FGFR1 Amplification Drives Endocrine Therapy Resistance and Is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.
Ueno et al., "Enhanced Expression of Fibroblast Growth Factor Receptor 3 IIIc Promotes Human Esophageal Carcinoma Cell Proliferation," Journal of Histochemistry & Cytochemistry, 2016, 64(1): 7-17.
Ukraine Office Action in Ukraine Application No. a 2019 12195, dated Nov. 11, 2021, 7 pages.
Ukraine Office Action in Ukraine Application No. a201500191, dated Dec. 13, 2016, 10 pages (with English translation).
Ukraine Office Action in Ukraine Application No. a201511370, dated Nov. 12, 2018, 6 pages (with English translation).
Ukraine Office Action in Ukraine Application No. a201709220, dated Dec. 9, 2019, 11 pages.
Ukraine Office Action in Ukraine Application No. a201801562, dated Jul. 28, 2021, 9 pages.
Ukraine Office Action in Ukraine Application No. a202007700, dated Sep. 13, 2022, 11 pages.
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
Van Oers et al., "FGFR3 Mutations Indicate Better Survival in Invasive Upper Urinary Tract and Bladder Tumours," European Urology, 2009, 650-658.
Våtsveen et al., "FGFR3 is expressed and is important for survival in INA-6, a human myeloma cell line without a t(4;14)," Eur. J. Haematol., 83:5, Jul. 6, 2009, 471-476 (Abstract Only).
Verstovsek et al., "Interim Results from Fight-203, a Phase 2, Open-Label, Multicenter Study Evaluating the Efficacy and Safety of Pemigatinib (INCB054828) in Patients with Myeloid/Lymphoid Neoplasms with Rearrangement of Fibroblast Growth Factor Receptor 1 (FGFR1)," Blood, Nov. 29, 2018, retrieved from URL <https://ashpublications.org/blood/article/132/Supplement%201/690/266005/Interim-Results-from-Fight203-a-Phase-2-OpenLabel>, 132(Supplement 1):690.
Vietnamese Office Action in Vietnamese Application No. 1-2015-00102, dated Mar. 18, 2015, 4 pages.
Vietnamese Office Action in Vietnamese Application No. 1-2022-03016, dated Jul. 8, 2022, 2 pages.
Vogt et al., "FGF23 and phosphate cardiovascular toxins in ckd," Toxins, Nov. 6, 2019, 11(11):647.
Von Massenhausen et al., "Evaluation of FGFR3 as a Therapeutic Target in Head and Neck Squamous Cell Carcinoma, " Targ. Oncol., 2016, 11: 631-642.
Walsky and Obach, "Validated assays for human cytochrome P450 activities," Drug Metab Dispos., 2004, 32(6):647-660.
Walsky et al., "Evaluation of 227 drugs for in vitro inhibition of cytochrome P450 2B6," J Clin Pharmacol., Dec. 2006, 46(12):1426-1438.
Wang and Becker, "Antisense targeting of basic fibroblast growth factor and fibroblast growth factor receptor-1 in human melanomas blocks intratumoral angiogenesis and tumor growth," Nature Medicine, Aug. 1997, 887-893.
Wang and Ding, "Fibroblast growth factor receptors in breast cancer," Tumor Biology, May 2017, 1-10.
Wang et al., "The fibroblast growth factor receptor-4 Arg388 allele is associated with prostate cancer initiation and progression," Clin Cancer Res. 2004, 10:6169-6178.
Ware et al., "Rapidly Acquired Resistance to EFGR Tyrosine Kinase Inhibitors in NSCLC Cell Lines through De-Repression of FGFR2 and FGFR3 Expression," PLoS, Nov. 2010, 5(11): 1-9.
Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.
Williams et al., "Oncogenic FGFR3 gene fusions in bladder cancer," Hum Mol Genet, 2013, 22:795-803.
Wu, "Urothelial Tumorigenesis: A Tale of Divergent Pathways," Nature Reviews, Sep. 2005, 5: 713-725.
Wuts et al., "Greene's Protective Groups in Organic Synthesis," 4th Ed., 2006, Chapter 7, 696-926.
Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFRI on cell proliferation, survival, and migration in a 3D mammary epithelial cell model," JCB, 2005, 171(4): 663-673.
Xin et al., "CHIR-258 Is Efficacious in a Newly Developed Fibroblast Growth Factor Receptor 3-Expressing Orthotopic Multiple Myeloma Model in Mice," Clin Cancer Res, Aug. 2006, 4908-4915.
Xu et al., "Fibroblast growth factor receptor 4 promotes progression and correlates to poor prognosis in cholangiocarcinoma," Biochemical and Biophysical Research Communications, 2014, 446: 54-60.

(56) References Cited

OTHER PUBLICATIONS

Xu et al. "Design, synthesis and biological evaluation of deuterated nintedanib for improving pharmacokinetic properties," J Label Compd Radiopharm., 2015, 58(7):308-312.
Yamani et al., "Discovery and optimization of novel pyrazole-benzimidazole CPL304110, as a potent and selective inhibitor of fibroblast growth factor receptors FGFR (1-3)," European Journal of Medicinal Chemistry, Jan. 2021, 210:112990.
Ye et al., "Combination of the FGFR4 inhibitor PD173074 and 5-fluorouracil reduces proliferation and promotes apoptosis in gastric cancer," Oncol Rep., Dec. 2013, 30(6):2777-2784.
Ying et al., "Genome-wide screening for genetic alterations in esophageal cancer by aCGH identifies 11q13 amplification oncogenes associated with nodal metastasis," PLoS One, Jun. 25, 2012, 7:e39797.
Yu et al., "Amorphous pharmaceutical solids: preparation, characterization and stabilization," Advanced Drug Delivery Reviews, May 16, 2001, 48(1):27-42.
Yu et al., "Analysis of the Biochemical Mechanisms for the Endocrine Actions of Fibroblast Growth Factor-23," Endocrinology, Nov. 2005, 146(11): 4647-4656.
Yu et al., "FGFR-4 Arg(3)(8)(8) enhances prostate cancer progression via extracellular signal-related kinase and serum response factor signaling," Clin Cancer Res., Jul. 2011, 17:4355-4366.
Zaid et al., "Identification of FGFR4 as a Potential Therapeutic Target for Advanced-Stage, High-Grade Serous Ovarian Cancer," Clin Cancer Res, 2013, 19(4): 809-820.
Zhang et al., "AZD4547, a potent and selective FGF-receptor inhibitor induces tumor regressions in a human primary model of FGF-receptor 2 amplified gastric cancer and is efficacious in combination with chemotherapy," 2012, AstraZeneca, 1 page.
Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.
Zhang et al., "Enhanced FGFR signalling predisposes pancreatic cancer to the effect of a potent FGFR inhibitor in preclinical models," British Journal of Cancer, 2014, 110: 320-329.
Zhang et al., "FP-1039 (FGFR1:Fc), A Soluble FGFRI Receptor Antagonist, Inhibits Tumor Growth and Angiogenesis," Mol Cancer Ther, 6, Nov. 2007, B55.
Zhang et al., "Predicting Drug-Drug Interactions: An FDA Perspective," The AAPS Journal, May 6, 2009, 11(2):300-306.
Zhang et al., "Recent progress in therapeutic and diagnostic applications of lanthanides," Mini-Reviews in Medicinal Chemistry, 2011, 11(8):678-694.
Zhang et al., "Receptor Specificity of the Fibroblast Growth Factor Family," Journal of Biological Chemistry, Jun. 2006, 281(23): 15694-15700.
Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.
Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.
Zhao et al., "Homozygous Deletions and Chromosome Amplifications in Human Lung Carcinomas Revealed by Single Nucleotide Polymorphism Array Analysis," Cancer Res, Jul. 2005, 5561-5570.
Zhou et al., "A Structure-Guided Approach to Creating Covalent FGFR Inhibitors," Chemistry and Biology, Mar. 2010, 285-295.
Zhu et al., "Fibroblast growth factor receptor 3 inhibition by short hairpin RNAs leads to apoptosis in multiple myeloma," Mol Cancer Ther, May 2005, 787-798.
Zieger et al., "Role of Activating Fibroblast Growth Factor Receptor 3 Mutations in the Development of Bladder Tumors," Clin Cancer Res, Nov. 2005, 7709-7719.
Zingone et al., "Ectopic expression of wild-type FGFR3 cooperates with MYC to accelerate development of B-cell lineage neoplasms," Leukemia, 2010, 1171-1178.
European Office Action in European Application No. 20834013.3, dated Jan. 28, 2025, 4 pages.

* cited by examiner

SEQUENCE LISTING

```
Sequence total quantity: 1
SEQ ID NO: 1            moltype = AA  length = 15
FEATURE                 Location/Qualifiers
source                  1..15
                        mol_type = protein
                        organism = synthetic construct
SEQUENCE: 1
EQEDEPEGDY FEWLE                                                    15
```

TRICYCLIC HETEROCYCLES AS FGFR INHIBITORS

FIELD

The present disclosure relates to tricyclic heterocycles, and pharmaceutical compositions of the same, that are inhibitors of the enzyme FGFR and are useful in the treatment of FGFR-associated diseases such as cancer.

SEQUENCE LISTING

This application contains a Sequence Listing that has been submitted electronically as an XML file named 20443-0658002_SL_ST26.xml. The XML file, created on Dec. 19, 2023, is 1,922 bytes in size. The material in the XML file is hereby incorporated by reference in its entirety.

BACKGROUND

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005, 16, 139-149). Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described (Reviewed in Knights and Cook, Pharmacology & Therapeutics, 2010, 125, 105-117; Turner and Grose, Nature Reviews Cancer, 2010, 10, 116-129). Large scale DNA sequencing of thousands of tumor samples has revealed that FGFR genes are altered in many cancers (Helsten et al. Clin Cancer Res. 2016, 22, 259-267). Some of these activating mutations are identical to germline mutations that lead to skeletal dysplasia syndromes (Gallo et al. Cytokine & Growth Factor Reviews 2015, 26, 425-449). Mechanisms that lead to aberrant ligand-dependent signaling in human disease include overexpression of FGFs and changes in FGFR splicing that lead to receptors with more promiscuous ligand binding abilities. Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, colorectal, endometrial, gastric, head and neck, kidney, lung, ovarian, prostate); hematopoietic malignancies (e.g., multiple myeloma, acute myelogenous leukemia, and myeloproliferative neoplasms); and other neoplasms (e.g., glioblastoma and sarcomas). In addition to a role in oncogenic neoplasms, FGFR activation has also been implicated in skeletal and chondrocyte disorders including, but not limited to, achrondroplasia and craniosynostosis syndromes.

There is a continuing need for the development of new drugs for the treatment of cancer, and the FGFR inhibitors described herein help address this need.

SUMMARY

The present disclosure is directed to compounds having Formula (I):

I

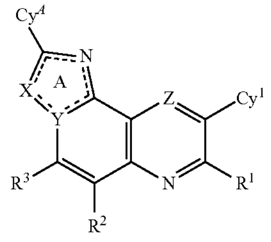

or pharmaceutically acceptable salts thereof, wherein constituent variables are defined herein.

The present disclosure is further directed to pharmaceutical compositions comprising a compound of Formula (I), or a pharmaceutically acceptable salt thereof, and at least one pharmaceutically acceptable carrier.

The present disclosure is further directed to methods of inhibiting an FGFR enzyme (e.g., an FGFR3 enzyme) comprising contacting the enzyme with a compound of Formula (I), or a pharmaceutically acceptable salt thereof.

The present disclosure is further directed to a method of treating a disease associated with abnormal activity or expression of an FGFR enzyme (e.g., an FGFR3 enzyme), comprising administering a compound of Formula (I), or a pharmaceutically acceptable salt thereof, to a patient in need thereof.

The present disclosure is further directed to compounds of Formula (I) for use in treating a disease associated with abnormal activity or expression of an FGFR enzyme (e.g., an FGFR3 enzyme).

The present disclosure is further directed to a method for treating a disorder mediated by an FGFR enzyme (e.g., an FGFR3 enzyme), or a mutant thereof, in a patient in need thereof, comprising the step of administering to said patient a compound of Formula (I), or pharmaceutically acceptable composition thereof.

The present disclosure is further directed to a method for treating a disorder mediated by an FGFR enzyme (e.g., an FGFR3 enzyme), or a mutant thereof, in a patient in need thereof, comprising the step of administering to the patient a compound of Formula (I), or a pharmaceutically acceptable salt thereof, or a composition comprising a compound of Formula (I), or a pharmaceutically acceptable salt thereof, in combination with another therapy or therapeutic agent as described herein.

The present disclosure is further directed to the use of compounds of Formula (I) in the preparation of a medicament for use in therapy.

DETAILED DESCRIPTION

Compounds

In one aspect, the present disclosure provides compounds of Formula (I):

I

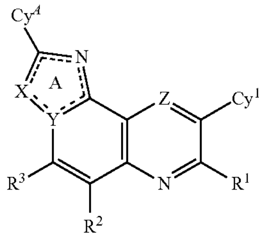

or a pharmaceutically acceptable salt thereof, wherein:

ring A is aromatic;

Y is N or C;

X is $CR^4$ when Y is N, or

X is $NR^5$ when Y is C;

==== represents a single bond or a double bond;

Z is N or $CR^6$;

$Cy^1$ is selected from $C_{6-10}$ aryl and 5-10 membered heteroaryl; wherein each 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

$Cy^A$ is selected from $C_{3-10}$ cycloalkyl, 4-10 membered heterocycloalkyl, $C_{6-10}$aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{20}$;

$R^1$, $R^2$, $R^3$, and $R^6$ are each independently selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a9}$, $SR^{a9}$, $C(O)R^{b9}$, $C(O)NR^{c9}R^{d9}$, $C(O)OR^{a9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{30}$;

$R^4$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a7}$, $SR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, $NR^{c7}C(O)OR^{a7}$, $NR^{c7}C(O)NR^{c7}R^{d7}$ $NR^{c7}S(O)R^{b7}$ $NR^{c7}S(O)_2$ $R^{b7}$ $NR^{c7}S(O)_2NR^{c7}R^{d7}$ $S(O)R^{b7}$, $S(O)NR^{c7}R^{d7}$, $S(O)_2R^{b7}$, and $S(O)_2NR^{c7}R^{d7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{40}$;

$R^5$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{50}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$ $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-6 membered heteroaryl, 4-7 membered heterocycloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$ $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-6 membered heteroaryl and 4-7 membered heterocycloalkyl, are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $NR^{c4}R^{d4}$ $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}C(O)NR^{c6}R^{d6}$ $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{30}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a10}$, $SR^{a10}$, $C(O)R^{b10}$, $C(O)NR^{c10}R^{d10}$, $C(O)OR^{a10}$, $NR^{c10}R^{d10}$, $NR^{c10}C(O)R^{b10}$, $NR^{c10}C(O)OR^{a10}$, $NR^{c10}C(O)NR^{c10}R^{d10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, and $S(O)_2NR^{c10}R^{d10}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{40}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $NR^{c8}C(O)OR^{a8}$, $NR^{c8}C(O)NR^{c8}R^{d8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, and $S(O)_2NR^{c8}R^{d8}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{50}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a11}$, $SR^{a11}$, $C(O)R^{b11}$, $C(O)NR^{c11}R^{b11}$, $C(O)OR^{a11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a2}$, $R^{c2}$ and $R^{d2}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

or any $R^{c2}$ and $R^{d2}$ attached to the same N atom, together with the N atom to which they are attached, form a 4-, 5-, 6- or 7-membered heterocycloalkyl group optionally substituted with 1, 2 or 3 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a3}$, $R^{c3}$ and $R^{d3}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{b3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^{12}$;

each $R^{a4}$, $R^{c4}$ and $R^{d4}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

each $R^{a5}$, $R^{c5}$ and $R^{d5}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c5}$ and $R^{d5}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a7}$, $R^{c7}$, and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c7}$ and $R^{d7}$ attached to the same N atom, together with the N atom to which they are attached, form a 4-, 5-, 6- or 7-membered heterocycloalkyl group optionally substituted with 1, 2 or 3 substituents independently selected from $R^{40}$;

each $R^{b7}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

each $R^{a8}$, $R^{c8}$ and $R^{d8}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b8}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a9}$, $R^{c9}$, and $R^{d9}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

or any $R^{c9}$ and $R^{d9}$ attached to the same N atom, together with the N atom to which they are attached, form a 4-, 5-, 6- or 7-membered heterocycloalkyl group optionally substituted with 1, 2 or 3 substituents independently selected from $R^{30}$;

each $R^{b9}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

each $R^{a10}$, $R^{c10}$ and $R^{d10}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b10}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a11}$, $R^{c11}$ and $R^{d11}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b11}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$; and each $R^9$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In another aspect, the present disclosure provides compounds of Formula (I):

I

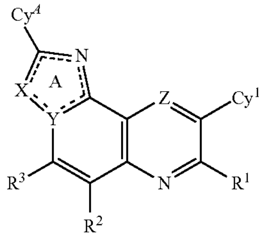

or a pharmaceutically acceptable salt thereof, wherein:

ring A is aromatic;

Y is N or C;

X is $CR^4$ when Y is N, or

X is $NR^5$ when Y is C;

$\overline{=\!=\!=}$ represents a single bond or a double bond;

Z is N or $CR^6$;

$Cy^1$ is selected from $C_{6-10}$ aryl and 5-10 membered heteroaryl; wherein each 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

$Cy^A$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{20}$;

$R^1$, $R^2$, $R^3$, and $R^6$ are each independently selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a9}$, $SR^{a9}$, $C(O)R^{b9}$, $C(O)NR^{c9}R^{d9}$, $C(O)OR^{a9}$, $NR^{c9}R^{d9}$ $NR^{c9}C(O)R^{b9}$, $NR^{c9}C(O)OR^{a9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{30}$;

$R^4$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a7}$, $SR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, $NR^{c7}C(O)OR^{a7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, and $S(O)_2NR^{c7}R^{d7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{40}$;

$R^5$ is selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{50}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{c1})NR^{c1}R^{d1}$ $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$ $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2$ $NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-6 membered heteroaryl, 4-7 membered heterocycloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$ $NR^{c5}C(O)R^{b5}$, $NR^{c5}C(O)OR^{a5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$ $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-6 membered heteroaryl and 4-7 membered heterocycloalkyl, are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$ $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2$ $NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{30}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a10}$, $SR^{a10}$, $C(O)R^{b10}$, $C(O)NR^{c10}R^{d10}$, $C(O)OR^{a10}$, $NR^{c10}R^{d10}$, $NR^{c10}C(O)R^{b10}$, $NR^{c10}C(O)OR^{a10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, and $S(O)_2NR^{c10}R^{d10}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{40}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $NR^{c8}C(O)OR^{a8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, and $S(O)_2NR^{c8}R^{d8}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{50}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a11}$, $SR^{a11}$, $C(O)R^{b11}$, $C(O)NR^{c11}R^{d11}$, $C(O)OR^{a11}$, $NR^{c11}R^{d11}$, $NR^{c11}C(O)R^{b11}$, $NR^{c11}C(O)OR^{a11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^1$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

or any $R^{c2}$ and $R^{d2}$ attached to the same N atom, together with the N atom to which they are attached, form a 4-, 5-, 6- or 7-membered heterocycloalkyl group optionally substituted with 1, 2 or 3 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

each $R^{a5}$, $R^{c5}$ and $R^{d5}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c5}$ and $R^{d5}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a7}$, $R^{c7}$, and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c7}$ and $R^{d7}$ attached to the same N atom, together with the N atom to which they are attached, form a 4-, 5-, 6- or 7-membered heterocycloalkyl group optionally substituted with 1, 2 or 3 substituents independently selected from $R^{40}$;

each $R^{b7}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

each $R^{a8}$, $R^{c8}$ and $R^{d8}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^{g}$;

each $R^{b8}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^{g}$;

each $R^{a9}$, $R^{c9}$, and $R^{d9}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

or any $R^{c9}$ and $R^{d9}$ attached to the same N atom, together with the N atom to which they are attached, form a 4-, 5-, 6- or 7-membered heterocycloalkyl group optionally substituted with 1, 2 or 3 substituents independently selected from $R^{30}$;

each $R^{b9}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

each $R^{a10}$, $R^{c10}$ and $R^{d10}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^{g}$;

each $R^{b10}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^{g}$;

each $R^{a11}$, $R^{c11}$ and $R^{d11}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^{g}$;

each $R^{b11}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^{g}$; and each $R^{g}$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In one embodiment, the present disclosure provides compounds of Formula (I) or a pharmaceutically acceptable salt thereof, wherein:

ring A is aromatic;

Y is N or C;

X is $CR^4$ when Y is N, or

X is $NR^5$ when Y is C;

$\overset{\cdots}{—}$ represents a single bond or a double bond;

Z is N or $CR^6$;

$Cy^1$ is selected from 5-10 membered heteroaryl; wherein each 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the 5-10 membered heteroaryl are each optionally substituted with 1, 2, 3 or 4 substituents independently selected from $R^{10}$;

$Cy^A$ is selected from $C_{6-10}$ aryl and 5-10 membered heteroaryl; wherein the 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{20}$;

$R^1$, $R^2$, $R^3$, and $R^6$ are each independently selected from H, D, $C_{1-6}$ alkyl, $C_{1-6}$ haloalkyl, halo, CN, $OR^{a9}$, and $NR^{c9}R^{d9}$;

$R^4$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a7}$, and $NR^{c7}R^{d7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{40}$;

$R^5$ is selected from $C_{1-6}$ alkyl, $C_{1-6}$ haloalkyl, $C_{3-10}$ cycloalkyl, and $C_{6-10}$ aryl; wherein said $C_{1-6}$ alkyl, $C_{3-10}$ cycloalkyl, and $C_{6-10}$ aryl, are each optionally substituted with 1, 2, 3, or 4 substituents independently selected from $R^{50}$;

each $R^{10}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a1}$, and $NR^{c1}R^{d1}$; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$;

each $R^{11}$ is independently selected from $C_{1-6}$ alkyl, $C_{1-6}$ haloalkyl, $C_{3-10}$ cycloalkyl, halo, D, CN, $OR^{a3}$, $C(O)R^{b3}$, $C(O)NR^{c3}R^{d3}$, $C(O)OR^{a3}$, $NR^{c3}R^{d3}$, and $NR^{c3}C(O)R^{b3}$; wherein said $C_{1-6}$ alkyl, and $C_{3-10}$ cycloalkyl, are each optionally substituted with 1, 2, 3, or 4 substituents independently selected from $R^{12}$;

each $R^{12}$ is independently selected from $C_{1-6}$ alkyl, halo, D, CN, $OR^{a5}$ and $NR^{c5}R^{d5}$;

each $R^{20}$ is independently selected from $C_{1-6}$ alkyl, $C_{1-6}$ haloalkyl, $C_{3-10}$ cycloalkyl, halo, D, CN, $OR^{a2}$, $C(O)R^{b2}$, $C(O)NR^{c2}R^{d2}$, $C(O)OR^{a2}$, $S(O)NR^{c2}R^{d2}$, and $S(O)_2R^{b2}$; wherein said $C_{1-6}$ alkyl, and $C_{3-10}$ cycloalkyl are each optionally substituted with 1, 2, 3, or 4 substituents independently selected from $R^{21}$;

each $R^{21}$ is independently selected from $C_{1-6}$ alkyl, $C_{1-6}$ haloalkyl, halo, D, CN, $OR^{a4}$, and $NR^{c4}R^{d4}$;

each $R^{40}$ is independently selected from $C_{1-6}$ alkyl, $C_{1-6}$ haloalkyl, halo, D, CN, $OR^{a8}$, and $NR^{c8}R^{d8}$;

each $R^{50}$ is independently selected from $C_{1-6}$ alkyl, $C_{1-6}$ haloalkyl, halo, D, CN, $OR^{a11}$, and $NR^{c11}R^{d11}$;

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, or 6-membered heterocycloalkyl group optionally substituted with 1, 2, 3, or 4 substituents independently selected from $R^{11}$;

each $R^{a2}$, $R^{c2}$ and $R^{d2}$ is independently selected from H, $C_{1-6}$ alkyl, $C_{1-6}$ haloalkyl, and $C_{3-10}$ cycloalkyl; wherein said $C_{1-6}$ alkyl and $C_{3-10}$ cycloalkyl, are each optionally substituted with 1, 2, 3, or 4 substituents independently selected from $R^{21}$;

each $R^{b2}$ is independently selected from $C_{1-6}$ alkyl, $C_{1-6}$ haloalkyl, and $C_{3-10}$ cycloalkyl; wherein said $C_{1-6}$ alkyl and $C_{3-10}$ cycloalkyl, are each optionally substituted with 1, 2, 3, or 4 substituents independently selected from $R^{21}$;

each $R^{a3}$, $R^{c3}$ and $R^{d3}$ is independently selected from H, $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1, 2, 3, or 4 substituents independently selected from $R^{12}$;

each $R^{b3}$ is independently selected from $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, and $C_{1-6}$ haloalkyl;

each $R^{a5}$, $R^{c5}$ and $R^{d5}$ is independently selected from H, $C_{1-6}$ alkyl, and $C_{1-6}$ haloalkyl;

each $R^{a7}$, $R^{c7}$, and $R^{d7}$ is independently selected from H, $C_{1-6}$ alkyl, and $C_{1-6}$ haloalkyl;

each $R^{a8}$, $R^{c8}$ and $R^{d8}$ is independently selected from H, $C_{1-6}$ alkyl, and $C_{1-6}$ haloalkyl;

each $R^{a9}$, $R^{c9}$, and $R^{d9}$ is independently selected from H, $C_{1-6}$ alkyl, and $C_{1-6}$ haloalkyl; and each $R^{a11}$, $R^{c11}$, and $R^{d11}$ is independently selected from H, $C_{1-6}$ alkyl, and $C_{1-6}$ haloalkyl.

In one embodiment, the present disclosure provides compounds of Formula (I) or a pharmaceutically acceptable salt thereof, wherein:

ring A is aromatic;

Y is N or C;

X is $CR^4$ when Y is N, or

X is $NR^5$ when Y is C;

$\equiv\equiv$ represents a single bond or a double bond;

Z is N or CH;

$Cy^1$ is selected from 5-6 membered heteroaryl; wherein each 5-6 membered heteroaryl has at least one ring-forming carbon atom and 1, 2, 3, or 4 ring-forming heteroatoms independently selected from N, O, and S; and wherein the 5-6 membered heteroaryl are each optionally substituted with 1, 2, 3 or 4 substituents independently selected from $R^{10}$;

$Cy^A$ is selected from phenyl and 5-6 membered heteroaryl; wherein the 5-6 membered heteroaryl each has at least one ring-forming carbon atom and 1, 2, 3, or 4 ring-forming heteroatoms independently selected from N, O, and S; and wherein the phenyl and 5-6 membered heteroaryl are each optionally substituted with 1, 2, 3 or 4 substituents independently selected from $R^{20}$;

$R^1$, $R^2$, $R^3$ are each H;

$R^4$ is selected from H, halo, CN, $C_{1-6}$ alkyl, $C_{2-6}$ alkenyl, $C_{3-7}$ cycloalkyl, phenyl, and 5-6 membered heteroaryl, wherein said $C_{1-6}$ alkyl, $C_{2-6}$ alkenyl, $C_{3-7}$ cycloalkyl, phenyl, and 5-6 membered heteroaryl are each optionally substituted with 1 or 2 substituents selected from $R^{40}$;

$R^5$ is $C_{1-6}$ alkyl;

each $R^{10}$ is independently selected from $C_{1-6}$ alkyl, 4-6 membered heterocycloalkyl, and $C_{3-7}$ cycloalkyl, each of which is optionally substituted with 1 or 2 substituents independently selected from $R^{11}$;

each $R^{11}$ is independently selected from $C_{1-6}$ alkyl, $C_{3-7}$ cycloalkyl, CN, $OR^{a3}$, $C(O)R^{b3}$, $C(O)NR^{c3}R^{d3}$, $C(O)OR^{a3}$, and $S(O)_2R^{b3}$; wherein said $C_{1-6}$ alkyl, and $C_{3-7}$ cycloalkyl are each optionally substituted with 1 or 2 substituents independently selected from $R^{12}$;

each $R^{12}$ is independently selected from $C_{1-6}$ alkyl, halo, D, CN, $OR^{a5}$ and $NR^{c5}R^{d5}$;

each $R^{20}$ is independently selected from halo, $C_{1-6}$ alkyl, and $OR^{a2}$ each $R^{21}$ is independently selected from $C_{1-6}$ alkyl, $C_{1-6}$ haloalkyl, halo, D, CN, $OR^{a4}$, and $NR^{c4}R^{d4}$.

each $R^{40}$ is independently selected from $C_{1-6}$ alkyl, $C_{1-6}$ haloalkyl, halo, D, CN, $OR^{a8}$, and $NR^{c8}R^{d8}$.

each $R^{a2}$ is selected from H, $C_{1-6}$ alkyl, $C_{1-6}$ haloalkyl, and $C_{3-10}$ cycloalkyl; wherein said $C_{1-6}$ alkyl and $C_{3-10}$ cycloalkyl, are each optionally substituted with 1, 2, 3, or 4 substituents independently selected from $R^{21}$;

each $R^{a3}$, $R^{c3}$ and $R^{d3}$ is independently selected from H, $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1, 2, 3, or 4 substituents independently selected from $R^{12}$;

each $R^{b3}$ is independently selected from $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, and $C_{1-6}$ haloalkyl;

each $R^{a5}$, $R^{c5}$ and $R^{d5}$ is independently selected from H, $C_{1-6}$ alkyl, and $C_{1-6}$ haloalkyl; and each $R^{a8}$, $R^{c8}$ and $R^{d8}$ is independently selected from H, $C_{1-6}$ alkyl, and $C_{1-6}$ haloalkyl.

In one embodiment, the present disclosure provides compounds of Formula (I) or a pharmaceutically acceptable salt thereof, wherein:

ring A is aromatic;

Y is N or C;

X is $CR^4$ when Y is N, or

X is $NR^5$ when Y is C;

---- represents a single bond or a double bond;

Z is N or CH;

$Cy^1$ is selected from phenyl and 5-6 membered heteroaryl; wherein each 5-6 membered heteroaryl has at least one ring-forming carbon atom and 1, 2, 3, or 4 ring-forming heteroatoms independently selected from N, O, and S; and wherein the phenyl and 5-6 membered heteroaryl are each optionally substituted with 1, 2, 3 or 4 substituents independently selected from $R^{10}$;

$Cy^A$ is selected from phenyl, 5-6 membered heteroaryl, 4-10 membered heterocycloalkyl, and $C_{3-7}$ cycloalkyl; wherein the 5-6 membered heteroaryl each has at least one ring-forming carbon atom and 1, 2, 3, or 4 ring-forming heteroatoms independently selected from N, O, and S; and wherein the phenyl, 5-6 membered heteroaryl, 4-10 membered heterocycloalkyl, and $C_{3-7}$ cycloalkyl are each optionally substituted with 1, 2, 3 or 4 substituents independently selected from $R^{20}$;

$R^1$ is H, $OR^{a9}$, or $NR^{c9}R^{d9}$;

$R^2$ and $R^3$ are each H;

$R^4$ is selected from H, halo, CN, $C_{1-6}$ alkyl, $C_{2-6}$ alkenyl, $C_{3-7}$ cycloalkyl, phenyl, and 5-6 membered heteroaryl, wherein said $C_{1-6}$ alkyl, $C_{2-6}$ alkenyl, $C_{3-7}$ cycloalkyl, phenyl, and 5-6 membered heteroaryl are each optionally substituted with 1 or 2 substituents selected from $R^{40}$;

$R^5$ is $C_{1-6}$ alkyl;

each $R^{10}$ is independently selected from $C_{1-6}$ alkyl, $C_{1-6}$ haloalkyl, phenyl, 4-6 membered heterocycloalkyl, and $C_{3-7}$ cycloalkyl, each of which is optionally substituted with 1 or 2 substituents independently selected from $R^{11}$;

each $R^{11}$ is independently selected from $C_{1-6}$ alkyl, CN, $C(O)R^{b3}$, $C(O)OR^{a3}$, $NR^{c3}C(O)R^{b3}$, $OR^{a3}$, $C(O)NR^{c3}R^{d3}$, $NR^{c3}R^{d3}$, $NR^{c3}C(O)NR^{c3}R^{d3}$, $S(O)_2NR^{c3}R^{d3}$, $S(O)_2R^{b3}$, phenyl, and 4-6 membered heterocycloalkyl; wherein said $C_{1-6}$ alkyl, phenyl, and 4-6 membered heterocycloalkyl are each optionally substituted with 1 or 2 substituents independently selected from $R^{12}$;

each $R^{12}$ is independently selected from $C_{1-6}$ alkyl, halo, D, CN, $OR^{a5}$, $NR^{c5}R^{d5}$ and 5-6 membered heteroaryl;

each $R^{20}$ is independently selected from halo, CN, $C_{1-6}$ alkyl, $C_{1-6}$ haloalkyl, and $NR^{c2}C(O)R^{b2}$ wherein the $C_{1-6}$ alkyl is optionally substituted with $OR^{a4}$;

each $R^{21}$ is independently selected from $C_{1-6}$ alkyl, $C_{1-6}$ haloalkyl, halo, D, CN, $OR^{a4}$, and $NR^{c4}R^{d4}$.

each $R^{40}$ is independently selected from $C_{1-6}$ alkyl, $C_{1-6}$ haloalkyl, halo, D, CN, $OR^{a8}$, and $NR^{c8}R^{d8}$;

each $R^{a2}$ is selected from H, $C_{1-6}$ alkyl, $C_{1-6}$ haloalkyl, and $C_{3-10}$ cycloalkyl; wherein said $C_{1-6}$ alkyl and $C_{3-10}$ cycloalkyl, are each optionally substituted with 1, 2, 3, or 4 substituents independently selected from $R^{21}$;

each $R^{a3}$, $R^{c3}$ and $R^{d3}$ is independently selected from H, $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1, 2, 3, or 4 substituents independently selected from $R^{12}$;

each $R^{b3}$ is independently selected from $C_{1-6}$ alkyl, $C_{1-6}$ haloalkyl, $C_{3-6}$ cycloalkyl, 5-6 membered heteroaryl, and 4-6 membered heterocycloalkyl; each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, and $C_{1-6}$ haloalkyl;

each $R^{a5}$, $R^{c5}$ and $R^{d5}$ is independently selected from H, $C_{1-6}$ alkyl, and $C_{1-6}$ haloalkyl; and each $R^{a8}$, $R^{c8}$ and $R^{d8}$ is independently selected from H, $C_{1-6}$ alkyl, and $C_{1-6}$ haloalkyl.

In one aspect, the present disclosure provides compounds of Formula (IA) or (IB):

IA

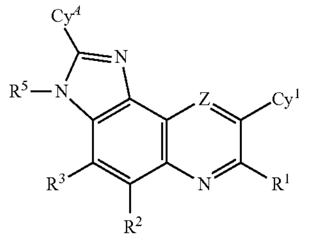

or

IB

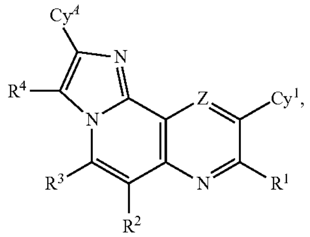

or a pharmaceutically acceptable salt thereof.

In one aspect, the present disclosure provides compounds of Formula (IA):

IA

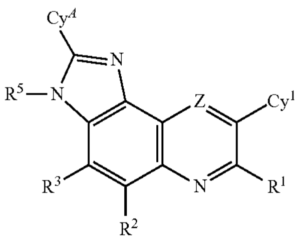

or a pharmaceutically acceptable salt thereof.

In one aspect, the present disclosure provides compounds of Formula (IB):

IB

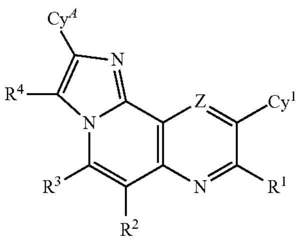

or a pharmaceutically acceptable salt thereof.

In one aspect, the present disclosure provides compounds of Formula (IA) or a pharmaceutically acceptable salt thereof, wherein:

Z is N;

$Cy^1$ is selected from $C_{6-10}$ aryl and 5-10 membered heteroaryl; wherein each 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

$Cy^A$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{20}$;

$R^1$, $R^2$, $R^3$, and $R^6$ are each independently selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a9}$, $SR^{a9}$, $C(O)R^{b9}$, $C(O)NR^{c9}R^{d9}$, $C(O)OR^{a9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{30}$;

$R^5$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{50}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-6 membered heteroaryl, 4-7 membered heterocycloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$ $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^5S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-6 membered heteroaryl and 4-7 membered heterocycloalkyl, are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$ $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{30}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a10}$, $SR^{a10}$, $C(O)R^{b10}$, $C(O)NR^{c10}R^{d10}$, $C(O)OR^{a10}$, $NR^{c10}R^{d10}$, $NR^{c10}C(O)R^{b10}$, $NR^{c10}C(O)OR^{a10}$, $NR^{c10}C(O)NR^{c10}R^{d10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, and $S(O)_2NR^{c10}R^{d10}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{50}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a11}$, $SR^{a11}$, $C(O)R^{b11}$, $C(O)NR^{c11}R^{d11}$, $C(O)OR^{a11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, and $S(O)_2NR^{c11}R^{d11}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a2}$, $R^{c2}$ and $R^{d2}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

or any $R^{c2}$ and $R^{d2}$ attached to the same N atom, together with the N atom to which they are attached, form a 4-, 5-, 6- or 7-membered heterocycloalkyl group optionally substituted with 1, 2 or 3 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a3}$, $R^{c3}$ and $R^{d3}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^{12}$;

each $R^{a4}$, $R^{c4}$ and $R^{d4}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

each $R^{a5}$, $R^{c5}$ and $R^{d5}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c5}$ and $R^{d5}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a9}$, $R^{c9}$, and $R^{d9}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

or any $R^{c9}$ and $R^{d9}$ attached to the same N atom, together with the N atom to which they are attached, form a 4-, 5-, 6- or 7-membered heterocycloalkyl group optionally substituted with 1, 2 or 3 substituents independently selected from $R^{30}$;

each $R^{b9}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

each $R^{a10}$, $R^{c10}$ and $R^{d10}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b10}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a11}$, $R^{c11}$ and $R^{d11}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b11}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$; and each $R^9$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In one aspect, the present disclosure provides compounds of Formula (IA), or a pharmaceutically acceptable salt thereof, wherein:

Z is N;

$Cy^1$ is selected from 5-10 membered heteroaryl; wherein each 5-10 membered heteroaryl has at least one ring-forming carbon atom and 1, 2, 3, or 4 ring-forming heteroatoms independently selected from N, O, and S; wherein a ring-forming carbon atom of 5-10 membered heteroaryl is optionally substituted by oxo to form a carbonyl group; and wherein the 5-10 membered heteroaryl are each optionally substituted with 1 or 2 substituents independently selected from $R^{10}$;

$Cy^A$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1, 2, or 3 substituents independently selected from $R^{20}$;

$R^1$, $R^2$, and $R^3$ are each independently selected from H, D, $C_{1-6}$ alkyl, $C_{1-6}$ haloalkyl halo, and CN;

$R^5$ is selected from H, D, $C_{1-6}$ alkyl, and $C_{1-6}$ haloalkyl;

each $R^{10}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a1}$, and $NR^{c1}R^{d1}$; wherein said $C_{1-6}$ alkyl, $C_{3-10}$ cycloalkyl, and 4-10 membered heterocycloalkyl, are each optionally substituted with 1, 2, or 3 substituents independently selected from $R^{11}$;

each $R^{11}$ is independently selected from $C_{1-6}$ alkyl, $C_{1-6}$ haloalkyl, halo, D, CN, $OR^3$, $C(O)R^{b3}$, $C(O)NR^{c3}R^{d3}$, and $NR^{c3}R^{d3}$;

each $R^{20}$ is independently selected from $C_{1-6}$ alkyl, $C_{1-6}$ haloalkyl, halo, D, CN, $OR^{a2}$, and $NR^{c2}R^{d2}$.

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1 or 2 substituents independently selected from $R^{11}$;

or any $R^{c1}$ and $R^{d1}$ attached to the same N atom, together with the N atom to which they are attached, form a 4-, 5-, or 6-membered heterocycloalkyl group optionally substituted with 1 or 2 substituents independently selected from $R^{11}$;

each $R^{a2}$, $R^{c2}$ and $R^{d2}$, is independently selected from H, $C_{1-6}$ alkyl, and $C_{1-6}$ haloalkyl;

each $R^{a3}$, $R^{c3}$ and $R^{d3}$, is independently selected from H, $C_{1-6}$ alkyl, and $C_{1-6}$ haloalkyl; and each $R^{b3}$ is independently selected from $C_{1-6}$ alkyl, and $C_{1-6}$ haloalkyl.

In one aspect, the present disclosure provides compounds of Formula (IA) or a pharmaceutically acceptable salt thereof, wherein:

Z is N;

$Cy^1$ is 5-10 membered heteroaryl; wherein each 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

$Cy^A$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{20}$;

$R^1$, $R^2$, and $R^3$ are each independently selected from H, D, $C_{1-6}$ alkyl, $C_{1-6}$ haloalkyl, halo, CN, $OR^{a9}$, and $NR^{c9}R^{d9}$;

$R^5$ is selected from $C_{1-6}$ alkyl, $C_{1-6}$ haloalkyl, $C_{3-10}$ cycloalkyl, and $C_{6-10}$ aryl; wherein said $C_{1-6}$ alkyl, $C_{3-10}$ cycloalkyl, and $C_{6-10}$ aryl, are each optionally substituted with 1, 2, 3, or 4 substituents independently selected from $R^{50}$;

each $R^{10}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a1}$, and $NR^{c1}R^{d1}$; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$;

each $R^{11}$ is independently selected from $C_{1-6}$ alkyl, $C_{1-6}$ haloalkyl, $C_{3-10}$ cycloalkyl, halo, D, CN, $OR^{a3}$, $C(O)R^{b3}$, $C(O)NR^{c3}R^{d3}$, $C(O)OR^{a3}$, $NR^{c3}R^{d3}$, and $S(O)_2R^{b3}$; wherein said $C_{1-6}$ alkyl, and $C_{3-10}$ cycloalkyl, are each optionally substituted with 1, 2, 3, or 4 substituents independently selected from $R^{12}$;

each $R^{12}$ is independently selected from $C_{1-6}$ alkyl, halo, D, CN, $OR^{a5}$ and $NR^{c5}R^{d5}$;

each $R^{20}$ is independently selected from $C_{1-6}$ alkyl, $C_{1-6}$ haloalkyl, $C_{3-10}$ cycloalkyl, halo, D, CN, $OR^{a2}$, $C(O)R^{b2}$, $C(O)NR^{c2}R^{d2}$, $C(O)OR^{a2}$, $S(O)NR^{c2}R^{d2}$, and $S(O)_2R^{b2}$; wherein said $C_{1-6}$ alkyl, and $C_{3-10}$ cycloalkyl are each optionally substituted with 1, 2, 3, or 4 substituents independently selected from $R^{21}$;

each $R^{21}$ is independently selected from $C_{1-6}$ alkyl, $C_{1-6}$ haloalkyl, halo, D, CN, $OR^{a4}$, and $NR^{c4}R^{d4}$;

each $R^{50}$ is independently selected from $C_{1-6}$ alkyl, $C_{1-6}$ haloalkyl, halo, D, CN, $OR^{a11}$, and $NR^{c11}R^{d11}$.

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$;

or any $R^{cc}$ and $R^{d1}$ attached to the same N atom, together with the N atom to which they are attached, form a 4-, 5-, or 6-membered heterocycloalkyl group optionally substituted with 1, 2, 3, or 4 substituents independently selected from $R^{11}$;

each $R^{a2}$, $R^{c2}$ and $R^{d2}$ is independently selected from H, $C_{1-6}$ alkyl, $C_{1-6}$ haloalkyl, and $C_{3-10}$ cycloalkyl; wherein said $C_{1-6}$ alkyl and $C_{3-10}$ cycloalkyl, are each optionally substituted with 1, 2, 3, or 4 substituents independently selected from $R^{21}$;

each $R^{b2}$ is independently selected from $C_{1-6}$ alkyl, $C_{1-6}$ haloalkyl, and $C_{3-10}$ cycloalkyl; wherein said $C_{1-6}$ alkyl and $C_{3-10}$ cycloalkyl, are each optionally substituted with 1, 2, 3, or 4 substituents independently selected from $R^{21}$;

each $R^{a3}$, $R^{c3}$ and $R^{d3}$ is independently selected from H, $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1, 2, 3, or 4 substituents independently selected from $R^{12}$;

each $R^{b3}$ is independently selected from $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, and $C_{1-6}$ haloalkyl;

each $R^{a5}$, $R^{c5}$ and $R^{d5}$ is independently selected from H, $C_{1-6}$ alkyl, and $C_{1-6}$ haloalkyl;

each $R^{a9}$, $R^{c9}$, and $R^{d9}$ is independently selected from H, $C_{1-6}$ alkyl, and $C_{1-6}$ haloalkyl; and each $R^{a11}$, $R^{c11}$ and $R^{d11}$ is independently selected from H, $C_{1-6}$ alkyl, and $C_{1-6}$ haloalkyl.

In one aspect, the present disclosure provides compounds of Formula (IB) or a pharmaceutically acceptable salt thereof, wherein:

Z is N or $CR^6$;

$Cy^1$ is selected from $C_{6-10}$ aryl and 5-10 membered heteroaryl; wherein each 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{10}$;

$Cy^A$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{20}$;

$R^1$, $R^2$, $R^3$, and $R^6$ are each independently selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a9}$, $SR^{a9}$, $C(O)R^{b9}$, $C(O)NR^{c9}R^{d9}$, $C(O)OR^{a9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{30}$;

$R^4$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a7}$, $SR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, and $S(O)_2NR^{c7}R^{d7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{40}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-6 membered heteroaryl, 4-7 membered heterocycloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$ $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^5S(O)_2R^{b5}$, $NR^5S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-6 membered heteroaryl and 4-7 membered heterocycloalkyl, are each optionally substituted with 1, 2, 3, or 4 substituents independently selected from $R^g$; each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$ $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, OR a, $SR^{a6}$, $C(O)R^{b6}$, $C(O)NR^{c6}R^{d6}$, $C(O)OR^{a6}$, $NR^{c6}R^{d6}$ $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{30}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a10}$, $SR^{a10}$, $C(O)R^{b10}$, $C(O)NR^{c10}R^{d10}$, $C(O)OR^{a10}$, $NR^{c10}R^{d10}$, $NR^{c10}C(O)R^{b10}$, $NR^{c10}C(O)OR^{a10}$, $NR^{c10}C(O)NR^{c10}R^{d10}$, $NR^{c10}S(O)R^{b10}$, $NR^{c10}$ $S(O)_2R^{b10}$, $NR^{C10}S(O)_2NR^{c10}R^{d10}$, $S(O)R^{b10}$, $S(O)NR^{c10}R^{d10}$, $S(O)_2R^{b10}$, and $S(O)_2NR^{c10}R^{d10}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{40}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $NR^{c8}C(O)OR^{a8}$, $NR^{c8}C(O)NR^{c8}R^{d8}$, $NR^{c8}$ $S(O)R^{b8}$, $NR^{c8}S(O)_2R^{b8}$ $NR^{c8}S(O)_2NR^{c8}R^{d8}$, $S(O)R^{b8}$, $S(O)NR^{c8}R^{d8}$, $S(O)_2R^{b8}$, and $S(O)_2NR^{c8}R^{d8}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^g$;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a2}$, $R^{c2}$ and $R^{d2}$, is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

or any $R^{c2}$ and $R^{d2}$ attached to the same N atom, together with the N atom to which they are attached, form a 4-, 5-, 6- or 7-membered heterocycloalkyl group optionally substituted with 1, 2 or 3 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

each $R^{e2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{a3}$, $R^{c3}$ and $R^{d3}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl, are each optionally substituted with 1, 2, 3, or 4 substituents independently selected from $R^{12}$;

each $R^{a4}$, $R^{c4}$ and $R^{d4}$, is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

each $R^{a5}$, $R^{c5}$ and $R^{d5}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c5}$ and $R^{d5}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$; each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a7}$, $R^{c7}$, and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

or any $R^{c7}$ and $R^{d7}$ attached to the same N atom, together with the N atom to which they are attached, form a 4-, 5-, 6- or 7-membered heterocycloalkyl group optionally substituted with 1, 2 or 3 substituents independently selected from $R^{40}$;

each $R^{b7}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{40}$;

each $R^{a8}$, $R^{c8}$ and $R^{d8}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b8}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a9}$, $R^{c9}$, and $R^{d9}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

or any $R^{c9}$ and $R^{d9}$ attached to the same N atom, together with the N atom to which they are attached, form a 4-, 5-, 6- or 7-membered heterocycloalkyl group optionally substituted with 1, 2 or 3 substituents independently selected from $R^{30}$;

each $R^{b9}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl, are each optionally substituted with 1, 2, 3, or 4 substituents independently selected from $R^{30}$;

each $R^{a10}$, $R^{c10}$ and $R^{d10}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b10}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$; and each $R^g$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In one aspect, the present disclosure provides compounds of Formula (IB) or a pharmaceutically acceptable salt thereof, wherein:

Z is N or $CR^6$;

$Cy^1$ is selected from 5-10 membered heteroaryl; wherein each 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the 5-10 membered heteroaryl are each optionally substituted with 1, 2, 3 or 4 substituents independently selected from $R^{10}$;

$Cy^A$ is selected from $C_{6-10}$ aryl and 5-10 membered heteroaryl; wherein the 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{20}$;

$R^1$, $R^2$, $R^3$, and $R^6$ are each independently selected from H, D, $C_{1-6}$ alkyl, $C_{1-6}$ haloalkyl, halo, CN, $OR^{a}$s, and $NR^{c9}R^{d9}$;

$R^4$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a7}$, and $NR^{c7}R^{d7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{40}$;

each $R^{10}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a1}$, and $NR^{c1}R^{d1}$; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$;

each $R^{11}$ is independently selected from $C_{1-6}$ alkyl, $C_{1-6}$ haloalkyl, $C_{3-10}$ cycloalkyl, halo, D, CN, $OR^{a3}$, $C(O)R^{b3}$, $C(O)NR^{c3}R^{d3}$, $C(O)OR^{a3}$, $NR^{c3}R^{d3}$, and $NR^{c3}C(O)R^{b3}$; wherein said $C_{1-6}$ alkyl, and $C_{3-10}$ cycloalkyl, are each optionally substituted with 1, 2, 3, or 4 substituents independently selected from $R^{12}$;

each $R^{12}$ is independently selected from $C_{1-6}$ alkyl, halo, D, CN, $OR^{a5}$ and $NR^{c5}R^{d5}$;

each $R^{20}$ is independently selected from $C_{1-6}$ alkyl, $C_{1-6}$ haloalkyl, $C_{3-10}$ cycloalkyl, halo, D, CN, $OR^{a2}$, $C(O)R^{b2}$, $C(O)NR^{c2}R^{d2}$, $C(O)OR^{a2}$, $S(O)NR^{c2}R^{d2}$, and $S(O)_2R^{b2}$; wherein said $C_{1-6}$ alkyl, and $C_{3-10}$ cycloalkyl are each optionally substituted with 1, 2, 3, or 4 substituents independently selected from $R^{21}$;

each $R^{21}$ is independently selected from $C_{1-6}$ alkyl, $C_{1-6}$ haloalkyl, halo, D, CN, $OR^{a4}$, and $NR^{c4}R^{d4}$.

each $R^{40}$ is independently selected from $C_{1-6}$ alkyl, $C_{1-6}$ haloalkyl, halo, D, CN, $OR^{a8}$, and $NR^{c8}R^{d8}$;

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, or 6-membered heterocycloalkyl group optionally substituted with 1, 2, 3, or 4 substituents independently selected from $R^{11}$;

each $R^{a2}$, $R^{c2}$ and $R^{d2}$ is independently selected from H, $C_{1-6}$ alkyl, $C_{1-6}$ haloalkyl, and $C_{3-10}$ cycloalkyl; wherein said $C_{1-6}$ alkyl and $C_{3-10}$ cycloalkyl, are each optionally substituted with 1, 2, 3, or 4 substituents independently selected from $R^{21}$;

each $R^{b2}$ is independently selected from $C_{1-6}$ alkyl, $C_{1-6}$ haloalkyl, and $C_{3-10}$ cycloalkyl; wherein said $C_{1-6}$ alkyl and $C_{3-10}$ cycloalkyl, are each optionally substituted with 1, 2, 3, or 4 substituents independently selected from $R^{21}$;

each $R^{a3}$, $R^{c3}$ and $R^{d3}$ is independently selected from H, $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1, 2, 3, or 4 substituents independently selected from $R^{12}$;

each $R^{b3}$ is independently selected from $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, and $C_{1-6}$ haloalkyl;

each $R^{a5}$, $R^{c5}$ and $R^{d5}$ is independently selected from H, $C_{1-6}$ alkyl, and $C_{1-6}$ haloalkyl;

each $R^{a7}$, $R^{c7}$, and $R^{d7}$ is independently selected from H, $C_{1-6}$ alkyl, and $C_{1-6}$ haloalkyl;

each $R^{a8}$, $R^{c8}$ and $R^{d8}$ is independently selected from H, $C_{1-6}$ alkyl, and $C_{1-6}$ haloalkyl; and each $R^{a9}$, $R^{c9}$, and $R^{d9}$ is independently selected from H, $C_{1-6}$ alkyl, and $C_{1-6}$ haloalkyl.

In one aspect, the present disclosure provides compounds of Formula (IB) or a pharmaceutically acceptable salt thereof, wherein:

Z is N or $CR^6$;

$Cy^1$ is selected from $C_{6-10}$ aryl and 5-10 membered heteroaryl; wherein each 5-10 membered heteroaryl has at least one ring-forming carbon atom and 1, 2, 3, or 4 ring-forming heteroatoms independently selected from N, O, and S; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1 or 2 substituents independently selected from $R^{10}$;

$Cy^A$ is selected from $C_{3-10}$ cycloalkyl, and $C_{6-10}$ aryl; wherein the $C_{3-10}$ cycloalkyl, and $C_6$. 10 aryl are each optionally substituted with 1, 2, or 3 substituents independently selected from $R^{20}$;

$R^1$ is independently selected from H, D, $C_{1-6}$ alkyl, $C_{1-6}$ haloalkyl halo, CN, $OR^{a9}$, and $NR^{c9}R^{d9}$.

$R^2$ and $R^3$ are each independently selected from H, D, and $C_{1-6}$ alkyl;

$R^6$ are each independently selected from H, D, $C_{1-6}$ alkyl, $C_{1-6}$ haloalkyl halo, CN, $OR^{a9}$, and $NR^{c9}R^{d9}$;

$R^4$ is selected from H, D, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, CN, $OR^{a7}$ and $NR^{c7}R^{d7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1 or 2 substituents independently selected from $R^{40}$;

each $R^{10}$ is independently selected from $C_{1-6}$ alkyl, $C_{1-6}$ haloalkyl, $C_{3-10}$ cycloalkyl, 4-10 membered heterocycloalkyl, $C_{6-10}$ aryl, and 5-10 membered heteroaryl, halo, D, CN, $OR^{a1}$, and $NR^{c1}R^{d1}$; wherein said $C_{1-6}$ alkyl, $C_{3-10}$ cycloalkyl, 4-10 membered heterocycloalkyl, $C_{6-10}$ aryl, and 5-10 membered heteroaryl, are each optionally substituted with 1, 2 or 3 substituents independently selected from $R^{11}$;

each $R^{11}$ is independently selected from $C_{1-6}$ alkyl, $C_{1-6}$ haloalkyl, 4-10 membered heterocycloalkyl, $C_{6-10}$ aryl, halo, D, CN, $OR^{a3}$, $C(O)R^{b3}$, $C(O)NR^{c3}R^{d3}$, $C(O)OR^{a3}$, $NR^{c3}R^{d3}$ $NR^{c3}C(O)R^{b3}$ $NR^{c3}C(O)NR^{c3}R^{d3}$, $S(O)_2R^{b3}$, and $S(O)_2NR^{c3}R^{d3}$; wherein said $C_{1-6}$ alkyl and $C_{6-10}$ aryl, are each optionally substituted with 1 or 2 substituents independently selected from $R^{12}$;

each $R^{12}$ is independently selected from $C_{1-6}$ alkyl, $C_{1-6}$ haloalkyl, 5-6 membered heteroaryl, halo, D, CN, $OR^{a5}$, $C(O)R^5$, $C(O)NR^{c5}R^{d5}$, $C(O)OR^{a5}$, and $NR^{c5}R^{d5}$;

each $R^{20}$ is independently selected from $C_{1-6}$ alkyl, $C_{1-6}$ haloalkyl, halo, D, CN, $OR^{a2}$, $C(O)R^{b2}$, $C(O)NR^{c2}R^{d2}$, $C(O)OR^{a2}$, $NR^{c2}R^{d2}$, and $NR^{c2}C(O)R^{b2}$; wherein said $C_{1-6}$ alkyl, is optionally substituted with 1 or 2 substituents independently selected from $R^{21}$;

each $R^{21}$ is independently selected from $C_{1-6}$ alkyl, $C_{1-6}$ haloalkyl, halo, D, CN, $OR^{a4}$, and $NR^{c4}R^{d4}$.

each $R^{40}$ is independently selected from $C_{1-6}$ alkyl, $C_{1-6}$ haloalkyl, halo, D, CN, $OR^{a8}$, and $NR^{c8}R^{d8}$.

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1 or 2 substituents independently selected from $R^{11}$;

or any $R^{c1}$ and $R^{d1}$ attached to the same N atom, together with the N atom to which they are attached, form a 4-, 5-, or 6-membered heterocycloalkyl group optionally substituted with 1 or 2 substituents independently selected from $R^{11}$;

each $R^{a2}$, $R^{c2}$ and $R^{d2}$, is independently selected from H, $C_{1-6}$ alkyl, and $C_{1-6}$ haloalkyl; wherein said $C_{1-6}$ alkyl, is optionally substituted with 1 or 2 substituents independently selected from $R^{21}$;

each $R^{b2}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl, are each optionally substituted with 1 or 2 substituents independently selected from $R^{21}$;

each $R^{a3}$, $R^{c3}$ and $R^{d3}$, is independently selected from H, $C_{1-6}$ alkyl, and $C_{1-6}$ haloalkyl; wherein said $C_{1-6}$ alkyl is optionally substituted with 1 or 2 substituents independently selected from $R^{12}$;

or any $R^{c3}$ and $R^{d3}$ attached to the same N atom, together with the N atom to which they are attached, form a 4-, 5-, 6-membered heterocycloalkyl group optionally substituted with 1 or 2 substituents independently selected from $R^{12}$;

each $R^{b3}$ is independently selected from $C_{1-6}$ alkyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{3-6}$ cycloalkyl, phenyl, 5-6 membered heteroaryl and 4-7 membered heterocycloalkyl, are each optionally substituted with 1 or 2 substituents independently selected from $R^{12}$;

each $R^{a4}$, $R^{c4}$ and $R^{d4}$, is independently selected from H, $C_{1-6}$ alkyl, and $C_{1-6}$ haloalkyl;

each $R^{a5}$, $R^{c5}$ and $R^{d5}$, is independently selected from H, $C_{1-6}$ alkyl, and $C_{1-6}$ haloalkyl;

each $R^{b5}$ is independently selected from $C_{1-6}$ alkyl, and $C_{1-6}$ haloalkyl;

each $R^{a7}$, $R^{c7}$, and $R^{d7}$ is independently selected from H, $C_{1-6}$ alkyl, and $C_{1-6}$ haloalkyl; wherein said $C_{1-6}$ alkyl, is optionally substituted with 1 or 2 substituents independently selected from $R^{40}$;

each $R^{a8}$, $R^{c8}$ and $R^{d8}$, is independently selected from H, $C_{1-6}$ alkyl, and $C_{1-6}$ haloalkyl; and each $R^{a9}$, $R^{c9}$, and $R^{d9}$ is independently selected from H, $C_{1-6}$ alkyl, $C_{1-6}$ haloalkyl, $C_{3-10}$ cycloalkyl, and 4-10 membered heterocycloalkyl;

or any $R^{c9}$ and $R^{d9}$ attached to the same N atom, together with the N atom to which they are attached, form a 4-, 5- or 6-membered heterocycloalkyl group.

In some embodiments, X is $CR^4$ and Y is N.

In some embodiments, X is $NR^5$ and Y is C.

In some embodiments, Z is N.

In some embodiments, Z is $CR^6$.

In some embodiments, $Cy^1$ is 5-10 membered heteroaryl; wherein each 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the 5-10 membered heteroaryl is optionally substituted with 1, 2, 3 or 4 substituents independently selected from $R^{10}$.

In some embodiments, $Cy^1$ is 5-6 membered heteroaryl; wherein each 5-6 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl is optionally substituted by oxo to form a carbonyl group; and wherein the 5-6 membered heteroaryl is optionally substituted with 1, 2, 3 or 4 substituents independently selected from $R^{10}$.

In some embodiments, $Cy^1$ is 5-10 membered heteroaryl optionally substituted with 1, 2, 3 or 4 substituents independently selected from $R^{10}$. In some embodiments, $Cy^1$ is 5-6 membered heteroaryl optionally substituted with 1, 2, 3 or 4 substituents independently selected from $R^{10}$.

In some embodiments, $Cy^1$ is 5-10 membered heteroaryl optionally substituted with 1 or 2 substituents independently selected from $R^{10}$. In some embodiments, $Cy^1$ is 5-6 membered heteroaryl optionally substituted with 1 or 2 substituents independently selected from $R^{10}$. In some embodiments, $Cy^1$ is 5 membered heteroaryl optionally substituted with 1 or 2 substituents independently selected from $R^{10}$. In some embodiments, $Cy^1$ is 6 membered heteroaryl optionally substituted with 1 or 2 substituents independently selected from $R^{10}$.

In some embodiments, $Cy^1$ is 5-10 membered heteroaryl or phenyl, each optionally substituted with 1, 2, 3 or 4 substituents independently selected from $R^{10}$. In some embodiments, $Cy^1$ is 5-10 membered heteroaryl or phenyl, each optionally substituted with 1 or 2 substituents independently selected from $R^{10}$.

In some embodiments, $Cy^1$ is 5-6 membered heteroaryl or phenyl, each optionally substituted with 1, 2, 3 or 4 substituents independently selected from $R^{10}$. In some embodiments, $Cy^1$ is 5-6 membered heteroaryl or phenyl, each optionally substituted with 1 or 2 substituents independently selected from $R^{10}$.

In some embodiments, $Cy^1$ is phenyl optionally substituted with 1, 2, 3 or 4 substituents independently selected from $R^{10}$. In some embodiments, $Cy^1$ is phenyl optionally substituted with 1 or 2 substituents independently selected from $R^{10}$.

In some embodiments, $Cy^1$ is pyrazolyl or pyridinyl, each optionally substituted with 1 or 2 substituents independently selected from $R^{10}$. In some embodiments, $Cy^1$ is pyrazolyl optionally substituted with 1 or 2 substituents independently selected from $R^{10}$. In some embodiments, $Cy^1$ is pyridinyl optionally substituted with 1 or 2 substituents independently selected from $R^{10}$ In some embodiments, $Cy^1$ is pyrazolyl, pyridinyl, or phenyl, each optionally substituted with 1 or 2 substituents independently selected from $R^{10}$.

In some embodiments, $Cy^1$ is selected from 1-methyl-1H-pyrazol-4-yl, 1,3-dimethyl-1H-pyrazol-4-yl, 1-(1-acetylpyrrolidin-3-yl)-1H-pyrazol-4-yl, 1-(4-carboxycyclohexyl)-1H-pyrazol-4-yl, 1-(4-acetamidocyclohexyl)-1H-pyrazol-4-yl, 1-(3-hydroxycyclobutyl)-1H-pyrazol-4-yl, and 6-(4-acetylpiperazin-1-yl)pyridin-3-yl.

In some embodiments, $Cy^1$ is selected from 1-methyl-1H-pyrazol-4-yl, 1,3-dimethyl-1H-pyrazol-4-yl, 1-(1-acetylpyrrolidin-3-yl)-1H-pyrazol-4-yl, 1-(4-carboxycyclohexyl)-1H-pyrazol-4-yl, 1-(4-acetamidocyclohexyl)-1H-pyrazol-4-yl, 1-(3-hydroxycyclobutyl)-1H-pyrazol-4-yl, 6-(4-acetylpiperazin-1-yl)pyridin-3-yl, 1-(1-(2-hydroxyacetyl)pyrrolidin-3-yl)-1H-pyrazol-4-yl, 1-(1-(1-aminocyclopropane-1-carbonyl)azetidin-3-yl)-1H-pyrazol-4-yl, 1-(1-(2-(1H-imidazol-1-yl)acetyl)azetidin-3-yl)-1H-pyrazol-4-yl, 1-(1-(oxazole-4-carbonyl)azetidin-3-yl)-1H-pyrazol-4-yl, 1-(1-(4-aminotetrahydro-2H-pyran-4-carbonyl)azetidin-3-yl)-1H-pyrazol-4-yl, 1-(1-(2-cyanoacetyl)azetidin-3-yl)-1H-pyrazol-4-yl, 1-(4-carboxy-3-fluorobenzyl)-1H-pyrazol-4-yl, 1-(4-(dimethylcarbamoyl)phenyl)-1H-pyrazol-4-yl, 1-((1r,4r)-4-(2-methoxyacetamido)cyclohexyl)-1H-pyrazol-4-yl, 1-((1r,4r)-4-(3,3-dimethylureido)cyclohexyl)-1H-pyrazol-4-yl, 1-(2-acetyl-2-azaspiro[3.5]nonan-7-yl)-1H-pyrazol-4-yl, 1-(tetrahydro-2H-pyran-4-yl)-1H-pyrazol-4-yl, 1-((1r,4r)-4-hydroxycyclohexyl)-1H-pyrazol-4-yl, 1-(4-carboxy-4-methylcyclohexyl)-1H-pyrazol-4-yl, 1-(1-(dimethylcarbamoyl)pyrrolidin-3-yl)-1H-pyrazol-4-yl, 1-(1-(N,N-dimethylsulfamoyl)pyrrolidin-3-yl)-1H-pyrazol-4-yl, 1-(3-(2-hydroxyacetyl)-3-azabicyclo[3.1.0]hexan-1-yl)-1H-pyrazol-4-yl, 1-(1-(morpholine-4-carbonyl)pyrrolidin-3-yl)-1H-pyrazol-4-yl, 1-(3-(2-hydroxyacetyl)-3-azabicyclo[4.1.0]heptan-6-yl)-1H-pyrazol-4-yl, 1-(3-acetyl-3-azabicyclo[4.1.0]heptan-1-yl)-1H-pyrazol-4-yl, 6-(1-(2-hydroxyacetyl)azetidin-3-yl)pyridin-3-yl, 5-(1-acetylazetidin-3-yl)pyridin-3-yl, 4-(1-acetylazetidin-3-yl)phenyl), 1-cyclopropyl-1H-pyrazol-4-yl, 1-(tetrahydrofuran-3-yl)-1H-pyrazol-4-yl, 1-(oxetan-3-yl)-1H-pyrazol-4-yl, 1-(2-(dimethylamino)ethyl)-1H-pyrazol-4-yl, 1-isopropyl-1H-pyrazol-4-yl, 1-(difluoromethyl)-1H-pyrazol-4-yl, 1-(2-cyanoethyl)-1H-pyrazol-4-yl, 1-(2-hydroxy-2-methylpropyl)-1H-pyrazol-4-yl, 1-(cyanomethyl)-1H-pyrazol-4-yl, 1-(1-methylpiperidin-4-yl)-1H-pyrazol-4-yl, 1-(1-hydroxy-2-methylpropan-2-yl)-1H-pyrazol-4-yl, 1-(2-(methylsulfonyl)ethyl)-1H-pyrazol-4-yl, 1-(2,2,2-trifluoroethyl)-1H-pyrazol-4-yl, 1-(2-morpholinoethyl)-1H-pyrazol-4-yl, and 1-(2-hydroxyethyl)-1H-pyrazol-4-yl.

In some embodiments, $Cy^1$ is selected from 1-methyl-1H-pyrazol-4-yl, 1,3-dimethyl-1H-pyrazol-4-yl, 1-(1-acetylpyrrolidin-3-yl)-1H-pyrazol-4-yl, 1-(4-carboxycyclohexyl)-1H-pyrazol-4-yl, 1-(4-acetamidocyclohexyl)-1H-pyrazol-4-yl, 1-(3-hydroxycyclobutyl)-1H-pyrazol-4-yl, 6-(4-acetylpiperazin-1-yl)pyridin-3-yl, 1-(1-(2-hydroxyacetyl)pyrrolidin-3-yl)-1H-pyrazol-4-yl, 1-(1-(1-aminocyclopropane-1-carbonyl)azetidin-3-yl)-1H-pyrazol-4-yl, 1-(1-(2-(1H-imidazol-1-yl)acetyl)azetidin-3-yl)-1H-pyrazol-4-yl, 1-(1-(oxazole-4-carbonyl)azetidin-3-yl)-1H-pyrazol-4-yl, 1-(1-(4-aminotetrahydro-2H-pyran-4-carbonyl)azetidin-3-yl)-1H-pyrazol-4-yl, 1-(1-(2-cyanoacetyl)azetidin-3-yl)-1H-pyrazol-4-yl, 1-(4-carboxy-3-fluorobenzyl)-1H-pyrazol-4-yl, 1-(4-(dimethylcarbamoyl)phenyl)-1H-pyrazol-4-yl, 1-((1r,4r)-4-(2-methoxyacetamido)cyclohexyl)-1H-pyrazol-4-yl, 1-((1r,4r)-4-(3,3-dimethylureido)cyclohexyl)-1H-pyrazol-4-yl, 1-(2-acetyl-2-azaspiro[3.5]nonan-7-yl)-1H-pyrazol-4-yl, 1-(tetrahydro-2H-pyran-4-yl)-1H-pyrazol-4-yl, 1-((1r,4r)-4-hydroxycyclohexyl)-1H-pyrazol-4-yl, 1-(4-carboxy-4-methylcyclohexyl)-1H-pyrazol-4-yl, 1-(1-(dimethylcarbamoyl)pyrrolidin-3-yl)-1H-pyrazol-4-yl, 1-(1-(N,N-dimethylsulfamoyl)pyrrolidin-3-yl)-1H-pyrazol-4-yl, 1-(3-(2-hydroxyacetyl)-3-azabicyclo[3.1.0]hexan-1-yl)-1H-pyrazol-4-yl, 1-(1-(morpholine-4-carbonyl)pyrrolidin-3-yl)-1H-pyrazol-4-yl, 1-(3-(2-hydroxyacetyl)-3-azabicyclo[4.1.0]heptan-6-yl)-1H-pyrazol-4-yl, 1-(3-acetyl-3-azabicyclo[4.1.0]heptan-1-yl)-1H-pyrazol-4-yl, 6-(1-(2-hydroxyacetyl)azetidin-3-yl)pyridin-3-yl, 5-(1-acetylazetidin-3-yl)pyridin-3-yl, 1-cyclopropyl-1H-pyrazol-4-yl, 1-(tetrahydrofuran-3-yl)-1H-pyrazol-4-yl, 1-(oxetan-3-yl)-1H-pyrazol-4-yl, 1-(2-(dimethylamino)ethyl)-1H-pyrazol-4-yl, 1-isopropyl-1H-pyrazol-4-yl, 1-(difluoromethyl)-1H-pyrazol-4-yl, 1-(2-cyanoethyl)-1H-pyrazol-4-yl, 1-(2-hydroxy-2-methylpropyl)-1H-pyrazol-4-yl, 1-(cyanomethyl)-1H-pyrazol-4-yl, 1-(1-methylpiperidin-4-yl)-1H-pyrazol-4-yl, 1-(1-hydroxy-2-methylpropan-2-yl)-1H-pyrazol-4-yl, 1-(2-(methylsulfonyl)ethyl)-1H-pyrazol-4-yl, 1-(2,2,2-trifluoroethyl)-1H-pyrazol-4-yl, 1-(2-morpholinoethyl)-1H-pyrazol-4-yl, and 1-(2-hydroxyethyl)-1H-pyrazol-4-yl.

In some embodiments, each $R^{10}$ is independently selected from $C_{1-6}$ alkyl, $C_{1-6}$ haloalkyl, $C_{3-10}$ cycloalkyl, 4-10 membered heterocycloalkyl, halo, D, CN, OR, and $NR^{c1}R^{d1}$; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$.

In some embodiments, each $R^{10}$ is independently selected from $C_{1-6}$ alkyl, $C_{1-6}$ haloalkyl, $C_{6-10}$ aryl, $C_{3-10}$ cycloalkyl, 4-10 membered heterocycloalkyl, halo, D, CN, $OR^{a1}$, and $NR^{c1}R^{d1}$; wherein said $C_{1-6}$ alkyl, $C_{6-10}$ aryl, $C_{3-10}$ cycloalkyl, and 4-10 membered heterocycloalkyl, are each optionally substituted with 1, 2, 3, or 4 substituents independently selected from $R^{11}$.

In some embodiments, each $R^{10}$ is independently selected from $C_{1-6}$ alkyl, $C_{1-6}$ haloalkyl, $C_{3-7}$ cycloalkyl, 4-6 membered heterocycloalkyl, halo, D, CN, $OR^{a1}$, and $NR^{c1}R^{d1}$; wherein said $C_{1-6}$ alkyl, $C_{3-7}$ cycloalkyl, and 4-6 membered heterocycloalkyl are each optionally substituted with 1 or 2 substituents independently selected from $R^{11}$.

In some embodiments, each $R^{10}$ is independently selected from $C_{1-6}$ alkyl, $C_{1-6}$ haloalkyl, 10 $C_{6-10}$ aryl, $C_{3-7}$ cycloalkyl, 4-6 membered heterocycloalkyl, halo, D, CN, $OR^{a1}$, and $NR^{c1}R^{d1}$; wherein said $C_{1-6}$ alkyl, $C_{6-10}$ aryl, $C_{3-7}$ cycloalkyl, and 4-6 membered heterocycloalkyl are each optionally substituted with 1 or 2 substituents independently selected from $R^{11}$.

In some embodiments, each $R^{10}$ is independently selected from $C_{1-6}$ alkyl, 4-10 membered heterocycloalkyl, and $C_{3-10}$ cycloalkyl, each of which is optionally substituted with 1 or 2 substituents independently selected from $R^{11}$.

In some embodiments, each $R^{10}$ is independently selected from $C_{1-6}$ alkyl, 4-10 membered heterocycloalkyl, $C_{6-10}$ aryl, and $C_{3-10}$ cycloalkyl, each of which is optionally substituted with 1 or 2 substituents independently selected from $R^{11}$.

In some embodiments, each $R^{10}$ is independently selected from $C_{1-6}$ alkyl, 4-6 membered heterocycloalkyl, and $C_{3-7}$ cycloalkyl, each of which is optionally substituted with 1 or 2 substituents independently selected from $R^{11}$. In some embodiments, each $R^{10}$ is independently selected from $C_{1-6}$ alkyl optionally substituted with 1 or 2 substituents independently selected from $R^{11}$. In some embodiments, each $R^{10}$ is independently selected from 4-6 membered heterocycloalkyl optionally substituted with 1 or 2 substituents independently selected from $R^{11}$. In some embodiments, each $R^{10}$ is independently selected from $C_{3-7}$ cycloalkyl optionally substituted with 1 or 2 substituents independently selected from $R^{11}$.

In some embodiments, each $R^{10}$ is independently selected from $C_{1-6}$ alkyl, 4-6 membered heterocycloalkyl, $C_{6-10}$ aryl, and $C_{3-7}$ cycloalkyl, each of which is optionally substituted with 1 or 2 substituents independently selected from $R^{11}$. In some embodiments, each $R^{10}$ is independently selected from $C_{1-6}$ alkyl, 4-6 membered heterocycloalkyl, phenyl, and $C_{3-7}$ cycloalkyl, each of which is optionally substituted with 1 or 2 substituents independently selected from $R^{11}$. In some embodiments, each $R^{10}$ is independently selected from methyl, pyrrolidinyl, cyclohexyl, cyclobutyl, and piperazinyl, each of which is optionally substituted with 1 or 2 substituents independently selected from $R^{11}$. In some embodiments, each $R^{10}$ is independently selected from methyl, pyrrolidinyl, cyclohexyl, and cyclobutyl, each of which is optionally substituted with 1 or 2 substituents independently selected from $R^{11}$. In some embodiments, each $R^{10}$ is independently selected from methyl and piperazinyl, each of which is optionally substituted with 1 or 2 substituents independently selected from $R^{11}$.

In some embodiments, each $R^{10}$ is independently selected from methyl, ethyl, isopropyl, 2-methylpropyl, difluoromethyl, cyclopropyl, cyclobutyl, cyclohexyl, phenyl, piperzinyl, azetidinyl, pyrrolidinyl, azaspiro[3.5]nonanyl, tetrahydro-2H-pyranyl, azabicyclo[3.1.0]hexanyl, azabicyclo[4.1.0]heptanyl, tetrahydrofuranyl, oxetanyl, and piperidinyl, each of which is optionally substituted with 1 or 2 substituents independently selected from $R^{11}$.

In some embodiments, each $R^{10}$ is independently selected from methyl, ethyl, isopropyl, 2-methylpropyl, and difluoromethyl, wherein each methyl and ethyl is optionally substituted with 1 or 2 substituents independently selected from $R^{11}$. In some embodiments, each $R^{10}$ is independently selected from methyl, ethyl, isopropyl, 2-methylpropyl, and difluoromethyl.

In some embodiments, each $R^{10}$ is independently selected from cyclopropyl, cyclobutyl, cyclohexyl, phenyl, piperzinyl, azetidinyl, pyrrolidinyl, azaspiro[3.5]nonanyl, tetrahydro-2H-pyranyl, azabicyclo[3.1.0]hexanyl, azabicyclo[4.1.0]heptanyl, tetrahydrofuranyl, oxetanyl, and piperidinyl, each of which is optionally substituted with 1 or 2 substituents independently selected from $R^{11}$.

In some embodiments, each $R^{11}$ is independently selected from $C_{1-6}$ alkyl, $C_{1-6}$ haloalkyl, $C_{6-10}$ aryl, halo, D, CN, $OR^{a}$, $C(O)R^{b3}$, $C(O)NR^{c3}R^{d3}$, $C(O)OR^{a3}$, $NR^{c3}R^{d3}$ $NR^{c3}C(O)R^{b3}$, $S(O)_2R^{b3}$, and $S(O)_2NR^{c3}R^{d3}$; wherein said $C_{1-6}$ alkyl and $C_{6-10}$ aryl are each optionally substituted with 1 or 2 substituents independently selected from $R^{12}$.

In some embodiments, each $R^{11}$ is independently selected from $C_{1-6}$ alkyl, $C_{3-7}$ cycloalkyl, CN, $OR^{a3}$, $C(O)R^{b3}$, $C(O)NR^{c3}R^{d3}$, $C(O)OR^{3}$, and $S(O)_2R^{b3}$; wherein said $C_{1-6}$ alkyl, and $C_{3-7}$ cycloalkyl are each optionally substituted with 1 or 2 substituents independently selected from $R^{12}$.

In some embodiments, each $R^{11}$ is independently selected from $C_{1-6}$ alkyl, $C_{1-6}$ haloalkyl, $C_{6-10}$ aryl, halo, D, CN, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $S(O)_2R^{b3}$, and $S(O)_2NR^{c3}R^{d3}$; wherein said $C_{1-6}$ alkyl and $C_{6-10}$ aryl, are each optionally substituted with 1 or 2 substituents independently selected from $R^{12}$ In some embodiments, each $R^{11}$ is independently selected from $C_{1-6}$ alkyl, $C_{1-6}$ haloalkyl, $C_{3-7}$ cycloalkyl, halo, D, CN, $OR^{a3}$, $C(O)R^{b3}$, $C(O)NR^{c3}R^{d3}$, $C(O)OR^{a3}$, $NR^{c3}R^{d3}$ and $S(O)_2R^{b}$.

In some embodiments, each $R^{11}$ is independently selected from $C(O)R^{b3}$, $C(O)OR^{a3}$, $NR^{c3}C(O)R^{b3}$, and $OR^{a3}$. In some embodiments, each $R^{11}$ is independently selected from $C(O)CH_3$, $C(O)OH$, $NHC(O)CH_3$, and OH.

each $R^{11}$ is independently selected from $C_{1-6}$ alkyl, CN, $C(O)R^{b3}$, $C(O)OR^{a3}$, $NR^{c3}C(O)R^{b3}$, $OR^{a3}$, $C(O)NR^{c3}R^{d3}$, $NR^{c3}R^{d3}$, $NR^{c3}C(O)NR^{c3}R^{d3}$, $S(O)_2NR^{c3}R^{d3}$, $S(O)_2R^{b3}$, phenyl, and 4-6 membered heterocycloalkyl, wherein said $C_{1-6}$ alkyl, phenyl, and 4-6 membered heterocycloalkyl are each optionally substituted with 1 or 2 substituents independently selected from $R^{12}$.

In some embodiments, each $R^{11}$ is independently selected from $C(O)R^{b3}$, $C(O)OR^{a3}$, $NR^{c3}C(O)R^{b3}$, $OR^{a3}$, $C(O)NR^{c3}R^{d3}$, $S(O)_2NR^{c3}R^{d3}$, $NR^{c3}R^{d3}$, CN, and $S(O)_2R^{b3}$.

In some embodiments, each $R^{11}$ is independently selected from $C(O)R^{b3}$, $C(O)OR^{a3}$, and $NR^{c3}C(O)R^{b3}$. In some embodiments, each $R^{11}$ is independently selected from $C(O)CH_3$, $C(O)OH$, and $NHC(O)CH_3$.

In some embodiments, each $R^{11}$ is independently selected from methyl, CN, OH, $C(O)CH_3$, $C(O)OH$, $NHC(O)CH_3$, $C(O)CH_2OH$, $C(O)N(CH_3)_2$, $NHC(O)CH_2OCH_3$, $NHC(O)N(CH_3)_2$, $S(O)_2N(CH_3)_2$, $N(CH_3)_2$, $S(O)_2CH_3$, 2-cyanoacetyl, morpholine-4-carbonyl, morpholinyl, 1-aminocyclopropane-1-carbonyl, (1H-imidazol-1-yl)acetyl, oxazole-4-carbonyl, 4-aminotetrahydro-2H-pyran-4-carbonyl, and 4-carboxy-3-fluorophenyl.

In some embodiments, $R^{11}$ is $OR^{a3}$. In some embodiments, $R^{11}$ is OH.

In some embodiments, each $R^{12}$ is independently selected from $C_{1-6}$ alkyl, halo, D, CN, $OR^{a5}$ and $NR^{c5}R^{d5}$.

In some embodiments, each $R^{12}$ is independently selected from $C_{1-6}$ alkyl, $C_{1-6}$ haloalkyl, 5-6 membered heteroaryl, halo, D, CN, $OR^{a5}$, $C(O)R^{b5}$, $C(O)NR^{c5}R^{d5}$, $C(O)OR^{a5}$, and $NR^{c5}R^{d5}$.

In some embodiments, $Cy^{A}$ is selected from $C_{3-7}$ cycloalkyl, 4-6 membered heterocycloalkyl, phenyl and 5-6 membered heteroaryl; wherein the 4-6 membered heterocycloalkyl and 5-6 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl and 4-6 membered heterocycloalkyl is optionally substituted by oxo to form a carbonyl group; and wherein the $C_{3-7}$ cycloalkyl, 4-6 membered heterocycloalkyl, phenyl and 5-6 membered heteroaryl are each optionally substituted with 1, 2, 3 or 4 substituents independently selected from $R^{20}$.

In some embodiments, $Cy^{A}$ is selected from $C_{3-7}$ cycloalkyl, 4-6 membered heterocycloalkyl, phenyl and 5-6 membered heteroaryl; wherein the 4-6 membered heterocycloalkyl and 5-6 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl and 4-6 membered heterocycloalkyl is optionally substituted by oxo to form a carbonyl group; and wherein the $C_{3-7}$ cycloalkyl, 4-6 membered heterocycloalkyl, phenyl and 5-6 membered heteroaryl are each optionally substituted with 1 or 2 substituents independently selected from $R^{20}$.

In some embodiments, $Cy^{A}$ is selected from $C_{6-10}$ aryl and 5-10 membered heteroaryl; wherein the 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{6-10}$ aryl and 5-10 membered heteroaryl are each optionally substituted with 1, 2, 3 or 4 substituents independently selected from $R^{20}$.

In some embodiments, $Cy^A$ is selected from phenyl and 5-6 membered heteroaryl; wherein the 5-6 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-6 membered heteroaryl is optionally substituted by oxo to form a carbonyl group; and wherein the phenyl and 5-6 membered heteroaryl are each optionally substituted with 1, 2, 3 or 4 substituents independently selected from $R^{20}$.

In some embodiments, $Cy^A$ is selected from phenyl and 5-6 membered heteroaryl, wherein the phenyl and 5-6 membered heteroaryl are each optionally substituted with 1, 2, 3 or 4 substituents independently selected from $R^{20}$. In some embodiments, $Cy^A$ is selected from phenyl and 5-6 membered heteroaryl, wherein the phenyl and 5-6 membered heteroaryl are each optionally substituted with 1 or 2 substituents independently selected from $R^{20}$.

In some embodiments, $Cy^A$ is phenyl or furanyl, each optionally substituted with 1, 2, or 3 substituents independently selected from $R^{20}$. In some embodiments, $Cy^A$ is phenyl or furanyl, each optionally substituted with 1 or 2 substituents independently selected from $R^{20}$.

In some embodiments, $Cy^A$ is phenyl, furanyl, piperidinyl, 2-oxo-3,8-diazabicyclo[3.2.1]octanyl, or cyclopropyl, each optionally substituted with 1, 2, or 3 substituents independently selected from $R^{20}$. In some embodiments, $Cy^A$ is phenyl, furanyl, piperidinyl, 2-oxo-3,8-diazabicyclo[3.2.1]octanyl, or cyclopropyl, each optionally substituted with 1 or 2 substituents independently selected from $R^{20}$.

In some embodiments, $Cy^A$ is phenyl optionally substituted with 1, 2, or 3 substituents independently selected from $R^{20}$. In some embodiments, $Cy^A$ is phenyl substituted with 1 or 2 substituents independently selected from $R^{20}$. In some embodiments, $Cy^A$ is phenyl substituted with 1 or 2 substituents independently selected from $R^{20}$ at the ortho and/or para positions of the phenyl. For example, $Cy^A$ is phenyl substituted with 2 substituents independently selected from $R^{20}$ at the ortho and para positions of the phenyl.

In some embodiments, $Cy^A$ is phenyl substituted with 1 or 2 substituents independently selected from $R^{20}$ at the ortho positions of the phenyl. For example, $Cy^A$ is phenyl substituted with 1 substituent independently selected from $R^{20}$ at the ortho position of the phenyl. For example, $Cy^A$ is phenyl substituted with 2 substituents independently selected from $R^{20}$ at the ortho positions of the phenyl.

In some embodiments, $Cy^A$ is selected from 2-chlorophenyl, 2,6-difluorophenyl, 2-chloro-6-fluorophenyl, 2,6-dichlorophenyl, 2-fluoro-6-methylphenyl, 2-chloro-4-methoxyphenyl, and 3-methylfuran-2-yl.

In some embodiments, $Cy^A$ is selected from 2-chlorophenyl, 2,6-difluorophenyl, 2-chloro-6-fluorophenyl, 2,6-dichlorophenyl, 2-fluoro-6-methylphenyl, 2-chloro-4-methoxyphenyl, 3-methylfuran-2-yl, 1-methylpiperidin-4-yl, (1S,5R)-2-oxo-3,8-diazabicyclo[3.2.1]octan-8-yl, 2-chloro-6-(trifluoromethyl)phenyl, 2,6-dimethylphenyl, 2-cyano-6-fluorophenyl, 2-fluoro-6-methoxyphenyl, 2,3-dimethylphenyl, 4-(hydroxymethyl)-2-methylphenyl, 3-acrylamido-2,6-dichlorophenyl, 3-acrylamidophenyl, 2-acrylamidophenyl, and cyclopropyl.

In some embodiments, each $R^{20}$ is independently selected from $C_{1-6}$ alkyl, $C_{1-6}$ haloalkyl, $C_{3-10}$ cycloalkyl, halo, D, CN, $OR^{a2}$, $C(O)R^{b2}$, $C(O)NR^{c2}R^{d2}$, $C(O)OR^{a2}$, $S(O)NR^{c2}R^{d2}$, and $S(O)_2R^{b2}$; wherein said $C_{1-6}$ alkyl and $C_{3-10}$ cycloalkyl are each optionally substituted with 1, 2, 3, or 4 substituents independently selected from $R^{21}$.

In some embodiments, each $R^{20}$ is independently selected from $C_{1-6}$ alkyl, $C_{1-6}$ haloalkyl, $C_{3-10}$ cycloalkyl, halo, D, CN, $OR^{a2}$, $C(O)R^{b2}$, $C(O)NR^{c2}R^{d2}$, $C(O)OR^{a2}$, $NR^{c2}C(O)R^{b2}$, $S(O)NR^{c2}R^{d2}$, and $S(O)_2R^{b2}$; wherein said $C_{1-6}$ alkyl and $C_{3-10}$ cycloalkyl are each optionally substituted with 1, 2, 3, or 4 substituents independently selected from $R^{21}$.

In some embodiments, each $R^{20}$ is independently selected from halo, CN, $C_{1-6}$ alkyl, $C_{1-6}$ haloalkyl, and $NR^{c2}C(O)R^{b2}$, wherein the $C_{1-6}$ alkyl is optionally substituted with $OR^{a4}$ In some embodiments, each $R^{20}$ is independently selected from halo, $C_{1-6}$ alkyl, and $OR^{a2}$.

In some embodiments, each $R^{20}$ is independently selected from chloro, fluoro, methyl, and methoxy.

In some embodiments, each $R^{20}$ is independently selected from CN, chloro, fluoro, methyl, methoxy, trifluoromethyl, hydroxymethyl, and acrylamido.

In some embodiments, each $R^{21}$ is independently selected from $C_{1-6}$ alkyl, $C_{1-6}$ haloalkyl, halo, D, CN, $OR^{a4}$, and $NR^{c4}R^{d4}$.

In some embodiments, $R^1$, $R^2$, $R^3$, and $R^6$ are each independently selected from H, D, $C_{1-6}$ alkyl, $C_{1-6}$ haloalkyl, halo, CN, $OR^{a9}$, and $NR^{c9}R^{d9}$.

In some embodiments, $R^1$, $R^2$, and $R^3$ are each independently selected from H, D, $C_{1-6}$ alkyl, $C_{1-6}$ haloalkyl, halo, CN, $OR^{a9}$, and $NR^{c9}R^{d9}$.

In some embodiments, $R^1$ is H. In some embodiments, $R^1$ is selected from H, D, $C_{1-6}$ alkyl, $C_{1-6}$ haloalkyl, halo, CN, $OR^{a9}$, and $NR^{c9}R^{d9}$.

In some embodiments, $R^1$ is H, $OR^{a9}$, or $NR^{c9}R^{d9}$. In some embodiments, $R^1$ is H, OH, or $N(CH_3)_2$.

In some embodiments, $R^2$ is H. In some embodiments, $R^2$ is selected from H, D, $C_{1-6}$ alkyl, $C_{1-6}$ haloalkyl, halo, CN, $OR^{a9}$, and $NR^{c9}R^{d9}$.

In some embodiments, $R^3$ is H. In some embodiments, $R^3$ is selected from H, D, $C_{1-6}$ alkyl, $C_{1-6}$ haloalkyl, halo, CN, $OR^{a9}$, and $NR^{c9}R^{d9}$.

In some embodiments, $R^4$ is selected from H, D, $C_{1-6}$ alkyl, $C_{2-6}$ alkenyl, $C_{2-6}$ alkynyl, $C_{1}$. 6 haloalkyl, $C_{3-10}$ cycloalkyl, 4-10 membered heterocycloalkyl, $C_{6-10}$ aryl, 5-10 membered heteroaryl, halo, CN, $OR^{a7}$, and $NR^{c7}R^{d7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl, are each optionally substituted with 1, 2, 3, or 4 substituents independently selected from $R^{40}$.

In some embodiments, $R^4$ is selected from H, halo, CN, $C_{1-6}$ alkyl, $C_{2-6}$ alkenyl, $C_{3-10}$ cycloalkyl, $C_{6-10}$ aryl, and 5-10 membered heteroaryl, wherein said $C_{1-6}$ alkyl, $C_{2-6}$ alkenyl, $C_{3-10}$ cycloalkyl, $C_{6-10}$ aryl, and 5-10 membered heteroaryl are each optionally substituted with 1 or 2 substituents selected from $R^{40}$.

In some embodiments, $R^4$ is selected from H, halo, CN, $C_{1-6}$ alkyl, $C_{2-6}$ alkenyl, $C_{3-7}$ cycloalkyl, phenyl, and 5-6 membered heteroaryl, wherein said $C_{1-6}$ alkyl, $C_{2-6}$ alkenyl, $C_{3-7}$ cycloalkyl, phenyl, and 5-6 membered heteroaryl are each optionally substituted with 1 or 2 substituents selected from $R^{40}$.

In some embodiments, $R^4$ is independently selected from H, methyl, ethyl, chloro, CN, cyclopropyl, cyclopentenyl, propenyl, phenyl, pyrazolyl, and furanyl; wherein said methyl, ethyl, cyclopropyl, cyclopentenyl, propenyl, phenyl, pyrazolyl, and furanyl are each optionally substituted with 1 or 2 substituents selected from $R^{40}$.

In some embodiments, $R^4$ is selected from H, methyl, ethyl, chloro, CN, cyclopent-1-en-1-yl, prop-1-en-1-yl, 3,5-dimethoxyphenyl, 1-methyl-1H-pyrazol-4-yl, furan-2-yl, and cyclopropyl.

In some embodiments, $R^4$ is selected from H, methyl, ethyl, isopropyl, hydroxymethyl, 1-hydroxyethyl, chloro, bromo, CN, cyclopent-1-en-1-yl, prop-1-en-1-yl, 3,5-dimethoxyphenyl, 1-methyl-1H-pyrazol-4-yl, furan-2-yl, and cyclopropyl.

In some embodiments, each $R^{40}$ is independently selected from $C_{1-6}$ alkyl, $C_{1-6}$ haloalkyl, halo, D, CN, $OR^a$s, and $NR^{c8}R^{d8}$.

In some embodiments, each $R^{40}$ is independently selected from $C_{1-6}$ alkyl and $OR^{a8}$.

In some embodiments, $R^5$ is selected from $C_{1-6}$ alkyl, $C_{1-6}$ haloalkyl, $C_{3-10}$ cycloalkyl, and $C_{6-10}$ aryl; wherein said $C_{1-6}$ alkyl, $C_{3-10}$ cycloalkyl, and $C_{6-10}$ aryl are each optionally substituted with 1, 2, 3, or 4 substituents independently selected from $R^{50}$.

In some embodiments, $R^5$ is $C_{1-6}$ alkyl.

In some embodiments, $R^5$ is methyl.

In some embodiments, each $R^{50}$ is independently selected from $C_{1-6}$ alkyl, $C_{1-6}$ haloalkyl, halo, D, CN, $OR^{a11}$, and $NR^{c11}R^{d11}$.

In some embodiments, $R^6$ is H.

In some embodiments, $R^6$ is H or $OR^{a9}$. In some embodiments, $R^6$ is H or (tetrahydrofuran-3-yl)oxy.

In some embodiments, each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl, are each optionally substituted with 1, 2, 3, or 4 substituents independently selected from $R^{11}$.

In some embodiments, each $R^{a1}$, $R^{c1}$ and $R^{d1}$ is independently selected from H, $C_{1-6}$ alkyl, and $C_{1-6}$ haloalkyl.

In some embodiments, any $R^{c1}$ and $R^{d1}$ attached to the same N atom, together with the N atom to which they are attached, form a 4-, 5-, or 6-membered heterocycloalkyl group optionally substituted with 1, 2, 3, or 4 substituents independently selected from $R^{11}$.

In some embodiments, each $R^{b1}$ is independently selected from $C_{1-6}$ alkyl and $C_{1-6}$ haloalkyl.

In some embodiments, each $R^{c1}$ is independently selected from H and $C_{1-6}$ alkyl.

In some embodiments, each $R^{a2}$, $R^{c2}$ and $R^{d2}$ is independently selected from H, $C_{1-6}$ alkyl, $C_{1-6}$ haloalkyl, and $C_{3-10}$ cycloalkyl; wherein said $C_{1-6}$ alkyl and $C_{3-10}$ cycloalkyl, are each optionally substituted with 1, 2, 3, or 4 substituents independently selected from $R^{21}$.

In some embodiments, each $R^{a2}$, $R^{c2}$ and $R^{d2}$ is independently selected from H, $C_{1-6}$ alkyl, and $C_{1-6}$ haloalkyl.

In some embodiments, each $R^{b2}$ is independently selected from $C_{1-6}$ alkyl, $C_{1-6}$ haloalkyl, and $C_{3-10}$ cycloalkyl; wherein said $C_{1-6}$ alkyl and $C_{3-10}$ cycloalkyl, are each optionally substituted with 1, 2, 3, or 4 substituents independently selected from $R^{21}$.

In some embodiments, each $R^{b2}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl, are each optionally substituted with 1 or 2 substituents independently selected from $R^{21}$. In some embodiments, each $R^{b2}$ is $C_{2-6}$ alkenyl, In some embodiments, each $R^{b2}$ is independently selected from $C_{1-6}$ alkyl and $C_{1-6}$ haloalkyl.

In some embodiments, each $R^{e2}$ is independently selected from H and $C_{1-6}$ alkyl.

In some embodiments, each $R^{a3}$, $R^{c3}$ and $R^{d3}$ is independently selected from H, $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1, 2, 3, or 4 substituents independently selected from $R^{12}$.

In some embodiments, each $R^{a3}$, $R^{c3}$ and $R^{d3}$ is independently selected from H, $C_{1-6}$ alkyl, and $C_{1-6}$ haloalkyl.

In some embodiments, any $R^{c3}$ and $R^{d3}$ attached to the same N atom, together with the N atom to which they are attached, form a 4-, 5-, 6-membered heterocycloalkyl group optionally substituted with 1 or 2 substituents independently selected from $R^{12}$. In some embodiments, any $R^{c3}$ and $R^{d3}$ attached to the same N atom, together with the N atom to which they are attached, form a 6-membered heterocycloalkyl group.

In some embodiments, each $R^{b3}$ is independently selected from $C_{1-6}$ alkyl, $C_{1-6}$ haloalkyl, and $C_{3-6}$ cycloalkyl; wherein said $C_{1-6}$ alkyl and $C_{3-6}$ cycloalkyl, are each optionally substituted with 1, 2, 3, or 4 substituents independently selected from $R^{12}$.

In some embodiments, each $R^{b3}$ is independently selected from $C_{1-6}$ alkyl and $C_{1-6}$ haloalkyl.

In some embodiments, each $R^{b3}$ is independently selected from $C_{1-6}$ alkyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{3-6}$ cycloalkyl, phenyl, 5-6 membered heteroaryl and 4-7 membered heterocycloalkyl are each optionally substituted with 1 or 2 substituents independently selected from $R^{12}$. In some embodiments, each $R^{b3}$ is independently selected from $C_{1-6}$ alkyl, $C_{1-6}$ haloalkyl, $C_{3-6}$ cycloalkyl, phenyl, 5-6 membered heteroaryl and 4-7 membered heterocycloalkyl.

In some embodiments, each $R^{a4}$, $R^{c4}$ and $R^{d4}$ is independently selected from H, $C_{1-6}$ alkyl, and $C_{1-6}$ haloalkyl.

In some embodiments, each $R^{b4}$ is independently selected from $C_{1-6}$ alkyl and $C_{1-6}$ haloalkyl.

In some embodiments, each $R^{a5}$, $R^{c5}$ and $R^{d5}$ is independently selected from H, $C_{1-6}$ alkyl, and $C_{1-6}$ haloalkyl.

In some embodiments, each $R^{b5}$ is independently selected from $C_{1-6}$ alkyl and $C_{1-6}$ haloalkyl.

In some embodiments, each $R^{a6}$, $R^{c6}$ and $R^{d6}$ is independently selected from H, $C_{1-6}$ alkyl, and $C_{1-6}$ haloalkyl.

In some embodiments, each $R^{b6}$ is independently selected from $C_{1-6}$ alkyl and $C_{1-6}$ haloalkyl.

In some embodiments, each $R^{a7}$, $R^{c7}$ and $R^{d7}$ is independently selected from H, $C_{1-6}$ alkyl, and $C_{1-6}$ haloalkyl.

In some embodiments, each $R^{b7}$ is independently selected from $C_{1-6}$ alkyl and $C_{1-6}$ haloalkyl.

In some embodiments, each $R^{a8}$, $R^{c8}$ and $R^{d8}$ is independently selected from H, $C_{1-6}$ alkyl, and $C_{1-6}$ haloalkyl.

In some embodiments, each $R^{b8}$ is independently selected from $C_{1-6}$ alkyl and $C_{1-6}$ haloalkyl.

In some embodiments, each $R^{a9}$, $R^{c9}$, and $R^{d9}$ is independently selected from H, $C_{1-6}$ alkyl, and $C_{1-6}$ haloalkyl.

In some embodiments, each $R^{a9}$, $R^{c9}$, and $R^{d9}$ is independently selected from H, $C_{1-6}$ alkyl, $C_{1-6}$ haloalkyl, $C_{3-10}$ cycloalkyl, and 4-10 membered heterocycloalkyl. In some embodiments, each $R^{a9}$, $R^{c9}$, and $R^{d9}$ is independently selected from H, $C_{1-6}$ alkyl, and 4-10 membered heterocycloalkyl.

In some embodiments, each $R^{b9}$ is independently selected from $C_{1-6}$ alkyl and $C_{1-6}$ haloalkyl.

In some embodiments, each $R^{a10}$, $R^{c10}$ and $R^{d10}$ is independently selected from H, $C_{1-6}$ alkyl, and $C_{1-6}$ haloalkyl.

In some embodiments, each $R^{b10}$ is independently selected from $C_{1-6}$ alkyl and $C_{1-6}$ haloalkyl.

In some embodiments, each $R^{a11}R^{c11}$ and $R^{d11}$ is independently selected from H, $C_{1-6}$ alkyl, and $C_{1-6}$ haloalkyl.

In some embodiments, each $R^{b11}$ is independently selected from $C_{1-6}$ alkyl and $C_{1-6}$ haloalkyl.

Provided herein is a compound of Formula IIa:

IIa

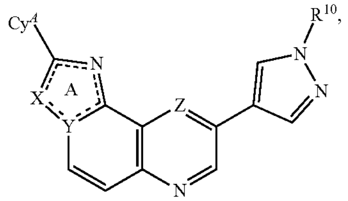

or a pharmaceutically acceptable salt thereof; wherein $Cy^A$, X, Y, Z, and $R^{10}$ are as defined herein, and wherein ring A is aromatic.

Provided herein is a compound of Formula IIb:

IIb

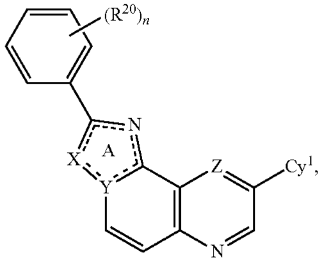

or a pharmaceutically acceptable salt thereof, wherein $Cy^1$, X, Y, Z, and each $R^{20}$ are as defined herein, wherein ring A is aromatic, and wherein n is 0, 1, 2, or 3. In some embodiments, n is 1 or 2.

Provided herein is a compound of Formula IIc:

IIc

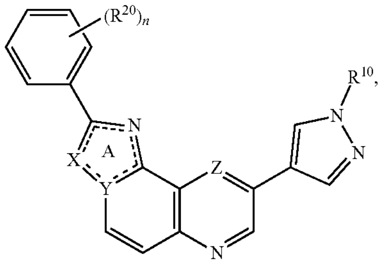

or a pharmaceutically acceptable salt thereof, wherein X, Y, Z, $R^{10}$, and each $R^{20}$ are as defined herein, wherein ring A is aromatic, and wherein n is 0, 1, 2, or 3. In some embodiments, n is 1 or 2.

Provided herein is a compound of Formula IIIa:

IIIa

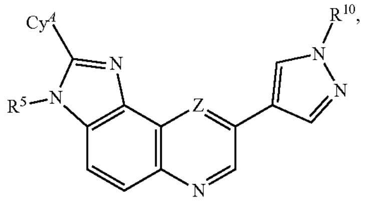

or a pharmaceutically acceptable salt thereof; wherein $Cy^A$, Z, $R^5$, and $R^{10}$ are as defined herein.

Provided herein is a compound of Formula IIIb:

IIIb

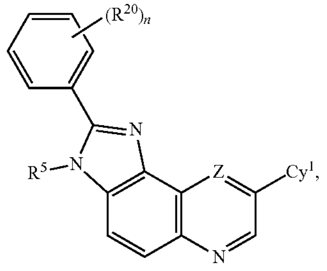

or a pharmaceutically acceptable salt thereof, wherein $Cy^1$, Z, $R^5$, and each $R^{20}$ are as defined herein, and wherein n is 0, 1, 2, or 3. In some embodiments, n is 1 or 2.

Provided herein is a compound of Formula IIIc:

IIIc

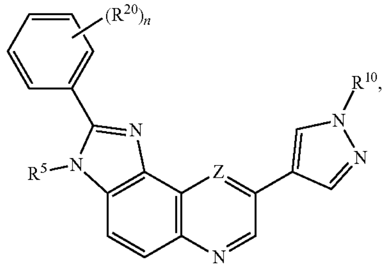

or a pharmaceutically acceptable salt thereof, wherein Z, $R^5$, $R^{10}$, and each $R^{20}$ are as defined herein, and wherein n is 0, 1, 2, or 3. In some embodiments, n is 1 or 2.

Provided herein is a compound of Formula IVa:

IVa

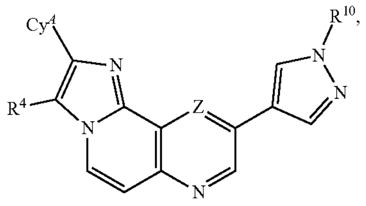

or a pharmaceutically acceptable salt thereof; wherein $Cy^A$, Z, $R^4$, and $R^{10}$ are as defined herein.

Provided herein is a compound of Formula IVb:

IVb

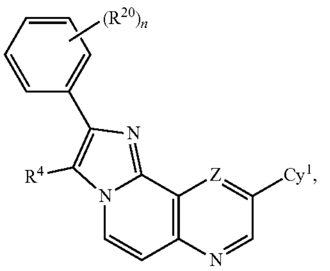

or a pharmaceutically acceptable salt thereof, wherein $Cy^1$, Z, $R^4$, and each $R^{20}$ are as defined herein, and wherein n is 0, 1, 2, or 3. In some embodiments, n is 1 or 2.

Provided herein is a compound of Formula IVc:

IVc

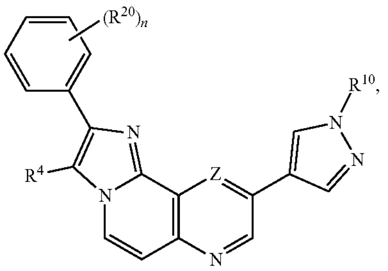

or a pharmaceutically acceptable salt thereof, wherein Z, $R^4$, $R^{10}$, and each $R^{20}$ are as defined herein, and wherein n is 0, 1, 2, or 3. In some embodiments, n is 1 or 2.

In some embodiments, provided herein is a compound selected from:

2-(2-Chlorophenyl)-3-methyl-9-(1-methyl-1H-pyrazol-4-yl)imidazo[2,1-f][1,6]naphthyridine;

2-(2-Chlorophenyl)-3-(cyclopent-1-en-1-yl)-9-(1-methyl-1H-pyrazol-4-yl)imidazo[2,1-f][1,6]naphthyridine;

2-(2-Chlorophenyl)-9-(1-methyl-1H-pyrazol-4-yl)-3-(prop-1-en-1-yl)imidazo[2,1-f][1,6]naphthyridine;

2-(2-Chlorophenyl)-3-(3,5-dimethoxyphenyl)-9-(1-methyl-1H-pyrazol-4-yl)imidazo[2,1-f][1,6]naphthyridine;

2-(2-Chlorophenyl)-3,9-bis(1-methyl-1H-pyrazol-4-yl)imidazo[2,1-f][1,6]naphthyridine;

2-(2-Chlorophenyl)-3-(furan-2-yl)-9-(1-methyl-1H-pyrazol-4-yl)imidazo[2,1-f][1,6]naphthyridine;

2-(2-Chlorophenyl)-9-(1-methyl-1H-pyrazol-4-yl)imidazo[2,1-f][1,6]naphthyridine-3-carbonitrile;

2-(2-Chlorophenyl)-3-cyclopropyl-9-(1-methyl-1H-pyrazol-4-yl)imidazo[2,1-f][1,6]naphthyridine;

2-(2-Chlorophenyl)-3-ethyl-9-(1-methyl-1H-pyrazol-4-yl)imidazo[2,1-f][1,6]naphthyridine;

3-Chloro-2-(2-chlorophenyl)-9-(1-methyl-1H-pyrazol-4-yl)imidazo[2,1-f][1,6]naphthyridine;

2-(2,6-Difluorophenyl)-9-(1-methyl-1H-pyrazol-4-yl)imidazo[2,1-f][1,6]naphthyridine;

2-(2-Chloro-6-fluorophenyl)-9-(1,3-dimethyl-1H-pyrazol-4-yl)imidazo[2,1-f][1,6]naphthyridine;

9-(2-Chlorophenyl)-8-cyclopropyl-2-(1-methyl-1H-pyrazol-4-yl)imidazo[1',2':1,2]pyrido[3,4-b]pyrazine;

9-(2-Chloro-6-fluorophenyl)-2-(1-methyl-1H-pyrazol-4-yl)imidazo[1',2':1,2]pyrido[3,4-b]pyrazine;

1-(3-(4-(2-(2,6-Dichlorophenyl)imidazo[2,1-f][1,6]naphthyridin-9-yl)-1H-pyrazol-1-yl)pyrrolidin-1-yl)ethan-1-one;

(1R,4R)-4-(4-(2-(2-Chlorophenyl)-3-cyclopropylimidazo[2,1-f][1,6]naphthyridin-9-yl)-1H-pyrazol-1-yl)cyclohexane-1-carboxylic acid;

N-((1R,4R)-4-(4-(2-(2-Chlorophenyl)-3-cyclopropylimidazo[2,1-f][1,6]naphthyridin-9-yl)-1H-pyrazol-1-yl)cyclohexyl)acetamide;

2-(2-Fluoro-6-methylphenyl)-3-methyl-8-(1-methyl-1H-pyrazol-4-yl)-3H-imidazo[4,5-f]quinoxaline;

2-(2-Chloro-4-methoxyphenyl)-3-methyl-8-(1-methyl-1H-pyrazol-4-yl)-3H-imidazo[4,5-f]quinoxaline;

3-Methyl-8-(1-methyl-1H-pyrazol-4-yl)-2-(3-methylfuran-2-yl)-3H-imidazo[4,5-f]quinoxaline;

3-(4-(2-(2-Chloro-6-fluorophenyl)-3-methyl-3H-imidazo[4,5-f]quinoxalin-8-yl)-1H-pyrazol-1-yl)cyclobutan-1-ol; and 1-(4-(5-(2-(2-Chloro-6-fluorophenyl)-3-methyl-3H-imidazo[4,5-f]quinoxalin-8-yl)pyridin-2-yl)piperazin-1-yl)ethan-1-one, or a pharmaceutically acceptable of any of the aforementioned.

In some embodiments, provided herein is a compound selected from:

3-Methyl-8-(1-methyl-1H-pyrazol-4-yl)-2-(1-methylpiperidin-4-yl)-3H-imidazo[4,5-f]quinoxaline;

(1S,5R)-8-(3-Methyl-8-(1-methyl-1H-pyrazol-4-yl)-3H-imidazo[4,5-f]quinoxalin-2-yl)-3,8-diazabicyclo[3.2.1]octan-2-one;

(S)-1-(3-(4-(2-(2-Chloro-6-(trifluoromethyl)phenyl)-3-methylimidazo[2,1-f][1,6]naphthyridin-9-yl)-1H-pyrazol-1-yl)pyrrolidin-1-yl)-2-hydroxyethan-1-one;

(S)-1-(3-(4-(2-(2,6-Dimethylphenyl)-3-methylimidazo[2,1-f][1,6]naphthyridin-9-yl)-1H-pyrazol-1-yl)pyrrolidin-1-yl)-2-hydroxyethan-1-one;

(S)-3-Fluoro-2-(9-(1-(1-(2-hydroxyacetyl)pyrrolidin-3-yl)-1H-pyrazol-4-yl)-3-methylimidazo[2,1-f][1,6]naphthyridin-2-yl)benzonitrile;

(S)-1-(3-(4-(2-(2-Fluoro-6-methoxyphenyl)-3-methylimidazo[2,1-f][1,6]naphthyridin-9-yl)-1H-pyrazol-1-yl)pyrrolidin-1-yl)-2-hydroxyethan-1-one;

2-(2,3-Dimethylphenyl)-3-methyl-9-(1-methyl-1H-pyrazol-4-yl)imidazo[2,1-f][1,6]naphthyridine;

(3-Methyl-4-(3-methyl-9-(1-methyl-1H-pyrazol-4-yl)imidazo[2,1-f][1,6]naphthyridin-2-yl)phenyl)methanol;

2-(2,6-Dichlorophenyl)-3-methyl-9-(1-methyl-1H-pyrazol-4-yl)imidazo[2,1-f][1,6]naphthyridin-8-ol;

(S)-2-(2,6-Dichlorophenyl)-3-methyl-9-(1-methyl-1H-pyrazol-4-yl)-10-((tetrahydrofuran-3-yl)oxy)imidazo[2,1-f][1,6]naphthyridine;

2-(2,6-Dichlorophenyl)-N,N,3-trimethyl-9-(1-methyl-1H-pyrazol-4-yl)imidazo[2,1-f][1,6]naphthyridin-8-amine;

N-(2,4-Dichloro-3-(3-methyl-9-(1-methyl-1H-pyrazol-4-yl)imidazo[2,1-f][1,6]naphthyridin-2-yl)phenyl)acrylamide;

N-(3-(3-Methyl-9-(1-methyl-1H-pyrazol-4-yl)imidazo[2,1-f][1,6]naphthyridin-2-yl)phenyl)acrylamide;

N-(2-(3-Methyl-9-(1-methyl-1H-pyrazol-4-yl)imidazo[2,1-f][1,6]naphthyridin-2-yl)phenyl)acrylamide;

(1-Aminocyclopropyl)(3-(4-(2-(2,6-dichlorophenyl)-3-methylimidazo[2,1-f][1,6]naphthyridin-9-yl)-1H-pyrazol-1-yl)azetidin-1-yl)methanone;

1-(3-(4-(2-(2,6-Dichlorophenyl)-3-methylimidazo[2,1-f][1,6]naphthyridin-9-yl)-1H-pyrazol-1-yl)azetidin-1-yl)-2-(1H-imidazol-1-yl)ethan-1-one;

(3-(4-(2-(2,6-Dichlorophenyl)-3-methylimidazo[2,1-f][1,6]naphthyridin-9-yl)-1H-pyrazol-1-yl)azetidin-1-yl)(oxazol-4-yl)methanone;

(4-Aminotetrahydro-2H-pyran-4-yl)(3-(4-(2-(2,6-dichlorophenyl)-3-methylimidazo[2,1-f][1,6]naphthyridin-9-yl)-1H-pyrazol-1-yl)azetidin-1-yl)methanone;

3-(3-(4-(2-(2,6-Dichlorophenyl)-3-methylimidazo[2,1-f][1,6]naphthyridin-9-yl)-1H-pyrazol-1-yl)azetidin-1-yl)-3-oxopropanenitrile;

4-((4-(2-(2,6-Dichlorophenyl)imidazo[2,1-f][1,6]naphthyridin-9-yl)-1H-pyrazol-1-yl)methyl)-2-fluorobenzoic acid;

4-(4-(2-(2,6-Dichlorophenyl)imidazo[2,1-f][1,6]naphthyridin-9-yl)-1H-pyrazol-1-yl)-N,N-dimethylbenzamide;

N-((1r,4r)-4-(4-(2-(2,6-Dichlorophenyl)imidazo[2,1-f][1,6]naphthyridin-9-yl)-1H-pyrazol-1-yl)cyclohexyl)-2-methoxyacetamide;

3-((1r,4r)-4-(4-(2-(2,6-Dichlorophenyl)imidazo[2,1-f][1,6]naphthyridin-9-yl)-1H-pyrazol-1-yl)cyclohexyl)-1,1-dimethylurea;

1-(7-(4-(2-(2,6-Dichlorophenyl)imidazo[2,1-f][1,6]naphthyridin-9-yl)-1H-pyrazol-1-yl)-2-azaspiro[3.5]nonan-2-yl)ethan-1-one;

2-(2,6-Dichlorophenyl)-3-methyl-9-(1-(tetrahydro-2H-pyran-4-yl)-1H-pyrazol-4-yl)imidazo[2,1-f][1,6]naphthyridine;

(1r,4r)-4-(4-(2-(2,6-Dichlorophenyl)-3-methylimidazo[2,1-f][1,6]naphthyridin-9-yl)-1H-pyrazol-1-yl)cyclohexan-1-ol;

4-(4-(2-(2,6-Dichlorophenyl)-3-methylimidazo[2,1-f][1,6]naphthyridin-9-yl)-1H-pyrazol-1-yl)-1-methylcyclohexane-1-carboxylic acid;

3-(4-(2-(2,6-Dichlorophenyl)imidazo[2,1-f][1,6]naphthyridin-9-yl)-1H-pyrazol-1-yl)-N,N-dimethylpyrrolidine-1-carboxamide;

3-(4-(2-(2,6-Dichlorophenyl)imidazo[2,1-f][1,6]naphthyridin-9-yl)-1H-pyrazol-1-yl)-N,N-dimethylpyrrolidine-1-sulfonamide;

(S)-1-(3-(4-(2-(2,6-Dichlorophenyl)-3-methylimidazo[2,1-f][1,6]naphthyridin-9-yl)-1H-pyrazol-1-yl)pyrrolidin-1-yl)ethan-1-one;

(S)-1-(3-(4-(2-(2,6-Dichlorophenyl)-3-methylimidazo[2,1-f][1,6]naphthyridin-9-yl)-1H-pyrazol-1-yl)pyrrolidin-1-yl)-2-hydroxyethan-1-one;

1-(1-(4-(2-(2,6-Dichlorophenyl)-3-methylimidazo[2,1-f][1,6]naphthyridin-9-yl)-1H-pyrazol-1-yl)-3-azabicyclo[3.1.0]hexan-3-yl)-2-hydroxyethan-1-one;

(S)-1-(3-(4-(2-(2,6-Dichlorophenyl)-3-(hydroxymethyl)imidazo[2,1-f][1,6]naphthyridin-9-yl)-1H-pyrazol-1-yl)pyrrolidin-1-yl)-2-hydroxyethan-1-one;

(S)-1-(3-(4-(2-(2,6-Dichlorophenyl)-3-(hydroxymethyl)imidazo[2,1-f][1,6]naphthyridin-9-yl)-1H-pyrazol-1-yl)pyrrolidin-1-yl)ethan-1-one;

(S)-(3-(4-(2-(2,6-Dichlorophenyl)-3-(hydroxymethyl)imidazo[2,1-f][1,6]naphthyridin-9-yl)-1H-pyrazol-1-yl)pyrrolidin-1-yl)(morpholino)methanone;

1-((3S)-3-(4-(2-(2,6-dichlorophenyl)-3-(1-hydroxyethyl)imidazo[2,1-f][1,6]naphthyridin-9-yl)-1H-pyrazol-1-yl)pyrrolidin-1-yl)-2-hydroxyethan-1-one;

1-(6-(4-(2-(2,6-Dichlorophenyl)-3-methylimidazo[2,1-f][1,6]naphthyridin-9-yl)-1H-pyrazol-1-yl)-3-azabicyclo[4.1.0]heptan-3-yl)-2-hydroxyethan-1-one;

1-(1-(4-(2-(2,6-Dichlorophenyl)-3-methylimidazo[2,1-f][1,6]naphthyridin-9-yl)-1H-pyrazol-1-yl)-3-azabicyclo[4.1.0]heptan-3-yl)ethan-1-one;

1-(3-(5-(2-(2,6-Dichlorophenyl)-3-methylimidazo[2,1-f][1,6]naphthyridin-9-yl)pyridin-2-yl)azetidin-1-yl)-2-hydroxyethan-1-one;

1-(3-(5-(2-(2,6-Dichlorophenyl)-3-methylimidazo[2,1-f][1,6]naphthyridin-9-yl)pyridin-3-yl)azetidin-1-yl)ethan-1-one;

1-(3-(5-(2-(2,6-Dichlorophenyl)-3-methylimidazo[2,1-f][1,6]naphthyridin-9-yl)phenyl)azetidin-1-yl)ethan-1-one;

(S)-1-(3-(4-(2-(2-Chlorophenyl)-3-(hydroxymethyl)imidazo[2,1-f][1,6]naphthyridin-9-yl)-1H-pyrazol-1-yl)pyrrolidin-1-yl)ethan-1-one;

(S)-1-(3-(4-(2-(2-Chlorophenyl)-3-isopropylimidazo[2,1-f][1,6]naphthyridin-9-yl)-1H-pyrazol-1-yl)pyrrolidin-1-yl)-2-hydroxyethan-1-one;

(S)-1-(3-(4-(3-Bromo-2-(2-chloro-6-fluorophenyl)imidazo[2,1-f][1,6]naphthyridin-9-yl)-1H-pyrazol-1-yl)pyrrolidin-1-yl)-2-hydroxyethan-1-one;

2-Cyclopropyl-3-methyl-9-(1-methyl-1H-pyrazol-4-yl)imidazo[2,1-f][1,6]naphthyridine;

(2-(2,6-Dichlorophenyl)-9-(1-methyl-1H-pyrazol-4-yl)imidazo[2,1-f][1,6]naphthyridin-3-yl)methanol;

(9-(1-Cyclopropyl-1H-pyrazol-4-yl)-2-(2,6-dichlorophenyl)imidazo[2,1-f][1,6]naphthyridin-3-yl)methanol;

(2-(2,6-Dichlorophenyl)-9-(1-(tetrahydrofuran-3-yl)-1H-pyrazol-4-yl)imidazo[2,1-f][1,6]naphthyridin-3-yl)methanol;

(2-(2,6-Dichlorophenyl)-9-(1-(oxetan-3-yl)-1H-pyrazol-4-yl)imidazo[2,1-f][1,6]naphthyridin-3-yl)methanol;

(2-(2,6-Dichlorophenyl)-9-(1-(2-(dimethylamino)ethyl)-1H-pyrazol-4-yl)imidazo[2,1-f][1,6]naphthyridin-3-yl)methanol;

(2-(2,6-Dichlorophenyl)-9-(1-isopropyl-1H-pyrazol-4-yl)imidazo[2,1-f][1,6]naphthyridin-3-yl)methanol;

(2-(2,6-Dichlorophenyl)-9-(1-(difluoromethyl)-1H-pyrazol-4-yl)imidazo[2,1-f][1,6]naphthyridin-3-yl)methanol;

3-(4-(2-(2,6-Dichlorophenyl)-3-(hydroxymethyl)imidazo[2,1-f][1,6]naphthyridin-9-yl)-1H-pyrazol-1-yl)propanenitrile;

1-(4-(2-(2,6-Dichlorophenyl)-3-(hydroxymethyl)imidazo[2,1-f][1,6]naphthyridin-9-yl)-1H-pyrazol-1-yl)-2-methylpropan-2-ol;

2-(4-(2-(2,6-Dichlorophenyl)-3-(hydroxymethyl)imidazo[2,1-f][1,6]naphthyridin-9-yl)-1H-pyrazol-1-yl)acetonitrile;

(2-(2,6-Dichlorophenyl)-9-(1-(1-methylpiperidin-4-yl)-1H-pyrazol-4-yl)imidazo[2,1-f][1,6]naphthyridin-3-yl)methanol;

2-(4-(2-(2,6-Dichlorophenyl)-3-(hydroxymethyl)imidazo[2,1-f][1,6]naphthyridin-9-yl)-1H-pyrazol-1-yl)-2-methylpropan-1-ol;

(2-(2,6-Dichlorophenyl)-9-(1-(2-(methylsulfonyl)ethyl)-1H-pyrazol-4-yl)imidazo[2,1-f][1,6]naphthyridin-3-yl)methanol;

(2-(2,6-Dichlorophenyl)-9-(1-(2,2,2-trifluoroethyl)-1H-pyrazol-4-yl)imidazo[2,1-f][1,6]naphthyridin-3-yl)methanol;

(2-(2,6-Dichlorophenyl)-9-(1-(2-morpholinoethyl)-1H-pyrazol-4-yl)imidazo[2,1-f][1,6]naphthyridin-3-yl)methanol; and 2-(4-(2-(2,6-Dichlorophenyl)-3-(hydroxymethyl)imidazo[2,1-f][1,6]naphthyridin-9-yl)-1H-pyrazol-1-yl)ethan-1-ol, or a pharmaceutically acceptable of any of the aforementioned.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the disclosure in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. A single divalent substituent, e.g., oxo, can replace two hydrogen atoms.

As used herein, the term "$C_{i-j}$," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. An alkyl group formally corresponds to an alkane with one C—H bond replaced by the point of attachment of the alkyl group to the remainder of the compound. In some embodiments, the alkyl group contains 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like. In some embodiments, the alkyl group is methyl, ethyl, or propyl.

As used herein, the term "$C_{i-j}$ alkylene," employed alone or in combination with other terms, means a saturated divalent linking hydrocarbon group that may be straight-chain or branched, having i to j carbons. In some embodiments, the alkylene group contains from 1 to 4 carbon atoms, from 1 to 3 carbon atoms, or from 1 to 2 carbon atoms. Examples of alkylene moieties include, but are not limited to, chemical groups such as methylene, ethylene, 1,1-ethylene, 1,2-ethylene, 1,3-propylene, 1,2-propylene, 1,1-propylene, isopropylene, and the like.

As used herein, "alkenyl," employed alone or in combination with other terms, refers to a straight-chain or branched hydrocarbon group corresponding to an alkyl group having one or more carbon-carbon double bonds. An alkenyl group formally corresponds to an alkene with one C—H bond replaced by the point of attachment of the alkenyl group to the remainder of the compound. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl," employed alone or in combination with other terms, refers to a straight-chain or branched hydrocarbon group corresponding to an alkyl group having one or more carbon-carbon triple bonds. An alkynyl group formally corresponds to an alkyne with one C—H bond replaced by the point of attachment of the alkyl group to the remainder of the compound. In some embodiments, the alkynyl moiety contains 2 to 6 or 2 to 4 carbon atoms. Example alkynyl groups include, but are not limited to, ethynyl, propyn-1-yl, propyn-2-yl, and the like.

As used herein, the terms "carbamoyl" and "carbamyl" interchangeably refer to a group of formula —C(O)$NH_2$.

As used herein, the term "carboxy" refers to a group of formula —C(O)OH.

The term "cyano" or "nitrile" refers to a group of formula —C≡N, which also may be written as —CN.

As used herein, the term "$C_{1-3}$ alkoxy-$C_{1-3}$ alkyl" refers to a group of formula —($C_{1-3}$ alkylene)-($C_{1-3}$ alkoxy).

As used herein, the term "$C_{1-3}$ alkoxy-$C_{1-3}$ alkoxy" refers to a group of formula —($C_{1-3}$ alkoxylene)-($C_{1-3}$ alkoxy).

As used herein, the term "HO—$C_{1-3}$ alkoxy" refers to a group of formula —($C_{1-3}$ alkoxylene)-OH.

As used herein, the term "HO—$C_{1-3}$ alkyl" refers to a group of formula —($C_{1-3}$ alkylene)-OH.

As used herein, the term "cyano-$C_{1-3}$ alkyl" refers to a group of formula —($C_{1-3}$ alkylene)-CN.

As used herein, the term "$H_2N$—$C_{1-3}$ alkyl" refers to a group of formula —($C_{1-3}$ alkylene)-$NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyloxy" refers to a group of formula —OC(O)-alkyl, wherein the alkyl group has n to m carbon atoms. In some embodiments, the alkyl group has 1 to 6, 1 to 4, or 1 to 3 carbon atoms.

As used herein, the term "aminocarbonyloxy" refers to a group of formula —OC(O)$NH_2$.

As used herein, the term "$C_{n-m}$ alkylaminocarbonyloxy" refers to a group of formula —OC(O)NH-alkyl, wherein the alkyl group has n to m carbon atoms. In some embodiments, the alkyl group has 1 to 6, 1 to 4, or 1 to 3 carbon atoms.

As used herein, the term "Cn-m alkylsulfonylamino" refers to a group of formula —$NHS(O)_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —$S(O)_2NH_2$.

As used herein, the term "$C_{n-m}$ alkylaminosulfonyl" refers to a group of formula —$S(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —$S(O)_2N$(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —$NHS(O)_2NH_2$.

As used herein, the term "$C_{n-m}$ alkylaminosulfonylamino" refers to a group of formula —$NHS(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —$NHS(O)_2N$(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —$NHC(O)NH_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —$S(O)_2$-alkyl, wherein the alkyl group has n to m carbon atoms. In some embodiments, the alkyl group has 1 to 6, 1 to 4, or 1 to 3 carbon atoms.

As used herein, "halo" or "halogen", employed alone or in combination with other terms, includes fluoro, chloro, bromo, and iodo. In some embodiments, halo is F or Cl. In some embodiments, halo is F.

As used herein, the term "haloalkyl," employed alone or in combination with other terms, refers to an alkyl group in which one or more of the hydrogen atoms has been replaced by a halogen atom, having up to the full valency of halogen atom substituents, which may either be the same or different. In some embodiments, the halogen atoms are fluoro atoms. In some embodiments, the alkyl group has 1 to 6, 1 to 4, or 1 to 3 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. In some embodiments, the alkyl group has 1 to 6, 1 to 4, or 1 to 3 carbon atoms. Example alkoxy groups include methoxy, ethoxy, propoxy (e.g., n-propoxy and isopropoxy), t-butoxy, and the like. In some embodiments, alkoxy is methoxy.

As used herein, "haloalkoxy," employed alone or in combination with other terms, refers to a group of formula —O-(haloalkyl). In some embodiments, the alkyl group has 1 to 6, 1 to 4, or 1 to 3 carbon atoms. An example haloalkoxy group is —$OCF_3$.

As used herein, "amino," employed alone or in combination with other terms, refers to $NH_2$.

As used herein, the term "alkylamino," employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "alkylthio," employed alone or in combination with other terms, refers to a group of formula —S-alkyl. In some embodiments, the alkyl group has 1 to 6 or 1 to 4 carbon atoms.

As used herein, the term "cycloalkyl," employed alone or in combination with other terms, refers to a non-aromatic cyclic hydrocarbon including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. A cycloalkyl group containing a fused aromatic ring can be attached through any ring-forming atom including a ring-forming atom of the fused aromatic ring. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5]octane and the like). In some embodiments, the cycloalkyl group has 3 to 10 ring members, or 3 to 7 ring members, or 3 to 6 ring members. In some embodiments, the cycloalkyl group is monocyclic or bicyclic. In some embodiments, the cycloalkyl group is monocyclic. In some embodiments, the cycloalkyl group is a $C_7$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus, and which has 4-14 ring members, 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or polycyclic (e.g., having 2, 3 or 4 fused, bridged, or spiro rings) or spirocyclic ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, 4 to 10 ring-forming atoms, or 3 to 8 ring forming atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{27}$ monocyclic heterocycloalkyl group. In some embodiments, the heterocycloalkyl group is a morpholine ring, pyrrolidine ring, piperazine ring, piperidine ring, dihydropyran ring, tetrahydropyran ring, tetrahyropyridine, azetidine ring, or tetrahydrofuran ring. In some embodiments, the heterocycloalkyl is a 4-7 membered heterocycloalkyl moiety having carbon and 1, 2, or 3 heteroatoms independently selected from N, O and S. In some embodiments, the heterocycloalkyl is 4-10 membered heterocycloalkyl moiety having carbon and 1, 2, or 3 heteroatoms independently selected from N, O and S.

As used herein, the term "aryl," employed alone or in combination with other terms, refers to a monocyclic or polycyclic (e.g., having 2 fused rings) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl.

As used herein, the term "heteroaryl" or "heteroaromatic" employed alone or in combination with other terms, refers to a monocyclic or polycyclic (e.g., having 2 or 3 fused rings) aromatic hydrocarbon moiety, having one or more heteroatom ring members independently selected from nitrogen, sulfur and oxygen. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl, pyridone, or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In one embodiment the heteroaryl group is a 5 to 10 membered heteroaryl group. In another embodiment the heteroaryl group is a 5 to 6 membered heteroaryl group. In some embodiments, the heteroaryl is a 5-6 membered heteroaryl moiety having carbon and 1, 2, or 3 heteroatoms independently selected from N, O and S. In some embodiments, the heteroaryl is a 5-10 membered heteroaryl moiety having carbon and 1, 2, or 3 heteroatoms independently selected from N, O and S. In some embodiments, the heteroaryl has 5-6 ring atoms and 1 or 2 heteroatom ring members independently selected from nitrogen, sulfur and oxygen. In some embodiments, no more than 2 heteroatoms of a 5-membered heteroaryl moiety are N.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized π (pi) electrons where n is an integer).

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Resolution of racemic mixtures of compounds can be carried out by methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the disclosure have the (R)-configuration. In other embodiments, the compounds have the (S)-configuration. In compounds with more than one chiral centers, each of the chiral centers in the compound may be independently (R) or (S), unless otherwise indicated.

Compounds of the disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide-imidic acid pairs, lactam—lactim pairs, enamine —imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the disclosure also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the disclosure can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et.al. *J. Med. Chem.* 2011, 54, 201-210; R. Xu et.al. *J. Label Compd. Radiopharm.* 2015, 58, 308-312).

The term, "compound," as used herein is meant to include all stereoisomers, geometric iosomers, tautomers, and isotopes of the structures depicted. The term is also meant to refer to compounds of the disclosure, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., in the form of hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the disclosure, or salts thereof, are substantially isolated. By "substantially isolated" is meant that the compound is at least partially or substantially separated from the environment in which it was formed or detected. Partial separation can include, for example, a composition enriched in the compounds of the disclosure. Substantial separation can include compositions containing at least about 50%, at least about 60%, at least about 70%, at least about 80%, at least about 90%, at least about 95%, at least about 97%, or at least about 99% by weight of the compounds of the disclosure, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The following abbreviations may be used herein: AcOH (acetic acid); $Ac_2O$ (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DEAD (diethyl azodicarboxylate); DIAD (N,N'-diisopropyl azidodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography—mass spectrometry); m (multiplet); M (molar); mCPBA (3-chloroperoxybenzoic acid); $MgSO_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); $NaHCO_3$ (sodium bicarbonate); NaOH (sodium hydroxide); $Na_2SO_4$ (sodium sulfate); $NH_4Cl$ (ammonium chloride); $NH_4OH$ (ammonium hydroxide); NIS (N-iodosuccinimide); nM (nanomolar); NMR (nuclear magnetic resonance spectroscopy); OTf (trifluoromethanesulfonate); Pd (palladium); Ph (phenyl); pM (picomolar); PMB (para-methoxybenzyl), $POCl_3$ (phosphoryl chloride); RP-HPLC (reverse phase high performance liquid chromatography); s (singlet); SEM (2-trimethylsilylethoxymethyl); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); μg (microgram(s)); μL (microliter(s)); μM (micromolar); wt % (weight percent).

Synthesis

As will be appreciated by those skilled in the art, the compounds provided herein, including salts and stereoisomers thereof, can be prepared using known organic synthesis techniques and can be synthesized according to any of numerous possible synthetic routes.

The reactions for preparing compounds of the disclosure can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "r.t.", as used herein, are understood in the art, and refer generally to a temperature, e.g. a reaction temperature, that is about the temperature of the room in which the reaction is carried out, for example, a temperature from about 20° C. to about 30° C.

Compounds of formula S-11 can be prepared via the synthetic route as outlined in Scheme 1. The commercially available starting material S-1 can undergo a coupling reaction to adduct S-2, in which M is a boronic acid, a boronic ester or an appropriately substituted metal (e.g., M is $B(OR)_2$, $Sn(Alkyl)_3$, Zn-Hal, etc.), under standard Suzuki cross-coupling conditions (e.g., in the presence of a palladium catalyst and a suitable base) (Tetrahedron 2002, 58, 9633-9695), or standard Stille cross-coupling conditions (e.g., in the presence of a palladium catalyst) (ACS Catalysis 2015, 5, 3040-3053), or standard Negishi cross-coupling conditions (e.g., in the presence of a palladium catalyst) (ACS Catalysis 2016, 6, 1540-1552), to give derivative S-3. Reduction of the nitro group of compound S-3 under appropriate conditions can deliver compound S-4. Compound S-4 can undergo a halogenation reaction, such as electrophilic aromatic substitution ($S_EAr$), with an appropriate reagent, such as N-bromosuccinimide (NBS), to afford compound S-5 (Hal is a halide, such as F, Cl, Br, or I). Halide displacement of reagent S-6 with intermediate S-5 via nucleophilic substitution ($S_N2$) generates intermediate S-7. Compound S-7 can undergo an amination reaction, such as a Buchwald-Hartwig coupling (Chem. Sci. 2011, 2, 27-50) in the presence of a palladium catalyst (e.g., tris(dibenzylideneacetone)dipalladium(0)), appropriate ligand (e.g., 2'-(di-tert-butylphosphino)-N,N-dimethylbiphenyl-2-amine), and a base (e.g., sodium tert-butoxide) to afford diamine S-8. Compound S-8 can be coupled with a carboxylic acid adduct of formula S-9, using an appropriate coupling reagent (e.g. HATU, BOP, or PyBOP), to afford compound S-10. Finally, cyclization of compound S-10 at elevated temperature in the presence of a suitable reagent, such as acetic acid, generates compound S-11.

Scheme 1

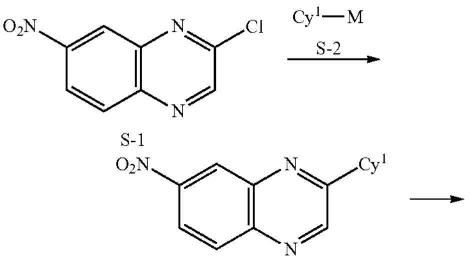

S-1
S-3

-continued

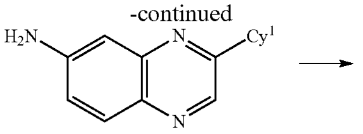

S-4

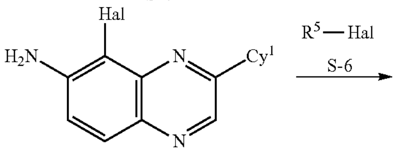

S-5

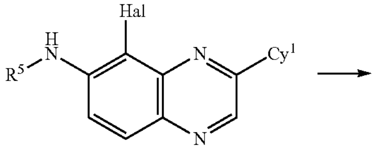

S-7

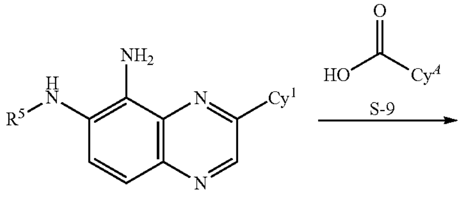

S-8

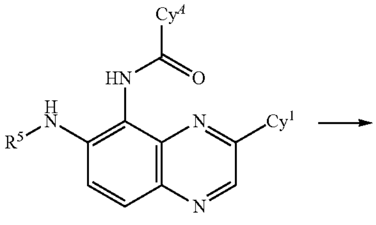

S-10

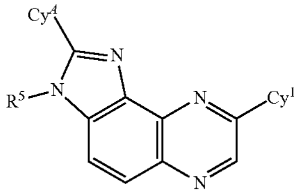

S-11

Alternatively, compound S-11 can be prepared via the synthetic route as outlined in Scheme 2. Acylation of compound S-8 with adduct S-12 (Hal is a halide, such as F, Cl, Br, or I) affords intermediate S-10. Cyclization of compound S-10 at elevated temperature in the presence of a suitable reagent, such as acetic acid, generates compound S-11.

Scheme 2

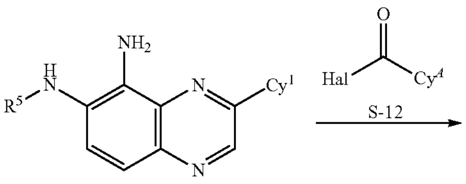

S-8

-continued

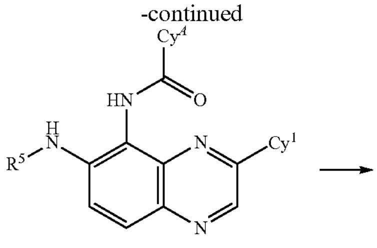

S-10

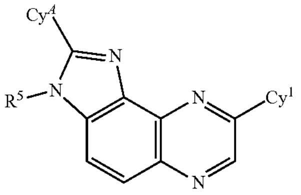

S-11

Compounds of formula S-21 can be prepared via the synthetic route as outlined in Scheme 3. Treatment of commercially available compound S-13 with an appropriate reagent, such as phosphoryl chloride ($POCl_3$), at elevated temperature can afford the chloride adduct S-14. Chloride displacement of compound S-14 via nucleophilic substitution with aqueous ammonia at elevated temperature can deliver amine S-15. Compound S-15 can then be selectively coupled to an adduct of formula S-2, in which M is a boronic acid, a boronic ester or an appropriately substituted metal (e.g., M is $B(OR)_2$, $Sn(Alkyl)_3$, Zn-Hal, etc.), under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst), to give derivative S-16. Condensation of compound S-16 with a carbonyl adduct S-17 (Hal is a halide, such as F, Cl, Br, or I) at elevated temperature can generate compound S-18. Tricyclic compound S-18 can undergo a halogenation reaction, such as electrophilic aromatic substitution ($S_EAr$), with an appropriate reagent, such as N-bromosuccinimide (NBS), to afford compound S-19 (Hal is a halide, such as F, Cl, Br, or I). Introduction of $R^1$ can then be achieved by the coupling of compound S-19 with an adduct S-20, using similar conditions as described for the preparation of compound S-16 from compound S-15, to afford compound S-21.

Scheme 3

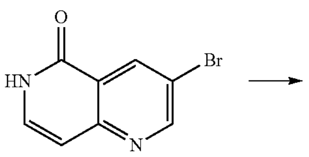

S-13

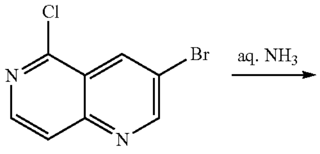

S-14

-continued

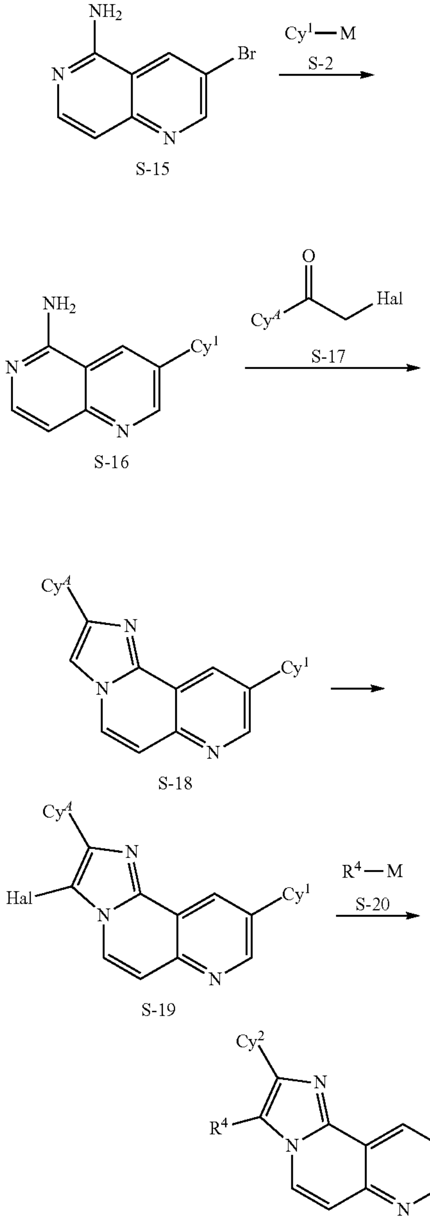

S-15, S-16, S-18, S-19, S-21

Alternatively, compounds of formula S-21 can be prepared via the synthetic route as outlined in Scheme 4. Condensation of compound S-15 with a carbonyl adduct of formula S-17 (Hal is a halide, such as Cl, Br, or I) at elevated temperature can generate compound S-22. Compound S-22 can then be selectively coupled to an adduct S-2, in which M is a boronic acid, a boronic ester or an appropriately substituted metal [e.g., M is $B(OR)_2$, $Sn(Alkyl)_3$, Zn-Hal, etc.], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst), to give a derivative of formula S-18. Compound S-21 can then be prepared from compound S-18 via the synthetic route as outlined in Scheme 3.

Scheme 4

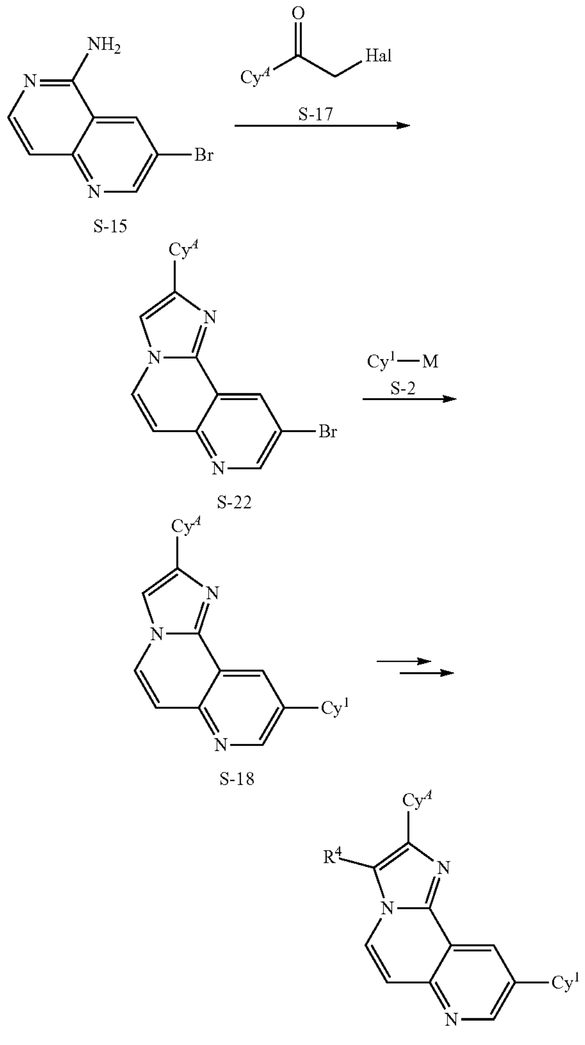

S-15, S-22, S-18, S-21

In addition, compound S-21 can be prepared by employing the steps described above in an alternative order. Initial halogenation of compound S-22 using an appropriate reagent, such as N-iodosuccinimide (NIS), can produce a dihalide intermediate which can undergo selective coupling to an adduct S-20 following the synthetic sequence from S-18 to S-21 as shown above in Scheme 3. A similar coupling strategy to an adduct S-2 as shown above in Scheme 4 can be followed to provide access to compound S-21.

Alternatively, compound S-21 can be prepared via the synthetic route as outlined in Scheme 5. Condensation of compound 5-15 with a carbonyl adduct S-23 (Hal is a halide, such as Cl, Br, or I) at elevated temperature can generate compound S-24. Compound S-24 can then be selectively coupled to an adduct S-2, in which M is a boronic acid, a boronic ester or an appropriately substituted metal [e.g., M is $B(OR)_2$, $Sn(Alkyl)_3$, Zn-Hal, etc.], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst), to give a derivative S-25. Compound S-25 can undergo a halogenation reaction, such as electrophilic aromatic substitution ($S_E$Ar), with an appropriate reagent, such as N-bromosuccinimide (NBS), to afford compound S-26 (Hal is a halide, such as Cl, Br, or I). Introduction of $R^1$ can then be achieved by the coupling of compound S-26 with an adduct S-20, using similar conditions as described for the preparation of compound S-25 from compound S-24, to afford compound S-27. Compound S-27 can undergo a second halogenation reaction, such as electrophilic aromatic substitution ($S_E$Ar), with an appropriate reagent, such as N-bromosuccinimide (NBS), to afford compound S-28 (Hal is a halide, such as Cl, Br, or I). Introduction of $Cy^2$ can then be achieved by the coupling of compound S-28 with an adduct S-29, using similar conditions as described for the preparation of compound S-25 from compound S-24, to afford compound S-21.

Scheme 5

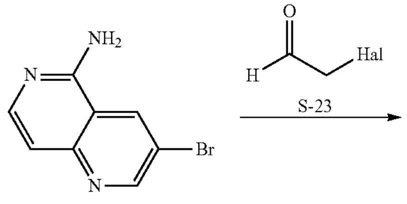

S-15

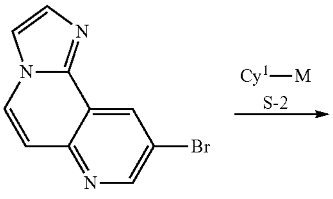

S-24

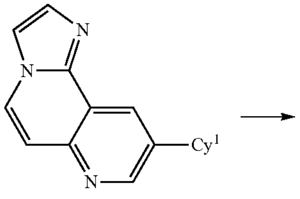

S-25

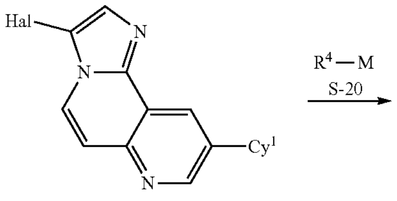

S-26

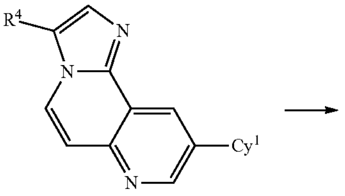

S-27

-continued

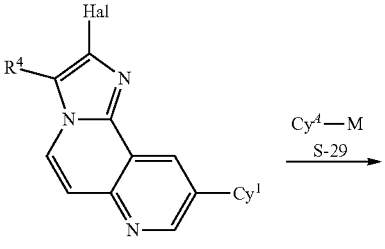

S-28

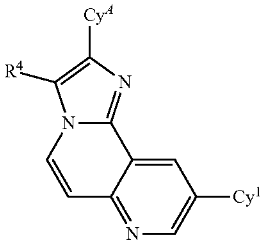

S-21

Compounds of formula 5-33 can be prepared via the synthetic route as outlined in Scheme 6. The commercially available starting material S-30 can undergo a selective coupling reaction with an adduct S-2, in which M is a boronic acid, a boronic ester or an appropriately substituted metal [e.g., M is $B(OR)_2$, $Sn(Alkyl)_3$, Zn-Hal, etc.], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst), to give a derivative S-31. Compound S-32 can be prepared by the reaction of compound S-31 with aqueous ammonia, using similar conditions as described for the preparation of compound 5-15 from compound S-14 in Scheme 3. Compound S-33 can then be prepared from compound S-32 via the synthetic route as outlined in Scheme 3 starting from compound S-16.

Scheme 6

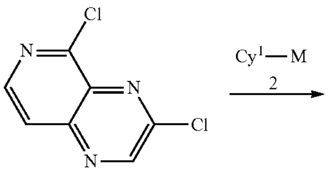

30

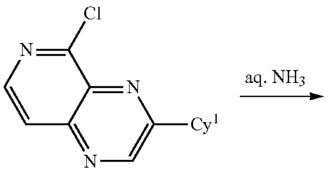

31

-continued

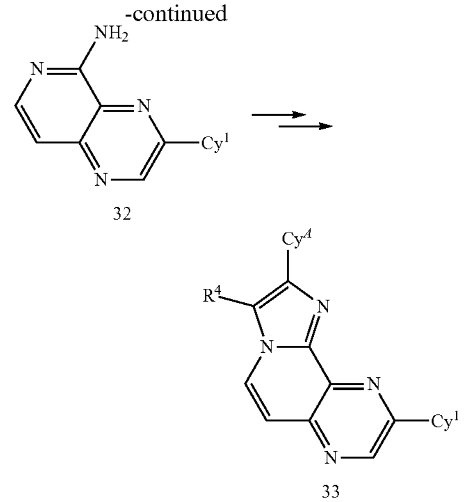

32

33

Methods of Use

Compounds of the present disclosure can inhibit the activity of the FGFR enzyme. For example, compounds of the present disclosure can be used to inhibit activity of an FGFR enzyme in a cell or in an individual or patient in need of inhibition of the enzyme by administering an inhibiting amount of one or more compounds of the present disclosure to the cell, individual, or patient. Compounds of the present disclosure can be used to inhibit activity of the FGFR3 enzyme in a cell or in an individual or patient in need of inhibition of the enzyme by administering an inhibiting amount of one or more compounds of the present disclosure to the cell, individual, or patient.

As FGFR inhibitors, the compounds of the present disclosure are useful in the treatment of various diseases associated with abnormal expression or activity of the FGFR enzyme or FGFR ligands. Compounds which inhibit FGFR will be useful in providing a means of preventing the growth or inducing apoptosis in tumors, particularly by inhibiting angiogenesis.

It is therefore anticipated that compounds of the present disclosure will prove useful in treating or preventing proliferative disorders such as cancers. In particular, tumors with activating mutants of receptor tyrosine kinases or upregulation of receptor tyrosine kinases may be particularly sensitive to the inhibitors.

In certain embodiments, the disclosure provides a method for treating a FGFR-mediated disorder in a patient in need thereof, comprising the step of administering to said patient a compound according to the disclosure, or a pharmaceutically acceptable composition thereof.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET), 8p11 myeloproliferative syndrome), myelodysplasia syndrome (MDS), T-cell acute lymphoblastic lymphoma (T-ALL), multiple myeloma, cutaneous T-cell lymphoma, adult T-cell leukemia, Waldenstrom's Macroglubulinemia, hairy cell lymphoma, marginal zone lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, lymphosarcoma, leiomyosarcoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, mesothelioma, pavicellular and non-pavicellular carcinoma, bronchial adenoma and pleuropulmonary blastoma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (exocrine pancreatic carcinoma, ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer, gall bladder cancer and anal cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) and urothelial carcinoma.

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors, neuro-ectodermal tumors), and spinal cord (neurofibroma, meningioma, glioma, sarcoma), neuroblastoma, Lhermitte-Duclos disease and pineal tumors.

Exemplary gynecological cancers include cancers of the breast (ductal carcinoma, lobular carcinoma, breast sarcoma, triple-negative breast cancer, HER2-positive breast cancer, inflammatory breast cancer, papillary carcinoma), uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers, tumors of the eye, tumors of the lips and mouth and squamous head and neck cancer.

The compounds of the present disclosure can also be useful in the inhibition of tumor metastases.

In addition to oncogenic neoplasms, the compounds of the disclosure are useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes. In some embodiments, the present disclosure provides a method for treating a patient suffering from a skeletal and chondrocyte disorder.

In some embodiments, compounds described herein can be used to treat Alzheimer's disease, HIV, or tuberculosis.

As used herein, the term "8p11 myeloproliferative syndrome" is meant to refer to myeloid/lymphoid neoplasms associated with eosinophilia and abnormalities of FGFR1.

As used herein, the term "cell" is meant to refer to a cell that is in vitro, ex vivo or in vivo.

In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR enzyme with a compound described herein includes the administration of a compound described herein to an individual or patient, such as a human, having FGFR, as well as, for example, introducing a compound described herein into a sample containing a cellular or purified preparation containing the FGFR enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

It is appreciated that certain features of the disclosure, which are, for clarity, described in the context of separate embodiments, can also be provided in combination in a single embodiment (while the embodiments are intended to be combined as if written in multiply dependent form). Conversely, various features of the disclosure which are, for brevity, described in the context of a single embodiment, can also be provided separately or in any suitable subcombination.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with compounds described herein for treatment of FGFR-associated diseases, disorders or conditions, or diseases or conditions as described herein. The agents can be combined with the present compounds in a single dosage form, or the agents can be administered simultaneously or sequentially as separate dosage forms.

Compounds described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the solid forms of the FGFR inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, compounds described herein can be used in combination with one or more inhibitors of the enzyme or protein receptors such as HPK1, SBLB, TUT4, A2A/A2B, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, compounds described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, compounds described herein can be used in combination with targeted therapies, including JAK kinase inhibitors (Ruxolitinib, additional JAK1/2 and JAK1-selective, baricitinib or INCB39110), Pim kinase inhibitors (e.g., LGH447, INCB053914 and SGI-1776), PI3 kinase inhibitors including PI3K-delta selective and broad spectrum PI3K inhibitors (e.g., INCB50465 and INCB54707), PI3K-gamma inhibitors such as PI3K-gamma selective inhibitors, MEK inhibitors, CSF1R inhibitors (e.g., PLX3397 and LY3022855), TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as OTX015, CPI-0610, INCB54329 or INCB57643), LSD1 inhibitors (e.g., GSK2979552, INCB59872 and INCB60003), arginase inhibitors (e.g., INCB1158), indoleamine 2,3-dioxygenase inhibitors (e.g., epacadostat, NLG919 or BMS-986205), PARP inhibiors (e.g., olaparib or rucaparib), and inhibitors of BTK such as ibrutinib. In addition, for treating cancer and other proliferative diseases, compounds described herein can be used in combination with targeted therapies such as, e.g., c-MET inhibitors (e.g., capmatinib), an anti-CD19 antibody (e.g., tafasitamab), an ALK2 inhibitor (e.g., INCB00928); or combinations thereof.

For treating cancer and other proliferative diseases, compounds described herein can be used in combination with chemotherapeutic agents, agonists or antagonists of nuclear receptors, or other anti-proliferative agents. Compounds described herein can also be used in combination with a medical therapy such as surgery or radiotherapy, e.g., gamma-radiation, neutron beam radiotherapy, electron beam radiotherapy, proton therapy, brachytherapy, and systemic radioactive isotopes.

Examples of suitable chemotherapeutic agents include any of: abarelix, abiraterone, afatinib, aflibercept, aldesleukin, alemtuzumab, alitretinoin, allopurinol, altretamine, amidox, amsacrine, anastrozole, aphidicolon, arsenic trioxide, asparaginase, axitinib, azacitidine, bevacizumab, bexarotene, baricitinib, bendamustine, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, didox, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lonafarnib, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, niraparib, nofetumomab, oserelin, oxaliplatin, paclitaxel, pamidronate, panitumumab, panobinostat, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, rucaparib, ruxolitinib, sorafenib, streptozocin, sunitinib, sunitinib maleate, tamoxifen, tegafur, temozolomide, teniposide, testolactone, tezacitabine, thalidomide, thioguanine, thiotepa, tipifarnib, topotecan, toremifene, tositumomab, trastuzumab, tretinoin, triapine, trimidox, triptorelin, uracil mustard, valrubicin, vandetanib, vinblastine, vincristine, vindesine, vinorelbine, vorinostat, veliparib, talazoparib, and zoledronate.

In some embodiments, compounds described herein can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is a small molecule PD-L1 inhibitor. In some embodiments, the small molecule PD-L1 inhibitor has an IC50 less than 1 μM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is MGA012 (retifanlimab), nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is nivolumab. In some embodiments, the anti-PD-1 monoclonal antibody is MGA012 (retifanlimab). In some embodiments, the anti-PD1 antibody is SHR-1210. Other anti-cancer agent(s) include antibody therapeutics such as 4-1BB (e.g. urelumab, utomilumab.

In some embodiments, the compounds of the disclosure can be used in combination with INCB086550.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

In some embodiments, the compounds described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with compounds described herein for the treatment of cancer include chemotherapeutic agents, targeted cancer therapies, immunotherapies or radiation therapy. Compounds described herein may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds described herein. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with FGFR inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds described herein. In some embodiments, the JAK inhibitor is selective for JAK1 over JAK2 and JAK3.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds described herein include steroids including 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure can be used in combination with bone marrow transplant for the treatment of a variety of tumors of hematopoietic origin.

Methods for the safe and effective administration of most of these chemotherapeutic agents are known to those skilled in the art. In addition, their administration is described in the standard literature. For example, the administration of many of the chemotherapeutic agents is described in the "Physicians'Desk Reference" (PDR, e.g., 1996 edition, Medical Economics Company, Montvale, NJ), the disclosure of which is incorporated herein by reference as if set forth in its entirety.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

When employed as pharmaceuticals, compounds described herein can be administered in the form of pharmaceutical compositions which refers to a combination of one or more compounds described herein, and at least one pharmaceutically acceptable carrier or excipient. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, one or more compounds described herein in combination with one or more pharmaceutically acceptable carriers or excipients. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is suitable for topical administration.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from, for example, about 5 mg to about 1000 mg, about 5 mg to about 100 mg, about 100 mg to about 500 mgor about 10 to about 30 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The therapeutic dosage of a compound of the present disclosure can vary according to, e.g., the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid pre-formulation composition containing a homogeneous mixture of one or more compounds described herein. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds, or compositions as described herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the disclosure. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of the compounds in a pharmaceutical composition can vary depending upon a number of factors including dosage, chemical characteristics (e.g., hydrophobicity), and the route of administration. For example, compounds of the present disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Compounds described herein can also be formulated in combination with one or more additional active ingredients, which can include any pharmaceutical agent such as antiviral agents, vaccines, antibodies, immune enhancers, immune suppressants, anti-inflammatory agents and the like.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating FGFR3 protein in tissue samples, including human, and for identifying FGFR3 ligands by inhibition binding of a labeled compound. Substitution of one or more of the atoms of the compounds of the present disclosure can also be useful in generating differentiated ADME (Adsorption, Distribution, Metabolism and Excretion). Accordingly, the present disclosure includes FGFR binding assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as $—CD_3$ being substituted for $—CH_3$). In some embodiments, alkyl groups in Formula (I) can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro adenosine receptor labeling and competition assays, compounds that incorporate $^{3}H$, $^{14}C$, $^{82}Br$, $^{125}I$, $^{131}I$ or $^{35}S$ can be useful. For radio-imaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments, the radionuclide is selected from the group consisting of $^{3}H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify and/or evaluate compounds. For example, a newly synthesized or identified compound (i.e., test compound) which is labeled can be evaluated for its ability to bind an FGFR3 protein by monitoring its concentration variation when contacting with the FGFR3, through tracking of the labeling. For example, a test compound (labeled) can be evaluated for its ability to reduce binding of another compound which is known to bind to a FGFR3 protein (i.e., standard compound). Accordingly, the ability of a test compound to compete with the standard compound for binding to the FGFR3 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of FGFR-associated diseases or disorders, such as cancer and other diseases referred to herein which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The disclosure will be described in greater detail by way of specific examples. The following examples are offered for illustrative purposes, and are not intended to limit the disclosure in any manner. Those of skill in the art will readily recognize a variety of non-critical parameters which can be changed or modified to yield essentially the same results. The compounds of the Examples were found to be inhibitors of FGFR3 as described below.

EXAMPLES

Experimental procedures for compounds of the disclosure are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 μm, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1. 2-(2-Chlorophenyl)-3-methyl-9-(1-methyl-1H-pyrazol-4-yl)imidazo[2,1-f][1,6]naphthyridine

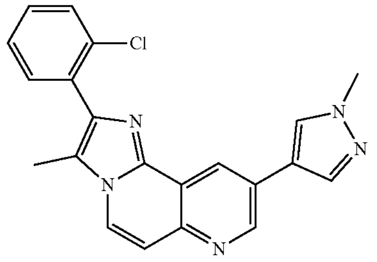 [SMILES: Cc1c(-c2ccccc2Cl)nc2c3cc(-c4cnn(C)c4)cnc3ccn12]

Step 1. 3-Bromo-5-chloro-1,6-naphthyridine

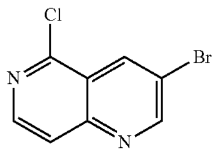 [SMILES: Clc1nccc2ncc(Br)cc12]

A flask containing a mixture of phosphorus(V) oxychloride (41.4 mL, 444 mmol) and 3-bromo-1,6-naphthyridin-5(6H)-one (5.0 g, 22.2 mmol) was stirred at 100° C. for 3 h. The reaction mixture was cooled to room temperature and the reaction mixture was concentrated in vacuo. The resulting residue was treated with saturated aqueous $NaHCO_3$ and the mixture was extracted with EtOAc. The organic phase was washed with brine, dried over $MgSO_4$, filtered and the solvent was evaporated in vacuo. The obtained crude product was used in the next step without further purification. LCMS calculated for $C_8H_5BrClN_2$ $(M+H)^+$: m/z=242.9/244.9; Found: 243.0/244.9.

Step 2. 3-Bromo-1,6-naphthyridin-5-amine

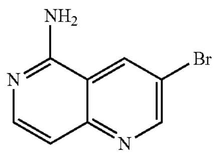 [SMILES: Nc1nccc2ncc(Br)cc12]

A mixture of 3-bromo-5-chloro-1,6-naphthyridine (2.68 g, 11.0 mmol), 1,4-dioxane (9 mL) and ammonium hydroxide solution (9 mL) in a sealed microwave vessel was irradiated at 150° C. for 3 h using a Biotage Initator+ Microwave Synthesizer. The reaction mixture was cooled to room temperature and the solvent was evaporated in vacuo. The obtained crude product was used in the next step without further purification. LCMS calculated for $C_8H_7BrN_3$ $(M+H)^+$: m/z=224.0/226.0; Found: 224.2/226.2.

Step 3. 3-(1-Methyl-1H-pyrazol-4-yl)-1,6-naphthyridin-5-amine

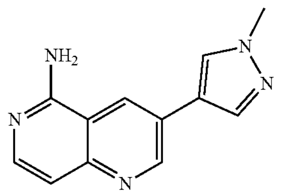 [SMILES: Cn1cc(-c2cnc3ccnc(N)c3c2)cn1]

A vial containing a mixture of 1-methyl-4-(4,4,5,5-tetramethyl-1,3,2-dioxaborolan-2-yl)-1H-pyrazole (1.0 g, 4.91 mmol), 3-bromo-1,6-naphthyridin-5-amine (1.0 g, 4.46 mmol), XPhos Pd G2 (351 mg, 0.45 mmol), and sodium carbonate (1.42 g, 13.4 mmol) was evacuated and backfilled with nitrogen three times, followed by the addition of 1,4-dioxane (20 mL) and water (2.0 mL). The vial was sealed and heated to 100° C. for 1 h. After cooling to room temperature the mixture was filtered directly, washing the filter cake with water, ether, and hexanes, followed by air drying overnight. The obtained crude product was used in the next step without further purification. LCMS calculated for $C_{12}H_{12}N_5$ $(M+H)^+$: m/z=226.1; Found: 226.3.

Step 4. 2-(2-Chlorophenyl)-9-(1-methyl-1H-pyrazol-4-yl)imidazo[2,1-f][1,6]naphthyridine

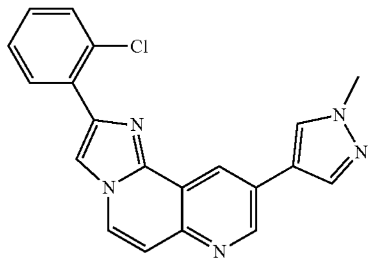 [SMILES: Cn1cc(-c2cnc3ccn4cc(-c5ccccc5Cl)nc4c3c2)cn1]

A vial containing a mixture of 3-(1-methyl-1H-pyrazol-4-yl)-1,6-naphthyridin-5-amine (255 mg, 1.13 mmol), sodium bicarbonate (1.43 g, 1.70 mmol), 2-bromo-1-(2-chlorophenyl)ethan-1-one (214 μL, 1.47 mmol) and absolute ethanol (3 mL) was heated to 100° C. for 3 h. After cooling to room temperature, the solvent was evaporated in vacuo and the remaining residue was filtered. The filter cake was washed with ether followed by air drying overnight. The obtained crude product was used in the next step without further purification. LCMS calculated for $C_{20}H_{15}ClN_5$ $(M+H)^+$: m/z=360.1/362.1; Found: 360.2/362.3.

Step 5. 3-Bromo-2-(2-chlorophenyl)-9-(1-methyl-1H-pyrazol-4-yl)imidazo[2,1-f][1,6]naphthyridine

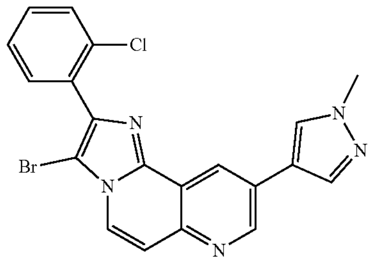 [SMILES: Cn1cc(-c2cnc3ccn4c(Br)c(-c5ccccc5Cl)nc4c3c2)cn1]

To a solution of 2-(2-chlorophenyl)-9-(1-methyl-1H-pyrazol-4-yl)imidazo[2,1-f][1,6]-naphthyridine (407 mg, 1.13 mmol) in $CH_2Cl_2$ (7.5 mL) at 0° C. was added N-bromosuccinimide (242 mg, 1.36 mmol), followed by stirring at room temperature for 10 min. The solvent was evaporated in vacuo and the resulting residue was purified by Biotage Isolera to give the desired product as a brown solid (411 mg, 83% yield). LCMS calculated for $C_{20}H_{14}BrClN_5$ $(M+H)^+$: m/z=438.0/440.0/442.0; found 438.0/439.9/442.0.

Step 6. 2-(2-Chlorophenyl)-3-methyl-9-(1-methyl-1H-pyrazol-4-yl)imidazo[2,1-f][1,6]naphthyridine A vial containing a mixture of 3-bromo-2-(2-chlorophenyl)-9-(1-methyl-1H-pyrazol-4-yl)imidazo[2,1-f][1,6]naphthyridine (10 mg, 0.023 mmol), tetrakis(triphenylphosphine)-palladium(0) (5.3 mg, 0.0046 mmol), and potassium carbonate (6.3 mg, 0.043 mmol) was evacuated and backfilled with nitrogen three times, followed by the addition of 1,4-dioxane (1 mL), water (150 μL), and trimethylboroxine (4.8 μL, 0.034 mmol). The vial was sealed and heated to 100° C. for 1.5 h. After cooling to room temperature, the mixture was filtered through Celite and washed with $CH_2Cl_2$, followed by concentration of the filtrate in vacuo. The reaction mixture was then diluted with $CH_3CN$ and water and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{21}H_{17}ClN_5$ $(M+H)^+$: m/z=374.1/376.1; found 374.3/376.3.

Example 2. 2-(2-Chlorophenyl)-3-(cyclopent-1-en-1-yl)-9-(1-methyl-1H-pyrazol-4-yl)imidazo[2,1-f][1,6]naphthyridine

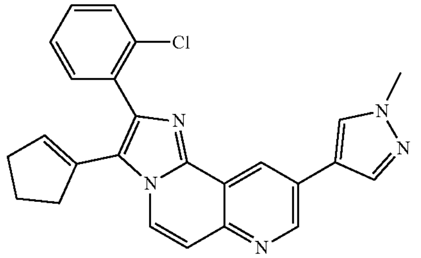 [SMILES: Cn1cc(-c2cnc3ccn4c(C5=CCCC5)c(-c5ccccc5Cl)nc4c3c2)cn1]

This compound was prepared according to the procedures described in Example 1, with 2-(cyclopent-1-en-1-yl)-4,4,5,5-tetramethyl-1,3,2-dioxaborolane replacing trimethylboroxine in Step 6. The title compound was isolated as the TFA salt. LCMS calculated for $C_{25}H_{21}ClN_5$ $(M+H)^+$: m/z=426.1/428.1; Found: 426.3/428.4.

Example 3. (E)-2-(2-Chlorophenyl)-9-(1-methyl-1H-pyrazol-4-yl)-3-(prop-1-en-1-yl)imidazo[2,1-f][1,6]naphthyridine

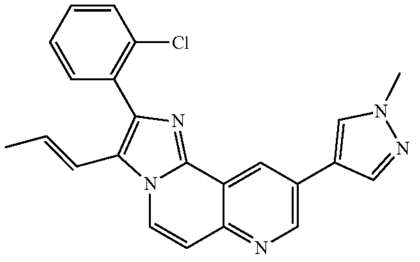 [SMILES: C/C=C/c1c(-c2ccccc2Cl)nc2c3cc(-c4cnn(C)c4)cnc3ccn12]

This compound was prepared according to the procedures described in Example 1, with potassium (E)-trifluoro(prop-1-en-1-yl)borate replacing trimethylboroxine in Step 6. The title compound was isolated as the TFA salt. LCMS calculated for $C_{23}H_{19}ClN_5$ $(M+H)^+$: m/z=400.1/402.1; Found: 400.3/402.4.

Example 4. 2-(2-Chlorophenyl)-3-(3,5-dimethoxyphenyl)-9-(1-methyl-1H-pyrazol-4-yl)imidazo[2,1-f][1,6]naphthyridine

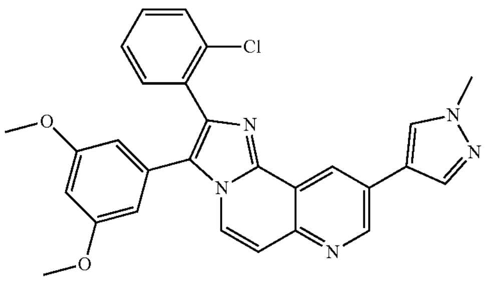 [SMILES: COc1cc(OC)cc(-c2c(-c3ccccc3Cl)nc3c4cc(-c5cnn(C)c5)cnc4ccn23)c1]

This compound was prepared according to the procedures described in Example 1, with 2-(3,5-dimethoxyphenyl)-4,4,5,5-tetramethyl-1,3,2-dioxaborolane replacing trimethylboroxine in Step 6. The title compound was isolated as the TFA salt. LCMS calculated for $C_{28}H_{23}ClN_5O_2$ $(M+H)^+$: m/z=496.2/498.2; Found: 496.1/498.1.

Example 5. 2-(2-Chlorophenyl)-3,9-bis(1-methyl-1H-pyrazol-4-yl)imidazo[2,1-f][1,6]naphthyridine

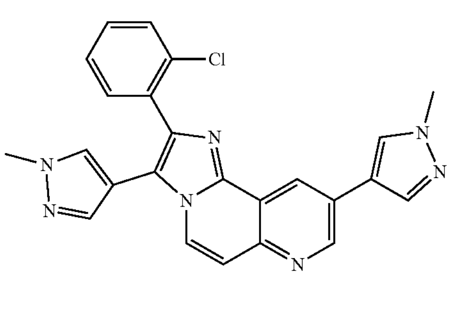 [SMILES: Cn1cc(-c2cnc3ccn4c(-c5cnn(C)c5)c(-c5ccccc5Cl)nc4c3c2)cn1]

This compound was prepared according to the procedures described in Example 1, with 1-methyl-4-(4,4,5,5-tetramethyl-1,3,2-dioxaborolan-2-yl)-1H-pyrazole replacing trimethylboroxine in Step 6. The title compound was isolated as the TFA salt. LCMS calculated for $C_{24}H_{19}ClN_7$ $(M+H)^+$: m/z=440.1/442.1; Found: 440.4/442.3.

Example 6. 2-(2-Chlorophenyl)-3-(furan-2-yl)-9-(1-methyl-1H-pyrazol-4-yl)imidazo[2,1-f][1,6]naphthyridine

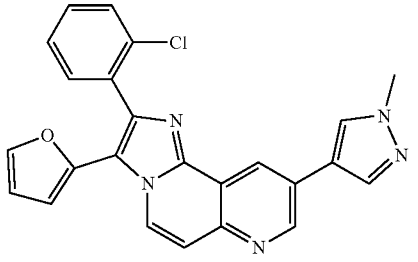 [SMILES: Cn1cc(-c2cnc3ccn4c(-c5ccco5)c(-c5ccccc5Cl)nc4c3c2)cn1]

A vial containing a mixture of 3-bromo-2-(2-chlorophenyl)-9-(1-methyl-1H-pyrazol-4-yl)imidazo[2,1-f][1,6]naphthyridine (10 mg, 0.023 mmol, Example 1, Step 5) and tetrakis(triphenylphosphine)palladium(0) (2.6 mg, 0.0023 mmol) was evacuated and backfilled with nitrogen three times, followed by the addition of 1,4-dioxane (1 mL) and tributyl(furan-2-yl)stannane (7.9 μL, 0.025 mmol). The vial was sealed and heated to 100° C. for 1 h. After cooling to room temperature the mixture was filtered through Celite and washed with $CH_2Cl_2$, followed by concentration of the filtrate in vacuo. The reaction mixture was then diluted with $CH_3CN$ and water and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{24}H_{17}ClN_5O$ $(M+H)^+$: m/z=426.1/428.1; found 426.2/428.1.

Example 7. 2-(2-Chlorophenyl)-9-(1-methyl-1H-pyrazol-4-yl)imidazo[2,1-f][1,6]naphthyridine-3-carbonitrile

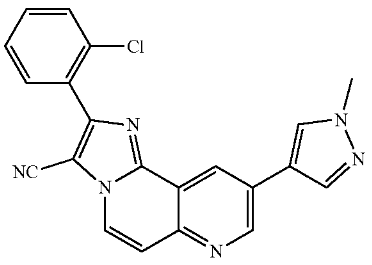 [SMILES: Cn1cc(-c2cnc3ccn4c(C#N)c(-c5ccccc5Cl)nc4c3c2)cn1]

A microwave vessel containing a mixture of 3-bromo-2-(2-chlorophenyl)-9-(1-methyl-1H-pyrazol-4-yl)imidazo[2,1-f][1,6]naphthyridine (Example 1, Step 5) (20 mg, 0.046 mmol), tris(dibenzylideneacetone)dipalladium(0) (2.1 mg, 2.3 μmol), 1,1'-bis(diphenylphosphino)ferrocene (2.5 mg, 4.5 μmol), zinc powder (1.2 mg, 0.02 mmol), and zinc cyanide (5.3 mg, 0.046 mmol) was evacuated and backfilled with nitrogen three times, followed by the addition of DMF (1 mL). The vial was sealed and irradiated at 150° C. for 2 h using a Biotage Initator+ Microwave Synthesizer. After cooling to room temperature, the mixture was filtered through Celite and washed with $CH_2Cl_2$, followed by concentration of the filtrate in vacuo. The reaction mixture was then diluted with $CH_3CN$ and water and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{21}H_{14}ClN_6$ $(M+H)^+$: m/z=385.1/387.1; found 385.1/387.1.

Example 8. 2-(2-Chlorophenyl)-3-cyclopropyl-9-(1-methyl-1H-pyrazol-4-yl)imidazo[2,1-f][1,6]naphthyridine

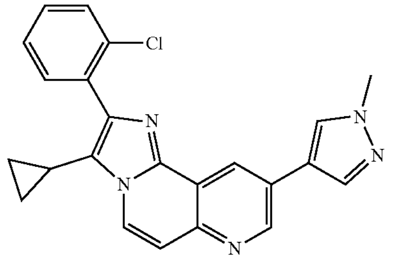 [SMILES: Cn1cc(-c2cnc3ccn4c(C5CC5)c(-c5ccccc5Cl)nc4c3c2)cn1]

A vial containing a mixture of 3-bromo-2-(2-chlorophenyl)-9-(1-methyl-1H-pyrazol-4-yl)imidazo[2,1-f][1,6]naphthyridine (Example 1, Step 5) (10 mg, 0.023 mmol), palladium(II) acetate (1.0 mg, 4.6 μmol), potassium cyclopropyltrifluoroborate (3.4 mg, 0.023 mmol), and di(1-adamantyl)-n-butylphosphine (2.0 mg, 5.7 μmol) was evacuated and backfilled with nitrogen three times, followed by the addition of 1,4-dioxane (1 mL) and water (100 μL). The vial was sealed and heated to 100° C. for 16 h. After cooling to room temperature, the mixture was filtered through Celite and washed with $CH_2Cl_2$, followed by concentration of the filtrate in vacuo. The reaction mixture was then diluted with $CH_3CN$ and water and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{23}H_{19}ClN_5$ $(M+H)^+$: m/z=400.1/402.1; found 400.2/402.2.

Example 9. 2-(2-Chlorophenyl)-3-ethyl-9-(1-methyl-1H-pyrazol-4-yl)imidazo[2,1-f][1,6]naphthyridine

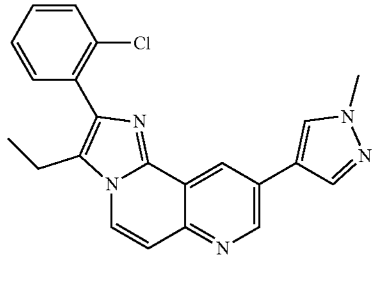 [SMILES: CCc1c(-c2ccccc2Cl)nc2c3cc(-c4cnn(C)c4)cnc3ccn12]

Step 1. 2-(2-Chlorophenyl)-9-(1-methyl-1H-pyrazol-4-yl)-3-vinylimidazo[2,1-f][1,6]naphthyridine

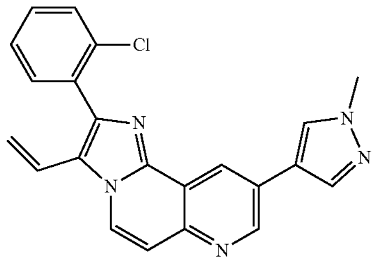 [SMILES: C=Cc1c(-c2ccccc2Cl)nc2c3cc(-c4cnn(C)c4)cnc3ccn12]

This compound was prepared according to the procedures described in Example 1, with 4,4,5,5-tetramethyl-2-vinyl-1,3,2-dioxaborolane replacing trimethylboroxine in Step 6. LCMS calculated for $C_{22}H_{17}ClN_5$ $(M+H)^+$: m/z=386.1/388.1; Found: 386.2/386.1.

Step 2. 2-(2-Chlorophenyl)-3-ethyl-9-(1-methyl-1H-pyrazol-4-yl)imidazo[2,1-f][1,6]naphthyridine Palladium hydroxide on carbon (20 wt %, 2.4 mg, 3.4 μmol) was added to a solution of 2-(2-chlorophenyl)-9-(1-methyl-1H-pyrazol-4-yl)-3-vinylimidazo[2,1-f][1,6]naphthyridine (13 mg, 0.034 mmol) in absolute ethanol (2 mL). The reaction flask was connected to a balloon with hydrogen and evacuated and backfilled three times. The reaction mixture was stirred at 60° C. for 2 h. After cooling to room temperature the mixture was filtered through Celite and washed with $CH_2Cl_2$, followed by concentration of the filtrate in vacuo. The reaction mixture was then diluted with $CH_3CN$ and water and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{22}H_{19}ClN_5$ $(M+H)^+$: m/z=388.1/390.1; found 388.2/390.2.

Example 10. 3-Chloro-2-(2-chlorophenyl)-9-(1-methyl-1H-pyrazol-4-yl)imidazo[2,1-f][1,6]naphthyridine

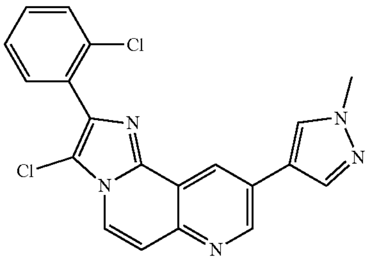 [SMILES: Cn1cc(-c2cnc3ccn4c(Cl)c(-c5ccccc5Cl)nc4c3c2)cn1]

To a solution of 2-(2-chlorophenyl)-9-(1-methyl-1H-pyrazol-4-yl)imidazo[2,1-f][1,6]naphthyridine (Example 1, Step 4) (10 mg, 0.028 mmol) in 1,2-dichloroethane (500 μL) was added N-chlorosuccinimide (4.5 mg, 0.033 mmol), followed by heating to 100° C. for 1 h. The solvent was evaporated in vacuo and the residue was then purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{20}H_{14}Cl_2N_5$ (M+H)$^+$: m/z=394.1/396.1; found 394.3/396.3.

Example 11. 2-(2,6-Difluorophenyl)-9-(1-methyl-1H-pyrazol-4-yl)imidazo[2,1-f][1,6]naphthyridine

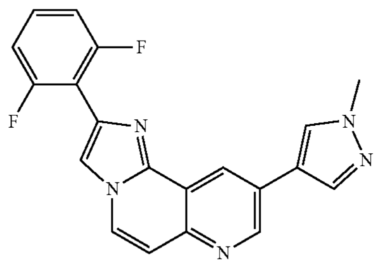 [SMILES: Cn1cc(-c2cnc3ccn4cc(-c5c(F)cccc5F)nc4c3c2)cn1]

This compound was prepared according to the procedures described in Example 1, with 2-bromo-1-(2,6-difluorophenyl)ethan-1-one replacing 2-bromo-1-(2-chlorophenyl)ethan-1-one in Step 4. The title compound was isolated as the TFA salt. LCMS calculated for $C_{20}H_{14}F_2N_5$ (M+H)$^+$: m/z=362.1; Found: 362.2.

Example 12. 2-(2-Chloro-6-fluorophenyl)-9-(1,3-dimethyl-1H-pyrazol-4-yl)imidazo[2,1-f][1,6]naphthyridine

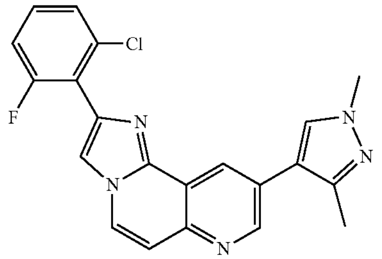 [SMILES: Cc1nn(C)cc1-c1cnc2ccn3cc(-c4c(F)cccc4Cl)nc3c2c1]

Step 1. 3-(1,3-Dimethyl-1H-pyrazol-4-yl)-1,6-naphthyridin-5-amine

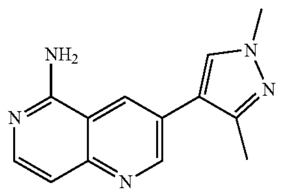 [SMILES: Cc1nn(C)cc1-c1cnc2ccnc(N)c2c1]

This compound was prepared according to the procedures described in Example 1, with 1,3-dimethyl-4-(4,4,5,5-tetramethyl-1,3,2-dioxaborolan-2-yl)-1H-pyrazole replacing 1-methyl-4-(4,4,5,5-tetramethyl-1,3,2-dioxaborolan-2-yl)-1H-pyrazole in Step 3. LCMS calculated for $C_{13}H_{14}N_5$ (M+H)$^+$: m/z=240.1; Found: 240.1.

Step 2. 2-(2-Chloro-6-fluorophenyl)-9-(1,3-dimethyl-1H-pyrazol-4-yl)imidazo[2,1-f][1,6]naphthyridine This compound was prepared according to the procedures described in Example 1, with 2-bromo-1-(2-chloro-6-fluorophenyl)ethan-1-one replacing 2-bromo-1-(2-chlorophenyl)ethan-1-one in Step 4. The title compound was isolated as the TFA salt. LCMS calculated for $C_{21}H_{16}ClFN_5$ (M+H)$^+$: m/z=392.1/394.1; Found: 392.2/394.2.

Intermediate 1. 3-(1-Methyl-1H-pyrazol-4-yl)pyrido[3,4-b]pyrazin-5-amine

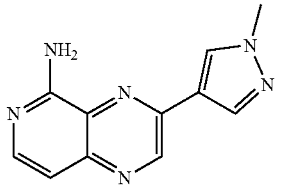 [SMILES: Cn1cc(-c2cnc3ccnc(N)c3n2)cn1]

Step 1. 5-Chloro-3-(1-methyl-1H-pyrazol-4-yl)pyrido[3,4-b]pyrazine

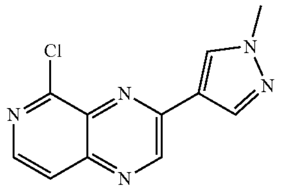 [SMILES: Cn1cc(-c2cnc3ccnc(Cl)c3n2)cn1]

This compound was prepared according to the procedures described in Example 1, with 3,5-dichloropyrido[3,4-b]pyrazine replacing 3-bromo-1,6-naphthyridin-5-amine in Step 3. LCMS calculated for $C_{11}H_9ClN_5$ (M+H)$^+$: m/z=246.1/248.1; Found: 246.2/248.2.

Step 2. 3-(1-Methyl-1H-pyrazol-4-yl)pyrido[3,4-b]pyrazin-5-amine

This compound was prepared according to the procedures described in Example 1, with 5-chloro-3-(1-methyl-1H-pyrazol-4-yl)pyrido[3,4-b]pyrazine replacing 3-bromo-5-chloro-1,6-naphthyridine in Step 2. LCMS calculated for $C_{11}H_{11}N_6$ (M+H)$^+$: m/z=227.1; Found: 227.2.

Example 13. 9-(2-Chlorophenyl)-8-cyclopropyl-2-(1-methyl-1H-pyrazol-4-yl)imidazo[1',2':1,2]pyrido[3,4-b]pyrazine

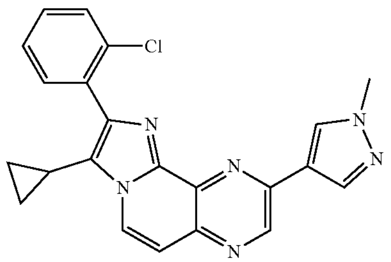

This compound was prepared according to the procedures described in Examples 1 and 8, with 3-(1-methyl-1H-pyrazol-4-yl)pyrido[3,4-b]pyrazin-5-amine replacing 3-(1-methyl-1H-pyrazol-4-yl)-1,6-naphthyridin-5-amine in Example 1, Step 4. The title compound was isolated as the TFA salt. LCMS calculated for $C_{22}H_{18}ClN_6$ $(M+H)^+$: m/z=401.1/403.1; Found: 401.2/403.1.

Example 14. 9-(2-Chloro-6-fluorophenyl)-2-(1-methyl-1H-pyrazol-4-yl)imidazo[1',2':1,2]pyrido[3,4-b]pyrazine

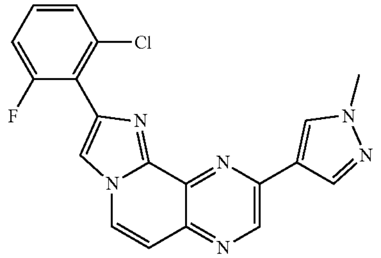 [SMILES: Cn1cc(-c2cnc3ccn4cc(-c5c(F)cccc5Cl)nc4c3n2)cn1]

This compound was prepared according to the procedures described in Example 1, with 3-(1-methyl-1H-pyrazol-4-yl)pyrido[3,4-b]pyrazin-5-amine replacing 3-(1-methyl-1H-pyrazol-4-yl)-1,6-naphthyridin-5-amine in Step 4. The title compound was isolated as the TFA salt. LCMS calculated for $C_{19}H_{13}ClFN_6$ $(M+H)^+$: m/z=379.1/381.1; Found: 379.2/381.1.

Example 15. 1-(3-(4-(2-(2,6-Dichlorophenyl)imidazo[2,1-f][1,6]naphthyridin-9-yl)-1H-pyrazol-1-yl)pyrrolidin-1-yl)ethan-1-one

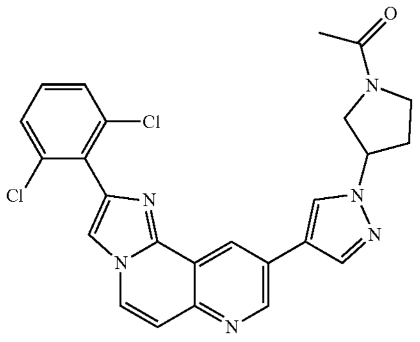 [SMILES: CC(=O)N1CCC(n2cc(-c3cnc4ccn5cc(-c6c(Cl)cccc6Cl)nc5c4c3)cn2)C1]

Step 1. 9-Bromo-2-(2,6-dichlorophenyl)imidazo[2,1-f][1,6]naphthyridine

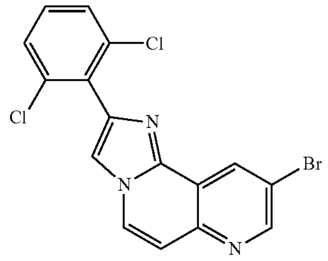 [SMILES: Clc1cccc(Cl)c1-c1cn2ccc3ncc(Br)cc3c2n1]

A microwave vessel containing a mixture of 3-bromo-1,6-naphthyridin-5-amine (Example 1, Step 2) (1.32 g, 5.89 mmol), sodium bicarbonate (742 mg, 8.84 mmol), 2-bromo-1-(2,6-dichlorophenyl)ethan-1-one (1.89 g, 7.07 mmol) and tert-butanol (8 mL) was irradiated at 150° C. for 9 h using a Biotage Initator+ Microwave Synthesizer. After cooling to room temperature the solid was filtered and washed with $CH_2Cl_2$, followed by concentration of the filtrate in vacuo. The resulting residue was purified by Biotage Isolera to give the desired product as an orange solid. LCMS calculated for $C_{16}H_9BrCl_2N_3$ $(M+H)^+$: m/z=391.9/393.9/395.9; found 392.1/394.1/396.1.

Step 2. 2-(2,6-Dichlorophenyl)-9-(1-(pyrrolidin-3-yl)-1H-pyrazol-4-yl)imidazo[2,1-f][1,6]naphthyridine

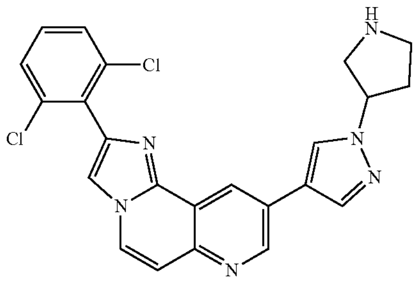 [SMILES: Clc1cccc(Cl)c1-c1cn2ccc3ncc(-c4cnn(C5CCNC5)c4)cc3c2n1]

A vial containing a mixture of tert-butyl 3-(4-(4,4,5,5-tetramethyl-1,3,2-dioxaborolan-2-yl)-1H-pyrazol-1-yl)pyrrolidine-1-carboxylate (102 mg, 0.280 mmol), 9-bromo-2-(2,6-dichlorophenyl)imidazo[2,1-f][1,6]naphthyridine (100 mg, 0.254 mmol), tetrakis(triphenylphosphine)palladium(0) (29 mg, 0.025 mmol), and potassium carbonate (81.0 mg, 0.763 mmol) was evacuated and backfilled with nitrogen three times, followed by the addition of 1,4-dioxane (2 mL) and water (200 μL). The vial was sealed and heated to 100° C. for 2 h. After cooling to room temperature the mixture was filtered through Celite and washed with $CH_2Cl_2$, followed by concentration of the filtrate in vacuo. The resulting residue was purified by Biotage Isolera to give the desired product as a brown solid. The purified material was then diluted with $CH_2Cl_2$ (3 mL) and TFA (1 mL) and left to stir at r.t. for 1 h. At completion, volatiles were removed in vacuo. The obtained product was used in the next step without further purification. LCMS calculated for $C_{23}H_{19}Cl_2N_6$ $(M+H)^+$: m/z=449.1/451.1; found 449.3/451.3.

Step 3. 1-(3-(4-(2-(2,6-Dichlorophenyl)imidazo[2,1-f][1,6]naphthyridin-9-yl)-1H-pyrazol-1-yl)pyrrolidin-1-yl)ethan-1-one To a vial containing a mixture of 2-(2,6-dichlorophenyl)-9-(1-(pyrrolidin-3-yl)-1H-pyrazol-4-yl)imidazo[2,1-f][1,6]naphthyridine (10 mg, 0.022 mmol) and diisopropylethylamine (19 μL, 0.111 mmol) as a solution in $CH_3CN$ (1 mL) was added acetyl chloride (3 μL, 0.049 mmol). The solution was left to stir at r.t. for 2 h. The reaction mixture was then diluted with $CH_3CN$ and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{25}H_{21}Cl_2N_6O$ $(M+H)^+$: m/z=491.1/493.1; found 491.1/493.1.

Example 16. (1R,4R)-4-(4-(2-(2-Chlorophenyl)-3-cyclopropylimidazo[2,1-f][1,6]naphthyridin-9-yl)-1H-pyrazol-1-yl)cyclohexane-1-carboxylic acid

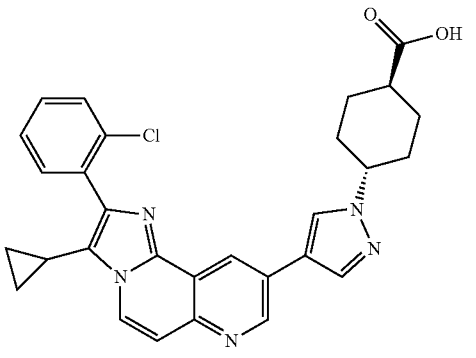 [SMILES: O=C(O)[C@H]1CC[C@H](n2cc(-c3cnc4ccn5c(C6CC6)c(-c6ccccc6Cl)nc5c4c3)cn2)CC1]

Step 1. 2-(2-Chlorophenyl)-3-cyclopropyl-9-(1-((2-(trimethylsilyl)ethoxy)methyl)-1H-pyrazol-4-yl)imidazo[2,1-f][1,6]naphthyridine

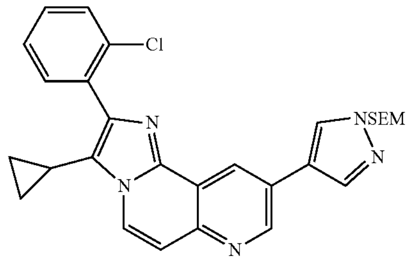 [SMILES: C[Si](C)(C)CCOCn1cc(-c2cnc3ccn4c(C5CC5)c(-c5ccccc5Cl)nc4c3c2)cn1]

This compound was prepared according to the procedures described in Examples 1 and 8, with 4-(4,4,5,5-tetramethyl-1,3,2-dioxaborolan-2-yl)-1-((2-(trimethylsilyl)ethoxy)methyl)-1H-pyrazole replacing 1-methyl-4-(4,4,5,5-tetramethyl-1,3,2-dioxaborolan-2-yl)-1H-pyrazole in Example 1, Step 3. LCMS calculated for $C_{28}H_{31}ClN_5OSi$ $(M+H)^+$: m/z=516.2/518.2; Found: 516.4/518.4.

Step 2. 2-(2-Chlorophenyl)-3-cyclopropyl-9-(1H-pyrazol-4-yl)imidazo[2,1-f][1,6]naphthyridine

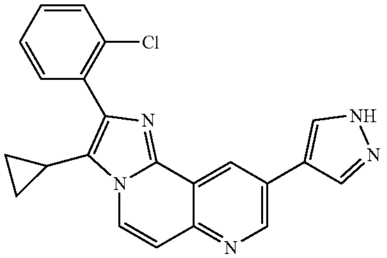 [SMILES: Clc1ccccc1-c1nc2c3cc(-c4cn[nH]c4)cnc3ccn2c1C1CC1]

To a vial containing a mixture of 2-(2-chlorophenyl)-3-cyclopropyl-9-(1-((2-(trimethylsilyl)ethoxy)methyl)-1H-pyrazol-4-yl)imidazo[2,1-f][1,6]naphthyridine (1.39 g, 2.70 mmol) as a solution in $CH_2Cl_2$ (10 mL) was added 4M HCl in dioxane (10 mL). The solution was left to stir at r.t. overnight. The reaction mixture was concentrated in vacuo. The resulting residue was treated with saturated aqueous $NaHCO_3$ and the organics were extracted into EtOAc. The organic phase was washed with brine, dried over $MgSO_4$, filtered and the solvent was evaporated in vacuo. The obtained crude product was used in the next step without further purification. LCMS calculated for $C_{22}H_{17}ClN_5$ $(M+H)^+$: m/z=386.1/388.1; found 386.1/388.1.

Step 3. (1R,4R)-4-(4-(2-(2-Chlorophenyl)-3-cyclopropylimidazo[2,1-f][1,6]naphthyridin-9-yl)-1H-pyrazol-1-yl)cyclohexane-1-carboxylic acid To a vial containing a mixture of 2-(2-chlorophenyl)-3-cyclopropyl-9-(1H-pyrazol-4-yl)imidazo[2,1-f][1,6]naphthyridine (20 mg, 0.052 mmol, and cesium carbonate (51 mg, 0.155 mmol) as a solution in $CH_3CN$ (1 mL) was added ethyl (1S,4S)-4-((methylsulfonyl)oxy)cyclohexane-1-carboxylate (19.5 mg, 0.078 mmol). The vial was sealed and heated to 80° C. for 16 h. After cooling to room temperature the mixture was filtered and washed with $CH_3CN$, followed by concentration of the filtrate in vacuo. The resulting residue was treated with 1,4-dioxane (1 mL) and 2M aq. LiOH (1 mL) and left to stir at r.t. for 2 h. The reaction mixture was then diluted with $CH_3CN$ and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{29}H_{27}ClN_5O_2$ $(M+H)^+$: m/z=512.2/514.2; found 512.4/514.4.

Example 17. N-((1R,4R)-4-(4-(2-(2-Chlorophenyl)-3-cyclopropylimidazo[2,1-f][1,6]naphthyridin-9-yl)-1H-pyrazol-1-yl)cyclohexyl)acetamide

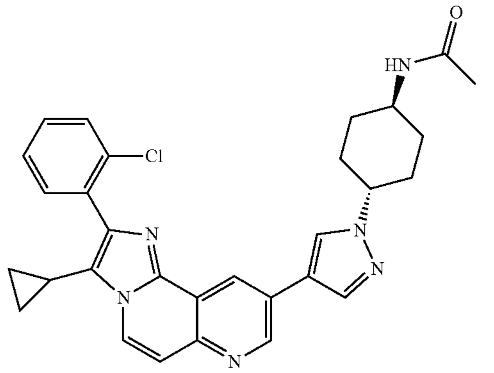 [SMILES: CC(=O)N[C@H]1CC[C@H](n2cc(-c3cnc4ccn5c(C6CC6)c(-c6ccccc6Cl)nc5c4c3)cn2)CC1]

Step 1. tert-Butyl ((1R,4R)-4-(4-(2-(2-chlorophenyl)-3-cyclopropylimidazo[2,1-f][1,6]naphthyridin-9-yl)-1H-pyrazol-1-yl)cyclohexyl)carbamate

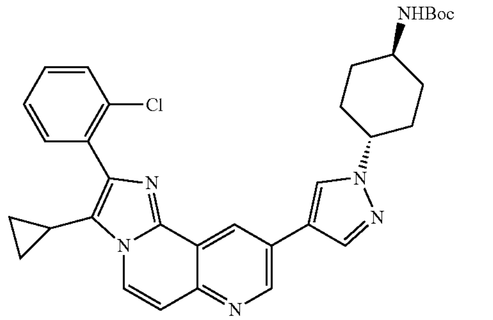 [SMILES: CC(C)(C)OC(=O)N[C@H]1CC[C@H](n2cc(-c3cnc4ccn5c(C6CC6)c(-c6ccccc6Cl)nc5c4c3)cn2)CC1]

To a vial containing a mixture of 2-(2-chlorophenyl)-3-cyclopropyl-9-(1H-pyrazol-4-yl)imidazo[2,1-f][1,6]naphthyridine (20 mg, 0.052 mmol, and cesium carbonate (51 mg, 0.155 mmol) as a solution in $CH_3CN$ (1 mL) was added (1S,4S)-4-((tert-butoxycarbonyl)amino)-cyclohexyl methanesulfonate (22.8 mg, 0.078 mmol). The vial was sealed and heated to 80° C. for 16 h. After cooling to room temperature the mixture was filtered and washed with $CH_3CN$, followed by concentration of the filtrate in vacuo. The obtained crude product was used in the next step without further purification. LCMS calculated for $C_{33}H_{36}ClN_6O_2$ $(M+H)^+$: m/z=583.3/585.3; Found: 583.4/585.4.

Step 2. (1R,4R)-4-(4-(2-(2-Chlorophenyl)-3-cyclopropylimidazo[2,1-f][1,6]naphthyridin-9-yl)-1H-pyrazol-1-yl)cyclohexan-1-amine

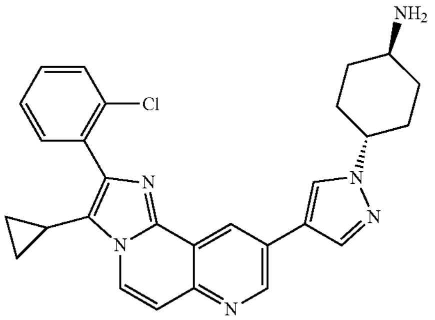 [SMILES: N[C@H]1CC[C@H](n2cc(-c3cnc4ccn5c(C6CC6)c(-c6ccccc6Cl)nc5c4c3)cn2)CC1]

To a vial containing a mixture of tert-butyl ((1R,4R)-4-(4-(2-(2-chlorophenyl)-3-cyclopropylimidazo[2,1-f][1,6]naphthyridin-9-yl)-1H-pyrazol-1-yl)cyclohexyl)carbamate (30 mg, 0.052 mmol) as a solution in $CH_2Cl_2$ (1 mL) was added TFA (1 mL). The solution was left to stir at r.t. for 1 h. The reaction mixture was concentrated in vacuo. The obtained crude product was used in the next step without further purification. LCMS calculated for $C_{28}H_{28}ClN_6$ $(M+H)^+$: m/z=483.2/485.2; found 483.2/485.2.

Step 3. N-((1R,4R)-4-(4-(2-(2-Chlorophenyl)-3-cyclopropylimidazo[2,1-f][1,6]naphthyridin-9-yl)-1H-pyrazol-1-yl)cyclohexyl)acetamide To a vial containing a mixture of (1R,4R)-4-(4-(2-(2-chlorophenyl)-3-cyclopropylimidazo[2,1-f][1,6]naphthyridin-9-yl)-1H-pyrazol-1-yl)cyclohexan-1-amine (23 mg, 0.048 mmol) and diisopropylethylamine (42 μL, 0.238 mmol) as a solution in $CH_3CN$ (1 mL) was added acetyl chloride (5 μL, 0.071 mmol). The solution was left to stir at r.t. for 2 h. The reaction mixture was then diluted with $CH_3CN$ and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{30}H_{30}ClN_6O$ $(M+H)^+$: m/z=525.2/527.2; found 525.3/527.3.

Example 18. 2-(2-Fluoro-6-methylphenyl)-3-methyl-8-(1-methyl-1H-pyrazol-4-yl)-3H-imidazo[4,5-f]quinoxaline

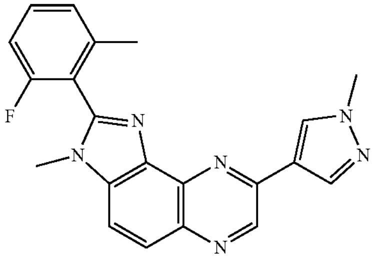 [SMILES: Cc1cccc(F)c1-c1nc2c3nc(-c4cnn(C)c4)cnc3ccc2n1C]

Step 1. 2-(1-Methyl-1H-pyrazol-4-yl)-7-nitroquinoxaline

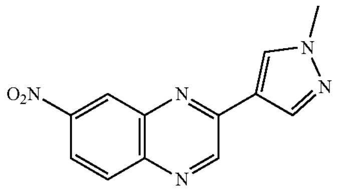 [SMILES: Cn1cc(-c2cnc3ccc(N)cc3n2)cn1]

A mixture of 2-chloro-7-nitroquinoxaline (Combi-Blocks Catalog, #QB-1085) (10 g, 48 mmol), XPhos Pd G2 (3.6 g, 4.8 mmol), and 1-methyl-4-(4,4,5,5-tetramethyl-1,3,2-dioxaborolan-2-yl)-1H-pyrazole (12 g, 57 mmol) in 1,4-dioxane (220 mL) and water (22 mL) was purged with nitrogen and stirred at 110° C. for 2 h. The reaction mixture was then cooled to room temperature, and filtered through a Celite plug with EtOAc. The volatiles were removed under reduced pressure and the crude material was taken forward without additional purification. LCMS calculated for $C_{12}H_{10}N_5O_2$ $(M+H)^+$: m/z=256.1; Found: 256.1.

Step 2. 3-(1-Methyl-1H-pyrazol-4-yl)quinoxalin-6-amine

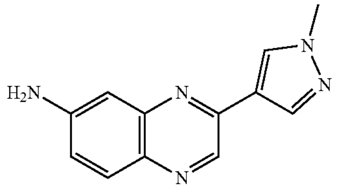

To a pressure vessel containing 2-(1-methyl-1H-pyrazol-4-yl)-7-nitroquinoxaline (12.2 g, 47.7 mmol) was added iron powder (13.3 g, 239 mmol) and ammonium chloride (15.3 g, 286 mmol), followed by THF (80 mL), MeOH (80 mL), and water (80 mL). The vessel was sealed and heated to 55° C. for 3 h. The reaction mixture was then cooled to room temperature, and filtered through a Celite plug with 10% MeOH/DCM. The volatiles were removed under reduced pressure and the crude material was taken forward without additional purification. LCMS calculated for $C_{12}H_{12}N_5$ $(M+H)^+$: m/z=226.1; Found: 226.3.

Step 3. 5-Bromo-3-(1-methyl-1H-pyrazol-4-yl)quinoxalin-6-amine

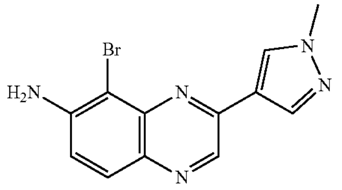 [SMILES: Cn1cc(-c2cnc3ccc(N)c(Br)c3n2)cn1]

To a mixture of 3-(1-methyl-1H-pyrazol-4-yl)quinoxalin-6-amine (8.50 g, 37.7 mmol) in DCM (190 mL) at 0° C. was added N-bromosuccinimide (6.72 g, 37.7 mmol) portion-wise. The reaction mixture was allowed to warm to room temperature, resulting in a homogenous solution. After stirring at room temperature for 30 min, the volatiles were removed under reduced pressure. The desired product was purified by column chromatography eluting with 0-100% EtOAc/hexanes containing 1% triethylamine. LCMS calculated for $C_{12}H_{11}BrN_5$ $(M+H)^+$: m/z=304.0; Found: 304.0.

Step 4. 5-Bromo-N-methyl-3-(1-methyl-1H-pyrazol-4-yl)quinoxalin-6-amine

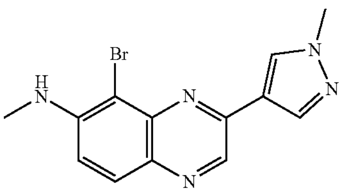 [SMILES: CNc1ccc2ncc(-c3cnn(C)c3)nc2c1Br]

To a solution of 5-bromo-3-(1-methyl-1H-pyrazol-4-yl)quinoxalin-6-amine (3.4 g, 11 mmol) in DMF (56 mL) cooled to 0° C. was added NaH (0.67 g, 17 mmol) as a 60% dispersion in mineral oil. The solution was stirred at 0° C. for 1 h, at which point iodomethane (0.42 mL, 6.8 mmol) was added drop wise. The reaction was stirred at room temperature for 2 h. The reaction was treated with saturated aq. $NaHCO_3$ and the organics were extracted with 5% isopropyl alcohol/DCM (3×). The combined organics were washed with water (3×) to remove excess DMF, then were dried over anhydrous magnesium sulfate, filtered, and concentrated under reduced pressure. The desired product was isolated by column chromatography eluting with 0-100% EtOAc/hexanes containing 1% triethylamine. LCMS calculated for $C_{13}H_{13}BrN_5$ $(M+H)^+$: m/z=318.0; Found: 318.0.

Step 5. $N^6$-Methyl-3-(1-methyl-1H-pyrazol-4-yl)quinoxaline-5,6-diamine

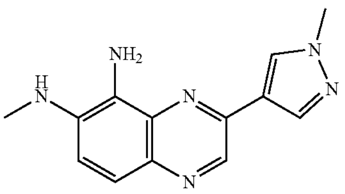 [SMILES: CNc1ccc2ncc(-c3cnn(C)c3)nc2c1N]

To a Schlenk flask was added t-BuDavePhos (0.86 g, 2.5 mmol), $Pd_2(dba)_3$ (0.68 g, 0.74 mmol), sodium tert-butoxide (1.4 g, 15 mmol), and 5-bromo-N-methyl-3-(1-methyl-1H-pyrazol-4-yl)quinoxalin-6-amine (2.4 g, 7.4 mmol). The flask was evacuated and back-filled with nitrogen, and an ammonia solution in dioxane (93 mL, 37.1 mmol) was added via syringe. The reaction mixture was then heated at 85° C. and stirred for 16 h. The reaction mixture was then cooled to room temperature, and filtered through a Celite plug with EtOAc. The filtrate was concentrated and the desired product was purified by column chromatography eluting with 0-10% MeOH/DCM. LCMS calculated for $C_{13}H_{15}N_6$ $(M+H)^+$: m/z=255.1; Found: 255.1.

Step 6. 2-Fluoro-6-methyl-N-(3-(1-methyl-1H-pyrazol-4-yl)-6-(methylamino)quinoxalin-5-yl)benzamide

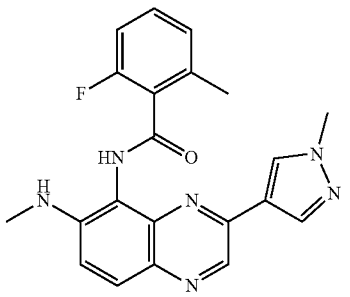 [SMILES: CNc1ccc2ncc(-c3cnn(C)c3)nc2c1NC(=O)c1c(C)cccc1F]

To a prestirred solution of 2-fluoro-6-methylbenzoic acid (18 mg, 0.094 mmol) in DCM (0.80 mL) was added a solution containing HATU (66 mg, 0.17 mmol), diisopropylethylamine (0.030 mL, 0.17 mmol) and DCM (0.80 mL). After the mixture was stirred for 30 min, $N^6$-methyl-3-(1-methyl-1H-pyrazol-4-yl)quinoxaline-5,6-diamine (20 mg, 0.079 mmol) was added and the reaction mixture was stirred for 2 h. At completion, water was added and the organics were extracted with DCM, then dried over anhydrous magnesium sulfate, filtered, and concentrated under reduced pressure. The crude material was taken forward without additional purification. LCMS calculated for $C_{21}H_{20}FN_6O$ $(M+H)^+$: m/z=391.2; Found: 391.1.

Step 7. 2-(2-Fluoro-6-methylphenyl)-3-methyl-8-(1-methyl-1H-pyrazol-4-yl)-3H-imidazo[4,5-f]quinoxaline To a solution of 2-fluoro-6-methyl-N-(3-(1-methyl-1H-pyrazol-4-yl)-6-(methylamino)-quinoxalin-5-yl)benzamide (25 mg, 0.064 mmol) in MeOH (1.0 mL) was added methanesulfonic acid (0.03 mL, 0.39 mmol). The reaction mixture was then heated at 80° C. for 2 h. At completion, the reaction mixture was diluted with $CH_3CN$ and water and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{21}H_{18}FN_6$ $(M+H)^+$: m/z=373.2; Found: 373.1.

Example 19. 2-(2-Chloro-4-methoxyphenyl)-3-methyl-8-(1-methyl-1H-pyrazol-4-yl)-3H-imidazo[4,5-f]quinoxaline

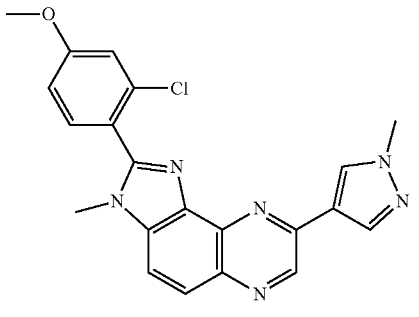 [SMILES: COc1ccc(-c2nc3c4nc(-c5cnn(C)c5)cnc4ccc3n2C)c(Cl)c1]

This compound was prepared using similar procedures as described for Example 18, with 2-chloro-4-methoxybenzoic acid replacing 2-fluoro-6-methylbenzoic acid in Step 6. The title compound was isolated as the TFA salt. LCMS calculated for $C_{21}H_{18}ClN_6O$ $(M+H)^+$: m/z=405.1; Found: 405.2.

Example 20. 3-Methyl-8-(1-methyl-1H-pyrazol-4-yl)-2-(3-methylfuran-2-yl)-3H-imidazo[4,5-f]quinoxaline

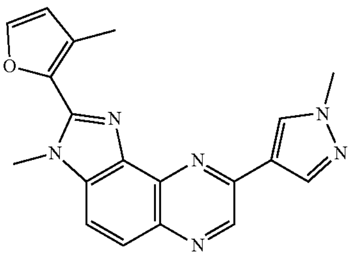 [SMILES: Cc1ccoc1-c1nc2c3nc(-c4cnn(C)c4)cnc3ccc2n1C]

This compound was prepared using similar procedures as described for Example 18, with 3-methylfuran-2-carboxylic acid replacing 2-fluoro-6-methylbenzoic acid in Step 6. The title compound was isolated as the TFA salt. LCMS calculated for $C_{19}H_{17}N_6O$ $(M+H)^+$: m/z=345.1; Found: 345.3.

Example 21. 3-(4-(2-(2-Chloro-6-fluorophenyl)-3-methyl-3H-imidazo[4,5-f]quinoxalin-8-yl)-1H-pyrazol-1-yl)cyclobutan-1-ol

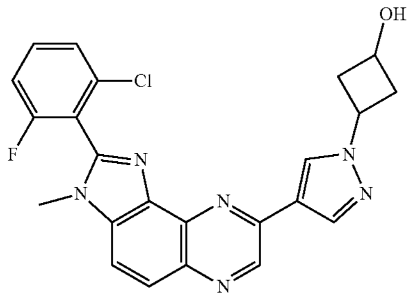 [SMILES: Cn1c(-c2c(F)cccc2Cl)nc2c3nc(-c4cnn(C5CC(O)C5)c4)cnc3ccc21]

Step 1. $N^6$-Methyl-3-(1-((2-(trimethylsilyl)ethoxy)methyl)-1H-pyrazol-4-yl)quinoxaline-5,6-diamine

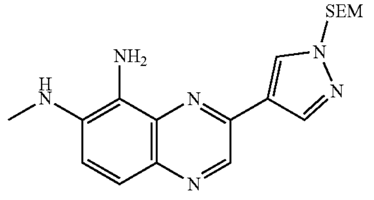 [SMILES: CNc1ccc2ncc(-c3cnn(COCC[Si](C)(C)C)c3)nc2c1N]

This compound was prepared using similar procedures as described for Example 15, Step 1 to Step 5, with 4-(4,4,5,5-tetramethyl-1,3,2-dioxaborolan-2-yl)-1-((2-(trimethylsilyl)ethoxy)methyl)-1H-pyrazole replacing 1-methyl-4-(4,4, 5,5-tetramethyl-1,3,2-dioxaborolan-2-yl)-1H-pyrazole in Step 1. LCMS calculated for $C_{18}H_{27}N_6OSi$ $(M+H)^+$: m/z=371.2; Found: 371.2.

Step 2. 2-Chloro-6-fluoro-N-(6-(methylamino)-3-(1-((2-(trimethylsilyl)ethoxy)methyl)-1H-pyrazol-4-yl)quinoxalin-5-yl)benzamide

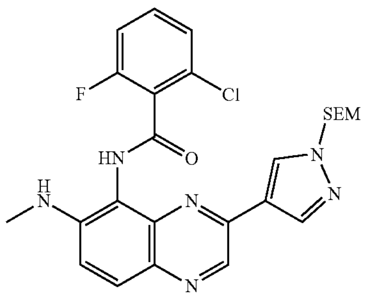 [SMILES: CNc1ccc2ncc(-c3cnn(COCC[Si](C)(C)C)c3)nc2c1NC(=O)c1c(F)cccc1Cl]

To a solution of $N^6$-methyl-3-(1-((2-(trimethylsilyl)ethoxy)methyl)-1H-pyrazol-4-yl)quinoxaline-5,6-diamine (0.75 g, 2.01 mmol) and diisopropylethylamine (0.53 mL, 3.02 mmol) in DCM (10 mL) cooled to 0° C. was added 2-chloro-6-fluorobenzoyl chloride (0.29 mL, 2.22 mmol) dropwise. The solution was stirred at 0° C. for 1 h, at which point the reaction was treated with saturated aq. $NaHCO_3$ and the organics were extracted with DCM. The combined organics were dried over anhydrous magnesium sulfate, filtered, and concentrated under reduced pressure. The crude material was taken forward without additional purification. LCMS calculated for $C_{25}H_{29}ClFN_6O_2Si$ $(M+H)^+$: m/z=527.2; Found: 527.1.

Step 3. 2-(2-Chloro-6-fluorophenyl)-3-methyl-8-(1-((2-(trimethylsilyl)ethoxy)methyl)-1H-pyrazol-4-yl)-3H-imidazo[4,5-f]quinoxaline

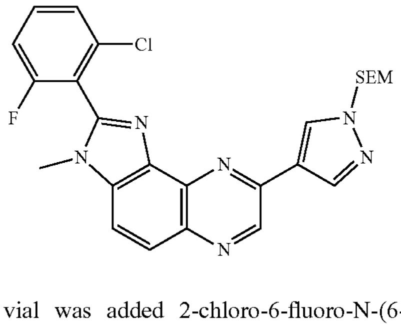

To a vial was added 2-chloro-6-fluoro-N-(6-(methylamino)-3-(1-((2-(trimethylsilyl)ethoxy)-methyl)-1H-pyrazol-4-yl)quinoxalin-5-yl)benzamide (0.850 g, 2.01 mmol) and acetic acid (8.0 mL). The vial was sealed and the reaction mixture was heated at 120° C. for 4 h. The reaction mixture was then cooled to room temperature, and concentrated under reduced pressure. The crude residue was dissolved in DCM and saturated $NaHCO_3$ was carefully added. The aqueous phase was extracted with DCM (3×) and the combined organics were dried over anhydrous magnesium sulfate, filtered, and concentrated under reduced pressure. The crude material was taken forward without additional purification. LCMS calculated for $C_{25}H_{27}ClFN_6OSi$ $(M+H)^+$: m/z=509.2; Found: 508.9.

Step 4. 2-(2-Chloro-6-fluorophenyl)-3-methyl-8-(1H-pyrazol-4-yl)-3H-imidazo[4,5-f]quinoxaline

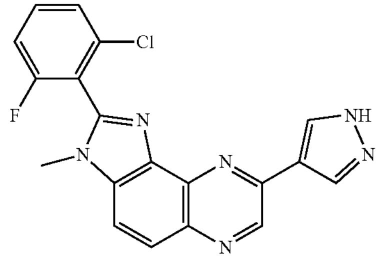 [SMILES: Cn1c(-c2c(F)cccc2Cl)nc2c3nc(-c4cn[nH]c4)cnc3ccc21]

In a flask, 2-(2-chloro-6-fluorophenyl)-3-methyl-8-(1-((2-(trimethylsilyl)ethoxy)methyl)-1H-pyrazol-4-yl)-3H-imidazo[4,5-f]quinoxaline (1.4 g, 2.8 mmol) was dissolved in DCM (28 mL). To the reaction mixture was added 4N HCl in dioxane (10 mL, 41 mmol). After stirring at ambient temperature for 3 h, the reaction mixture was concentrated under reduced pressure. The resultant material was purified by column chromatography eluting with 0-10% MeOH/DCM. LCMS calculated for $C_{19}H_{13}ClFN_6$ $(M+H)^+$: m/z=379.1; Found: 379.1.

Step 5. 3-(4-(2-(2-Chloro-6-fluorophenyl)-3-methyl-3H-imidazo[4,5-f]quinoxalin-8-yl)-1H-pyrazol-1-yl)cyclobutan-1-ol To a mixture of 2-(2-chloro-6-fluorophenyl)-3-methyl-8-(1H-pyrazol-4-yl)-3H-imidazo[4,5-f]quinoxaline (40 mg, 0.11 mmol), 3-((tert-butyldimethylsilyl)oxy)cyclobutan-1-ol (70 μL, 0.32 mmol), and triphenylphosphine (55 mg, 0.21 mmol) in THF (1.0 mL) was added DIAD (62 μL, 0.32 mmol). The reaction mixture was purged with nitrogen and stirred at 80° C. for 16 h. At completion, water was added and the organics were extracted with DCM. The combined organics were dried over anhydrous magnesium sulfate, filtered, and concentrated under reduced pressure. To the resulting residue was added $CH_3CN$ (1.0 mL) and 6N HCl (0.20 mL, 1.2 mmol). The reaction mixture was stirred for 30 min at room temperature. The reaction mixture was then diluted with $CH_3CN$ and water and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{23}H_{19}ClFN_6O$ $(M+H)^+$: m/z=449.1; Found: 449.1.

Example 22. 1-(4-(5-(2-(2-Chloro-6-fluorophenyl)-3-methyl-3H-imidazo[4,5-f]quinoxalin-8-yl)pyridin-2-yl)piperazin-1-yl)ethan-1-one

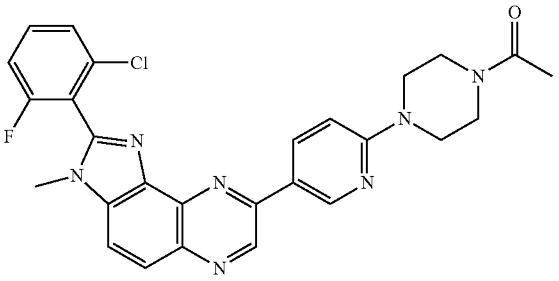 [SMILES: CC(=O)N1CCN(c2ccc(-c3cnc4ccc5c(nc(-c6c(F)cccc6Cl)n5C)c4n3)cn2)CC1]

Step 1. 5-Bromo-3-(6-fluoropyridin-3-yl)quinoxalin-6-amine

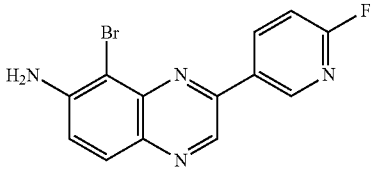 [SMILES: Nc1ccc2ncc(-c3ccc(F)nc3)nc2c1Br]

This compound was prepared using similar procedures as described for Example 18, Step 1 to Step 3, with 2-fluoro-5-(4,4,5,5-tetramethyl-1,3,2-dioxaborolan-2-yl)pyridine replacing 1-methyl-4-(4,4,5,5-tetramethyl-1,3,2-dioxaborolan-2-yl)-1H-pyrazole in Step 1. LCMS calculated for $C_{13}H_9BrFN_4$ $(M+H)^+$: m/z=319.0; Found: 319.0.

Step 2. N-(5-Bromo-3-(6-fluoropyridin-3-yl)quinoxalin-6-yl)-2-chloro-6-fluorobenzamide

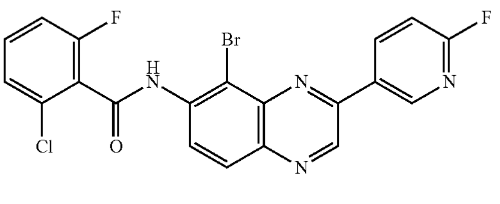 [SMILES: O=C(Nc1ccc2ncc(-c3ccc(F)nc3)nc2c1Br)c1c(F)cccc1Cl]

To a solution of 5-bromo-3-(6-fluoropyridin-3-yl)quinoxalin-6-amine (1.9 g, 6.0 mmol) and diisopropylethylamine (1.6 mL, 9.0 mmol) in DCM (30 mL) cooled to 0° C. was added 2-chloro-6-fluorobenzoyl chloride (0.80 mL, 6.0 mmol) dropwise. The solution was stirred at 0° C. for 1 h, at which point the reaction was treated with saturated $NaHCO_3$ and the organics were extracted with DCM. The combined organics were dried over anhydrous magnesium sulfate, filtered, and concentrated under reduced pressure. The desired product was isolated by column chromatography eluting with 0-100% EtOAc/hexanes containing 1% triethylamine. LCMS calculated for $C_{20}H_{11}BrClF_2N_4O$ $(M+H)^+$: m/z=475.0; Found: 475.0.

Step 3. N-(5-Bromo-3-(6-fluoropyridin-3-yl)quinoxalin-6-yl)-2-chloro-6-fluoro-N-methylbenzamide

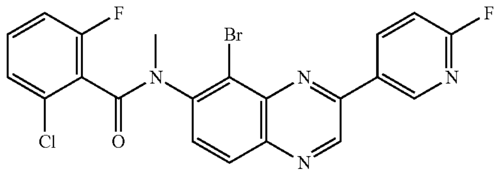 [SMILES: CN(C(=O)c1c(F)cccc1Cl)c1ccc2ncc(-c3ccc(F)nc3)nc2c1Br]

To a solution of N-(5-bromo-3-(6-fluoropyridin-3-yl)quinoxalin-6-yl)-2-chloro-6-fluorobenzamide (1.2 g, 2.5 mmol) in DMF (10 mL) cooled to 0° C. was added NaH (0.20 g, 5.1 mmol) as a 60% dispersion in mineral oil. The solution was stirred at 0° C. for 10 min, at which point iodomethane (0.31 mL, 5.1 mmol) was added dropwise. The reaction was stirred at room temperature for 1 h. The reaction was treated with saturated aqueous $NaHCO_3$ and the organics were extracted with EtOAc (3×). The combined organics were dried over anhydrous magnesium sulfate, filtered, and concentrated under reduced pressure. The desired product was isolated by column chromatography eluting with 0-100% EtOAc/hexanes containing 1% triethylamine. LCMS calculated for $C_{21}H_{13}BrClF_2N_4O$ $(M+H)^+$: m/z=489.0; Found: 489.0.

Step 4. tert-Butyl 4-(5-(8-bromo-7-(2-chloro-6-fluoro-N-methylbenzamido)quinoxalin-2-yl)pyridin-2-yl)piperazine-1-carboxylate

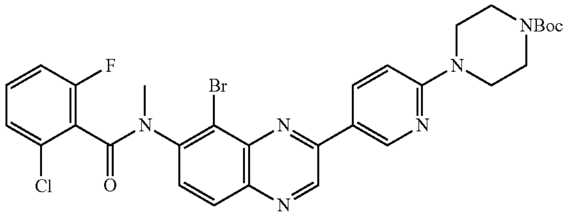 [SMILES: CN(C(=O)c1c(F)cccc1Cl)c1ccc2ncc(-c3ccc(N4CCN(C(=O)OC(C)(C)C)CC4)nc3)nc2c1Br]

To a vial was added N-(5-bromo-3-(6-fluoropyridin-3-yl)quinoxalin-6-yl)-2-chloro-6-fluoro-N-methylbenzamide (0.20 g, 0.41 mmol), tert-butyl piperazine-1-carboxylate (0.11 g, 0.61 mmol), and diisopropylethylamine (0.21 mL, 1.23 mmol) in DMSO (2.0 mL). The vial was sealed and the reaction mixture was heated at 100° C. for 16 h. At completion the reaction mixture was diluted with water and the organics were extracted with EtOAc (3×). The combined organics were dried over anhydrous magnesium sulfate, filtered, and concentrated under reduced pressure. The desired product was isolated by column chromatography eluting with 0-100% EtOAc/hexanes containing 1% triethylamine. LCMS calculated for $C_{30}H_{30}BrClFN_6O_3$ $(M+H)^+$: m/z=655.1; Found: 655.1.

Step 5. tert-Butyl 4-(5-(8-amino-7-(2-chloro-6-fluoro-N-methylbenzamido)quinoxalin-2-yl)pyridin-2-yl)piperazine-1-carboxylate

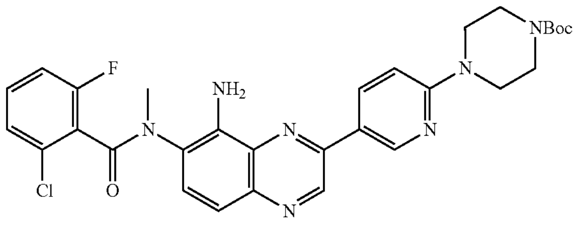

To a vial was added t-BuDavePhos (33 mg, 0.096 mmol), $Pd_2(dba)_3$ (26 mg, 0.028 mmol), sodium tert-butoxide (54 mg, 0.56 mmol), and tert-butyl 4-(5-(8-bromo-7-(2-chloro-6-fluoro-N-methylbenzamido)quinoxalin-2-yl)pyridin-2-yl) piperazine-1-carboxylate (190 mg, 0.28 mmol). The vial was evacuated and back-filled with nitrogen, and an ammonia solution in dioxane (3.5 mL, 1.4 mmol) was added via syringe. The reaction mixture was then heated at 85° C. for 16 h. The reaction mixture was then cooled to room temperature, and filtered through a Celite plug with EtOAc. The filtrate was concentrated and the desired product was purified by column chromatography eluting with 0-10% MeOH/DCM. LCMS calculated for $C_{30}H_{32}ClFN_7O_3$ $(M+H)^+$: m/z=592.2; Found: 592.4.

Step 6. 1-(4-(5-(2-(2-Chloro-6-fluorophenyl)-3-methyl-3H-imidazo[4,5-f]quinoxalin-8-yl)pyridin-2-yl)piperazin-1-yl)ethan-1-one To a vial was added tert-butyl 4-(5-(8-amino-7-(2-chloro-6-fluoro-N-methylbenzamido)quinoxalin-2-yl)pyridin-2-yl) piperazine-1-carboxylate (30 mg, 0.09 mmol) and acetic acid (1.0 mL). The vial was sealed and the reaction mixture was heated at 120° C. for 16 h. The reaction mixture was then diluted with $CH_3CN$ and water and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{27}H_{24}ClFN_7O$ $(M+H)^+$: m/z=516.2; Found: 516.4.

Example 23. 3-Methyl-8-(1-methyl-1H-pyrazol-4-yl)-2-(1-methylpiperidin-4-yl)-3H-imidazo[4,5-f]quinoxaline

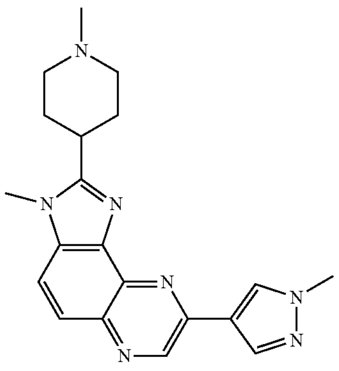

Step 1. 1-Methyl-N-(3-(1-methyl-1H-pyrazol-4-yl)-6-(methylamino)quinoxalin-5-yl)piperidine-4-carboxamide

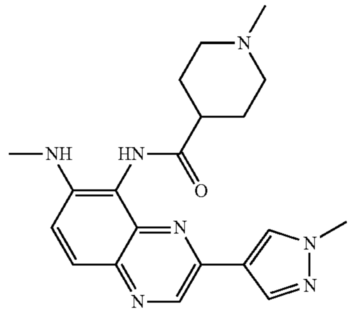

To a vial containing a mixture of $N^6$-methyl-3-(1-methyl-1H-pyrazol-4-yl)quinoxaline-5,6-diamine (20 mg, 0.079 mmol, Example 18, Step 5) as a solution in $CH_2Cl_2$ (0.5 mL) at 0° C. was added diisopropylethylamine (34 μL, 0.197 mmol), followed by 1-methylpiperidine-4-carbonyl chloride hydrochloride (16 mg, 0.079 mmol). The solution was left to stir at 0° C. for 1 h. The reaction mixture was warmed to r.t. and the solvent was removed in vacuo. The residue was then diluted with $CH_3CN$ and purified with prep-LCMS(XBridge C18 column, eluting with a gradient of acetonitrile/water containing 0.1% TFA, at flow rate of 60 mL/min). LCMS calculated for $C_{20}H_{26}N_{70}$ $(M+H)^+$: m/z=380.2; found 380.4.

Step 2. 3-Methyl-8-(1-methyl-1H-pyrazol-4-yl)-2-(1-methylpiperidin-4-yl)-3H-imidazo[4,5-f]quinoxaline A vial containing a 1-methyl-N-(3-(1-methyl-1H-pyrazol-4-yl)-6-(methylamino)quinoxalin-5-yl)piperidine-4-carboxamide (5 mg, 0.013 mmol) as a solution in AcOH (0.5 mL) was heated to 120° C. for 16 h. The solution was cooled to r.t., then diluted with $CH_3CN$ and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{20}H_{24}N_7$ $(M+H)^+$: m/z=362.2; found 362.3.

Example 24. (1S,5R)-8-(3-Methyl-8-(1-methyl-1H-pyrazol-4-yl)-3H-imidazo[4,5-f]quinoxalin-2-yl)-3,8-diazabicyclo[3.2.1]octan-2-one

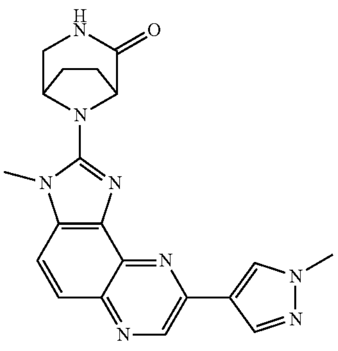

Step 1. 3-Methyl-8-(1-methyl-1H-pyrazol-4-yl)-1,3-dihydro-2H-imidazo[4,5-f]quinoxalin-2-one

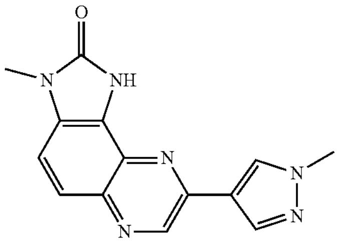

A vial containing a mixture of $N^6$-methyl-3-(1-methyl-1H-pyrazol-4-yl)quinoxaline-5,6-diamine (Example 18, Step 5, 100 mg, 0.393 mmol) as a solution in THF (4 mL) was added diisopropylethylamine (103 μL, 0.590 mmol), followed by 1,1'-carbonyldiimidazole (77 mg, 0.472 mmol). The solution was left to stir for 16 h. The volatiles were removed under reduced pressure and the crude material was taken forward without additional purification. LCMS calculated for $C_{14}H_{13}N_6O$ $(M+H)^+$: m/z=281.1; Found: 281.1.

Step 2. 2-Chloro-3-methyl-8-(1-methyl-1H-pyrazol-4-yl)-3H-imidazo[4,5-f]quinoxaline

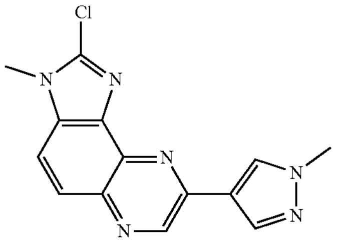

A vial containing a 3-methyl-8-(1-methyl-1H-pyrazol-4-yl)-1,3-dihydro-2H-imidazo[4,5-f]quinoxalin-2-one (110 mg, 0.392 mmol) as a solution in phosphoryl chloride (2 mL, 21.5 mmol) was heated to 100° C. for 1 h. The volatiles were removed in vacuo and the resulting residue was purified by Biotage Isolera to give the desired product as a brown foam (56 mg, 48% yield). LCMS calculated for $C_{14}H_{12}ClN_6$ $(M+H)^+$: m/z=299.1/301.1; found 299.2/301.2.

Step 3. (1S,5R)-8-(3-Methyl-8-(1-methyl-1H-pyrazol-4-yl)-3H-imidazo[4,5-f]quinoxalin-2-yl)-3,8-diazabicyclo[3.2.1]octan-2-one A microwave vessel containing 2-chloro-3-methyl-8-(1-methyl-1H-pyrazol-4-yl)-3H-imidazo[4,5-f]quinoxaline (30 mg, 0.100 mmol) as a solution in t-BuOH (1 mL) was added diisopropylethylamine (53 μL, 0.301 mmol), followed by (1S,5R)-3,8-diazabicyclo[3.2.1]octan-2-one (25 mg, 0.201 mmol). The vial was sealed and irradiated at 150° C. for 5 h using a Biotage Initator+ Microwave Synthesizer. After cooling to room temperature, the mixture was diluted with $CH_3CN$ and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{20}H_{21}N_8O$ $(M+H)^+$: m/z=389.2; found 389.3.

Example 25. (S)-1-(3-(4-(2-(2-Chloro-6-(trifluoromethyl)phenyl)-3-methylimidazo[2,1-f][1,6]naphthyridin-9-yl)-1H-pyrazol-1-yl)pyrrolidin-1-yl)-2-hydroxyethan-1-one

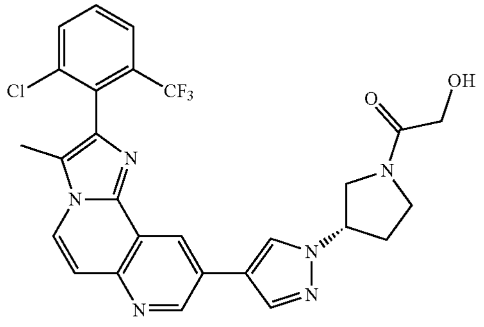 [SMILES: Cc1c(-c2c(Cl)cccc2C(F)(F)F)nc2c3cc(-c4cnn([C@H]5CCN(C(=O)CO)C5)c4)cnc3ccn12]

Step 1. 9-Bromoimidazo[2,1-f][1,6]naphthyridine

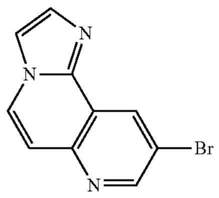 [SMILES: Brc1cnc2ccn3ccnc3c2c1]

To a flask containing a mixture of 3-bromo-1,6-naphthyridin-5-amine (Example 1, Step 2, 4.32 g, 19.3 mmol) as a solution in EtOH (77 mL) was added sodium bicarbonate (3.24 g, 38.6 mmol), followed by chloroacetaldehyde (50% in $H_2O$, 4.9 mL, 38.6 mmol). The solution was heated to 80° C. and left to stir for 2 h. After cooling to room temperature, the volatiles were removed in vacuo and the crude material was dissolved in DCM and filtered through Celite and washed with $CH_2Cl_2$. The volatiles were removed under reduced pressure and the crude material was taken forward without additional purification. LCMS calculated for $C_{10}H_7BrN_3$ $(M+H)^+$: m/z=248.0/250.0; Found: 248.1/250.1.

Step 2. 9-(1-((2-(Trimethylsilyl)ethoxy)methyl)-1H-pyrazol-4-yl)imidazo[2,1-f][1,6]naphthyridine

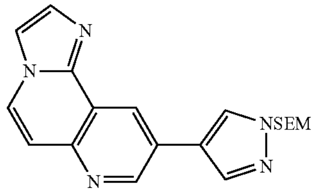 [SMILES: C[Si](C)(C)CCOCn1cc(-c2cnc3ccn4ccnc4c3c2)cn1]

A vial containing a mixture of 9-bromoimidazo[2,1-f][1,6]naphthyridine (1.1 g, 4.43 mmol), 4-(4,4,5,5-tetramethyl-1,3,2-dioxaborolan-2-yl)-1-((2-(trimethylsilyl)ethoxy)methyl)-1H-pyrazole (1.51 g, 4.66 mmol), XPhos Pd G2 (349 mg, 0.443 mmol), and potassium phosphate, tribasic (2.82 g, 13.3 mmol) was evacuated and backfilled with nitrogen three times, followed by the addition of 1,4-dioxane (14 mL) and water (3.5 mL). The vial was sealed and heated to 80° C. for 30 min. After cooling to room temperature, the mixture was filtered through Celite and washed with $CH_2Cl_2$, followed by concentration of the filtrate in vacuo. The obtained crude product was purified by Biotage Isolera to give the desired product. LCMS calculated for $C_{19}H_{24}N_5OSi$ $(M+H)^+$: m/z=366.2; found 366.2.

Step 3. 3-Bromo-9-(1-((2-(trimethylsilyl)ethoxy)methyl)-1H-pyrazol-4-yl)imidazo[2,1-f][1,6]naphthyridine

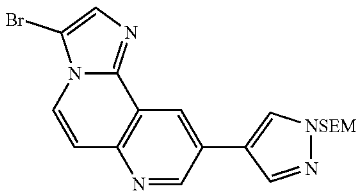 [SMILES: C[Si](C)(C)CCOCn1cc(-c2cnc3ccn4c(Br)cnc4c3c2)cn1]

To a flask containing 9-(1-((2-(trimethylsilyl)ethoxy)methyl)-1H-pyrazol-4-yl)imidazo[2,1-f][1,6]naphthyridine (1.62 g, 4.43 mmol) as a solution in $CH_2Cl_2$ (44 mL) was added NBS (947 mg, 5.32 mmol) and left to stir at r.t. for 30 min. The volatiles were removed under reduced pressure and the obtained crude product was purified by Biotage Isolera to give the desired product. LCMS calculated for $C_{19}H_{23}BrN_5OSi$ $(M+H)^+$: m/z=444.1/446.1; Found: 444.3/446.3.

Step 4. 3-Methyl-9-(1H-pyrazol-4-yl)imidazo[2,1-f][1,6]naphthyridine

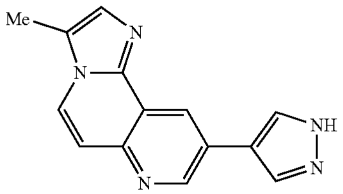 [SMILES: Cc1cnc2c3cc(-c4cn[nH]c4)cnc3ccn12]

A vial containing a mixture of 3-bromo-9-(1-((2-(trimethylsilyl)ethoxy)methyl)-1H-pyrazol-4-yl)imidazo[2,1-f][1,6]naphthyridine (1.97 g, 4.43 mmol), XPhos Pd G2 (349 mg, 0.443 mmol), and potassium phosphate, tribasic (2.82 g, 13.3 mmol) was evacuated and backfilled with nitrogen three times, followed by the addition of 1,4-dioxane (35 mL), water (9 mL), and trimethylboroxine (1.24 mL, 8.87 mmol). The vial was sealed and heated to 100° C. for 5 h. After cooling to room temperature, the mixture was filtered through Celite and washed with $CH_2Cl_2$, followed by concentration of the filtrate in vacuo. The obtained crude product was purified by Biotage Isolera to give the desired product (1.46 g, 87% yield). The purified material was then dissolved in $CH_2Cl_2$ (10 mL) and TFA (2 mL) and left to stir at r.t. for 2 h. The reaction mixture was concentrated in vacuo, then dissolved in MeOH (2 mL) and added to a stirring solution of saturated aqueous $NaHCO_3$ (50 mL). The resulting brown solid precipitate was filtered and collected, followed by drying under vacuum overnight. LCMS calculated for $C_{14}H_{12}N_5$ $(M+H)^+$: m/z=250.1; found 250.2.

Step 5. tert-Butyl (S)-3-(4-(3-methylimidazo[2,1-f][1,6]naphthyridin-9-yl)-1H-pyrazol-1-yl)pyrrolidine-1-carboxylate

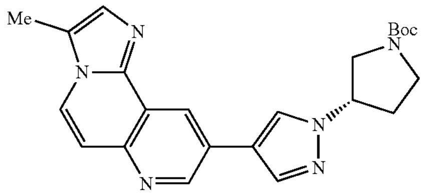 [SMILES: Cc1cnc2c3cc(-c4cnn([C@H]5CCN(C(=O)OC(C)(C)C)C5)c4)cnc3ccn12]

To a vial containing 3-methyl-9-(1H-pyrazol-4-yl)imidazo[2,1-f][1,6]naphthyridine (964 mg, 3.87 mmol) as a solution in MeCN (19 mL) was added cesium carbonate (2.52 g, 7.73 mmol) and tert-butyl (R)-3-((methylsulfonyl)oxy)pyrrolidine-1-carboxylate (1.54 g, 5.80 mmol). The vial was sealed and heated to 80° C. for 3 h. After cooling to room temperature, the mixture was filtered and washed with MeCN, followed by concentration of the filtrate in vacuo. The obtained crude product was purified by Biotage Isolera to give the desired product as a brown solid (1.09 g, 67% yield). LCMS calculated for $C_{23}H_{27}N_6O_2$ $(M+H)^+$: m/z=419.2; found 419.2.

Step 6. tert-Butyl (S)-3-(4-(2-bromo-3-methylimidazo[2,1-f][1,6]naphthyridin-9-yl)-1H-pyrazol-1-yl)pyrrolidine-1-carboxylate

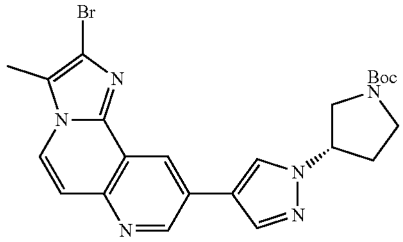 [SMILES: Cc1c(Br)nc2c3cc(-c4cnn([C@H]5CCN(C(=O)OC(C)(C)C)C5)c4)cnc3ccn12]

To a vial containing tert-butyl (S)-3-(4-(3-methylimidazo[2,1-f][1,6]naphthyridin-9-yl)-1H-pyrazol-1-yl)pyrrolidine-1-carboxylate (222 mg, 0.530 mmol) as a solution in $CH_2Cl_2$ (26 mL) was added NBS (113 mg, 0.637 mmol). The vial was sealed and heated to 80° C. for 2 h. After cooling to room temperature, the solvent was evaporated in vacuo and the resulting residue was purified by Biotage Isolera to give the desired product as a yellow solid (206 mg, 78% yield). LCMS calculated for $C_{23}H_{26}BrN_6O_2$ $(M+H)^+$: m/z=497.1/499.1; found 497.3/499.3.

Step 7. (S)-2-(2-Chloro-6-(trifluoromethyl)phenyl)-3-methyl-9-(1-(pyrrolidin-3-yl)-1H-pyrazol-4-yl)imidazo[2,1-f][1,6]naphthyridine

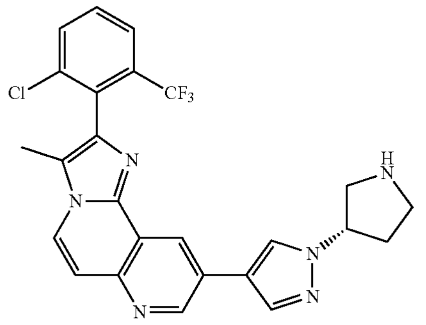 [SMILES: Cc1c(-c2c(Cl)cccc2C(F)(F)F)nc2c3cc(-c4cnn([C@H]5CCNC5)c4)cnc3ccn12]

A vial containing a mixture of tert-butyl (S)-3-(4-(2-bromo-3-methylimidazo[2,1-f][1,6]naphthyridin-9-yl)-1H-pyrazol-1-yl)pyrrolidine-1-carboxylate (20 mg, 0.040 mmol), (2-fluoro-6-(trifluoromethyl)phenyl)boronic acid (17 mg, 0.080 mmol), XPhos Pd G2 (3 mg, 4.00 μmol), and potassium phosphate, tribasic (26 mg, 0.121 mmol) was evacuated and backfilled with nitrogen three times, followed by the addition of 1,4-dioxane (1 mL) and water (250 μL). The vial was sealed and heated to 100° C. for 3 h. After cooling to room temperature, the mixture was filtered through Celite and washed with $CH_2Cl_2$, followed by concentration of the filtrate in vacuo. The obtained crude product was then dissolved in $CH_2Cl_2$(2 mL) and TFA (1 mL) and left to stir at r.t. for 1 h. The reaction mixture was concentrated in vacuo, then dissolved in MeOH (1 mL) and added to a stirring solution of saturated aqueous $NaHCO_3$ (5 mL). The resulting precipitate was filtered and collected, followed by drying under vacuum. LCMS calculated for $C_{25}H_{21}ClF_3N_6$ $(M+H)^+$: m/z=497.1/499.1; found 497.3/499.3.

Step 8. (S)-1-(3-(4-(2-(2-Chloro-6-(trifluoromethyl)phenyl)-3-methylimidazo[2,1-f][1,6]naphthyridin-9-yl)-1H-pyrazol-1-yl)pyrrolidin-1-yl)-2-hydroxyethan-1-one To a vial containing (S)-2-(2-chloro-6-(trifluoromethyl)phenyl)-3-methyl-9-(1-(pyrrolidin-3-yl)-1H-pyrazol-4-yl)imidazo[2,1-f][1,6]naphthyridine (20 mg, 0.040 mmol) as a solution in DMF (0.5 mL) was added 2-hydroxyacetic acid (6 mg, 0.080 mmol), diisopropylethylamine (14 μL, 0.080 mmol), and HATU (23 mg, 0.060 mmol). The reaction mixture was left to stir at r.t. for 1 h, upon which time water was added and the resulting solid was collected by filtration and washed with water. The solid was then dissolved with $CH_3CN$ and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{27}H_{23}ClF_3N_6O_2$ $(M+H)^+$: m/z=555.2; found 555.3.

Example 26. (S)-1-(3-(4-(2-(2,6-Dimethylphenyl)-3-methylimidazo[2,1-f][1,6]naphthyridin-9-yl)-1H-pyrazol-1-yl)pyrrolidin-1-yl)-2-hydroxyethan-1-one

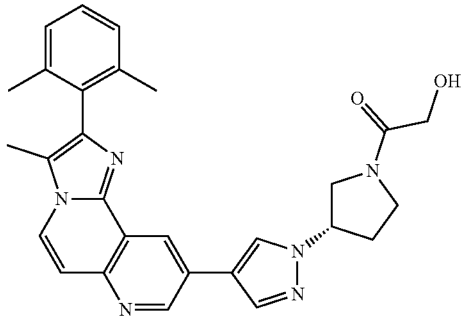 [SMILES: Cc1cccc(C)c1-c1nc2c3cc(-c4cnn([C@H]5CCN(C(=O)CO)C5)c4)cnc3ccn2c1C]

This compound was prepared according to the procedures described in Example 25, with (2,6-dimethylphenyl)boronic acid replacing (2-fluoro-6-(trifluoromethyl)phenyl)boronic acid in Step 7. The title compound was isolated as the TFA salt. LCMS calculated for $C_{28}H_{29}N_6O_2$ $(M+H)^+$: m/z=481.2; Found: 481.4.

Example 27. (S)-3-Fluoro-2-(9-(1-(1-(2-hydroxyacetyl)pyrrolidin-3-yl)-1H-pyrazol-4-yl)-3-methylimidazo[2,1-f][1,6]naphthyridin-2-yl)benzonitrile

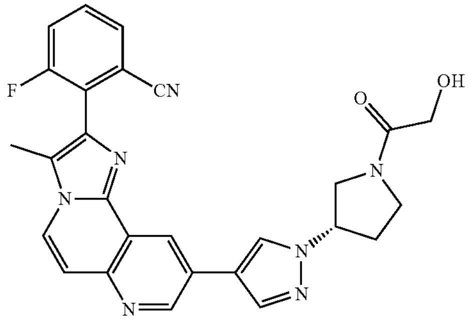 [SMILES: Cc1c(-c2c(F)cccc2C#N)nc2c3cc(-c4cnn([C@H]5CCN(C(=O)CO)C5)c4)cnc3ccn12]

This compound was prepared according to the procedures described in Example 25, with (2-cyano-6-fluorophenyl)boronic acid replacing (2-fluoro-6-(trifluoromethyl)phenyl)boronic acid in Step 7. The title compound was isolated as the TFA salt. LCMS calculated for $C_{27}H_{23}FN_7O_2$ $(M+H)^+$: m/z=496.2; Found: 496.3.

Example 28. (S)-1-(3-(4-(2-(2-Fluoro-6-methoxyphenyl)-3-methylimidazo[2,1-f][1,6]naphthyridin-9-yl)-1H-pyrazol-1-yl)pyrrolidin-1-yl)-2-hydroxyethan-1-one

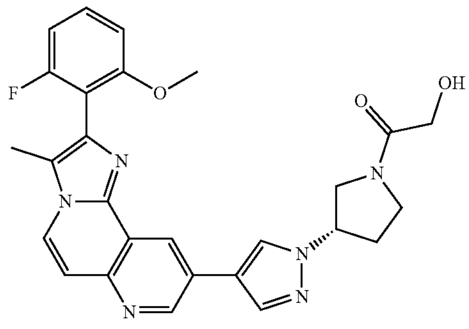 [SMILES: COc1cccc(F)c1-c1nc2c3cc(-c4cnn([C@H]5CCN(C(=O)CO)C5)c4)cnc3ccn2c1C]

This compound was prepared according to the procedures described in Example 25, with (2-fluoro-6-methoxyphenyl) boronic acid replacing (2-fluoro-6-(trifluoromethyl)phenyl) boronic acid in Step 7. The title compound was isolated as the TFA salt. LCMS calculated for $C_{27}H_{26}FN_6O_3$ $(M+H)^+$: m/z=501.2; Found: 501.2.

Intermediate 2. 2-Bromo-3-methyl-9-(1-methyl-1H-pyrazol-4-yl)imidazo[2,1-f][1,6]naphthyridine

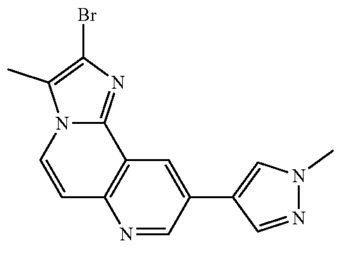

This compound was prepared according to the procedures described in Example 25, Steps 1 through 6, with 1-methyl-4-(4,4,5,5-tetramethyl-1,3,2-dioxaborolan-2-yl)-1H-pyrazole replacing 4-(4,4,5,5-tetramethyl-1,3,2-dioxaborolan-2-yl)-1-((2-(trimethylsilyl)ethoxy)methyl)-1H-pyrazole in Step 2. The title compound was isolated as the TFA salt. LCMS calculated for $C_{15}H_{13}BrN_5$ $(M+H)^+$: m/z=342.0/344.0; Found: 342.0/344.0.

Example 29. 2-(2,3-Dimethylphenyl)-3-methyl-9-(1-methyl-1H-pyrazol-4-yl)imidazo[2,1-f][1,6]naphthyridine

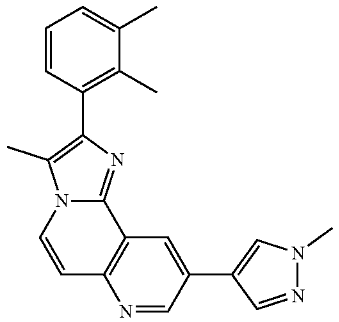

A vial containing a mixture of 2-bromo-3-methyl-9-(1-methyl-1H-pyrazol-4-yl)imidazo[2,1-f][1,6]naphthyridine (Intermediate 2, 10 mg, 0.029 mmol), (2,3-dimethylphenyl) boronic acid (9 mg, 0.058 mmol), XPhos Pd G2 (2 mg, 2.9 μmol), and potassium phosphate, tribasic (19 mg, 0.088 mmol) was evacuated and backfilled with nitrogen three times, followed by the addition of 1,4-dioxane (1 mL) and water (250 μL). The vial was sealed and heated to 80° C. for 2 h. After cooling to room temperature, the mixture was diluted with $CH_3CN$ and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{23}H_{22}N_5$ $(M+H)^+$: m/z=368.2; Found: 368.2. $^1H$ NMR (400 MHz, DMSO-$d_6$) δ 9.34 (d, J=2.2 Hz, 1H), 8.98 (d, J=2.3 Hz, 1H), 8.60 (d, J=7.3 Hz, 1H), 8.48 (s, 1H), 8.12 (s, 1H), 7.64 (d, J=7.5 Hz, 1H), 7.36 (d, J=4.6 Hz, 1H), 7.29 (d, J=4.5 Hz, 2H), 3.94 (s, 3H), 2.48 (s, 3H), 2.37 (s, 3H), 2.21 (s, 3H).

Example 30. (3-Methyl-4-(3-methyl-9-(1-methyl-1H-pyrazol-4-yl)imidazo[2,1-f][1,6]naphthyridin-2-yl)phenyl)methanol

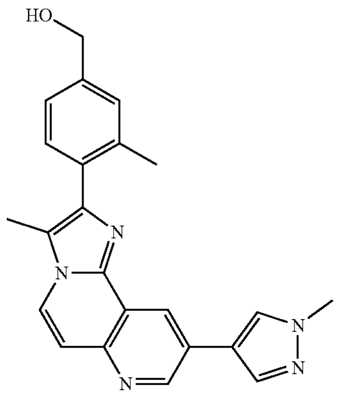

This compound was prepared according to the procedures described in Example 29, with (4-(hydroxymethyl)-2-methylphenyl)boronic acid replacing (2,3-dimethylphenyl)boronic acid. The title compound was isolated as the TFA salt. LCMS calculated for $C_{23}H_{22}N_5O$ $(M+H)^+$: m/z=384.2; Found: 384.3.

Example 31. 2-(2,6-Dichlorophenyl)-3-methyl-9-(1-methyl-1H-pyrazol-4-yl)imidazo[2,1-f][1,6]naphthyridin-8-ol

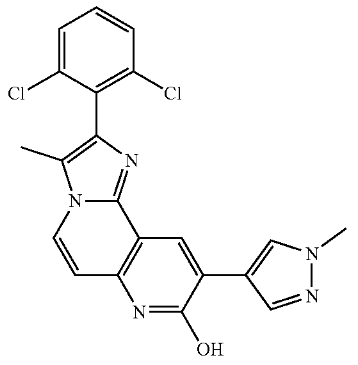

Step 1. 2-(2,6-Dichlorophenyl)-3-methyl-9-(1-methyl-1H-pyrazol-4-yl)imidazo[2,1-f][1,6]naphthyridine

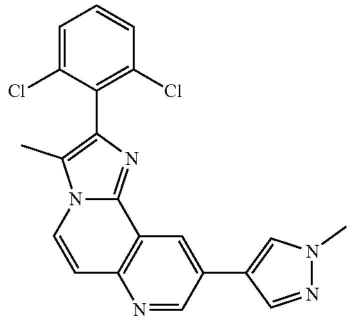

A vial containing a mixture of 2-bromo-3-methyl-9-(1-methyl-1H-pyrazol-4-yl)imidazo[2,1-f][1,6]naphthyridine (Intermediate 2, 600 mg, 1.75 mmol), (2,6-dichlorophenyl) boronic acid (836 mg, 4.38 mmol), potassium fluoride (336 mg, 5.79 mmol) and $Pd_2(dba)_3$ (321 mg, 0.351 mmol) was evacuated and backfilled with nitrogen three times, followed by the addition of 1,4-dioxane (16 mL), water (1.6 mL), and tri-tert-butylphosphine (1.0 M in toluene, 700 μL, 0.7 mmol). The vial was sealed and heated to 100° C. for 1 h. After cooling to room temperature, the mixture was filtered through Celite and washed with $CH_2Cl_2$, followed by concentration of the filtrate in vacuo. The obtained crude product was purified by Biotage Isolera to give the desired product as a yellow solid. LCMS calculated for $C_{21}H_{16}Cl_2N_5$ $(M+H)^+$: m/z=408.1/410.1; Found: 408.1/410.1.

Step 2. 2-(2,6-Dichlorophenyl)-3-methyl-9-(1-methyl-1H-pyrazol-4-yl)imidazo[2,1-f][1,6]naphthyridine 7-oxide

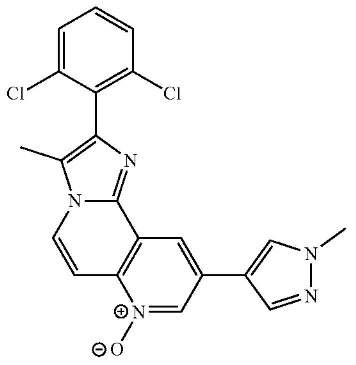

To a vial containing 2-(2,6-dichlorophenyl)-3-methyl-9-(1-methyl-1H-pyrazol-4-yl)imidazo[2,1-f][1,6]naphthyridine (400 mg, 0.980 mmol) as a solution in $CH_2Cl_2$ (10 mL) was added m-CPBA (220 mg, 0.980 mmol) and left to stir at r.t. After 1 h, added a second portion of m-CPBA (220 mg, 0.980 mmol) and left to stir for 1 h. The volatiles were removed in vacuo and the crude residue was purified by Biotage Isolera to give the desired product as a yellow solid (260 mg, 62.5% yield). LCMS calculated for $C_{21}H_{16}Cl_2N_5O$ $(M+H)^+$: m/z=424.1/426.1; Found: 424.0/426.1.

Step 3. 8-Chloro-2-(2,6-dichlorophenyl)-3-methyl-9-(1-methyl-1H-pyrazol-4-yl)imidazo[2,1-f][1,6]naphthyridine & 10-chloro-2-(2,6-dichlorophenyl)-3-methyl-9-(1-methyl-1H-pyrazol-4-yl)imidazo[2,1-f][1,6]naphthyridine

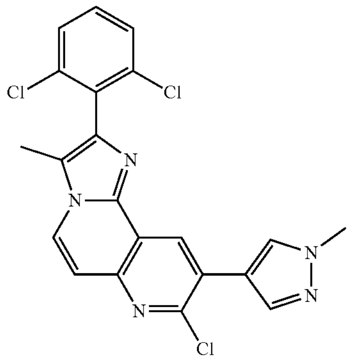

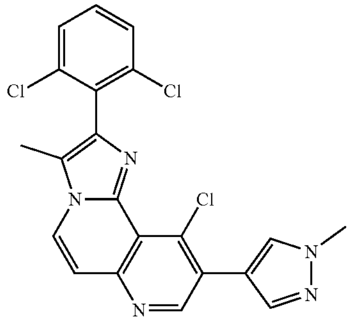

To a vial containing 2-(2,6-dichlorophenyl)-3-methyl-9-(1-methyl-1H-pyrazol-4-yl)imidazo[2,1-f][1,6]naphthyridine 7-oxide (100 mg, 0.236 mmol) as a solution in $CH_2Cl_2$ (2 mL) was added phosphoryl chloride (879 μL, 9.43 mmol) and left to stir at r.t. for 1 h. The volatiles were removed in vacuo and the resulting residue was treated with saturated aqueous $NaHCO_3$ and extracted with $CH_2Cl_2$. The organic phase was washed with brine, dried over $MgSO_4$, filtered and the solvent was evaporated in vacuo. The resulting residue was purified by Biotage Isolera to give the desired products as yellow solids. LCMS calculated for $C_{21}H_{15}Cl_3N_5$ $(M+H)^+$: m/z=442.0/444.0; Found: 442.2/444.2.

Step 4. 2-(2,6-Dichlorophenyl)-3-methyl-9-(1-methyl-1H-pyrazol-4-yl)imidazo[2,1-f][1,6]naphthyridin-8-ol To a vial containing 8-chloro-2-(2,6-dichlorophenyl)-3-methyl-9-(1-methyl-1H-pyrazol-4-yl)imidazo[2,1-f][1,6]naphthyridine (10 mg, 0.023 mmol) as a solution in 1,4-dioxane (0.5 mL) was added lithium hydroxide (2.0 M in $H_2O$, 500 μL, 1.00 mmol). The vial was sealed and heated to 100° C. for 16 h. After cooling to room temperature, the mixture was diluted with $CH_3CN$ and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{21}H_{16}Cl_2N_5O$ $(M+H)^+$: m/z=424.1/426.1; Found: 424.0/426.1.

Example 32. (S)-2-(2,6-Dichlorophenyl)-3-methyl-9-(1-methyl-1H-pyrazol-4-yl)-10-((tetrahydrofuran-3-yl)oxy)imidazo[2,1-f][1,6]naphthyridine

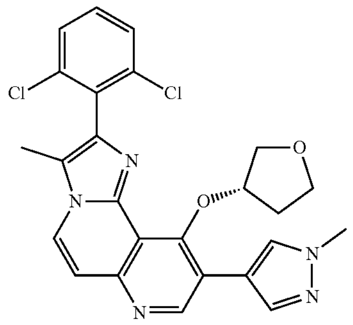

To a vial containing 10-chloro-2-(2,6-dichlorophenyl)-3-methyl-9-(1-methyl-1H-pyrazol-4-yl)imidazo[2,1-f][1,6]naphthyridine (Example 31, Step 3, 15 mg, 0.034 mmol) as a solution in 1,4-dioxane (1 mL) was added cesium carbonate (110 mg, 0.339 mmol) and (S)-tetrahydrofuran-3-ol (27 μL, 0.339 mmol). The vial was sealed and heated to 100° C. for 16 h. After cooling to room temperature, the mixture was diluted with $CH_3CN$ and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{25}H_{22}Cl_2N_5O_2$ $(M+H)^+$: m/z=494.1/496.1; Found: 494.2/496.2.

Example 33. 2-(2,6-Dichlorophenyl)-N,N,3-trimethyl-9-(1-methyl-1H-pyrazol-4-yl)imidazo[2,1-f][1,6]naphthyridin-8-amine

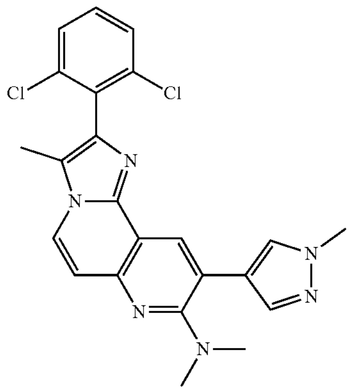

To a vial containing 8-chloro-2-(2,6-dichlorophenyl)-3-methyl-9-(1-methyl-1H-pyrazol-4-yl)imidazo[2,1-f][1,6]naphthyridine (Example 31, Step 3, 25 mg, 0.056 mmol) as a solution in DMSO (565 μL) was added diisopropylethylamine (15 μL, 0.085 mmol) and dimethylamine (2.0 M in THF, 31 μL, 0.062 mmol). The vial was sealed and heated to 100° C. for 16 h. After cooling to room temperature, the mixture was diluted with $CH_3CN$ and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{23}H_{21}Cl_2N_6$ $(M+H)^+$: m/z=451.1/453.1; Found: 451.1/453.2.

Example 34. N-(2,4-Dichloro-3-(3-methyl-9-(1-methyl-1H-pyrazol-4-yl)imidazo[2,1-f][1,6]naphthyridin-2-yl)phenyl)acrylamide

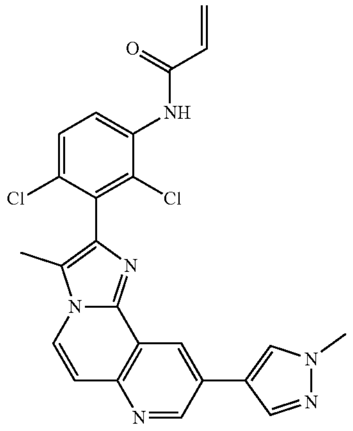

Step 1. (3-Amino-2,6-dichlorophenyl)boronic acid

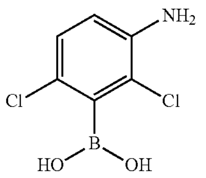 [SMILES: Nc1ccc(Cl)c(B(O)O)c1Cl]

A vial containing (2,6-dichloro-3-nitrophenyl)boronic acid (300 mg, 1.27 mmol) and palladium on carbon (10 wt %, 2.4 mg, 3.4 μmol) as a solution in methanol (10 mL) was connected to a balloon with hydrogen and evacuated and backfilled three times. The reaction mixture was left to stir for 1 h, then filtered through Celite and washed with methanol, followed by concentration of the filtrate in vacuo. The obtained crude product was used in the next step without further purification.

Step 2. 2,4-Dichloro-3-(3-methyl-9-(1-methyl-1H-pyrazol-4-yl)imidazo[2,1-f][1.6]naphthyridin-2-yl) aniline

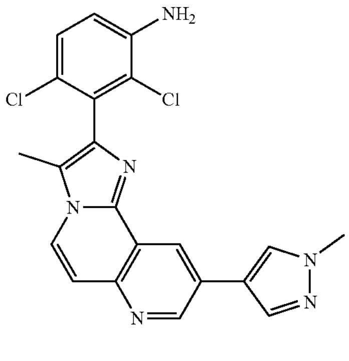

A vial containing a mixture of 2-bromo-3-methyl-9-(1-methyl-1H-pyrazol-4-yl)imidazo[2,1-f][1,6]naphthyridine (Intermediate 2, 20 mg, 0.058 mmol), (3-amino-2,6-dichlorophenyl)boronic acid (12 mg, 0.058 mmol), XPhos Pd G2 (4.2 mg, 5.8 μmol), and potassium phosphate, tribasic (37 mg, 0.175 mmol) was evacuated and backfilled with nitrogen three times, followed by the addition of 1,4-dioxane (1 mL) and water (250 μL). The vial was sealed and heated to 80° C. for 1 h. After cooling to room temperature, the mixture was filtered through Celite and washed with $CH_2Cl_2$, followed by concentration of the filtrate in vacuo. The obtained crude product was used in the next step without further purification. LCMS calculated for $C_{21}H_{17}Cl_2N_6$ $(M+H)^+$: m/z=423.1/425.1; Found: 423.2/425.2.

Step 3. N-(2,4-Dichloro-3-(3-methyl-9-(1-methyl-1H-pyrazol-4-yl)imidazo[2,1-f][1,6]naphthyridin-2-yl)phenyl)acrylamide To a vial containing 2,4-dichloro-3-(3-methyl-9-(1-methyl-1H-pyrazol-4-yl)imidazo[2,1-f][1,6]naphthyridin-2-yl)aniline (25 mg, 0.058 mmol) as a solution in $CH_2Cl_2$ (1 mL) was added diisopropylethylamine (30 μL, 0.174 mmol) and acryloyl chloride (6 μL, 0.075 mmol). The vial was left to stir at r.t. for 1 h. After the volatiles were removed in vacuo, the mixture was diluted with $CH_3CN$ and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{24}H_{19}Cl_2N_6O$ $(M+H)^+$: m/z=477.1/479.1; Found: 477.1/479.0.

Example 35. N-(3-(3-Methyl-9-(1-methyl-1H-pyrazol-4-yl)imidazo[2,1-f][1,6]naphthyridin-2-yl)phenyl)acrylamide

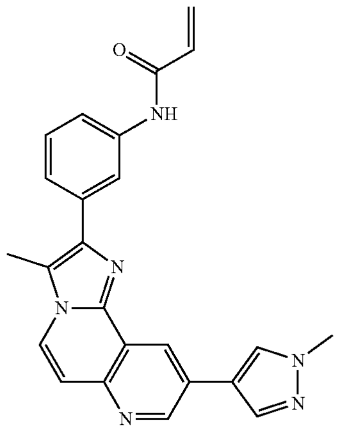

This compound was prepared according to the procedures described in Example 34, with (3-aminophenyl)boronic acid replacing (3-amino-2,6-dichlorophenyl)boronic acid in Step 2. The title compound was isolated as the TFA salt. LCMS calculated for $C_{24}H_{21}N_6O$ $(M+H)^+$: m/z=409.2; Found: 409.1. $^1H$ NMR (400 MHz, DMSO-$d_6$) δ 10.34 (s, 1H), 9.25 (d, J=2.2 Hz, 1H), 8.95 (d, J=2.2 Hz, 1H), 8.51 (d, J=7.6 Hz, 2H), 8.24 (d, J=1.9 Hz, 1H), 8.17 (s, 1H), 7.73 (dd, J=8.1, 2.0 Hz, 1H), 7.61-7.55 (m, 1H), 7.52 (d, J=7.9 Hz, 1H), 7.50-7.43 (m, 1H), 6.50 (dd, J=17.0, 10.1 Hz, 1H), 6.31 (dd, J=17.0, 2.0 Hz, 1H), 5.81 (dd, J=10.1, 2.0 Hz, 1H), 3.94 (s, 3H), 2.75 (s, 3H).

Example 36. N-(2-(3-Methyl-9-(1-methyl-1H-pyrazol-4-yl)imidazo[2,1-f][1,6]naphthyridin-2-yl)phenyl)acrylamide

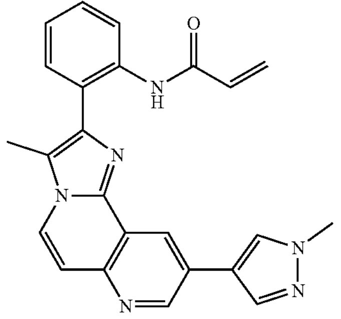

This compound was prepared according to the procedures described in Example 34, with 2-(4,4,5,5-tetramethyl-1,3,2-dioxaborolan-2-yl)aniline replacing (3-amino-2,6-dichlorophenyl)boronic acid in Step 2. The title compound was isolated as the TFA salt. LCMS calculated for $C_{24}H_{21}N_6O$ $(M+H)^+$: m/z=409.2; Found: 409.1.

Example 37. (1-Aminocyclopropyl)(3-(4-(2-(2,6-dichlorophenyl)-3-methylimidazo[2,1-f][1,6]naphthyridin-9-yl)-1H-pyrazol-1-yl)azetidin-1-yl)methanone

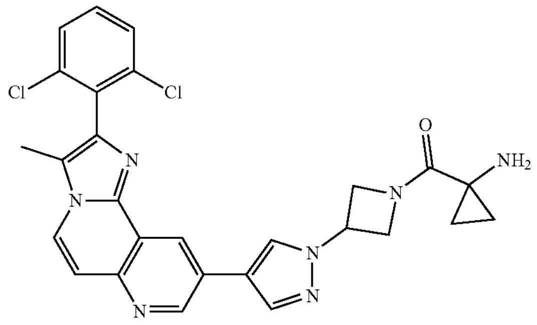 [SMILES: Cc1c(-c2c(Cl)cccc2Cl)nc2c3cc(-c4cnn(C5CN(C(=O)C6(N)CC6)C5)c4)cnc3ccn12]

Step 1. 2-(2,6-Dichlorophenyl)-9-(1-((2-(trimethylsilyl)ethoxy)methyl)-1H-pyrazol-4-yl)imidazo[2,1-f][1.6]naphthyridine

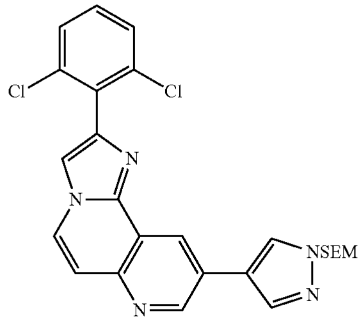 [SMILES: C[Si](C)(C)CCOCn1cc(-c2cnc3ccn4cc(-c5c(Cl)cccc5Cl)nc4c3c2)cn1]

A vial containing a mixture of 9-bromo-2-(2,6-dichlorophenyl)imidazo[2,1-f][1,6]naphthyridine (Example 15, Step 1, 1.0 g, 2.54 mmol), 4-(4,4,5,5-tetramethyl-1,3,2-dioxaborolan-2-yl)-1-((2-(trimethylsilyl)ethoxy)methyl)-1H-pyrazole (866 mg, 2.67 mmol), (1,1'-bis(diphenylphosphino)ferrocene)-dichloropalladium(II) (208 mg, 0.254 mmol), and potassium phosphate, tribasic (1.62 g, 7.63 mmol) was evacuated and backfilled with nitrogen three times, followed by the addition of 1,4-dioxane (13.5 mL) and water (3.5 mL). The vial was sealed and heated to 80° C. for 30 min. After cooling to room temperature, the mixture was filtered through Celite and washed with $CH_2Cl_2$, followed by concentration of the filtrate in vacuo. The obtained crude residue was purified by Biotage Isolera to give the desired product. LCMS calculated for $C_{25}H_{26}Cl_2N_5OSi$ $(M+H)^+$: m/z=510.1/512.1; found 510.1/512.1.

Step 2. 3-Bromo-2-(2,6-dichlorophenyl)-9-(1-((2-(trimethylsilyl)ethoxy)methyl)-1H-pyrazol-4-yl)imidazo[2,1-f][1.6]naphthyridine

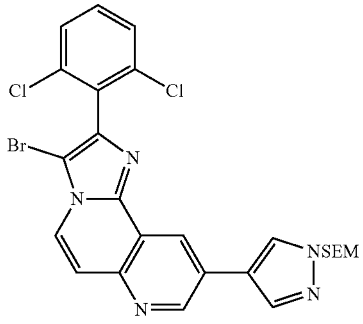 [SMILES: C[Si](C)(C)CCOCn1cc(-c2cnc3ccn4c(Br)c(-c5c(Cl)cccc5Cl)nc4c3c2)cn1]

This compound was prepared according to the procedures described in Example 25, with 2-(2,6-dichlorophenyl)-9-(1-((2-(trimethylsilyl)ethoxy)methyl)-1H-pyrazol-4-yl)imidazo[2,1-f][1,6]naphthyridine replacing 9-(1-((2-(trimethylsilyl)ethoxy)methyl)-1H-pyrazol-4-yl)imidazo[2,1-f][1,6]naphthyridine in Step 3. LCMS calculated for $C_{25}H_{25}BrCl_2N_5OSi$ $(M+H)^+$: m/z=588.0/590.0/592.0; Found: 588.2/590.2/592.2.

Step 3. 2-(2,6-Dichlorophenyl)-3-methyl-9-(1-((2-(trimethylsilyl)ethoxy)methyl)-1H-pyrazol-4-yl)imidazo[2,1-f][1.6]naphthyridine

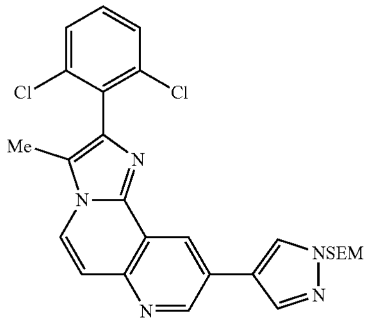 [SMILES: Cc1c(-c2c(Cl)cccc2Cl)nc2c3cc(-c4cnn(COCC[Si](C)(C)C)c4)cnc3ccn12]

This compound was prepared according to the procedures described in Example 1, with 3-bromo-2-(2,6-dichlorophenyl)-9-(1-((2-(trimethylsilyl)ethoxy)methyl)-1H-pyrazol-4-yl)imidazo[2,1-f][1,6]naphthyridine replacing 3-bromo-2-(2-chlorophenyl)-9-(1-methyl-1H-pyrazol-4-yl)imidazo[2,1-f][1,6]naphthyridine in Step 6. LCMS calculated for $C_{26}H_{28}Cl_2N_5OSi$ $(M+H)^+$: m/z=524.1/526.1; Found: 524.1/526.1.

Step 4. 2-(2,6-Dichlorophenyl)-3-methyl-9-(1H-pyrazol-4-yl)imidazo[2,1-f][1,6]naphthyridine

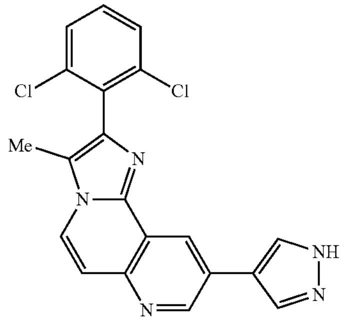 [SMILES: Cc1c(-c2c(Cl)cccc2Cl)nc2c3cc(-c4cn[nH]c4)cnc3ccn12]

To a vial containing a mixture of 2-(2,6-dichlorophenyl)-3-methyl-9-(1-((2-(trimethylsilyl)ethoxy)methyl)-1H-pyrazol-4-yl)imidazo[2,1-f][1,6]naphthyridine (1.33 g, 2.54 mmol) as a solution in $CH_2Cl_2$ (10 mL) was added TFA (3 mL). The reaction mixture was stirred at r.t. for 3 h, concentrated in vacuo, then dissolved in MeOH (2 mL) and added to a stirring solution of saturated aqueous $NaHCO_3$ (50 mL). The resulting tan precipitate was filtered and collected, washed with water, followed by drying under vacuum overnight. LCMS calculated for $C_{20}H_{14}Cl_2N_5$ $(M+H)^+$: m/z=394.1/396.1; found 394.0/396.0.

Step 5. 9-(1-(Azetidin-3-yl)-1H-pyrazol-4-yl)-2-(2,6-dichlorophenyl)-3-methylimidazo[2,1-f][1,6]naphthyridine

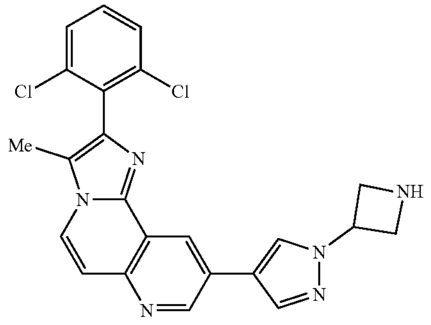 [SMILES: Cc1c(-c2c(Cl)cccc2Cl)nc2c3cc(-c4cnn(C5CNC5)c4)cnc3ccn12]

To a vial containing a mixture of 2-(2,6-dichlorophenyl)-3-methyl-9-(1H-pyrazol-4-yl)imidazo[2,1-f][1,6]naphthyridine (250 mg, 0.634 mmol), tert-butyl 3-((methylsulfonyl)oxy)azetidine-1-carboxylate (319 mg, 1.27 mmol), cesium carbonate (620 mg, 1.90 mmol) was added MeCN (6.3 mL). The vial was sealed and heated to 80° C. for 16 h. After cooling to room temperature, the mixture was filtered through Celite and washed with MeCN, followed by concentration of the filtrate in vacuo. The resulting residue was purified by Biotage Isolera to give the desired product as a tan solid. The purified material was then dissolved in $CH_2Cl_2$(3 mL) and TFA (1 mL) and left to stir at r.t. for 1 h. The reaction mixture was concentrated in vacuo, then dissolved in MeOH (3 mL) and added to a stirring solution of saturated aqueous $NaHCO_3$ (15 mL). The resulting solid precipitate was filtered and collected, followed by drying under vacuum overnight. LCMS calculated for $C_{23}H_{19}Cl_2N_6$ $(M+H)^+$: m/z=449.1/451.1; Found: 449.1/451.1.

Step 6. (1-Aminocyclopropyl)(3-(4-(2-(2,6-dichlorophenyl)-3-methylimidazo[2,1-f][1,6]naphthyridin-9-yl)-1H-pyrazol-1-yl)azetidin-1-yl)methanone To a vial containing 9-(1-(azetidin-3-yl)-1H-pyrazol-4-yl)-2-(2,6-dichlorophenyl)-3-methylimidazo[2,1-f][1,6]naphthyridine (50 mg, 0.111 mmol) as a solution in DMF (1 mL) was added 1-((tert-butoxycarbonyl)amino)cyclopropane-1-carboxylic acid (34 mg, 0.167 mmol), diisopropylethylamine (39 μL, 0.223 mmol), and HATU (64 mg, 0.167 mmol). The reaction mixture was left to stir at r.t. for 1 h, upon which time water was added and the resulting solid was collected by filtration and washed with water, followed by hexanes and drying under vacuum. The solid was then dissolved with TFA and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{27}H_{24}Cl_2N_7O$ $(M+H)^+$: m/z=532.1/534.1; found 532.2/534.2. $^1H$ NMR (400 MHz, DMSO-$d_6$) δ 9.25 (d, J=2.3 Hz, 1H), 8.96 (d, J=2.3 Hz, 1H), 8.81 (s, 1H), 8.53 (s, 2H), 8.46 (d, J=7.5 Hz, 1H), 8.41 (s, 1H), 7.69-7.61 (m, 2H), 7.55 (dd, J=8.9, 7.3 Hz, 1H), 7.41 (d, J=7.5 Hz, 1H), 5.36-5.25 (m, 1H), 4.80-4.25 (m, 4H), 2.39 (s, 3H), 1.56 (m, 2H), 1.29-1.23 (m, 2H).

Example 38. 1-(3-(4-(2-(2,6-Dichlorophenyl)-3-methylimidazo[2,1-f][1,6]naphthyridin-9-yl)-1H-pyrazol-1-yl)azetidin-1-yl)-2-(1H-imidazol-1-yl)ethan-1-one

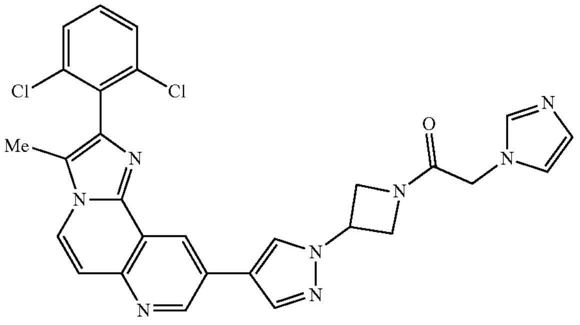 [SMILES: Cc1c(-c2c(Cl)cccc2Cl)nc2c3cc(-c4cnn(C5CN(C(=O)Cn6ccnc6)C5)c4)cnc3ccn12]

This compound was prepared according to the procedures described in Example 37, with 2-(1H-imidazol-1-yl)acetic acid replacing 1-((tert-butoxycarbonyl)amino)cyclopropane-1-carboxylic acid in Step 6. The title compound was isolated as the TFA salt. LCMS calculated for $C_{28}H_{23}Cl_2N_8O$ $(M+H)^+$: m/z=557.1/559.1; Found: 557.2/559.3.

Example 39. (3-(4-(2-(2,6-Dichlorophenyl)-3-methylimidazo[2,1-f][1,6]naphthyridin-9-yl)-1H-pyrazol-1-yl)azetidin-1-yl)(oxazol-4-yl)methanone

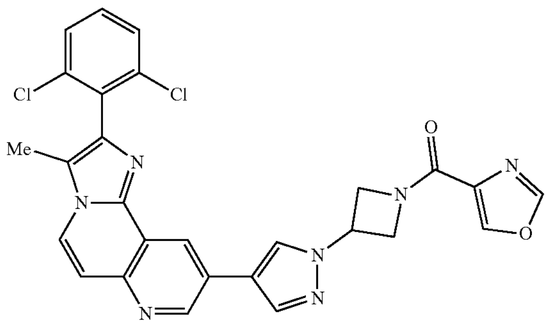 [SMILES: Cc1c(-c2c(Cl)cccc2Cl)nc2c3cc(-c4cnn(C5CN(C(=O)c6cocn6)C5)c4)cnc3ccn12]

This compound was prepared according to the procedures described in Example 37, with oxazole-4-carboxylic acid replacing 1-((tert-butoxycarbonyl)amino)cyclopropane-1-carboxylic acid in Step 6. The title compound was isolated as the TFA salt. LCMS calculated for $C_{27}H_{20}Cl_2N_7O_2$ $(M+H)^+$: m/z=544.1/546.1; Found: 544.1/546.3.

Example 40. (4-Aminotetrahydro-2H-pyran-4-yl)(3-(4-(2-(2,6-dichlorophenyl)-3-methylimidazo[2,1-f][1,6]naphthyridin-9-yl)-1H-pyrazol-1-yl)azetidin-1-yl)methanone

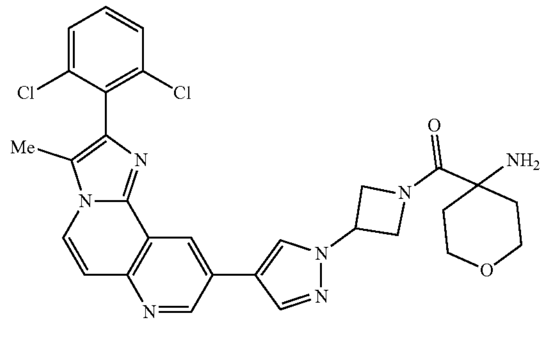 [SMILES: Cc1c(-c2c(Cl)cccc2Cl)nc2c3cc(-c4cnn(C5CN(C(=O)C6(N)CCOCC6)C5)c4)cnc3ccn12]

This compound was prepared according to the procedures described in Example 37, with 4-((tert-butoxycarbonyl)amino)tetrahydro-2H-pyran-4-carboxylic acid replacing 1-((tert-butoxycarbonyl)amino)cyclopropane-1-carboxylic acid in Step 6. The title compound was isolated as the TFA salt. LCMS calculated for $C_{29}H_{28}Cl_2N_7O_2$ $(M+H)^+$: m/z=576.2/578.2; Found: 576.2/578.2.

Example 41. 3-(3-(4-(2-(2,6-Dichlorophenyl)-3-methylimidazo[2,1-f][1,6]naphthyridin-9-yl)-1H-pyrazol-1-yl)azetidin-1-yl)-3-oxopropanenitrile

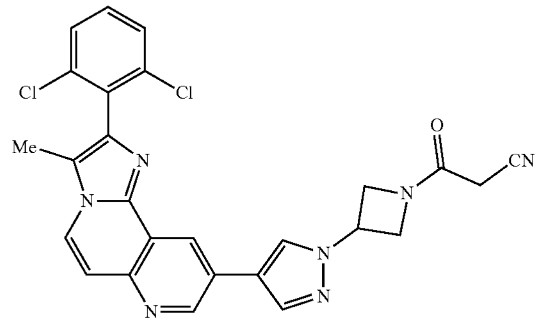 [SMILES: Cc1c(-c2c(Cl)cccc2Cl)nc2c3cc(-c4cnn(C5CN(C(=O)CC#N)C5)c4)cnc3ccn12]

To a vial containing 9-(1-(azetidin-3-yl)-1H-pyrazol-4-yl)-2-(2,6-dichlorophenyl)-3-methylimidazo[2,1-f][1,6]naphthyridinene (Example 37, Step 5, 10 mg, 0.022 mmol) as a solution in ethanol (200 μL) was added DBU (4 μL, 0.022 mmol) and ethyl 2-cyanoacetate (24 μL, 0.223 mmol). The vial was sealed and heated to 100° C. for 4 h. After cooling to room temperature, the mixture was then diluted with $CH_3CN$ and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{26}H_{20}Cl_2N_7O$ $(M+H)^+$: m/z=516.1/518.1; found 516.2/518.1.

Example 42. 4-((4-(2-(2,6-Dichlorophenyl)imidazo[2,1-f][1,6]naphthyridin-9-yl)-1H-pyrazol-1-yl)methyl)-2-fluorobenzoic acid

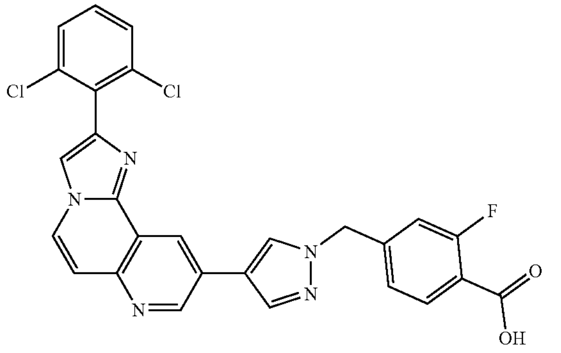 [SMILES: O=C(O)c1ccc(Cn2cc(-c3cnc4ccn5cc(-c6c(Cl)cccc6Cl)nc5c4c3)cn2)cc1F]

To a vial containing a mixture of 2-(2,6-dichlorophenyl)-9-(1H-pyrazol-4-yl)imidazo[2,1-f][1,6]naphthyridine (20 mg, 0.053 mmol, Example 55, Step 2), methyl 4-(bromomethyl)-2-fluorobenzoate (16 mg, 0.063 mmol), and cesium carbonate (34 mg, 0.105 mmol) was added MeCN (1 mL). The vial was sealed and heated to 80° C. for 16 h. After cooling to room temperature, the mixture was filtered through Celite and washed with MeCN, followed by concentration of the filtrate in vacuo. The resulting residue was then dissolved in 1,4-dioxane (1 mL) and lithium hydroxide solution (2 M in $H_2O$, 0.5 mL) and heated to 50° C. for 1 h. After cooling to room temperature, the volatiles were removed in vacuo and the mixture was diluted with TFA and $CH_3CN$ and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{27}H_{17}Cl_2FN_5O_2$ $(M+H)^+$: m/z=532.1/534.1; Found: 532.1/534.2.

Example 43. 4-(4-(2-(2,6-Dichlorophenyl)imidazo[2,1-f][1,6]naphthyridin-9-yl)-1H-pyrazol-1-yl)-N,N-dimethylbenzamide

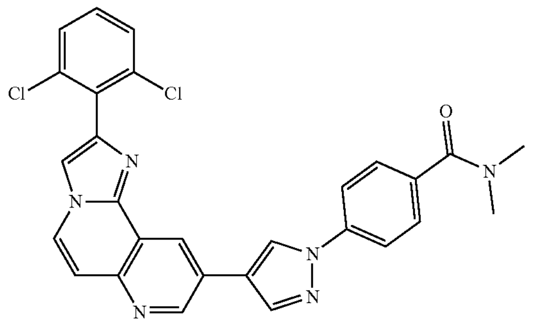 [SMILES: CN(C)C(=O)c1ccc(-n2cc(-c3cnc4ccn5cc(-c6c(Cl)cccc6Cl)nc5c4c3)cn2)cc1]

A vial containing a mixture of 2-(2,6-dichlorophenyl)-9-(1H-pyrazol-4-yl)imidazo[2,1-f][1,6]naphthyridine (15 mg, 0.039 mmol, Example 55, Step 2), 4-bromo-N,N-dimethylbenzamide (16 mg, 0.063 mmol), cesium carbonate (26 mg, 0.079 mmol), and copper(I) iodide (2 mg, 7.9 μmol) was evacuated and backfilled with nitrogen three times, followed by the addition of 1,4-dioxane (1 mL), and trans-N,N'-dimethylcyclohexane-1,2-diamine (5 mg, 0.016 mmol). The vial was sealed and heated to 100° C. for 2 h. After cooling to room temperature, the mixture was diluted with $CH_2Cl_2$ (1 mL), ammonium hydroxide solution (1 mL) and stirred vigorously for 10 min. The organic layer was then separated and concentrated in vacuo. The resulting residue was then diluted with $CH_3CN$ and water and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{28}H_{21}Cl_2N_6O$ $(M+H)^+$: m/z=527.1/529.1; found 527.3/529.3.

Example 44. N-((1r,4r)-4-(4-(2-(2,6-Dichlorophenyl)imidazo[2,1-f][1,6]naphthyridin-9-yl)-1H-pyrazol-1-yl)cyclohexyl)-2-methoxyacetamide

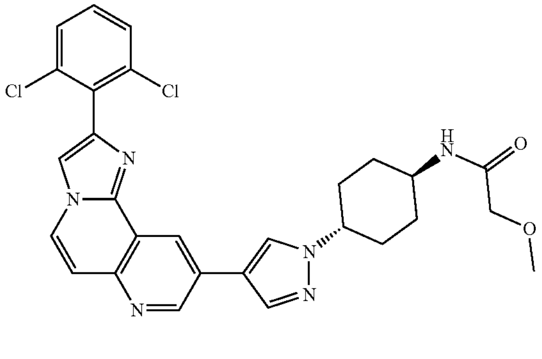 [SMILES: COCC(=O)N[C@H]1CC[C@H](n2cc(-c3cnc4ccn5cc(-c6c(Cl)cccc6Cl)nc5c4c3)cn2)CC1]

Step 1. (1r,4r)-4-(4-(2-(2,6-Dichlorophenyl)imidazo[2,1-f][1,6]naphthyridin-9-yl)-1H-pyrazol-1-yl)cyclohexan-1-amine

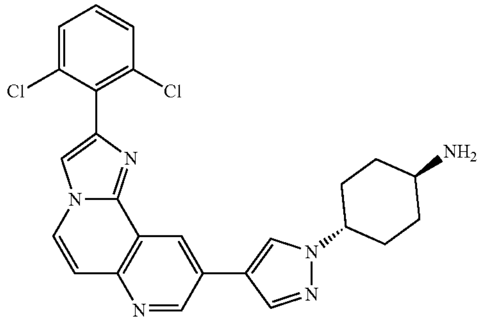 [SMILES: N[C@H]1CC[C@H](n2cc(-c3cnc4ccn5cc(-c6c(Cl)cccc6Cl)nc5c4c3)cn2)CC1]

To a vial containing a mixture of 2-(2,6-dichlorophenyl)-9-(1H-pyrazol-4-yl)imidazo[2,1-f][1,6]naphthyridine (100 mg, 0.263 mmol, Example 55, Step 2), and cesium carbonate (257 mg, 0.789 mmol) as a suspension in $CH_3CN$ (1.3 mL) was added (1s,4s)-4-((tert-butoxycarbonyl)amino)cyclohexyl 4-methylbenzenesulfonate (97 mg, 0.263 mmol). The vial was sealed and heated to 80° C. for 2 h. After cooling to room temperature, the mixture was filtered and washed with $CH_3CN$, followed by concentration of the filtrate in vacuo. The resulting residue was purified by Biotage Isolera to give a yellow solid. The purified material was then dissolved in $CH_2Cl_2$(3 mL) and TFA (1 mL) and left to stir at r.t. for 1 h. The reaction mixture was concentrated in vacuo, then dissolved in MeOH (1 mL) and added to a stirring solution of saturated aqueous $NaHCO_3$ (5 mL). The resulting solid precipitate was filtered and collected, followed by drying under vacuum overnight. LCMS calculated for $C_{25}H_{23}Cl_2N_6$ $(M+H)^+$: m/z=477.1/479.1; Found: 477.2/479.3.

Step 2. N-((1r,4r)-4-(4-(2-(2,6-Dichlorophenyl)imidazo[2,1-f][1,6]naphthyridin-9-yl)-1H-pyrazol-1-yl)cyclohexyl)-2-methoxyacetamide To a vial containing (1r,4r)-4-(4-(2-(2,6-dichlorophenyl)imidazo[2,1-f][1,6]naphthyridin-9-yl)-1H-pyrazol-1-yl)cyclohexan-1-amine (15 mg, 0.031 mmol) as a solution in DMF (0.5 mL) was added 2-methoxyacetic acid (3 μL, 0.031 mmol), diisopropylethylamine (17 μL, 0.094 mmol), and HATU (18 mg, 0.047 mmol). The reaction mixture was left to stir at r.t. for 1 h, upon which time water was added and the resulting solid was collected by filtration and washed with water. The solid was then dissolved with $CH_3CN$ and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{28}H_{27}Cl_2N_6O_2$ $(M+H)^+$: m/z=549.2/551.2; Found: 549.3/551.3. $^1H$ NMR (400 MHz, DMSO-$d_6$) δ 9.25 (d, J=2.3 Hz, 1H), 8.93 (d, J=2.3 Hz, 1H), 8.69 (s, 1H), 8.61 (d, J=7.4 Hz, 1H), 8.21 (d, J=6.7 Hz, 2H), 7.67 (d, J=8.2 Hz, 1H), 7.66-7.61 (m, 2H), 7.53 (dd, J=8.8, 7.3 Hz, 1H), 7.38 (d, J=7.4 Hz, 1H), 4.22-4.11 (m, 1H), 3.80 (s, 2H), 3.78-3.70 (m, 1H), 3.31 (s, 3H), 2.18-2.10 (m, 2H), 1.94-1.81 (m, 4H), 1.61-1.47 (m, 2H).

Example 45. 3-((1r,4r)-4-(4-(2-(2,6-Dichlorophenyl)imidazo[2,1-f][1,6]naphthyridin-9-yl)-1H-pyrazol-1-yl)cyclohexyl)-1,1-dimethylurea

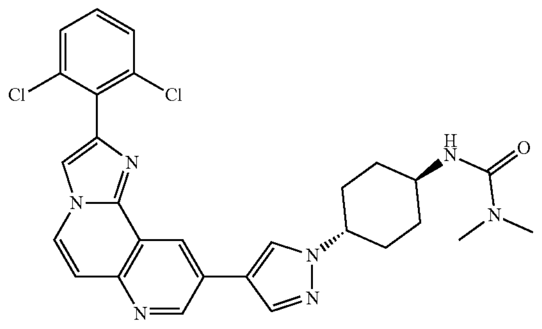 [SMILES: CN(C)C(=O)N[C@H]1CC[C@H](n2cc(-c3cnc4ccn5cc(-c6c(Cl)cccc6Cl)nc5c4c3)cn2)CC1]

To a vial containing a mixture of (1r,4r)-4-(4-(2-(2,6-dichlorophenyl)imidazo[2,1-f][1,6]naphthyridin-9-yl)-1H-pyrazol-1-yl)cyclohexan-1-amine (15 mg, 0.031 mmol, Example 44, Step 1) and diisopropylethylamine (27 μL, 0.157 mmol) as a solution in $CH_3CN$ (1 mL) was added dimethylcarbamyl chloride (6 μL, 0.063 mmol). The solution was left to stir at r.t. for 2 h. The reaction mixture was then diluted with $CH_3CN$ and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{28}H_{28}Cl_2N_7O$ $(M+H)^+$: m/z=548.2/550.2; found 548.3/550.3.

Example 46. 1-(7-(4-(2-(2,6-Dichlorophenyl)imidazo[2,1-f][1,6]naphthyridin-9-yl)-1H-pyrazol-1-yl)-2-azaspiro[3.5]nonan-2-yl)ethan-1-one

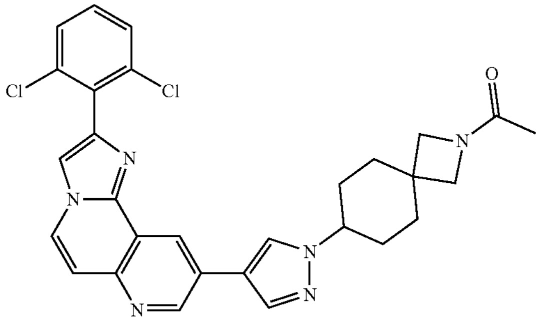 [SMILES: CC(=O)N1CC2(CCC(n3cc(-c4cnc5ccn6cc(-c7c(Cl)cccc7Cl)nc6c5c4)cn3)CC2)C1]

Step 1. 9-(1-(2-Azaspiro[3.5]nonan-7-yl)-1H-pyrazol-4-yl)-2-(2,6-dichlorophenyl)imidazo[2,1-f][1,6]naphthyridine

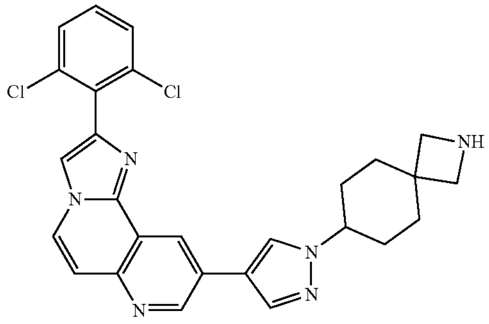 [SMILES: Clc1cccc(Cl)c1-c1cn2ccc3ncc(-c4cnn(C5CCC6(CC5)CNC6)c4)cc3c2n1]

This compound was prepared according to the procedures described in Example 44, with tert-butyl 7-(tosyloxy)-2-azaspiro[3.5]nonane-2-carboxylate replacing (1s,4s)-4-((tert-butoxycarbonyl)amino)cyclohexyl 4-methylbenzenesulfonate in Step 1. LCMS calculated for $C_{27}H_{25}Cl_2N_6$ $(M+H)^+$: m/z=503.2/505.1; Found: 503.2/505.2.

Step 2. 1-(7-(4-(2-(2,6-Dichlorophenyl)imidazo[2,1-f][1,6]naphthyridin-9-yl)-1H-pyrazol-1-yl)-2-azaspiro[3.5]nonan-2-yl)ethan-1-one This compound was prepared according to the procedures described in Example 15, with 9-(1-(2-azaspiro[3.5]nonan-7-yl)-1H-pyrazol-4-yl)-2-(2,6-dichlorophenyl)imidazo[2,1-f][1,6]naphthyridine replacing 2-(2,6-dichlorophenyl)-9-(1-(pyrrolidin-3-yl)-1H-pyrazol-4-yl)imidazo[2,1-f][1,6]naphthyridine in Step 3. The title compound was isolated as the TFA salt. LCMS calculated for $C_{29}H_{27}Cl_2N_6O$ $(M+H)^+$: m/z=545.2/547.2; Found: 545.2/547.2.

Example 47. 2-(2,6-Dichlorophenyl)-3-methyl-9-(1-(tetrahydro-2H-pyran-4-yl)-1H-pyrazol-4-yl)imidazo[2,1-f][1,6]naphthyridine

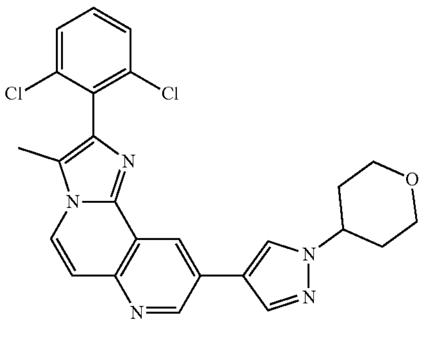 [SMILES: Cc1c(-c2c(Cl)cccc2Cl)nc2c3cc(-c4cnn(C5CCOCC5)c4)cnc3ccn12]

This compound was prepared according to the procedures described in Example 37, Steps 1 through 3, with 1-(tetrahydro-2H-pyran-4-yl)-4-(4,4,5,5-tetramethyl-1,3,2-dioxaborolan-2-yl)-1H-pyrazole replacing 4-(4,4,5,5-tetramethyl-1,3,2-dioxaborolan-2-yl)-1-((2-(trimethylsilyl)ethoxy)methyl)-1H-pyrazole in Step 1. The title compound was isolated as the TFA salt. LCMS calculated for $C_{25}H_{22}Cl_2N_5O$ $(M+H)^+$: m/z=478.1/480.1; Found: 478.3/480.4.

Example 48. (1r,4r)-4-(4-(2-(2,6-Dichlorophenyl)-3-methylimidazo[2,1-f][1,6]naphthyridin-9-yl)-1H-pyrazol-1-yl)cyclohexan-1-ol

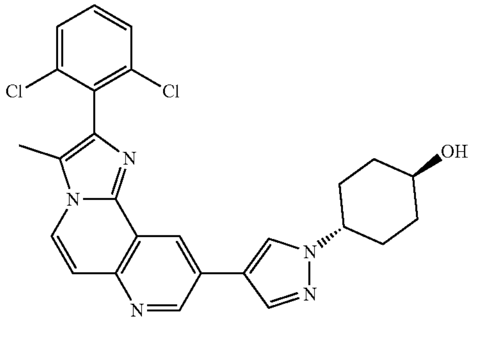 [SMILES: Cc1c(-c2c(Cl)cccc2Cl)nc2c3cc(-c4cnn([C@H]5CC[C@H](O)CC5)c4)cnc3ccn12]

Step 1. 9-(1-((1 r,4r)-4-((tert-Butyldimethylsilyl)oxy)cyclohexyl)-1H-pyrazol-4-yl)-2-(2,6-dichlorophenyl)-3-methylimidazo[2,1-f][1,6]naphthyridine

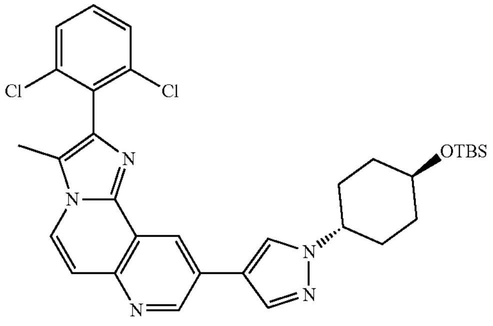 [SMILES: Cc1c(-c2c(Cl)cccc2Cl)nc2c3cc(-c4cnn([C@H]5CC[C@H](O[Si](C)(C)C(C)(C)C)CC5)c4)cnc3ccn12]

This compound was prepared according to the procedures described in Example 37, Steps 1 through 3, with 1-((1r,4r)-4-((tert-butyldimethylsilyl)oxy)cyclohexyl)-4-(4,4,5,5-tetramethyl-1,3,2-dioxaborolan-2-yl)-1H-pyrazole replacing 4-(4,4,5,5-tetramethyl-1,3,2-dioxaborolan-2-yl)-1-((2-(trimethylsilyl)ethoxy)methyl)-1H-pyrazole in Step 1. LCMS calculated for $C_{32}H_{38}Cl_2N_5OSi$ $(M+H)^+$: m/z=606.2/608.2; Found: 606.3/608.3.

Step 2. (1r,4r)-4-(4-(2-(2,6-Dichlorophenyl)-3-methylimidazo[2,1-f][1,6]naphthyridin-9-yl)-1H-pyrazol-1-yl)cyclohexan-1-ol To a vial containing 9-(1-((1r,4r)-4-((tert-butyldimethylsilyl)oxy)cyclohexyl)-1H-pyrazol-4-yl)-2-(2,6-dichlorophenyl)-3-methylimidazo[2,1-f][1,6]naphthyridine (33 mg, 0.055 mmol) as a solution in 1,4-dioxane (1 mL) was added 5N HCl (0.5 mL). The solution was left to stir at r.t. for 30 min, then diluted with $CH_3CN$ and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{26}H_{24}Cl_2N_5O$ $(M+H)^+$: m/z=492.1/494.1; found 492.1/494.1. $^1H$ NMR (400 MHz, DMSO-$d_6$) δ 9.25 (d, J=2.3 Hz, 1H), 8.93 (d, J=2.2 Hz, 1H), 8.65 (s, 1H), 8.46 (d, J=7.5 Hz, 1H), 8.20 (s, 1H), 7.71-7.61 (m, 2H), 7.56 (dd, J=8.9, 7.2 Hz, 1H), 7.43 (d, J=7.5 Hz, 1H), 4.17 (tt, J=11.5, 3.9 Hz, 1H), 3.56-3.44 (m, 1H), 2.40 (s, 3H), 2.08 (d, J=12.6 Hz, 2H), 1.98-1.91 (m, 2H), 1.83 (qd, J=13.0, 3.5 Hz, 2H), 1.44-1.31 (m, 2H).

Example 49. 4-(4-(2-(2,6-Dichlorophenyl)-3-methylimidazo[2,1-f][1,6]naphthyridin-9-yl)-1H-pyrazol-1-yl)-1-methylcyclohexane-1-carboxylic acid

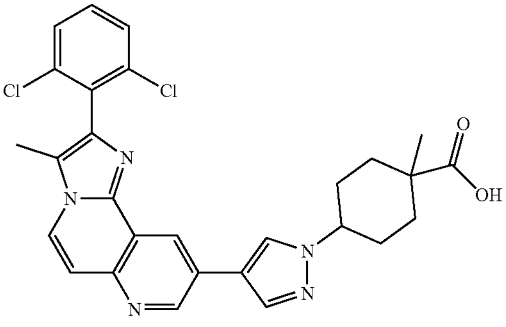 [SMILES: Cc1c(-c2c(Cl)cccc2Cl)nc2c3cc(-c4cnn(C5CCC(C)(C(=O)O)CC5)c4)cnc3ccn12]

Step 1. Ethyl 1-methyl-4-(tosyloxy)cyclohexane-1-carboxylate

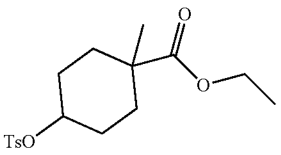 [SMILES: CCOC(=O)C1(C)CCC(OS(=O)(=O)c2ccc(C)cc2)CC1]

To a vial containing ethyl 4-hydroxy-1-methylcyclohexane-1-carboxylate (5.05 g, 27.1 mmol) as a solution in pyridine (27 mL) was added tosyl chloride (6.72 g, 35.2 mmol) and left to stir for 16 h. At completion, 10% aqueous citric acid solution was added and the organics were extracted with EtOAc. The combined organics were then back-extracted with $H_2O$ three times and dried over anhydrous $MgSO_4$, filtered, and concentrated in vacuo. The crude material was taken forward without additional purification.

Step 2. 4-(4-(2-(2,6-Dichlorophenyl)-3-methylimidazo[2,1-f][1,6]naphthyridin-9-yl)-1H-pyrazol-1-yl)-1-methylcyclohexane-1-carboxylic acid To a vial containing a mixture of 2-(2,6-dichlorophenyl)-3-methyl-9-(1H-pyrazol-4-yl)imidazo[2,1-f][1,6]naphthyridine (230 mg, 0.605 mmol, Example 37, Step 4), ethyl 1-methyl-4-(tosyloxy)cyclohexane-1-carboxylate (412 mg, 1.21 mmol), and cesium carbonate (394 mg, 1.21 mmol) was added MeCN (2.4 mL). The vial was sealed and heated to 80° C. for 16 h. After cooling to room temperature, the mixture was filtered through Celite and washed with MeCN, followed by concentration of the filtrate in vacuo. The resulting residue was purified by Biotage Isolera to give a white solid, which was dissolved in 1,4-dioxane (3 mL) and lithium hydroxide solution (2 M in $H_2O$, 1.5 mL) and heated to 80° C. for 2 h. After cooling to room temperature, the volatiles were removed in vacuo and the mixture was diluted with TFA and $CH_3CN$ and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{28}H_{26}Cl_2N_5O_2$ $(M+H)^+$: m/z=534.1/536.1; Found: 534.3/536.3.

Example 50. 3-(4-(2-(2,6-Dichlorophenyl)imidazo[2,1-f][1,6]naphthyridin-9-yl)-1H-pyrazol-1-yl)-N,N-dimethylpyrrolidine-1-carboxamide

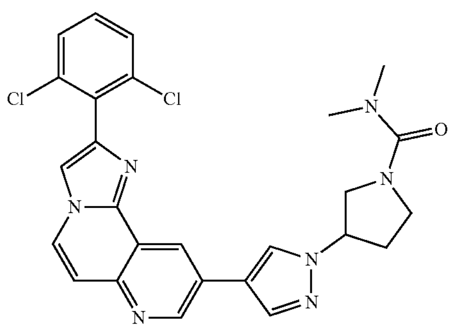 [SMILES: CN(C)C(=O)N1CCC(n2cc(-c3cnc4ccn5cc(-c6c(Cl)cccc6Cl)nc5c4c3)cn2)C1]

This compound was prepared according to the procedures described in Example 15, with dimethylcarbamyl chloride replacing acetyl chloride in Step 3. The title compound was isolated as the TFA salt. LCMS calculated for $C_{26}H_{24}Cl_2N_7O$ $(M+H)^+$: m/z=520.1/522.1; Found: 520.1/522.1.

Example 51. 3-(4-(2-(2,6-Dichlorophenyl)imidazo[2,1-f][1,6]naphthyridin-9-yl)-1H-pyrazol-1-yl)-N,N-dimethylpyrrolidine-1-sulfonamide

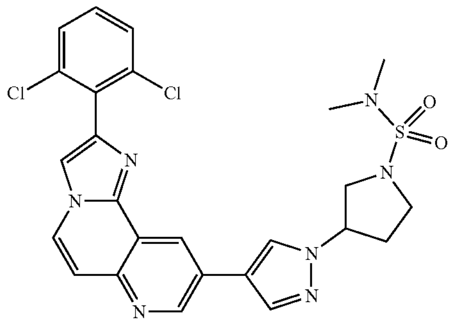 [SMILES: CN(C)S(=O)(=O)N1CCC(n2cc(-c3cnc4ccn5cc(-c6c(Cl)cccc6Cl)nc5c4c3)cn2)C1]

This compound was prepared according to the procedures described in Example 15, with N,N-dimethylsulfamoyl chloride replacing acetyl chloride in Step 3. The title compound was isolated as the TFA salt. LCMS calculated for $C_{25}H_{24}Cl_2N_7O_2S$ $(M+H)^+$: m/z=556.1/558.1; Found: 556.1/558.1.

Example 52. (S)-1-(3-(4-(2-(2,6-Dichlorophenyl)-3-methylimidazo[2,1-f][1,6]naphthyridin-9-yl)-1H-pyrazol-1-yl)pyrrolidin-1-yl)ethan-1-one

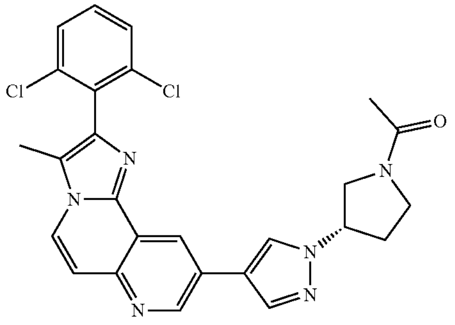 [SMILES: CC(=O)N1CC[C@H](n2cc(-c3cnc4ccn5c(C)c(-c6c(Cl)cccc6Cl)nc5c4c3)cn2)C1]

Step 1. (S)-2-(2,6-Dichlorophenyl)-3-methyl-9-(1-(pyrrolidin-3-yl)-1H-pyrazol-4-yl)imidazo[2,1-f][1,6]naphthyridine

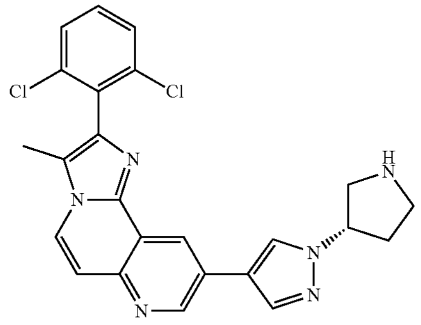 [SMILES: Cc1c(-c2c(Cl)cccc2Cl)nc2c3cc(-c4cnn([C@H]5CCNC5)c4)cnc3ccn12]

This compound was prepared according to the procedures described in Example 37, with tert-butyl (R)-3-((methylsulfonyl)oxy)pyrrolidine-1-carboxylate replacing tert-butyl 3-((methylsulfonyl)oxy)azetidine-1-carboxylate in Step 5. LCMS calculated for $C_{24}H_{21}Cl_2N_6$ $(M+H)^+$: m/z=463.1/465.1; Found: 463.0/465.0.

Step 2. (S)-1-(3-(4-(2-(2,6-Dichlorophenyl)-3-methylimidazo[2,1-f][1,6]naphthyridin-9-yl)-1H-pyrazol-1-yl)pyrrolidin-1-yl)ethan-1-one This compound was prepared according to the procedures described in Example 15, with (S)-2-(2,6-dichlorophenyl)-3-methyl-9-(1-(pyrrolidin-3-yl)-1H-pyrazol-4-yl)imidazo[2,1-f][1,6]naphthyridine replacing 2-(2,6-dichlorophenyl)-9-(1-(pyrrolidin-3-yl)-1H-pyrazol-4-yl)imidazo[2,1-f][1,6]naphthyridine in Step 3. The title compound was isolated as the TFA salt. LCMS calculated for $C_{26}H_{23}Cl_2N_6O$ $(M+H)^+$: m/z=505.1/507.1; Found: 505.3/507.3.

Example 53. (S)-1-(3-(4-(2-(2,6-Dichlorophenyl)-3-methylimidazo[2,1-f][1,6]naphthyridin-9-yl)-1H-pyrazol-1-yl)pyrrolidin-1-yl)-2-hydroxyethan-1-one

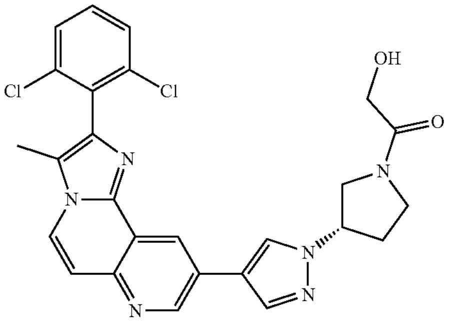 [SMILES: Cc1c(-c2c(Cl)cccc2Cl)nc2c3cc(-c4cnn([C@H]5CCN(C(=O)CO)C5)c4)cnc3ccn12]

This compound was prepared according to the procedures described in Example 25, with (S)-2-(2,6-dichlorophenyl)-3-methyl-9-(1-(pyrrolidin-3-yl)-1H-pyrazol-4-yl)imidazo[2,1-f][1,6]naphthyridine (Example 52, Step 1) replacing (S)-2-(2-chloro-6-(trifluoromethyl)phenyl)-3-methyl-9-(1-(pyrrolidin-3-yl)-1H-pyrazol-4-yl)imidazo[2,1-f][1,6]naphthyridine in Step 8. The title compound was isolated as the TFA salt. LCMS calculated for $C_{26}H_{23}Cl_2N_6O_2$ $(M+H)^+$: m/z=521.1/523.1; Found: 521.1/523.1. $^1H$ NMR (400 MHz, DMSO-$d_6$) δ 9.26 (d, J=2.2 Hz, 1H), 8.95 (d, J=2.3 Hz, 1H), 8.72 (d, J=4.6 Hz, 1H), 8.46 (d, J=7.5 Hz, 1H), 8.29 (d, J=5.5 Hz, 1H), 7.69-7.63 (m, 2H), 7.56 (dd, J=8.9, 7.2 Hz, 1H), 7.43 (d, J=7.5 Hz, 1H), 5.05 (dt, J=26.1, 5.2 Hz, 2H), 3.92 (dd, J=11.1, 6.4 Hz, 1H), 3.81 (dt, J=15.6, 4.9 Hz, 2H), 3.67-3.50 (m, 3H), 2.50-2.42 (m, 1H), 2.39 (s, 4H).

Example 54. 1-(1-(4-(2-(2,6-Dichlorophenyl)-3-methylimidazo[2,1-f][1,6]naphthyridin-9-yl)-1H-pyrazol-1-yl)-3-azabicyclo[3.1.0]hexan-3-yl)-2-hydroxyethan-1-one

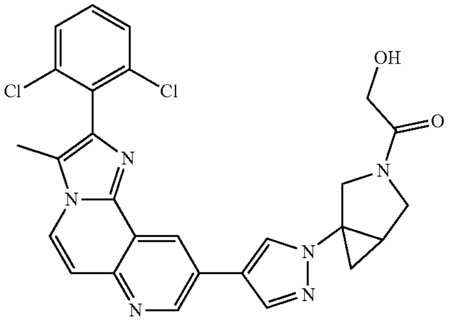 [SMILES: Cc1c(-c2c(Cl)cccc2Cl)nc2c3cc(-c4cnn(C56CC5CN(C(=O)CO)C6)c4)cnc3ccn12]

Step 1. 9-(1-(3-Azabicyclo[3.1.0]hexan-1-yl)-1H-pyrazol-4-yl)-2-(2,6-dichlorophenyl)-3-methylimidazo[2,1-f][1.6]naphthyridine

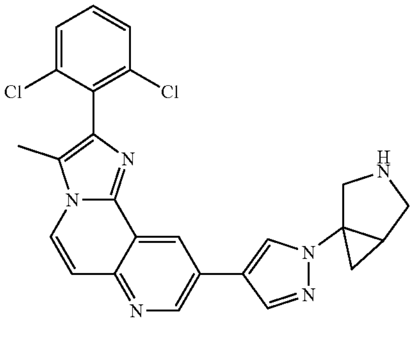 [SMILES: Cc1c(-c2c(Cl)cccc2Cl)nc2c3cc(-c4cnn(C56CNCC5C6)c4)cnc3ccn12]

A vial containing copper(II) acetate (55 mg, 0.304 mmol) and 1,10-phenanthroline monohydrate (60 mg, 0.304 mmol) as a suspension in DCE (2 mL) was sealed and heated to 60° C. for 20 min. A separate vial was charged with a mixture of 2-(2,6-dichlorophenyl)-3-methyl-9-(1H-pyrazol-4-yl)imidazo[2,1-f][1,6]naphthyridine (100 mg, 0.254 mmol, Example 37, Step 4), potassium (3-(tert-butoxycarbonyl)-3-azabicyclo[3.1.0]hexan-1-yl)trifluoroborate (73 mg, 0.254 mmol), and potassium phosphate, tribasic (162 mg, 0.761 mmol). Transferred the copper-ligand solution to the vial containing 2-(2,6-dichlorophenyl)-3-methyl-9-(1H-pyrazol-4-yl)imidazo[2,1-f][1,6]naphthyridine, then added DCE (6 mL) and water (700 μL). The vial was sealed and heated to 80° C. for 16 h. After cooling to room temperature, the mixture was filtered through Celite and washed with $CH_2Cl_2$, followed by concentration of the filtrate in vacuo. The resulting residue was purified by Biotage Isolera to give the desired product as a yellow solid (98 mg, 67% yield). The purified material was then dissolved in $CH_2Cl_2$ (3 mL) and TFA (1 mL) and left to stir at r.t. for 1 h. The reaction mixture was concentrated in vacuo, then dissolved in MeOH (1 mL) and added to a stirring solution of saturated aqueous $NaHCO_3$ (5 mL). The resulting solid precipitate was filtered and collected, followed by drying under vacuum overnight. LCMS calculated for $C_{25}H_{21}Cl_2N_6$ $(M+H)^+$: m/z=475.1/477.1; Found: 475.1/477.1.

Step 2. 1-(1-(4-(2-(2,6-Dichlorophenyl)-3-methylimidazo[2,1-f][1.6]naphthyridin-9-yl)-1H-pyrazol-1-yl)-3-azabicyclo[3.1.0]hexan-3-yl)-2-hydroxyethan-1-one This compound was prepared according to the procedures described in Example 25, with 9-(1-(3-azabicyclo[3.1.0]hexan-1-yl)-1H-pyrazol-4-yl)-2-(2,6-dichlorophenyl)-3-methylimidazo[2,1-f][1,6]naphthyridine replacing (S)-2-(2-chloro-6-(trifluoromethyl)phenyl)-3-methyl-9-(1-(pyrrolidin-3-yl)-1H-pyrazol-4-yl)imidazo[2,1-f][1,6]naphthyridine in Step 8. The title compound was isolated as the TFA salt. LCMS calculated for $C_{27}H_{23}Cl_2N_6O_2$ $(M+H)^+$: m/z=533.1/535.1; Found: 533.2/535.2. $^1H$ NMR (400 MHz, DMSO-$d_6$) δ 9.27 (d, J=2.3 Hz, 1H), 8.97 (d, J=2.3 Hz, 1H), 8.81 (d, J=6.4 Hz, 1H), 8.47 (d, J=7.5 Hz, 1H), 8.31 (d, J=4.2 Hz, 1H), 7.70-7.63 (m, 2H), 7.56 (dd, J=8.9, 7.3 Hz, 1H), 7.44 (d, J=7.5 Hz, 1H), 4.22 (d, J=11.2 Hz, 1H), 4.13-4.02 (m, 2H), 3.96 (dd, J=15.4, 1.9 Hz, 1H), 3.87-3.55 (m, 3H), 2.40 (s, 3H), 2.37-2.26 (m, 1H), 1.70-1.62 (m, 1H), 1.07 (td, J=5.5, 3.3 Hz, 1H).

Example 55. (S)-1-(3-(4-(2-(2,6-Dichlorophenyl)-3-(hydroxymethyl)imidazo[2,1-f][1,6]naphthyridin-9-yl)-1H-pyrazol-1-yl)pyrrolidin-1-yl)-2-hydroxyethan-1-one

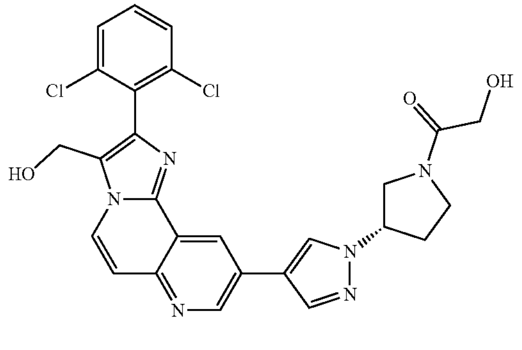 [SMILES: O=C(CO)N1CC[C@H](n2cc(-c3cnc4ccn5c(CO)c(-c6c(Cl)cccc6Cl)nc5c4c3)cn2)C1]

Step 1. 3-(1-((2-(Trimethylsilyl)ethoxy)methyl)-1H-pyrazol-4-yl)-1,6-naphthyridin-5-amine

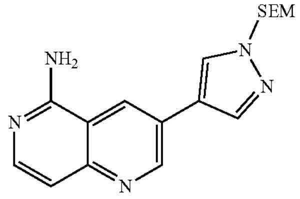 [SMILES: C[Si](C)(C)CCOCn1cc(-c2cnc3ccnc(N)c3c2)cn1]

This compound was prepared according to the procedures described in Example 25, with 3-bromo-1,6-naphthyridin-5-amine (Example 1, Step 2) replacing 9-bromoimidazo[2,1-f][1,6]naphthyridine in Step 2. LCMS calculated for $C_{17}H_{24}N_5OSi$ $(M+H)^+$: m/z=342.2; Found: 342.2.

Step 2. 2-(2,6-Dichlorophenyl)-9-(1H-pyrazol-4-yl)imidazo[2,1-f][1,6]naphthyridine

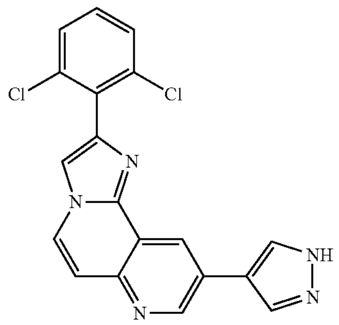 [SMILES: Clc1cccc(Cl)c1-c1cn2ccc3ncc(-c4cn[nH]c4)cc3c2n1]

A microwave vial containing a mixture of 3-(1-((2-(trimethylsilyl)ethoxy)methyl)-1H-pyrazol-4-yl)-1,6-naphthyridin-5-amine (2 g, 5.86 mmol), 2-bromo-1-(2,6-dichlorophenyl)ethan-1-one (1.7 g, 6.44 mmol), sodium bicarbonate (0.738 g, 8.79 mmol), and tert-butanol (10 mL) was irradiated at 150° C. for 14 h using a Biotage Initator+ Microwave Synthesizer. After cooling to room temperature, the solvent was removed in vacuo and the remaining residue was suspended in $CH_2Cl_2$, filtered, and the filtrate was concentrated in vacuo. The resulting residue was purified by Biotage Isolera to give the desired product as a brown solid. The purified material was then dissolved with $CH_2Cl_2$ (3 mL) and TFA (2 mL) and left to stir at r.t. for 1 h. At completion, the volatiles were removed in vacuo. The obtained product was used in the next step without further purification. LCMS calculated for $C_{19}H_{12}Cl_2N_5$ $(M+H)^+$: m/z=380.0/382.0; found 380.1/382.0.

Step 3. tert-Butyl (S)-3-(4-(2-(2,6-dichlorophenyl)imidazo[2,1-f][1,6]naphthyridin-9-yl)-1H-pyrazol-1-yl)pyrrolidine-1-carboxylate

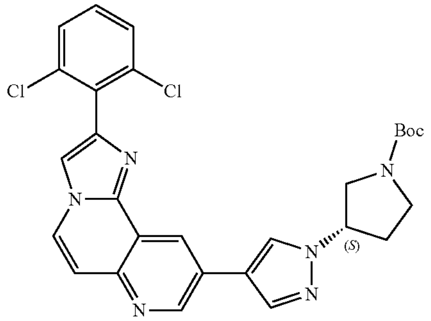

A vial containing 2-(2,6-dichlorophenyl)-9-(1H-pyrazol-4-yl)imidazo[2,1-f][1,6]naphthyridine (2.5 g, 6.57 mmol), tert-butyl (R)-3-((methylsulfonyl)oxy)pyrrolidine-1-carboxylate (2.62 g, 9.86 mmol), cesium carbonate (4.28 g, 13.15 mmol), and acetonitrile (33 mL) was heated to 80° C. and stirred for 16 h. The solution was subsequently cooled to r.t., filtered and the filtrate was concentrated in vacuo then purified by Biotage Isolera to give the desired product as a brown solid. LCMS calculated for $C_{28}H_{27}Cl_2N_6O_2$ $(M+H)^+$: m/z=549.2/551.2; found 549.1/551.1.

Step 4. tert-Butyl (S)-3-(4-(3-bromo-2-(2,6-dichlorophenyl)imidazo[2,1-f][1,6]naphthyridin-9-yl)-1H-pyrazol-1-yl)pyrrolidine-1-carboxylate

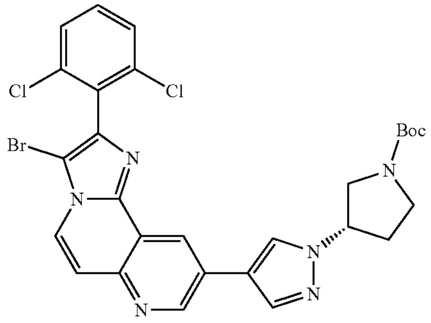 [SMILES: CC(C)(C)OC(=O)N1CC[C@H](n2cc(-c3cnc4ccn5c(Br)c(-c6c(Cl)cccc6Cl)nc5c4c3)cn2)C1]

This compound was prepared according to the procedures described in Example 25, with tert-butyl (S)-3-(4-(2-(2,6-dichlorophenyl)imidazo[2,1-f][1,6]naphthyridin-9-yl)-1H-pyrazol-1-yl)pyrrolidine-1-carboxylate replacing 9-(1-((2-(trimethylsilyl)ethoxy)methyl)-1H-pyrazol-4-yl)imidazo[2, 1-f][1,6]naphthyridine in Step 3. LCMS calculated for $C_{28}H_{26}BrCl_2N_6O_2$ $(M+H)^+$: m/z=627.1/629.0/631.0; found 627.2/629.2/631.2.

Step 5. tert-Butyl (S)-3-(4-(2-(2,6-dichlorophenyl)-3-vinylimidazo[2,1-f][1,6]naphthyridin-9-yl)-1H-pyrazol-1-yl)pyrrolidine-1-carboxylate

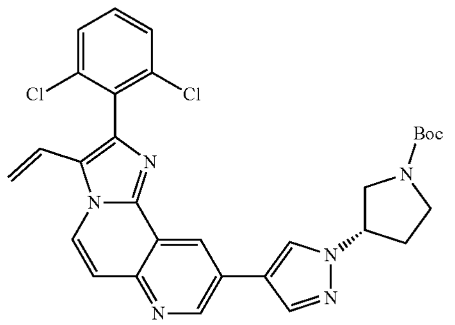 [SMILES: C=Cc1c(-c2c(Cl)cccc2Cl)nc2c3cc(-c4cnn([C@H]5CCN(C(=O)OC(C)(C)C)C5)c4)cnc3ccn12]

A vial containing tert-butyl 3-(4-(3-bromo-2-(2,6-dichlorophenyl)imidazo[2,1-f][1,6]naphthyridin-9-yl)-1H-pyrazol-1-yl)pyrrolidine-1-carboxylate (800 mg, 1.27 mmol), potassium phosphate, tribasic (540 mg, 2.55 mmol), (1,1'-bis(diphenylphosphino)ferrocene)-dichloropalladium(II) (93 mg, 0.127 mmol), and 4,4,5,5-tetramethyl-2-vinyl-1,3,2-dioxaborolane (432 μL, 2.55 mmol) as a solution in 1,4-dioxane (6 mL), and water (600 μL) was purged with nitrogen for 30 sec. and heated to 80° C. for 3 h. Upon cooling to r.t. the solution was diluted with $CH_2Cl_2$, filtered through Celite and concentrated the filtrate in vacuo. The resulting residue was purified by Biotage Isolera to give the desired product as a brown solid. LCMS calculated for $C_{30}H_{29}Cl_2N_6O_2$ $(M+H)^+$: m/z=575.2/577.2; found 575.1/577.2.

Step 6. (S)-(2-(2,6-Dichlorophenyl)-9-(1-(pyrrolidin-3-yl)-1H-pyrazol-4-yl)imidazo[2,1-f][1,6]naphthyridin-3-yl)methanol

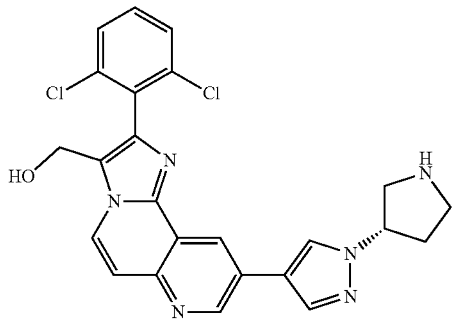 [SMILES: OCc1c(-c2c(Cl)cccc2Cl)nc2c3cc(-c4cnn([C@H]5CCNC5)c4)cnc3ccn12]

To a vial was added tert-butyl (S)-3-(4-(2-(2,6-dichlorophenyl)-3-vinylimidazo[2,1-f][1,6]naphthyridin-9-yl)-1H-pyrazol-1-yl)pyrrolidine-1-carboxylate (600 mg, 1.04 mmol), THF (16 mL), water (5 mL) and osmium tetroxide (4 wt. % in $H_2O$, 409 μL, 0.052 mmol), followed by sodium periodate (1.11 g, 5.21 mmol). The reaction mixture was stirred at r.t. for 3 h, and upon completion the reaction was quenched with saturated aqueous $Na_2S_2O_3$ and extracted into EtOAc. The combined organic layers were concentrated in vacuo and the residue was dissolved in isopropanol (10 mL), cooled to 0° C., and $NaBH_4$ (39 mg, 1.04 mmol) was added with stirring while allowing the reaction to slowly warm to r.t. The reaction was then cooled to 0° C. and quenched by addition of saturated aqueous $NH_4Cl$. The volatiles were removed in vacuo and the resulting residue was purified by Biotage Isolera to give a yellow solid. This product was taken up in $CH_2Cl_2$(3 mL) and TFA (1 mL) and stirred at r.t. for 1 h. The volatiles were removed in vacuo and the obtained product was used in the next step without further purification. LCMS calculated for $C_{24}H_{21}Cl_2N_6O$ $(M+H)^+$: m/z=479.1/481.1; found 479.1/481.1.

Step 7. (S)-1-(3-(4-(2-(2,6-Dichlorophenyl)-3-(hydroxymethyl)imidazo[2,1-f][1,6]naphthyridin-9-yl)-1H-pyrazol-1-yl)pyrrolidin-1-yl)-2-hydroxyethan-1-one To a vial containing (S)-(2-(2,6-dichlorophenyl)-9-(1-(pyrrolidin-3-yl)-1H-pyrazol-4-yl)imidazo[2,1-f][1,6]naphthyridin-3-yl)methanol (15 mg, 0.031 mmol) was added 2-hydroxyacetic acid (3 mg, 0.031 mmol), DMF (0.5 mL) and DIPEA (11 μL, 0.063 mmol). This solution was stirred for 1 min before HATU (18 mg, 0.047 mmol) was added and left to stir for 1 h. Upon completion the reaction mixture was then diluted with acetonitrile/methanol and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{26}H_{23}Cl_2N_6O_3$ $(M+H)^+$: m/z=537.1/539.1; found 537.1/539.1. $^1H$ NMR (400 MHz, DMSO-$d_6$) δ 9.28 (d, J=2.3 Hz, 1H), 8.98 (d, J=2.3 Hz, 1H), 8.73 (d, J=4.4 Hz, 1H), 8.54 (d, J=7.5 Hz, 1H), 8.30 (d, J=5.4 Hz, 1H), 7.68-7.62 (m, 2H), 7.55 (dd, J=9.0, 7.2 Hz, 1H), 7.45 (d, J=7.5 Hz, 1H), 5.05 (dt, J=26.1, 5.5 Hz, 1H), 4.68 (s, 2H), 4.04 (d, J=9.4 Hz, 2H), 3.96-3.77 (m, 2H), 3.67-3.52 (m, 2H), 2.47 (d, J=6.3 Hz, 1H), 2.38 (d, J=6.6 Hz, 1H).

Example 56. (S)-1-(3-(4-(2-(2,6-Dichlorophenyl)-3-(hydroxymethyl)imidazo[2,1-f][1,6]naphthyridin-9-yl)-1H-pyrazol-1-yl)pyrrolidin-1-yl)ethan-1-one

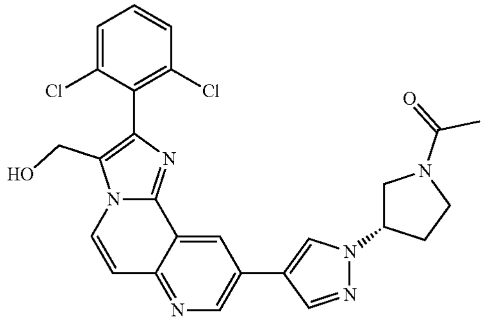 [SMILES: CC(=O)N1CC[C@H](n2cc(-c3cnc4ccn5c(CO)c(-c6c(Cl)cccc6Cl)nc5c4c3)cn2)C1]

This compound was prepared according to the procedures described in Example 55, with acetic acid replacing 2-hydroxyacetic acid in Step 7. The title compound was isolated as the TFA salt. LCMS calculated for $C_{26}H_{23}Cl_2N_6O_2$ $(M+H)^+$: m/z=521.1/523.1; Found: 521.1/523.1.

Example 57. (S)-(3-(4-(2-(2,6-Dichlorophenyl)-3-(hydroxymethyl)imidazo[2,1-f][1,6]naphthyridin-9-yl)-1H-pyrazol-1-yl)pyrrolidin-1-yl)(morpholino) methanone

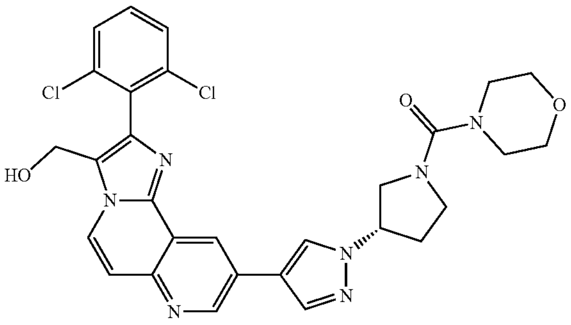 [SMILES: O=C(N1CCOCC1)N1CC[C@H](n2cc(-c3cnc4ccn5c(CO)c(-c6c(Cl)cccc6Cl)nc5c4c3)cn2)C1]

To a vial containing (S)-(2-(2,6-dichlorophenyl)-9-(1-(pyrrolidin-3-yl)-1H-pyrazol-4-yl)imidazo[2,1-f][1,6]naphthyridin-3-yl)methanol (10 mg, 0.021 mmol, Example 55, Step 6) was added morpholine-4-carbonyl chloride (3 μL, 0.025 mmol), DMF (0.5 mL) and diisopropylethylamine (5 μL, 0.025 mmol) and left to stir for 1 h. Upon completion the reaction mixture was then diluted with acetonitrile and methanol and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{29}H_{28}Cl_2N_7O_3$ $(M+H)^+$: m/z=592.2/594.2; found 592.2/594.1.

Example 58. 1-((3S)-3-(4-(2-(2,6-dichlorophenyl)-3-(1-hydroxyethyl)imidazo[2,1-f][1,6]naphthyridin-9-yl)-1H-pyrazol-1-yl)pyrrolidin-1-yl)-2-hydroxyethan-1-one

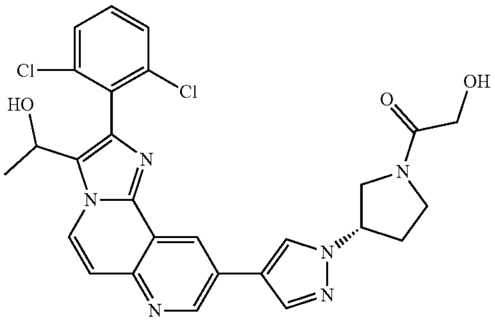 [SMILES: CC(O)c1c(-c2c(Cl)cccc2Cl)nc2c3cc(-c4cnn([C@H]5CCN(C(=O)CO)C5)c4)cnc3ccn12]

Step 1. tert-Butyl (S)-3-(4-(2-(2,6-dichlorophenyl)-3-(prop-1-en-2-yl)imidazo[2,1-f][1,6]naphthyridin-9-yl)-1H-pyrazol-1-yl)pyrrolidine-1-carboxylate

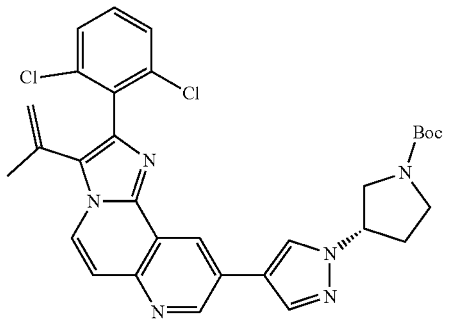 [SMILES: C=C(C)c1c(-c2c(Cl)cccc2Cl)nc2c3cc(-c4cnn([C@H]5CCN(C(=O)OC(C)(C)C)C5)c4)cnc3ccn12]

A mixture of tert-butyl (S)-3-(4-(3-bromo-2-(2,6-dichlorophenyl)imidazo[2,1-f][1,6]naphthyridin-9-yl)-1H-pyrazol-1-yl)pyrrolidine-1-carboxylate (200 mg, 0.318 mmol, Example 55, Step 6), potassium phosphate, tribasic (135 mg, 0.637 mmol), (1,1'-bis(diphenylphosphino)ferrocene)-dichloropalladium(II) (23 mg, 0.032 mmol), and isopropenylboronic acid pinacol ester (120 μL, 0.637 mmol) was suspended in 1,4-dioxane (1.4 mL), and water (0.145 mL). The reaction vial was purged with nitrogen for 30 sec., sealed and heated to 80° C. for 3 h. Upon cooling to r.t. the reaction mixture was diluted with $CH_2Cl_2$, filtered through Celite and concentrated in vacuo. The resulting residue was purified by Biotage Isolera to give the desired product as a brown solid, LCMS calculated for $C_{31}H_{31}Cl_2N_6O_2$ $(M+H)^+$: m/z=589.2/591.2; found 589.2/591.2.

Step 2. 1-(2-(2,6-Dichlorophenyl)-9-(1-((S)-pyrrolidin-3-yl)-1H-pyrazol-4-yl)imidazo[2,1-f][1,6]naphthyridin-3-yl)ethan-1-ol

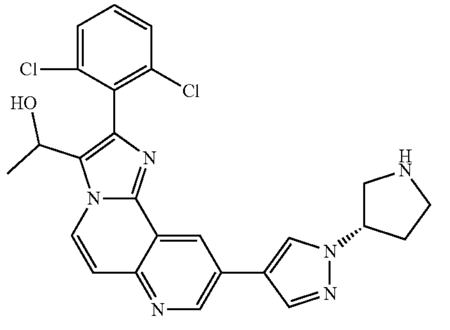 [SMILES: CC(O)c1c(-c2c(Cl)cccc2Cl)nc2c3cc(-c4cnn([C@H]5CCNC5)c4)cnc3ccn12]

This compound was prepared according to the procedures described in Example 55, with tert-butyl (S)-3-(4-(2-(2,6-dichlorophenyl)-3-(prop-1-en-2-yl)imidazo[2,1-f][1,6] naphthyridin-9-yl)-1H-pyrazol-1-yl)pyrrolidine-1-carboxylate replacing tert-butyl (S)-3-(4-(2-(2,6-dichlorophenyl)-3-vinylimidazo[2,1-f][1,6]naphthyridin-9-yl)-1H-pyrazol-1-yl)pyrrolidine-1-carboxylate in Step 6. LCMS calculated for $C_{25}H_{23}Cl_2N_6O$ $(M+H)^+$: m/z=493.1/495.1; found 493.3/495.3.

Step 3. 1-((3S)-3-(4-(2-(2,6-Dichlorophenyl)-3-(1-hydroxyethyl)imidazo[2,1-f][1,6]naphthyridin-9-yl)-1H-pyrazol-1-yl)pyrrolidin-1-yl)-2-hydroxyethan-1-one This compound was prepared according to the procedures described in Example 25, with 1-(2-(2,6-dichlorophenyl)-9-(1-((S)-pyrrolidin-3-yl)-1H-pyrazol-4-yl)imidazo[2,1-f][1,6]naphthyridin-3-yl)ethan-1-ol replacing (S)-2-(2-chloro-6-(trifluoromethyl)phenyl)-3-methyl-9-(1-(pyrrolidin-3-yl)-1H-pyrazol-4-yl)imidazo[2,1-f][1,6]naphthyridine in Step 8. The title compound was isolated as the TFA salt. LCMS calculated $C_{27}H_{25}Cl_2N_6O_3$ $(M+H)^+$: m/z=551.1/553.1; found 551.2/553.2.

Example 59. 1-(6-(4-(2-(2,6-Dichlorophenyl)-3-methylimidazo[2,1-f][1,6]naphthyridin-9-yl)-1H-pyrazol-1-yl)-3-azabicyclo[4.1.0]heptan-3-yl)-2-hydroxyethan-1-one

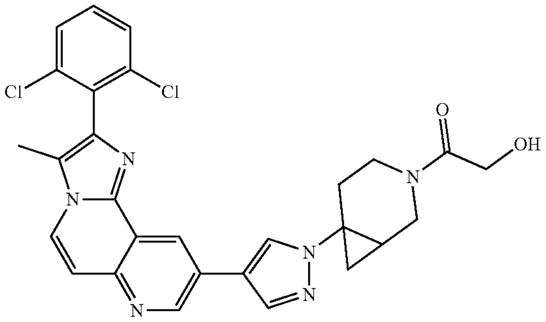 [SMILES: Cc1c(-c2c(Cl)cccc2Cl)nc2c3cc(-c4cnn(C56CCN(C(=O)CO)CC5C6)c4)cnc3ccn12]

This compound was prepared according to the procedures described in Example 54, with potassium (3-(tert-butoxycarbonyl)-3-azabicyclo[4.1.0]heptan-6-yl)trifluoroborate replacing potassium (3-(tert-butoxycarbonyl)-3-azabicyclo[3.1.0]hexan-1-yl)trifluoroborate in Step 1. The title compound was isolated as the TFA salt. LCMS calculated for $C_{28}H_{25}Cl_2N_6O_2$ $(M+H)^+$: m/z=547.1/549.1; found 547.1/549.1. $^1H$ NMR (400 MHz, DMSO-$d_6$) δ 9.28 (d, J=2.2 Hz, 1H), 8.97 (d, J=2.2 Hz, 1H), 8.75 (s, 1H), 8.49 (d, J=7.5 Hz, 1H), 8.24 (s, 1H), 7.71-7.64 (m, 2H), 7.57 (dd, J=8.9, 7.2 Hz, 1H), 7.46 (d, J=7.5 Hz, 1H), 4.11 (t, J=4.6 Hz, 2H), 3.89 (dd, J=13.7, 5.4 Hz, 1H), 3.83-3.55 (m, 1H), 3.54-3.19 (m, 2H), 2.41 (s, 3H), 2.33 (s, 1H), 2.26 (s, 1H), 1.89 (s, 1H), 1.55-1.45 (m, 1H), 1.06 (d, J=9.7 Hz, 1H).

Example 60. 1-(1-(4-(2-(2,6-Dichlorophenyl)-3-methylimidazo[2,1-f][1,6]naphthyridin-9-yl)-1H-pyrazol-1-yl)-3-azabicyclo[4.1.0]heptan-3-yl)ethan-1-one

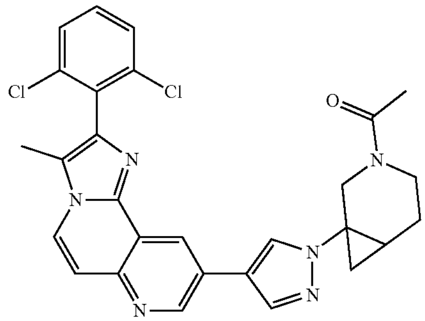 [SMILES: CC(=O)N1CCC2CC2(n2cc(-c3cnc4ccn5c(C)c(-c6c(Cl)cccc6Cl)nc5c4c3)cn2)C1]

Step 1. 9-(1-(3-Azabicyclo[4.1.0]heptan-1-yl)-1H-pyrazol-4-yl)-2-(2,6-dichlorophenyl)-3-methylimidazo[2,1-f][1.6]naphthyridine

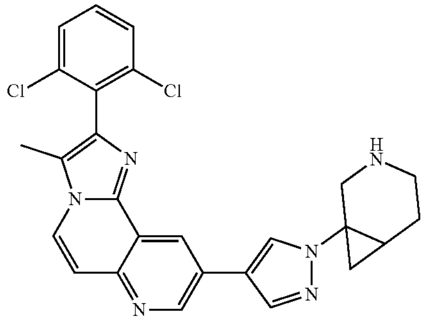 [SMILES: Cc1c(-c2c(Cl)cccc2Cl)nc2c3cc(-c4cnn(C56CNCCC5C6)c4)cnc3ccn12]

This compound was prepared according to the procedures described in Example 54, with potassium (3-(tert-butoxycarbonyl)-3-azabicyclo[4.1.0]heptan-1-yl)trifluoroborate replacing potassium (3-(tert-butoxycarbonyl)-3-azabicyclo[3.1.0]hexan-1-yl)trifluoroborate in Step 1. LCMS calculated for $C_{26}H_{23}Cl_2N_6$ $(M+H)^+$: m/z=489.1/491.1; found 489.1/491.

Step 2. 1-(1-(4-(2-(2,6-Dichlorophenyl)-3-methylimidazo[2,1-f][1.6]naphthyridin-9-yl)-1H-pyrazol-1-yl)-3-azabicyclo[4.1.0]heptan-3-yl)ethan-1-one To a vial containing 9-(1-(3-azabicyclo[4.1.0]heptan-1-yl)-1H-pyrazol-4-yl)-2-(2,6-dichlorophenyl)-3-methylimidazo[2,1-f][1,6]naphthyridine (15 mg, 0.031 mmol) was added acetic acid (2 μL, 0.031 mmol), DMF (0.5 mL) and DIPEA (11 μL, 0.061 mmol). This was stirred for 1 min before HATU (18 mg, 0.046 mmol) was added and left to stir for 1 h. Upon completion the reaction mixture was then diluted with acetonitrile/methanol and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{28}H_{25}Cl_2N_6O_2$ (M+H)+: m/z=531.1/533.1; found 531.2/533.1.

Example 61. 1-(3-(5-(2-(2,6-Dichlorophenyl)-3-methylimidazo[2,1-f][1,6]naphthyridin-9-yl)pyridin-2-yl)azetidin-1-yl)-2-hydroxyethan-1-one

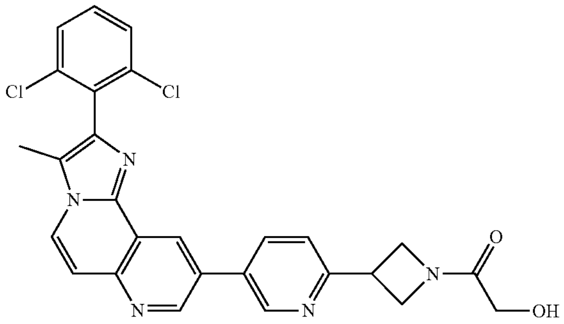 [SMILES: Cc1c(-c2c(Cl)cccc2Cl)nc2c3cc(-c4ccc(C5CN(C(=O)CO)C5)nc4)cnc3ccn12]

Step 1. tert-Butyl 3-(5-(4,4,5,5-tetramethyl-1,3,2-dioxaborolan-2-yl)pyridin-2-yl)azetidine-1-carboxylate

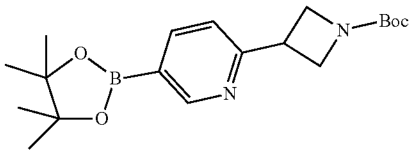 [SMILES: CC(C)(C)OC(=O)N1CC(c2ccc(B3OC(C)(C)C(C)(C)O3)cn2)C1]

A vial containing zinc(0) dust (173 mg, 2.65 mmol), 1,2-dibromoethane (15 μL, 0.177 mmol), TMSCl (22 μL, 0.177 mmol) in THF (3.53 mL) was purged with nitrogen for 30 sec., sealed and heated to 60° C. for 15 min. After cooling to room temperature, a solution of tert-butyl 3-iodoazetidine-1-carboxylate (500 mg, 1.76 mmol) in DMA (3.5 mL) was added. The vial was sealed and heated to 60° C. for another 15 min and, upon subsequent cooling to room temperature, 2,5-dibromopyridine (439 mg, 1.85 mmol), [1,1'-bis(diphenylphosphino)ferrocene]dichloropalladium (II) (72 mg, 0.088 mmol) and copper(I) iodide (17 mg, 0.088 mmol) were added. The vial was sealed and heated to 80° C. for 4 h. After cooling to r.t., the reaction mixture was diluted with $CH_2Cl_2$, filtered through Celite and the filtrate was concentrated in vacuo. The residue was purified by Biotage Isolera to give tert-butyl 3-(5-bromopyridin-2-yl)azetidine-1-carboxylate (400 mg, 1.277 mmol), which was added to a vial with [1,1'-bis(diphenylphosphino)ferrocene]dichloropalladium(II) (104 mg, 0.128 mmol), bis(pinacolato)diboron (0.649 g, 2.55 mmol), and potassium acetate (307 mg, 3.19 mmol), followed by 1,4-dioxane (4 mL). The solution was purged with nitrogen for 30 sec., then sealed and heated to 80° C. for 2 h. At completion, the volatiles were removed in vacuo to give the desired product which was used directly for the next step. LCMS calculated for the corresponding boronic acid, 3-(5-boronopyridin-2-yl)azetidine-1-carboxylic acid, observed $C_9H_{12}BN_2O_4$ $(M+H-tBu)^+$: m/z=223.1; found=223.1.

Step 2. tert-Butyl 3-(5-(2-(2,6-dichlorophenyl)imidazo[2,1-f][1,6]naphthyridin-9-yl)pyridin-2-yl)azetidine-1-carboxylate

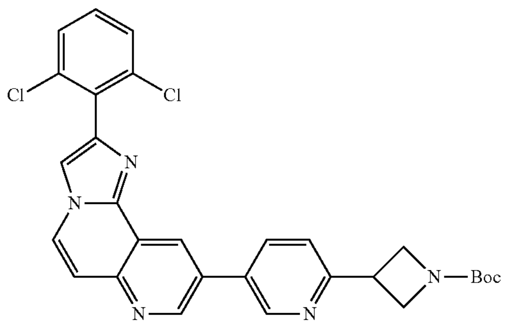 [SMILES: CC(C)(C)OC(=O)N1CC(c2ccc(-c3cnc4ccn5cc(-c6c(Cl)cccc6Cl)nc5c4c3)cn2)C1]

This compound was prepared according to the procedures described in Example 37, with tert-butyl 3-(5-(4,4,5,5-tetramethyl-1,3,2-dioxaborolan-2-yl)pyridin-2-yl)azetidine-1-carboxylate replacing 4-(4,4,5,5-tetramethyl-1,3,2-dioxaborolan-2-yl)-1-((2-(trimethylsilyl)ethoxy)methyl)-1H-pyrazole in Step 1. LCMS calculated for $C_{29}H_{26}Cl_2N_5O_2$ (M+H)+: m/z=546.1/548.1; found 546.2/548.2.

Step 3. tert-Butyl 3-(5-(3-bromo-2-(2,6-dichlorophenyl)imidazo[2,1-f][1.6]naphthyridin-9-yl)pyridin-2-yl)azetidine-1-carboxylate

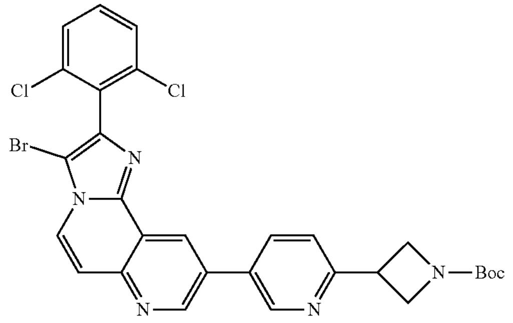 [SMILES: CC(C)(C)OC(=O)N1CC(c2ccc(-c3cnc4ccn5c(Br)c(-c6c(Cl)cccc6Cl)nc5c4c3)cn2)C1]

This compound was prepared according to the procedures described in Example 25, with tert-butyl 3-(5-(2-(2,6-dichlorophenyl)imidazo[2,1-f][1,6]naphthyridin-9-yl)pyridin-2-yl)azetidine-1-carboxylate replacing 9-(1-((2-(trimethylsilyl)ethoxy)methyl)-1H-pyrazol-4-yl)imidazo[2,1-f][1,6] naphthyridine in Step 3. LCMS calculated for $C_{29}H_{25}BrCl_2N_5O_2$ $(M+H)^+$: m/z=624.1/626.1/628.1; Found: 624.2/626.2/628.2.

Step 4. 9-(6-(Azetidin-3-yl)pyridin-3-yl)-2-(2,6-dichlorophenyl)-3-methylimidazo[2,1-f][1,6]naphthyridine

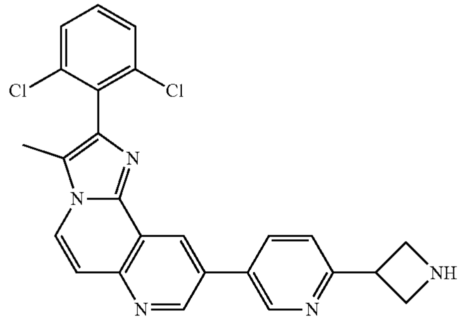 [SMILES: Cc1c(-c2c(Cl)cccc2Cl)nc2c3cc(-c4ccc(C5CNC5)nc4)cnc3ccn12]

A mixture of tert-butyl 3-(5-(3-bromo-2-(2,6-dichlorophenyl)imidazo[2,1-f][1,6]naphthyridin-9-yl)pyridin-2-yl) azetidine-1-carboxylate (500 mg, 0.800 mmol), potassium phosphate, tribasic (339 mg, 1.60 mmol), and RuPhos Pd G2 (62 mg, 0.080 mmol) was suspended in 1,4-dioxane (3.6 mL), and water (0.360 mL). The vial was purged with nitrogen for 30 sec., followed by the addition of trimethylboroxine (447 μL, 3.20 mmol). The vial was sealed and heated to 80° C. for 2 h. After cooling to room temperature, the reaction mixture was diluted with $CH_2Cl_2$, filtered through Celite and the filtrate was concentrated in vacuo. The resulting residue was purified by Biotage Isolera. The purified material was then dissolved in $CH_2Cl_2$ (4 mL) and TFA (1 mL) and stirred at r.t. for 1 h. At completion, the volatiles were removed in vacuo to give the desired product. LCMS calculated for $C_{25}H_{20}Cl_2N_5$ $(M+H)^+$: m/z=460.1/462.1; 460.1/462.1.

Step 5. 1-(3-(5-(2-(2,6-Dichlorophenyl)-3-methylimidazo[2,1-f][1.6]naphthyridin-9-yl)pyridin-2-yl) azetidin-1-yl)-2-hydroxyethan-1-one To a vial containing 9-(6-(azetidin-3-yl)pyridin-3-yl)-2-(2,6-dichlorophenyl)-3-methylimidazo[2,1-f][1,6]naphthyridine (10 mg, 0.022 mmol) was added 2-hydroxyacetic acid (2 mg, 0.022 mmol), DMF (0.5 mL) and diisopropylethylamine (8 μL, 0.043 mmol). This was stirred for 1 min before HATU (13 mg, 0.033 mmol) was added and left to stir for 1 h. Upon completion, the reaction mixture was then diluted with acetonitrile and methanol and purified with prep-LCMS (XBridge C18 column, eluting with a gradient of acetonitrile/water containing 0.1% $NH_4OH$, at flow rate of 60 mL/min). The title compound was isolated as the TFA salt. LCMS calculated for $C_{27}H_{22}Cl_2N_5O_2$ $(M+H)^+$: m/z=518.1/520.1; found 518.2/520.1. $^1H$ NMR (400 MHz, DMSO-$d_6$) δ 9.32 (d, J=2.4 Hz, 1H), 9.18 (d, J=2.4 Hz, 1H), 9.05 (d, J=2.4 Hz, 1H), 8.55 (d, J=7.5 Hz, 1H), 8.36 (dd, J=8.1, 2.4 Hz, 1H), 7.69-7.62 (m, 2H), 7.59-7.50 (m, 2H), 7.47 (d, J=7.2 Hz, 1H), 4.94 (t, J=6.0 Hz, 1H), 4.58 (t, J=8.3 Hz, 1H), 4.40 (dd, J=8.8, 5.3 Hz, 1H), 4.33-4.25 (m, 1H), 4.15-4.09 (m, 2H), 3.96 (d, J=6.0 Hz, 2H), 2.41 (s, 3H).

Example 62. 1-(3-(5-(2-(2,6-Dichlorophenyl)-3-methylimidazo[2,1-f][1,6]naphthyridin-9-yl)pyridin-3-yl)azetidin-1-yl)ethan-1-one

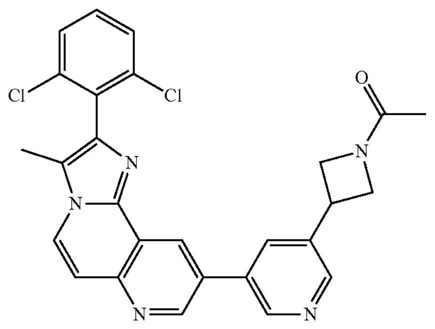 [SMILES: CC(=O)N1CC(c2cncc(-c3cnc4ccn5c(C)c(-c6c(Cl)cccc6Cl)nc5c4c3)c2)C1]

Step 1. 9-(5-(Azetidin-3-yl)pyridin-3-yl)-2-(2,6-dichlorophenyl)-3-methylimidazo[2,1-f][1,6]naphthyridine

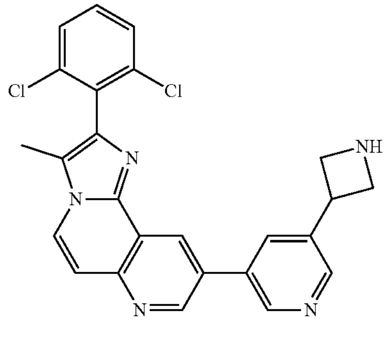 [SMILES: Cc1c(-c2c(Cl)cccc2Cl)nc2c3cc(-c4cncc(C5CNC5)c4)cnc3ccn12]

This compound was prepared according to the procedures described in Example 61, with 3,5-dibromopyridine replacing 2,5-dibromopyridine in Step 1. LCMS calculated for $C_{25}H_{20}Cl_2N_5$ $(M+H)^+$: m/z=460.1/462.1; 460.1/462.0.

Step 2. 1-(3-(5-(2-(2,6-Dichlorophenyl)-3-methylimidazo[2,1-f][1.6]naphthyridin-9-yl)pyridin-3-yl) azetidin-1-yl)ethan-1-one To a vial containing 9-(5-(azetidin-3-yl)pyridin-3-yl)-2-(2,6-dichlorophenyl)-3-methylimidazo[2,1-f][1,6]naphthyridine (10 mg, 0.022 mmol) was added acetic acid (2 μL, 0.022 mmol), DMF (0.5 mL) and diisopropylethylamine (8 μL, 0.043 mmol). This was stirred for 1 min before HATU (13 mg, 0.033 mmol) was added and left to stir for 1 h. Upon completion, the reaction mixture was then diluted with acetonitrile and methanol and purified with prep-LCMS (XBridge C18 column, eluting with a gradient of acetonitrile/water containing 0.1% $NH_4OH$, at flow rate of 60 mL/min). The title compound was isolated as the TFA salt. LCMS calculated for $C_{27}H_{22}Cl_2N_5O$ $(M+H)^+$: m/z=502.1/504.1; Found: 502.2/504.2.

Example 63. 1-(3-(5-(2-(2,6-Dichlorophenyl)-3-methylimidazo[2,1-f][1,6]naphthyridin-9-yl)phenyl) azetidin-1-yl)ethan-1-one

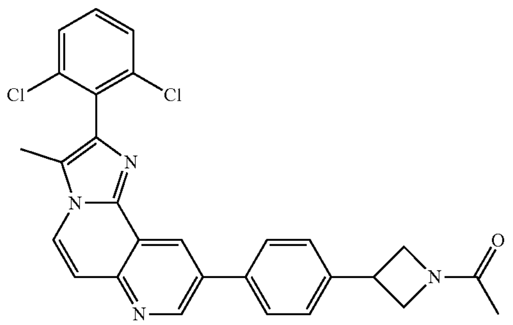 [SMILES: CC(=O)N1CC(c2ccc(-c3cnc4ccn5c(C)c(-c6c(Cl)cccc6Cl)nc5c4c3)cc2)C1]

Step 1. tert-Butyl 3-(4-chlorophenyl)azetidine-1-carboxylate

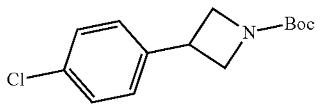 [SMILES: CC(C)(C)OC(=O)N1CC(c2ccc(Cl)cc2)C1]

A vial containing zinc(0) dust (0.346 g, 5.30 mmol), 1,2-dibromoethane (30 μL, 0.353 mmol), TMSCl (45 μL, 0.353 mmol) in THF (7.06 mL) was purged with $N_2$ for 30 sec., sealed and heated to 60° C. for 15 min. After which a solution of tert-butyl 3-iodoazetidine-1-carboxylate (1 g, 3.53 mmol) in DMA (3.5 mL) was added. This mixture was heated at 60° C. for another 15 min and, upon subsequent cooling to room temperature, 1-chloro-4-iodobenzene (0.842 g, 13.5 mmol), [11,11'-bis(diphenylphosphino)ferrocene]dichloropalladium(II) (0.144 g, 0.177 mmol) and CuI (34 mg, 0.177 mmol) were added. Following addition the reaction was heated to 80° C. and stirred for 4 h. Upon completion this was diluted with DCM, filtered through celite and concentrated in vacuo. The residue was purified by Biotage Isolera and concentrated in vacuo. LCMS calculated for $C_{10}H_{11}ClNO_2$ $(M+H-t-Bu)^+$: m/z=212.0/214.0; found=212.1/214.1.

Step 2. tert-Butyl 3-(4-(4,4,5,5-tetramethyl-1,3,2-dioxaborolan-2-yl)phenyl)azetidine-1-carboxylate

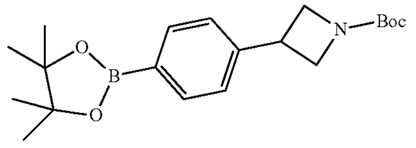 [SMILES: CC(C)(C)OC(=O)N1CC(c2ccc(B3OC(C)(C)C(C)(C)O3)cc2)C1]

To a vial was added tert-butyl 3-(4-chlorophenyl)azetidine-1-carboxylate (0.5 g, 1.867 mmol), XPhos Pd G2 (0.147 g, 0.187 mmol), bis(pinacolato)diboron (0.711 g, 2.80 mmol), potassium acetate (0.448 g, 4.67 mmol) in 1,4-dioxane (6 ml) The solution was purged with $N_2$ for 30 sec., sealed and heated to 80° C. for 2 h. At completion, volatiles were removed in vacuo to give the desired product, which was used directly for the next step. LCMS calculated for $C_{16}H_{23}BNO_4$ $(M+H-t-Bu)^+$: m/z=304.2 found=304.1.

Step 3. 9-(4-(Azetidin-3-yl)phenyl)-2-(2,6-dichlorophenyl)-3-methylimidazo[2,1-f][1,6]naphthyridine

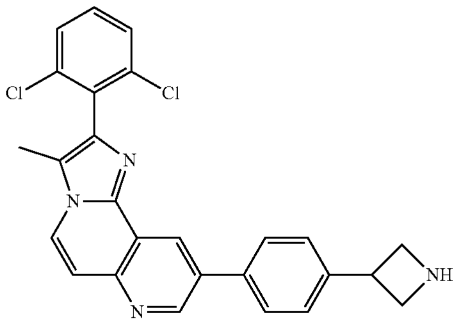

This compound was prepared according to the procedures described in Example 61, with tert-butyl 3-(4-(4,4,5,5-tetramethyl-1,3,2-dioxaborolan-2-yl)phenyl)azetidine-1-carboxylate replacing tert-butyl 3-(5-(4,4,5,5-tetramethyl-1,3,2-dioxaborolan-2-yl)pyridin-2-yl)azetidine-1-carboxylate in Step 2. LCMS calculated for $C_{26}H_{21}Cl_2N_4$ $(M+H)^+$: m/z=459.1/461.1; 459.1/461.1.

Step 4. 1-(3-(4-(2-(2,6-Dichlorophenyl)-3-methylimidazo[2,1-f][1.6]naphthyridin-9-yl)phenyl)azetidin-1-yl)ethan-1-one This compound was prepared according to the procedures described in Example 62 step 2, with 9-(4-(azetidin-3-yl)phenyl)-2-(2,6-dichlorophenyl)-3-methylimidazo[2,1-f][1,6]naphthyridine replacing 9-(5-(azetidin-3-yl)pyridin-3-yl)-2-(2,6-dichlorophenyl)-3-methylimidazo[2,1-f][1,6]naphthyridine. The title compound was isolated as the TFA salt. LCMS calculated for $C_{28}H_{23}Cl_2N_4O$ $(M+H)^+$: m/z=501.1/503.1; Found: 501.2/503.2

Example 64. (S)-1-(3-(4-(2-(2-Chlorophenyl)-3-(hydroxymethyl)imidazo[2,1-f][1,6]naphthyridin-9-yl)-1H-pyrazol-1-yl)pyrrolidin-1-yl)ethan-1-one

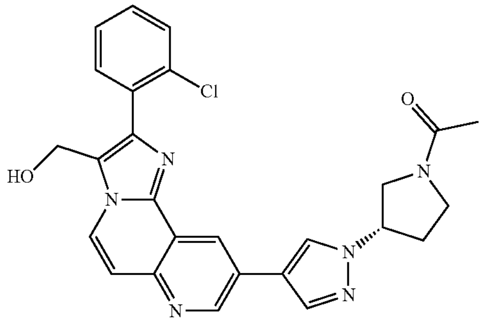 [SMILES: CC(=O)N1CC[C@H](n2cc(-c3cnc4ccn5c(CO)c(-c6ccccc6Cl)nc5c4c3)cn2)C1]

Step 1. (S)-(2-(2-Chlorophenyl)-9-(1-(pyrrolidin-3-yl)-1H-pyrazol-4-yl)imidazo[2,1-f][1,6]naphthyridin-3-yl)methanol

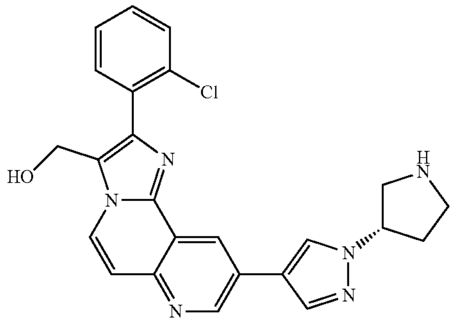 [SMILES: OCc1c(-c2ccccc2Cl)nc2c3cc(-c4cnn([C@H]5CCNC5)c4)cnc3ccn12]

This compound was prepared according to the procedures described in Example 55, with 2-bromo-1-(2-chlorophenyl)ethan-1-one replacing 2-bromo-1-(2,6-dichlorophenyl)ethan-1-one in Step 2. LCMS calculated for $C_{24}H_{22}Cl N_6O$ $(M+H)^+$: m/z=445.2/447.2; Found: 445.1/447.1.

Step 2. (S)-1-(3-(4-(2-(2-Chlorophenyl)-3-(hydroxymethyl)imidazo[2,1-f][1,6]naphthyridin-9-yl)-1H-pyrazol-1-yl)pyrrolidin-1-yl)ethan-1-one To a vial containing (S)-(2-(2-chlorophenyl)-9-(1-(pyrrolidin-3-yl)-1H-pyrazol-4-yl)imidazo[2,1-f][1,6]naphthyridin-3-yl)methanol (10 mg, 0.022 mmol) was added acetic acid (2 μL, 0.022 mmol), DMF (0.5 mL) and DIPEA (8 μL, 0.045 mmol). This was stirred for 1 min before HATU (13 mg, 0.034 mmol) was added and left to stir for 1 h. Upon completion the reaction mixture was then diluted with acetonitrile/methanol and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{26}H_{24}Cl N_6O_2$ $(M+H)^+$: m/z=487.2/489.2; Found: 487.1/489.2.

Example 65. (S)-1-(3-(4-(2-(2-Chlorophenyl)-3-isopropylimidazo[2,1-f][1,6]naphthyridin-9-yl)-1H-pyrazol-1-yl)pyrrolidin-1-yl)-2-hydroxyethan-1-one

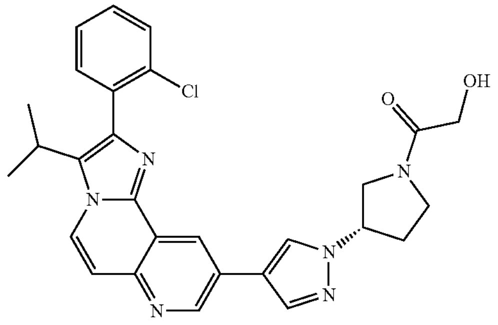 [SMILES: CC(C)c1c(-c2ccccc2Cl)nc2c3cc(-c4cnn([C@H]5CCN(C(=O)CO)C5)c4)cnc3ccn12]

Step 1. tert-Butyl (S)-3-(4-(2-(2-chlorophenyl)-3-(prop-1-en-2-yl)imidazo[2,1-f][1,6]naphthyridin-9-yl)-1H-pyrazol-1-yl)pyrrolidine-1-carboxylate

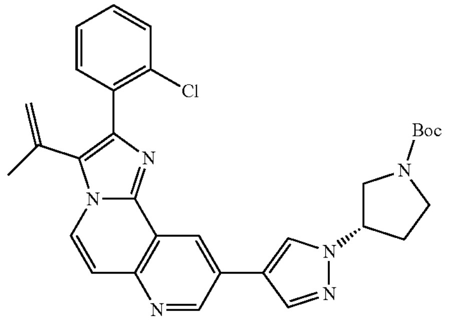 [SMILES: C=C(C)c1c(-c2ccccc2Cl)nc2c3cc(-c4cnn([C@H]5CCN(C(=O)OC(C)(C)C)C5)c4)cnc3ccn12]

This compound was prepared according to the procedures described in Examples 55 and 58, with 2-bromo-1-(2-chlorophenyl)ethan-1-one replacing 2-bromo-1-(2,6-dichlorophenyl)ethan-1-one in Example 55, Step 2. LCMS calculated for $C_{31}H_{32}Cl\,N_6O_2$ $(M+H)^+$: m/z=555.2/557.2; Found: 555.2/557.2.

Step 2. (S)-2-(2-Chlorophenyl)-3-isopropyl-9-(1-(pyrrolidin-3-yl)-1H-pyrazol-4-yl)imidazo[2,1-f][1,6]naphthyridine

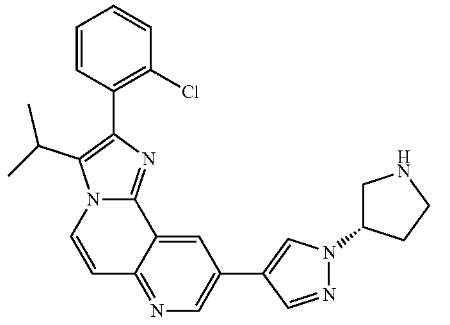 [SMILES: CC(C)c1c(-c2ccccc2Cl)nc2c3cc(-c4cnn([C@H]5CCNC5)c4)cnc3ccn12]

A vial containing tert-butyl (S)-3-(4-(2-(2-chlorophenyl)-3-(prop-1-en-2-yl)imidazo[2,1-f][1,6]naphthyridin-9-yl)-1H-pyrazol-1-yl)pyrrolidine-1-carboxylate (60 mg, 0.108 mmol) and palladium hydroxide (20 wt %, 12 mg, 0.017 mmol) as a solution in ethanol (540 μL) was purged with hydrogen gas for 1 min and left to stir under an atmosphere of hydrogen gas (balloon pressure) for 18 h. Upon completion the reaction mixture was diluted with $CH_2Cl_2$, filtered through celite and the filtrate was concentrated in vacuo. The resulting residue was dissolved in $CH_2Cl_2$ (1 mL) and TFA (0.5 mL) and stirred at r.t. for 1 h. At completion, the volatiles were removed in vacuo to give the desired product. LCMS calculated for $C_{26}H_{26}Cl\,N_6$ $(M+H)^+$: m/z=457.2/459.2; Found: 457.4/459.4.

Step 3. (S)-1-(3-(4-(2-(2-Chlorophenyl)-3-isopropylimidazo[2,1-f][1,6]naphthyridin-9-yl)-1H-pyrazol-1-yl)pyrrolidin-1-yl)-2-hydroxyethan-1-one This compound was prepared according to the procedures described in Example 25, with (S)-2-(2-chlorophenyl)-3-isopropyl-9-(1-(pyrrolidin-3-yl)-1H-pyrazol-4-yl)imidazo[2,1-f][1,6]naphthyridine replacing (S)-2-(2-chloro-6-(trifluoromethyl)phenyl)-3-methyl-9-(1-(pyrrolidin-3-yl)-1H-pyrazol-4-yl)imidazo[2,1-f][1,6]naphthyridine in Step 8. The title compound was isolated as the TFA salt. LCMS calculated for $C_{28}H_{28}Cl\,N_6O_2$ $(M+H)^+$: m/z=515.2/517.2; found 515.3/517.3.

Example 66. (S)-1-(3-(4-(3-Bromo-2-(2-chloro-6-fluorophenyl)imidazo[2,1-f][1,6]naphthyridin-9-yl)-1H-pyrazol-1-yl)pyrrolidin-1-yl)-2-hydroxyethan-1-one

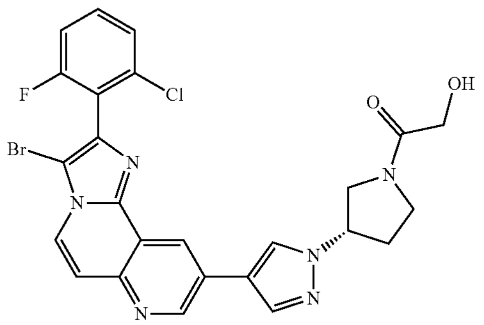 [SMILES: O=C(CO)N1CC[C@H](n2cc(-c3cnc4ccn5c(Br)c(-c6c(F)cccc6Cl)nc5c4c3)cn2)C1]

Step 1. tert-Butyl (S)-3-(4-(3-bromo-2-(2-chloro-6-fluorophenyl)imidazo[2,1-f][1,6]naphthyridin-9-yl)-1H-pyrazol-1-yl)pyrrolidine-1-carboxylate

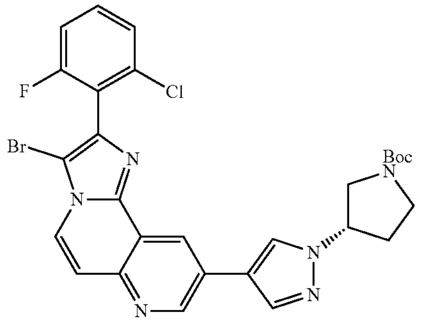 [SMILES: CC(C)(C)OC(=O)N1CC[C@H](n2cc(-c3cnc4ccn5c(Br)c(-c6c(F)cccc6Cl)nc5c4c3)cn2)C1]

This compound was prepared according to the procedures described in Example 56, Steps 1 through 4, with 2-bromo-1-(2-chloro-6-fluorophenyl)ethan-1-one replacing 2-bromo-1-(2,6-dichlorophenyl)ethan-1-one in Step 2. LCMS calculated for $C_{28}H_{26}BrClFN_6O_2$ $(M+H)^+$: m/z=611.1/613; found 611.2/613.3.

Step 2. (S)-1-(3-(4-(3-Bromo-2-(2-chloro-6-fluorophenyl)imidazo[2,1-f][1,6]naphthyridin-9-yl)-1H-pyrazol-1-yl)pyrrolidin-1-yl)-2-hydroxyethan-1-one tert-Butyl (S)-3-(4-(3-bromo-2-(2-chloro-6-fluorophenyl)imidazo[2,1-f][1,6]naphthyridin-9-yl)-1H-pyrazol-1-yl)pyrrolidine-1-carboxylate (15 mg, 0.024 mmol) was dissolved in $CH_2Cl_2$ (1 mL) and TFA (0.5 mL) and stirred at r.t. for 1 hr. At completion, the volatiles were removed in vacuo to give (S)-3-bromo-2-(2-chloro-6-fluorophenyl)-9-(1-(pyrrolidin-3-yl)-1H-pyrazol-4-yl)imidazo[2,1-f][1,6]naphthyridine (10 mg, 0.022 mmol), to which was added 2-hydroxyacetic acid (1.7 mg, 0.022 mmol), DMF (0.5 mL) and diisopropylethylamine (8 µL, 0.043 mmol). The reaction mixture was stirred for 1 min before HATU (12.4 mg, 0.147 mmol) was added and left to stir at r.t. for 1 h. Upon completion the reaction mixture was then diluted with acetonitrile and methanol and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{25}H_{20}BrClFN_6O_2$ $(M+H)^+$: m/z=569.1/571.0; found 569.2/571.2.

Example 67. 2-Cyclopropyl-3-methyl-9-(1-methyl-1H-pyrazol-4-yl)imidazo[2,1-f][1,6]naphthyridine

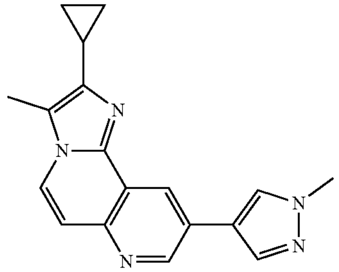

Step 1. 2-Cyclopropyl-3-methyl-9-(1H-pyrazol-4-yl)imidazo[2,1-f][1,6]naphthyridine

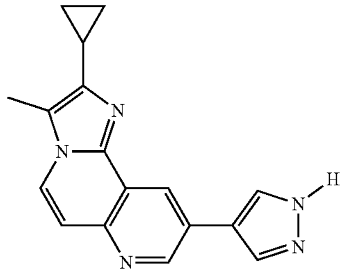 [SMILES: Cc1c(C2CC2)nc2c3cc(-c4cn[nH]c4)cnc3ccn12]

This compound was prepared according to the procedures described in Examples 37 and 55, with 2-bromo-1-cyclopropylethan-1-one replacing 2-bromo-1-(2,6-dichlorophenyl)ethan-1-one in Example 55, Step 2. LCMS calculated for $C_{17}H_{16}N_5$ $(M+H)^+$: m/z=290.1; found 290.1.

Step 2. 2-Cyclopropyl-3-methyl-9-(1-methyl-1H-pyrazol-4-yl)imidazo[2,1-f][1,6]naphthyridine A vial containing a mixture of 2-cyclopropyl-3-methyl-9-(1H-pyrazol-4-yl)imidazo[2,1-f][1,6]naphthyridine (20 mg, 0.069 mmol), methyl iodide (2M in tert-butyl methyl ether, 38 µL, 0.076 mmol), cesium carbonate (34 mg, 0.104 mmol), in acetonitrile (0.346 mL) was heated to 40° C. Upon completion, the reaction mixture was diluted with $CH_2Cl_2$ and filtered through Celite, followed by concentration of the filtrate in vacuo. The residue was diluted with acetonitrile and methanol and purified with prep-LCMS(XBridge C18 column, eluting with a gradient of acetonitrile/water containing 0.1% TFA, at flow rate of 60 mL/min). The title compound was isolated as the TFA salt. LCMS calculated for $C_{18}H_{18}N_5$ $(M+H)^+$: m/z=304.2; found 304.1.

Example 68. (2-(2,6-Dichlorophenyl)-9-(1-methyl-1H-pyrazol-4-yl)imidazo[2,1-f][1,6]naphthyridin-3-yl)methanol

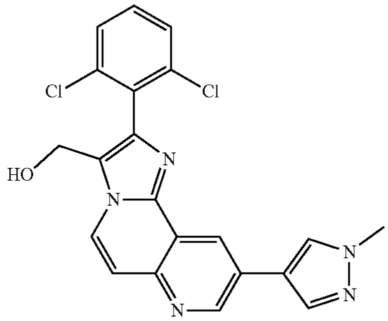 [SMILES: Cn1cc(-c2cnc3ccn4c(CO)c(-c5c(Cl)cccc5Cl)nc4c3c2)cn1]

Step 1. 9-Bromo-2-(2,6-dichlorophenyl)-3-iodoimidazo[2,1-f][1,6]naphthyridine

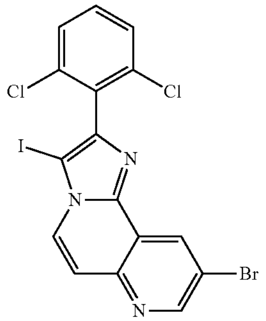 [SMILES: Clc1cccc(Cl)c1-c1nc2c3cc(Br)cnc3ccn2c1I]

A vial containing 9-bromo-2-(2,6-dichlorophenyl)imidazo[2,1-f][1,6]naphthyridine (Example 15, Step 1, 200 mg, 0.509 mmol), NIS (114 mg, 0.509 mmol) in acetonitrile (2 mL) was stirred at 60° C. for 4 h. The solution was subsequently cooled to room temperature, concentrated in vacuo and purified by Biotage Isolera to give the desired product as a brown solid. LCMS calculated for $C_{16}H_8BrCl_2IN_3$ (M+H)$^+$: m/z=517.8/519.8; found 517.9/519.7.

Step 2. 9-Bromo-2-(2,6-dichlorophenyl)-3-vinylimidazo[2,1-f][1,6]naphthyridine

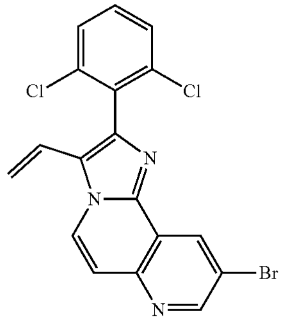 [SMILES: C=Cc1c(-c2c(Cl)cccc2Cl)nc2c3cc(Br)cnc3ccn12]

A vial containing 9-bromo-2-(2,6-dichlorophenyl)-3-iodoimidazo[2,1-f][1,6]naphthyridine (150 mg, 0.289 mmol), potassium phosphate, tribasic (123 mg, 0.578 mmol), tetrakis(triphenylphosphine)palladium(0) (33 mg, 0.029 mmol) and 4,4,5,5-tetramethyl-2-vinyl-1,3,2-dioxaborolane (49 μL, 0.289 mmol) was suspended in 1,4-dioxane (2 mL), and water (200 μL). This was purged with nitrogen for 30 sec. and heated to 70° C. for 2 h. Upon cooling to room temperature, the solution was diluted with $CH_2Cl_2$, filtered through Celite and the filtrate was concentrated in vacuo. The resulting residue was purified by Biotage Isolera to give the desired product as a brown solid. LCMS calculated for $C_{18}H_{11}BrCl_2N_3$ (M+H)$^+$: m/z=418.0/419.9; found 418.1/420.1.

Step 3. (9-Bromo-2-(2,6-dichlorophenyl)imidazo[2,1-f][1,6]naphthyridin-3-yl)methanol

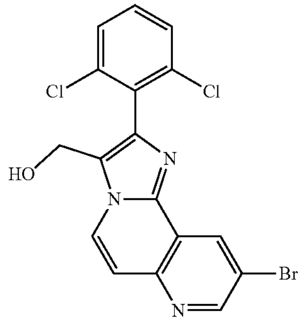 [SMILES: OCc1c(-c2c(Cl)cccc2Cl)nc2c3cc(Br)cnc3ccn12]

To a vial was added 9-bromo-2-(2,6-dichlorophenyl)-3-vinylimidazo[2,1-f][1,6]naphthyridine (80 mg, 0.191 mmol), THF (3 mL), water (1 mL) and osmium tetroxide (4 wt. % in $H_2O$, 75 μL, 9.54 μmol), followed by sodium periodate (204 mg, 0.954 mmol). The reaction mixture was stirred at room temperature for 3 h, and upon completion the reaction was quenched with saturated aqueous $Na_2S_2O_3$ and extracted into EtOAc. The combined organic layers were concentrated in vacuo and the residue was dissolved in isopropanol (4 mL), cooled to 0° C., and $NaBH_4$ (7.22 mg, 0.191 mmol) was added with stirring while allowing the reaction to slowly warm to room temperature. The reaction was then cooled to 0° C. and quenched by addition of saturated aqueous $NH_4Cl$. The volatiles were removed in vacuo and the residue was extracted into 20:1 $CH_2Cl_2$/MeOH. The resulting organic layers were combined and concentrated in vacuo. The obtained product was used in the next step without further purification. LCMS calculated for $C_{17}H_{11}BrCl_2N_3O$ (M+H)$^+$: m/z=421.9/423.9; found 421.9/424.0.

Step 4. (2-(2,6-Dichlorophenyl)-9-(1-methyl-1H-pyrazol-4-yl)imidazo[2,1-f][1,6]naphthyridin-3-yl)methanol To a vial was added (9-bromo-2-(2,6-dichlorophenyl)imidazo[2,1-f][1,6]naphthyridin-3-yl)methanol (20 mg, 0.047 mmol), 1-methyl-4-(4,4,5,5-tetramethyl-1,3,2-dioxaborolan-2-yl)-1H-pyrazole (10 mg, 0.047 mmol), potassium phosphate, tribasic (30 mg, 0.142 mmol), and (1,1'-bis(diphenylphosphino)ferrocene)dichloropalladium(II) (3 mg, 4.73 μmol) in 1,4-dioxane (1 mL) and water (100 μL). This was purged with nitrogen for 1 min, sealed and heated to 80° C. for 30 min. Upon completion the reaction mixture was cooled to room temperature and flushed through a SiliaPrep SPE thiol cartridge (SPE-R51030B-06P), diluted with acetonitrile/methanol and purified with prep-LCMS (XBridge C18 column, eluting with a gradient of acetonitrile/water containing 0.1% TFA, at flow rate of 60 mL/min). The title compound was isolated as the TFA salt. LCMS calculated for $C_{21}H_{16}Cl_2N_5O$ (M+H)$^+$: m/z=424.1/426.1; found 424.0/426.1.

Example 69. (9-(1-Cyclopropyl-1H-pyrazol-4-yl)-2-(2,6-dichlorophenyl)imidazo[2,1-f][1,6]naphthyridin-3-yl)methanol

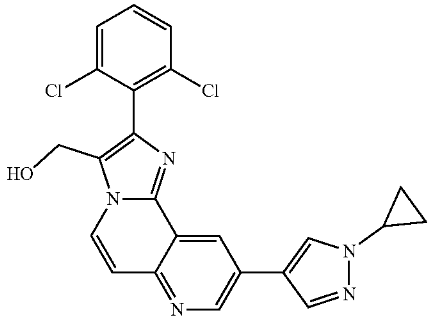 [SMILES: OCc1c(-c2c(Cl)cccc2Cl)nc2c3cc(-c4cnn(C5CC5)c4)cnc3ccn12]

This compound was prepared according to the procedures described in Example 68, with 1-cyclopropyl-4-(4,4,5,5-tetramethyl-1,3,2-dioxaborolan-2-yl)-1H-pyrazole replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{23}H_{18}Cl_2N_5O$ (M+H)$^+$: m/z=450.1/452.1; Found: 450.1/452.0.

Example 70. (2-(2,6-Dichlorophenyl)-9-(1-(tetrahydrofuran-3-yl)-1H-pyrazol-4-yl)imidazo[2,1-f][1,6]naphthyridin-3-yl)methanol

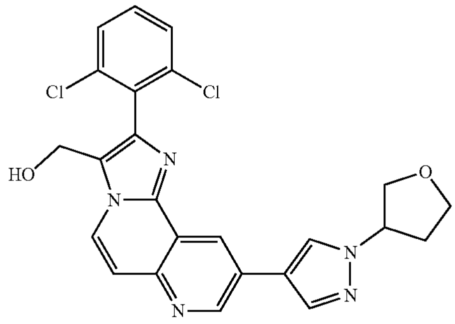 [SMILES: OCc1c(-c2c(Cl)cccc2Cl)nc2c3cc(-c4cnn(C5CCOC5)c4)cnc3ccn12]

This compound was prepared according to the procedures described in Example 68, with 1-(tetrahydrofuran-3-yl)-4-(4,4,5,5-tetramethyl-1,3,2-dioxaborolan-2-yl)-1H-pyrazole replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{24}H_{20}Cl_2N_5O_2$ $(M+H)^+$: m/z=480.1/482.1; Found: 480.1/482.0.

Example 71. (2-(2,6-Dichlorophenyl)-9-(1-(oxetan-3-yl)-1H-pyrazol-4-yl)imidazo[2,1-f][1,6]naphthyridin-3-yl)methanol

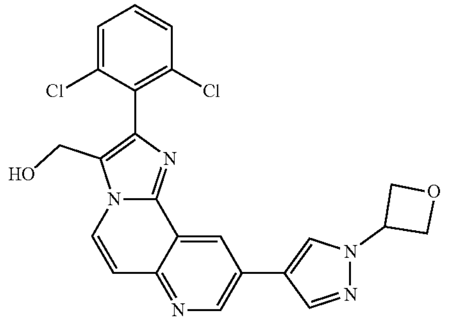 [SMILES: OCc1c(-c2c(Cl)cccc2Cl)nc2c3cc(-c4cnn(C5COC5)c4)cnc3ccn12]

This compound was prepared according to the procedures described in Example 68, with 1-(oxetan-3-yl)-4-(4,4,5,5-tetramethyl-1,3,2-dioxaborolan-2-yl)-1H-pyrazole replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{23}H_{18}Cl_2N_5O_2$ $(M+H)^+$: m/z=466.1/468.1; Found: 466.0/468.0.

Example 72. (2-(2,6-Dichlorophenyl)-9-(1-(2-(dimethylamino)ethyl)-1H-pyrazol-4-yl)imidazo[2,1-f][1,6]naphthyridin-3-yl)methanol

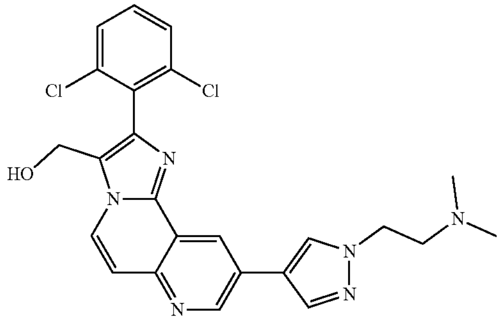 [SMILES: CN(C)CCn1cc(-c2cnc3ccn4c(CO)c(-c5c(Cl)cccc5Cl)nc4c3c2)cn1]

This compound was prepared according to the procedures described in Example 68, with N,N-dimethyl-2-(4-(4,4,5,5-tetramethyl-1,3,2-dioxaborolan-2-yl)-1H-pyrazol-1-yl)ethan-1-amine replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{24}H_{23}Cl_2N_6O$ $(M+H)^+$: m/z=481.1/483.1; Found: 481.1/483.1.

Example 73. (2-(2,6-Dichlorophenyl)-9-(1-isopropyl-1H-pyrazol-4-yl)imidazo[2,1-f][1,6]naphthyridin-3-yl)methanol

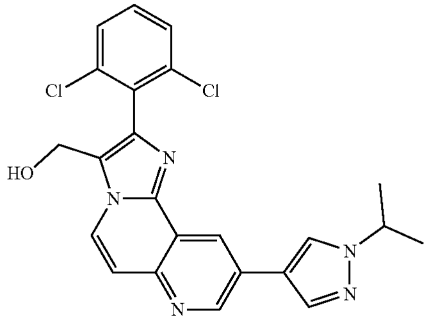 [SMILES: CC(C)n1cc(-c2cnc3ccn4c(CO)c(-c5c(Cl)cccc5Cl)nc4c3c2)cn1]

This compound was prepared according to the procedures described in Example 68, with 1-isopropyl-4-(4,4,5,5-tetramethyl-1,3,2-dioxaborolan-2-yl)-1H-pyrazole replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{23}H_{20}Cl_2N_5O$ $(M+H)^+$: m/z=452.1/454.1; Found: 452.1/454.0.

Example 74. (2-(2,6-Dichlorophenyl)-9-(1-(difluoromethyl)-1H-pyrazol-4-yl)imidazo[2,1-f][1,6]naphthyridin-3-yl)methanol

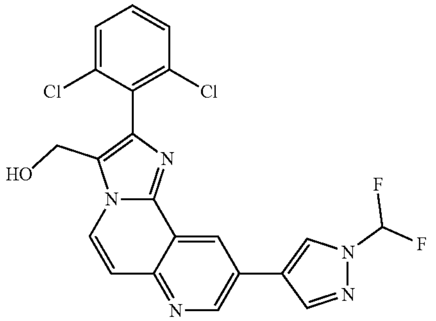 [SMILES: OCc1c(-c2c(Cl)cccc2Cl)nc2c3cc(-c4cnn(C(F)F)c4)cnc3ccn12]

This compound was prepared according to the procedures described in Example 68, with 1-(difluoromethyl)-4-(4,4,5,5-tetramethyl-1,3,2-dioxaborolan-2-yl)-1H-pyrazole replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{21}H_{14}Cl_2F_2N_5O$ $(M+H)^+$: m/z=460.1/462.1; Found: 460.0/462.0.

Example 75. 3-(4-(2-(2,6-Dichlorophenyl)-3-(hydroxymethyl)imidazo[2,1-f][1,6]naphthyridin-9-yl)-1H-pyrazol-1-yl)propanenitrile

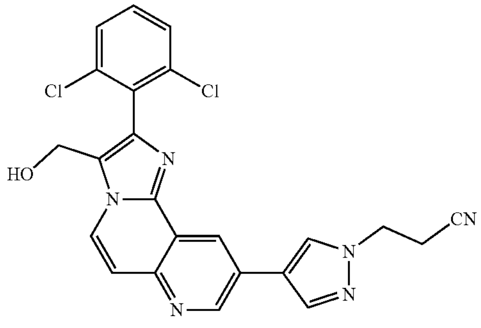

This compound was prepared according to the procedures described in Example 68, with 3-(4-(4,4,5,5-tetramethyl-1,3,2-dioxaborolan-2-yl)-1H-pyrazol-1-yl)propanenitrile replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{23}H_{17}Cl_2N_6O$ $(M+H)^+$: m/z=463.1/465.1; Found: 463.1/465.0.

Example 76. 1-(4-(2-(2,6-Dichlorophenyl)-3-(hydroxymethyl)imidazo[2,1-f][1,6]naphthyridin-9-yl)-1H-pyrazol-1-yl)-2-methylpropan-2-ol

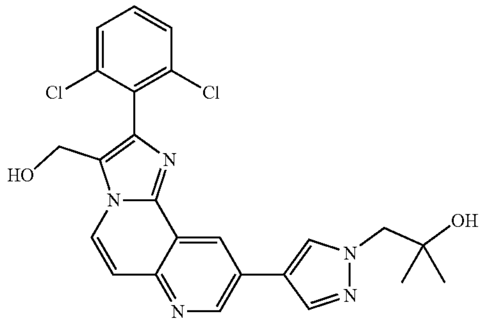 [SMILES: CC(C)(O)Cn1cc(-c2cnc3ccn4c(CO)c(-c5c(Cl)cccc5Cl)nc4c3c2)cn1]

This compound was prepared according to the procedures described in Example 68, with 2-methyl-1-(4-(4,4,5,5-tetramethyl-1,3,2-dioxaborolan-2-yl)-1H-pyrazol-1-yl)propan-2-ol replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{24}H_{22}Cl_2N_5O_2$ $(M+H)^+$: m/z=482.1/484.1; Found: 482.1/484.0.

Example 77. 2-(4-(2-(2,6-Dichlorophenyl)-3-(hydroxymethyl)imidazo[2,1-f][1,6]naphthyridin-9-yl)-1H-pyrazol-1-yl)acetonitrile

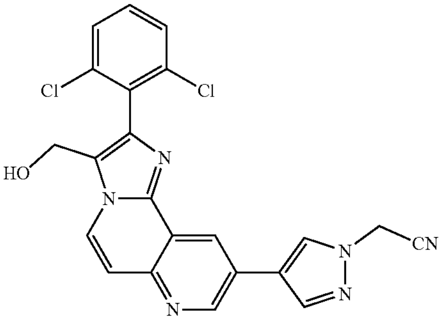

This compound was prepared according to the procedures described in Example 68, with 2-(4-(4,4,5,5-tetramethyl-1,3,2-dioxaborolan-2-yl)-1H-pyrazol-1-yl)acetonitrile replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{22}H_{15}Cl_2N_6O$ $(M+H)^+$: m/z=449.1/451.1; Found: 449.2/451.2.

Example 78. (2-(2,6-Dichlorophenyl)-9-(1-(1-methylpiperidin-4-yl)-1H-pyrazol-4-yl)imidazo[2,1-f][1,6]naphthyridin-3-yl)methanol

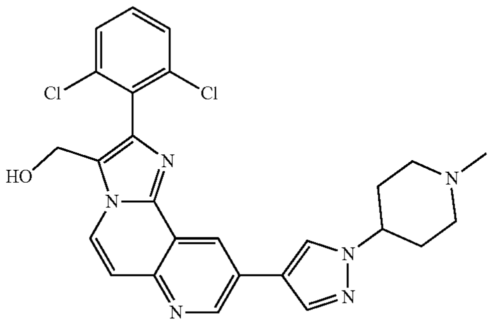 [SMILES: CN1CCC(n2cc(-c3cnc4ccn5c(CO)c(-c6c(Cl)cccc6Cl)nc5c4c3)cn2)CC1]

This compound was prepared according to the procedures described in Example 68, with 1-methyl-4-(4-(4,4,5,5-tetramethyl-1,3,2-dioxaborolan-2-yl)-1H-pyrazol-1-yl)piperidine replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{26}H_{25}Cl_2N_6O$ $(M+H)^+$: m/z=507.1/509.1; Found: 507.3/509.2.

Example 79. 2-(4-(2-(2,6-Dichlorophenyl)-3-(hydroxymethyl)imidazo[2,1-f][1,6]naphthyridin-9-yl)-1H-pyrazol-1-yl)-2-methylpropan-1-ol

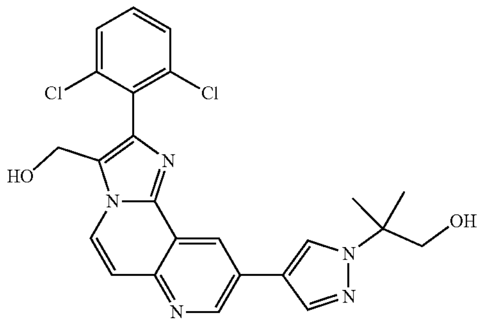 [SMILES: CC(C)(CO)n1cc(-c2cnc3ccn4c(CO)c(-c5c(Cl)cccc5Cl)nc4c3c2)cn1]

This compound was prepared according to the procedures described in Example 68, with 2-methyl-2-(4-(4,4,5,5-tetramethyl-1,3,2-dioxaborolan-2-yl)-1H-pyrazol-1-yl)propan-1-ol replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{24}H_{22}Cl_2N_5O_2$ $(M+H)^+$: m/z=482.1/484.1; Found: 482.3/484.3.

Example 80. (2-(2,6-Dichlorophenyl)-9-(1-(2-(methylsulfonyl)ethyl)-1H-pyrazol-4-yl)imidazo[2,1-f][1,6]naphthyridin-3-yl)methanol

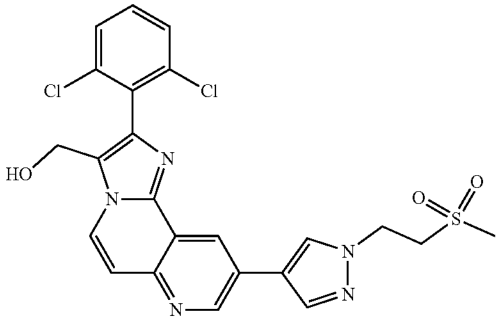 [SMILES: CS(=O)(=O)CCn1cc(-c2cnc3ccn4c(CO)c(-c5c(Cl)cccc5Cl)nc4c3c2)cn1]

This compound was prepared according to the procedures described in Example 68, with 1-(2-(methylsulfonyl)ethyl)-4-(4,4,5,5-tetramethyl-1,3,2-dioxaborolan-2-yl)-1H-pyrazole replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{23}H_{20}Cl_2N_5O_3S$ $(M+H)^+$: m/z=516.1/518.1; Found: 516.1/518.1.

Example 81. (2-(2,6-Dichlorophenyl)-9-(1-(2,2,2-trifluoroethyl)-1H-pyrazol-4-yl)imidazo[2,1-f][1,6]naphthyridin-3-yl)methanol

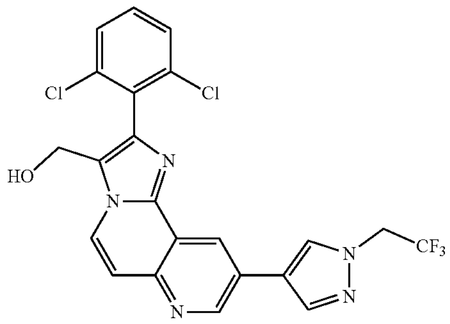 [SMILES: OCc1c(-c2c(Cl)cccc2Cl)nc2c3cc(-c4cnn(CC(F)(F)F)c4)cnc3ccn12]

This compound was prepared according to the procedures described in Example 68, with 4-(4,4,5,5-tetramethyl-1,3,2-dioxaborolan-2-yl)-1-(2,2,2-trifluoroethyl)-1H-pyrazole replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{22}H_{15}Cl_2F_3N_5O$ $(M+H)^+$: m/z=492.1/494.1; Found: 492.2/494.2.

Example 82. (2-(2,6-Dichlorophenyl)-9-(1-(2-morpholinoethyl)-1H-pyrazol-4-yl)imidazo[2,1-f][1,6]naphthyridin-3-yl)methanol

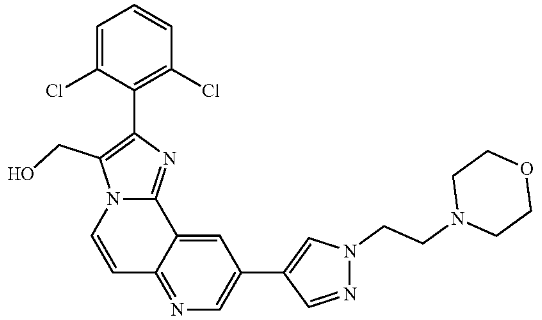 [SMILES: OCc1c(-c2c(Cl)cccc2Cl)nc2c3cc(-c4cnn(CCN5CCOCC5)c4)cnc3ccn12]

This compound was prepared according to the procedures described in Example 68, with 4-(2-(4-(4,4,5,5-tetramethyl-1,3,2-dioxaborolan-2-yl)-1H-pyrazol-1-yl)ethyl)morpholine replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{26}H_{25}Cl_2N_6O_2$ $(M+H)^+$: m/z=523.1/525.1; Found: 523.2/525.2.

Example 83. 2-(4-(2-(2,6-Dichlorophenyl)-3-(hydroxymethyl)imidazo[2,1-f][1,6]naphthyridin-9-yl)-1H-pyrazol-1-yl)ethan-1-ol

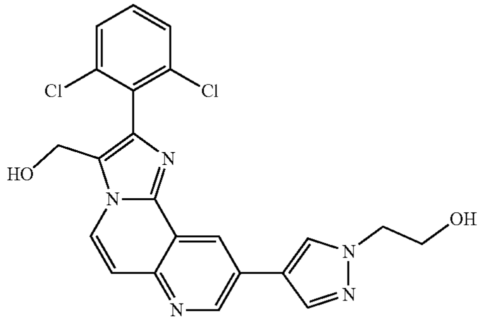 [SMILES: OCCn1cc(-c2cnc3ccn4c(CO)c(-c5c(Cl)cccc5Cl)nc4c3c2)cn1]

This compound was prepared according to the procedures described in Example 68, with 2-(4-(4,4,5,5-tetramethyl-1,3,2-dioxaborolan-2-yl)-1H-pyrazol-1-yl)ethan-1-ol replacing 1-methyl-4-(4,4,5,5-tetramethyl-1,3,2-dioxaborolan-2-yl)-1H-pyrazole in Step 4. The title compound was isolated as the TFA salt. LCMS calculated for $C_{22}H_{18}Cl_2N_5O_2$ $(M+H)^+$: m/z=454.1/456.1; Found: 454.2/456.2.

Example A: FGFR Enzymatic Assay

The inhibitor potency of the exemplified compounds was determined in an enzyme discontinuous assay that measures peptide phosphorylation using FRET measurements to detect product formation. Inhibitors were serially diluted in DMSO and a volume of 0.2 μL was transferred to the wells of a 384-well plate. A 5 μL/well volume of enzyme isoforms of FGFR (−1, −2, −3 wild-type and mutant isoforms, −4) including phosphorylated and un-phosphorylated proteins diluted in assay buffer (50 mM HEPES, 10 mM $MgCl_2$, 1 mM EGTA, 0.01% Tween-20, 5 mM DTT, pH 7.5) was added to the plate and pre-incubated with inhibitor for 5 to 15 minutes at ambient temperature. Appropriate controls (enzyme blank and enzyme with no inhibitor) were included on the plate. The reaction was initiated by the addition of a 5 μL/well volume containing both biotinylated EQEDEPEGDYFEWLE peptide substrate (SEQ ID NO: 1) and ATP in assay buffer. The 10 μL/well reaction concentration of the peptide substrate was 500 nM whereas the ATP concentration was maintained near or below the ATP Km. The ATP Km values were pre-determined in a separate series of experiments. The reaction plate was incubated at 25° C. for 1 hr and the reactions were ended with the addition of 5 μL/well of quench solution (50 mM Tris, 150 mM NaCl, 0.5 mg/mL BSA, pH 7.8; 45 mM EDTA, 600 nM staurosporin, with Perkin Elmer Lance Reagents at 3.75 nM Eu-antibody PY20 and 180 nM APC-Streptavidin). The plate was allowed to equilibrate for ~10 minutes at ambient temperature before scanning on a PheraStar plate reader (BMG Labtech) instrument.

Either GraphPad prism or XLfit was used to analyze the data. The $IC_{50}$ values were derived by fitting the data to a four parameter logistic equation producing a sigmoidal dose-response curve with a variable Hill coefficient. Prism equation: Y=Bottom+(Top−Bottom)/(1+10^((LogIC$_{50}$−X)*Hill slope)); XLfit equation: Y=(A+((B−A)/(1+((X/C)^D)))) where X is the logarithm of inhibitor concentration and Y is the response. Compounds having an $IC_{50}$ of 1 μM or less are considered active.

Table 1 provides $IC_{50}$ data for compounds of the disclosure assayed in the FGFR Enzymatic Assay after dilution in assay buffer, added to the plate and pre-incubated for 4 hours. The symbol: "+" indicates an $IC_{50}$ less than 10 nM; "++" indicates an $IC_{50}$ greater than or equal to 10 nM but less than 100 nM; "+++" indicates an $IC_{50}$ greater than or equal to 100 nM but less than 400 nM; and "++++" indicates an $IC_{50}$ greater than or equal to 400 nM.

The data in Table 1 was measured in wild-type un-phosphorylated FGFR3 protein.

TABLE 1

| Example | FGFR3_Ki, nM |
|---|---|
| 1 | ++ |
| 2 | +++ |
| 3 | ++ |
| 4 | + |
| 5 | +++ |
| 6 | ++ |
| 7 | +++ |
| 8 | + |
| 9 | ++ |
| 10 | ++ |
| 11 | ++ |
| 12 | ++ |
| 13 | + |
| 14 | ++ |
| 15 | + |
| 16 | + |
| 17 | + |
| 18 | ++ |
| 19 | +++ |
| 20 | +++ |
| 21 | + |
| 22 | + |
| 23 | ++++ |
| 24 | ++++ |
| 25 | + |
| 26 | + |
| 27 | ++ |
| 28 | ++ |

TABLE 1-continued

| Example | FGFR3_Ki, nM |
|---|---|
| 29 | ++ |
| 30 | ++ |
| 31 | ++ |
| 32 | +++ |
| 33 | ++ |
| 34 | + |
| 35 | ++ |
| 36 | +++ |
| 37 | + |
| 38 | + |
| 39 | + |
| 40 | + |
| 41 | + |
| 42 | + |
| 43 | ++ |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | + |
| 61 | ++ |
| 62 | ++ |
| 63 | + |
| 64 | + |
| 65 | ++ |
| 66 | + |
| 67 | +++ |
| 68 | + |
| 69 | + |
| 70 | + |
| 71 | + |
| 72 | + |
| 73 | + |
| 74 | + |
| 75 | + |
| 76 | + |
| 77 | + |
| 78 | + |
| 79 | + |
| 80 | + |
| 81 | + |
| 82 | + |
| 83 | + |

Example B: Luminescent Viability Assay

RT112 cells are purchased from ATCC (Manassas, VA) and maintained in RPMI, 10% FBS (Gibco/Life Technologies). To measure the effect of test compounds on the viability of cells, the cells are plated with RPMI 10% FBS ($5\times10^3$ cells/well/in 50 μL) into black 96-well Greiner polystyrene in the presence or absence of 50 ul of a concentration range of test compounds. After 3 days, 100 ul of CellTiter-Glo Reagent (Promega) is added. Luminescence is read with a TopCount (PerkinElmer). $IC_{50}$ determination is performed by fitting the curve of percent inhibition versus the log of the inhibitor concentration using the GraphPad Prism 5.0 software.

Example C: pFGFR2 and pFGFR1,3 Functional Cell HTRF Assay

To measure phosphorylated Fibroblast Growth Factor Receptor 2 (FGFR2), KATOIII cells (Human Gastric Carcinoma) are purchased from ATCC and maintained in Iscove's with 20% FBS (Gibco/Life Technologies). For the pFGFR2 assay, KATOIII cells are plated overnight in 5% FBS and Iscove's medium at $5\times10^4$ cells/well into Corning 96-well flat-bottom tissue culture treated plates. The next morning, 50 μl of fresh media with 0.5% FBS is incubated in the presence or absence of a concentration range of test compounds also at 50 ul, for 1 hour at 37° C., 5% CO2. Cell are washed with PBS, lysed with Cell Signaling Lysis Buffer with standard Protease inhibitors for 45 min at room temperature. 4 μl total of Cis Bio Anti Phospho-YAP d2 and Cis Bio Anti Phospho-YAP Cryptate together are added to the lysate and mixed well (following directions of the kit). 16 μl is then transferred to 384 well Greiner white plates and stored at 4° C. overnight in the dark. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 5.0 software.

To measure phosphorylated Fibroblast Growth Factor Receptor 3 (FGFR3), in house stable cell lines BAF3-TEL-FGFR1 or BAF3-TEL-FGFR3 are maintained in RPMI with 10% FBS and 1 ug/ml puromycin (Gibco/Life Technologies). For the assay, 12 nl of BAF3-TEL-FGFR1 or BAF3-TEL-FGFR3 cells in serum free and puromycin free RPMI media at $1\times10^6$ cell/ml are added to 384 Greiner white plate already containing 20 nl dots of compounds at a concentration range. The plates are gently shaken (100 rpm) for 2 minutes at room temperature to mix well and incubate for 2 hours in a single layer at 37° C., 5% CO2. 4 μl/well of 1/25 dilution of lysis buffer #3 (Cis Bio) is added with standard Protease inhibitors and shaken at 200 rpm at room temperature for 20 minutes. 4 μl total of the Cis Bio Tb-pFGFR Ab (10 ng) and d2-FGFR3 (1 ng) together are added to the lysate and mixed well. The plates are sealed and incubated at room temperature overnight in the dark. The plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 5.0 software.

Example D: pFGFR3 Functional Whole Blood HTRF Assay

To measure phosphorylated Fibroblast Growth Factor Receptor 3 (FGFR3) in a whole blood assay, in house stable cell lines BAF3-TEL-FGFR3 are maintained in RPMI with 10% FBS and 1 μg/ml puromycin (Gibco/Life Technologies). For the assay, 100 ul BAF3-TEL-FGFR3 cells in 10% FBS and puromycin free RPMI media at $5\times10^4$ cell/well are added to fibronectin coated 96 well tissue culture plate (5 ug/ml) overnight at 37° C., 5% CO2. The next day, serum is separated from the top of the blood by a low speed spin, 1200, RPM, and heat inactivated by incubating at 56° C. for 15 minutes. 30 μl of the cooled serum is added to a 96 well plate pre dotted with 70 nM dots of compounds at a concentration range. Cell plates are washed gently with media, all the blood/compound mixture is added to the plates, and the plates are incubated for 2 hours at 37° C., 5% CO2. Blood from the plate is gently washed twice by adding media to the side of the wells and then dumping media from the plate, and allowing the plate to briefly sit on a paper towel to drain. 70 μl/well of 1× of lysis buffer #1 (Cis Bio) are added with standard Protease inhibitors, and are shaken at 400 rpm at room temperature for 30 minutes. Following lysis, the plate is spun down for 5 minutes and 16 uL of lysate is transferred into a 384-well small volume plate. 4 μl total of the Cis Bio Tb-pFGFR Ab (10 ng) and d2-FGFR3 (1 ng) together are added to the lysate and mixed well. The plates are sealed and incubated at room temperature overnight in the dark. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 5.0 software.

Example E: KATOIII Whole Blood pFGFR2a ELISA Assay

To measure tyrosine-phosphorylated Fibroblast Growth Factor Receptor 2 alpha (FGFR2α) in KATO III spiked whole blood assay, KATO III cells are purchased from ATCC and maintained in Iscove's medium with 20% FBS (Gibco/Life Technologies). To measure the inhibition of FGFR2α activity of test compounds, the cells are resuspended with Iscove's, 0.2% FBS at $5\times10^6$ cells/ml. 50 μL of the cells are then spiked into a 96-deep well 2 ml polypropylene assay block (Costar,) in the presence or absence of a concentration range of test compounds and 300 ul human heparinized whole blood (Biological Specialty Corp, Colmar PA). After 4 hours incubation in 37° C., the red cells are lysed using Qiagen EL buffer and the cell lysates are resuspended in lysis buffer (Cell Signaling) containing standard protease inhibitor cocktail (Calbiochem/EMD,) and PMSF (Sigma) for 30 minutes ice. The lysates are transferred to a standard V bottom propylene tissue culture plate and frozen overnight at −80° C. Samples are tested an in an R & D Systems DuoSet IC Human Phospho-FGF R2α ELISA and the plate is measured using a SpectraMax M5 microplate set to 450 nm with a wavelength correction of 540. $IC_{50}$ determination is performed by fitting the curve of inhibitor percent inhibition versus the log of the inhibitor concentration using the GraphPad Prism 5.0 software.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound having Formula (I):

I

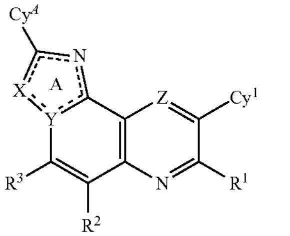

or a pharmaceutically acceptable salt thereof, wherein:

X is $NR^5$;

Y is C;

$\overline{\overline{----}}$ represents a single bond or a double bond;

Z is N;

$Cy^1$ is 5-10 membered heteroaryl; wherein each 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the 5-10 membered heteroaryl is optionally substituted with 1, 2, 3 or 4 substituents independently selected from R10;

$Cy^A$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{20}$;

$R^1$, $R^2$, and $R^3$ are each independently selected from H, D, $C_{1-6}$ alkyl, $C_{1-6}$ haloalkyl, $C_{3-10}$ cycloalkyl, halo, CN, $OR^{a9}$, and $NR^{c9}R^{d9}$;

$R^5$ is selected from $C_{1-6}$ alkyl, $C_{1-6}$ haloalkyl, $C_{3-10}$ cycloalkyl, and $C_{6-10}$ aryl; wherein said $C_{1-6}$ alkyl, $C_{3-10}$ cycloalkyl, and $C_{6-10}$ aryl are each optionally substituted with 1, 2, 3, or 4 substituents independently selected from $R^{50}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{e1}R^{d1}$, $NR^{e1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{e1}R^{d1}$, wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-6 membered heteroaryl, 4-7 membered heterocycloalkyl, halo, D, CN, $OR^{a5}$, $SR^{a5}$, $C(O)R^{b5}$, $C(O)NR^{c5}R^{d5}$, $C(O)OR^{a5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{3-6}$ cycloalkyl, $C_{6-10}$ aryl, 5-6 membered heteroaryl and 4-7 membered heterocycloalkyl are each optionally substituted with 1, 2, 3, or 4 substituents independently selected from $R^g$;

each $R^{20}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NOR^{a2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{21}$;

each $R^{21}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{22}$;

each $R^{22}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}OR^{d6}$, $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^{50}$ is independently selected from $C_{1-6}$ alkyl, $C_{1-6}$ haloalkyl, halo, D, CN, $OR^{a11}$ and $NR^{c11}R^{d11}$;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

each $R^{c1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl) carbamyl, aminosulfonyl, $C_{1-6}$ alkylaminosulfonyl and di($C_{1-6}$ alkyl)aminosulfonyl;

each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

or any $R^{c2}$ and $R^{d2}$ attached to the same N atom, together with the N atom to which they are attached, form a 4-, 5-, 6- or 7-membered heterocycloalkyl group optionally substituted with 1, 2 or 3 substituents independently selected from $R^{21}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{21}$;

each $R^{c2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl) carbamyl, aminosulfonyl, $C_{1-6}$ alkylaminosulfonyl and di($C_{1-6}$ alkyl)aminosulfonyl;

each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c3}$ and $R^{d3}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $R^{22}$, each $R^{b4}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{22}$;

each $R^{a5}$, $R^{c5}$ and $R^{d5}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

or any $R^{c5}$ and $R^{d5}$ attached to the same N atom, together with the N atom to which they are attached, form a 4-, 5-, 6- or 7-membered heterocycloalkyl group optionally substituted with 1, 2, 3, or 4 substituents independently selected from $R^g$;

each $R^{b5}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$, is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a9}$, $R^{e9}$, and $R^{d9}$ is independently selected from H, $C_{1-6}$ alkyl, and $C_{1-6}$ haloalkyl;

each $R^{a11}$, $R^{c11}$ and $R^{d11}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$; and each $R^g$ is independently selected from D, OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkoxycarbonylamino, $C_{1-6}$ alkylcarbonyloxy, aminocarbonyloxy, $C_{1-6}$ alkylaminocarbonyloxy, di($C_{1-6}$ alkyl)aminocarbonyloxy, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The compound of claim 1, or a pharmaceutically acceptable salt thereof, wherein:

ring A is aromatic.

3. The compound of claim 1, or a pharmaceutically acceptable salt thereof, wherein $Cy^1$ is pyrazolyl or pyridinyl, each optionally substituted with 1 or 2 substituents independently selected from $R^{10}$.

4. The compound of claim 1, or a pharmaceutically acceptable salt thereof, wherein $Cy^1$ is selected from 1-methyl-1H-pyrazol-4-yl, 1,3-dimethyl-1H-pyrazol-4-yl, 1-(1-acetylpyrrolidin-3-yl)-1H-pyrazol-4-yl, 1-(4-carboxycyclohexyl)-1H-pyrazol-4-yl, 1-(4-acetamidocyclohexyl)-1H-pyrazol-4-yl, 1-(3-hydroxycyclobutyl)-1H-pyrazol-4-yl, and 6-(4-acetylpiperazin-1-yl)pyridin-3-yl.

5. The compound of claim 1, or a pharmaceutically acceptable salt thereof, wherein $Cy^1$ is selected from 1-methyl-1H-pyrazol-4-yl, 1,3-dimethyl-1H-pyrazol-4-yl, 1-(1-acetylpyrrolidin-3-yl)-1H-pyrazol-4-yl, 1-(4-carboxycyclohexyl)-1H-pyrazol-4-yl, 1-(4-acetamidocyclohexyl)-1H-pyrazol-4-yl, 1-(3-hydroxycyclobutyl)-1H-pyrazol-4-yl, 6-(4-acetylpiperazin-1-yl)pyridin-3-yl, 1-(1-(2-hydroxyacetyl)pyrrolidin-3-yl)-1H-pyrazol-4-yl, 1-(1-(1-aminocyclopropane-1-carbonyl)azetidin-3-yl)-1H-pyrazol-4-yl, 1-(1-(2-(1H-imidazol-1-yl)acetyl)azetidin-3-yl)-1H-pyrazol-4-yl, 1-(1-(oxazole-4-carbonyl)azetidin-3-yl)-1H-pyrazol-4-yl, 1-(1-(4-aminotetrahydro-2H-pyran-4-carbonyl)azetidin-3-yl)-1H-pyrazol-4-yl, 1-(1-(2-cyanoacetyl)azetidin-3-yl)-1H-pyrazol-4-yl, 1-(4-carboxy-3-fluorobenzyl)-1H-pyrazol-4-yl, 1-(4-(dimethylcarbamoyl)phenyl)-1H-pyrazol-4-yl, 1-((1r,4r)-4-(2-methoxyacetamido)cyclohexyl)-1H-pyrazol-4-yl, 1-((1r,4r)-4-(3,3-dimethylureido)cyclohexyl)-1H-pyrazol-4-yl, 1-(2-acetyl-2-azaspiro[3.5]nonan-7-yl)-1H-pyrazol-4-yl, 1-(tetrahydro-2H-pyran-4-yl)-1H-pyrazol-4-yl, 1-((1r,4r)-4-hydroxycyclohexyl)-1H-pyrazol-4-yl, 1-(4-carboxy-4-methylcyclohexyl)-1H-pyrazol-4-yl, 1-(1-(dimethylcarbamoyl)pyrrolidin-3-yl)-1H-pyrazol-4-yl, 1-(1-(N,N-dimethylsulfamoyl)pyrrolidin-3-yl)-1H-pyrazol-4-yl, 1-(3-(2-hydroxyacetyl)-3-azabicyclo[3.1.0]hexan-1-yl)-1H-pyrazol-4-yl, 1-(1-(morpholine-4-carbonyl)pyrrolidin-3-yl)-1H-pyrazol-4-yl, 1-(3-(2-hydroxyacetyl)-3-azabicyclo[4.1.0]heptan-6-yl)-1H-pyrazol-4-yl, 1-(3-acetyl-3-azabicyclo[4.1.0]heptan-1-yl)-1H-pyrazol-4-yl, 6-(1-(2-hydroxyacetyl)azetidin-3-yl)pyridin-3-yl, 5-(1-acetylazetidin-3-yl)pyridin-3-yl, 1-cyclopropyl-1H-pyrazol-4-yl, 1-(tetrahydrofuran-3-yl)-1H-pyrazol-4-yl, 1-(oxetan-3-yl)-1H-pyrazol-4-yl, 1-(2-(dimethylamino)ethyl)-1H-pyrazol-4-yl, 1-isopropyl-1H-pyrazol-4-yl, 1-(difluoromethyl)-1H-pyrazol-4-yl, 1-(2-cyanoethyl)-1H-pyrazol-4-yl, 1-(2-hydroxy-2-methylpropyl)-1H-pyrazol-4-yl, 1-(cyanomethyl)-1H-pyrazol-4-yl, 1-(1-methylpiperidin-4-yl)-1H-pyrazol-4-yl, 1-(1-hydroxy-2-methylpropan-2-yl)-1H-pyrazol-4-yl, 1-(2-(methylsulfonyl)ethyl)-1H-pyrazol-4-yl, 1-(2,2,2-trifluoroethyl)-1H-pyrazol-4-yl, 1-(2-morpholinoethyl)-1H-pyrazol-4-yl, and 1-(2-hydroxyethyl)-1H-pyrazol-4-yl.

6. The compound of claim 1, or a pharmaceutically acceptable salt thereof, wherein each $R^{10}$ is independently selected from $C_{1-6}$ alkyl, 4-10 membered heterocycloalkyl, and $C_{3-10}$ cycloalkyl, each of which is optionally substituted with 1 or 2 substituents independently selected from $R^{11}$.

7. The compound of claim 1, or a pharmaceutically acceptable salt thereof, wherein each $R^{10}$ is independently selected from $C_{1-6}$ alkyl, $C_{1-6}$ haloalkyl, phenyl, 4-10 membered heterocycloalkyl, and $C_{3-10}$ cycloalkyl, each of which is optionally substituted with 1 or 2 substituents independently selected from $R^{11}$.

8. The compound of claim 1, or a pharmaceutically acceptable salt thereof, wherein each $R^{10}$ is independently selected from methyl, ethyl, isopropyl, 2-methylpropyl, difluoromethyl, cyclopropyl, cyclobutyl, cyclohexyl, phenyl, piperzinyl, azetidinyl, pyrrolidinyl, azaspiro[3.5]nonanyl, tetrahydro-2H-pyranyl, azabicyclo[3.1.0]hexanyl, azabicyclo[4.1.0]heptanyl, tetrahydrofuranyl, oxetanyl, and piperidinyl, each of which is optionally substituted with 1 or 2 substituents independently selected from $R^{11}$.

9. The compound of claim 1, or a pharmaceutically acceptable salt thereof, wherein each $R^{11}$ is independently selected from $C(O)R^{b3}$, $C(O)OR^{a3}$, $NR^3C(O)R^{b3}$, and $OR^{a3}$.

10. The compound of claim 1, or a pharmaceutically acceptable salt thereof, wherein each $R^{11}$ is independently selected from $C_{1-6}$ alkyl, CN, $C(O)R^{b3}$, $C(O)OR^{a3}$, $NR^{c3}C(O)R^{b3}$, $OR^{a3}$, $C(O)NR^{c3}R^{d3}$, $NR^{c3}R^{d3}$, $NR^{c3}C(O)NR^{c3}R^{d3}$, $S(O)_2NR^{c3}R^{d3}$, $S(O)_2R^{b3}$, phenyl, and 4-6 membered heterocycloalkyl, wherein said $C_{1-6}$ alkyl, phenyl, and 4-6 membered heterocycloalkyl are each optionally substituted with 1 or 2 substituents independently selected from $R^{12}$.

11. The compound of claim 1, or a pharmaceutically acceptable salt thereof, wherein each $R^{11}$ is independently selected from $C(O)CH_3$, $C(O)OH$, $NHC(O)CH_3$, and OH.

12. The compound of claim 1, or a pharmaceutically acceptable salt thereof, wherein each $R^{11}$ is independently selected from methyl, CN, OH, $C(O)CH_3$, $C(O)OH$, $NHC(O)CH_3$, $C(O)CH_2OH$, $C(O)N(CH_3)_2$, $NHC(O)CH_2OCH_3$, $NHC(O)N(CH_3)_2$, $S(O)_2N(CH_3)_2$, $N(CH_3)_2$, $S(O)_2CH_3$, 2-cyanoacetyl, morpholine-4-carbonyl, morpholinyl, 1-aminocyclopropane-1-carbonyl, (1H-imidazol-1-yl)acetyl, oxazole-4-carbonyl, 4-aminotetrahydro-2H-pyran-4-carbonyl, and 4-carboxy-3-fluorophenyl.

13. The compound of claim 1, or a pharmaceutically acceptable salt thereof, wherein $Cy^A$ is selected from phenyl and 5-6 membered heteroaryl, wherein the phenyl and 5-6 membered heteroaryl are each optionally substituted with 1, 2, 3 or 4 substituents independently selected from $R^{20}$.

14. The compound of claim 1, or a pharmaceutically acceptable salt thereof, wherein $Cy^A$ is phenyl or furanyl, each optionally substituted with 1, 2, or 3 substituents independently selected from $R^{20}$.

15. The compound of claim 1, or a pharmaceutically acceptable salt thereof, wherein $Cy^A$ is selected from 2-chlorophenyl, 2,6-difluorophenyl, 2-chloro-6-fluorophenyl, 2,6-dichlorophenyl, 2-fluoro-6-methylphenyl, 2-chloro-4-methoxyphenyl, and 3-methylfuran-2-yl.

16. The compound of claim 1, or a pharmaceutically acceptable salt thereof, wherein $Cy^A$ is selected from 2-chlorophenyl, 2,6-difluorophenyl, 2-chloro-6-fluorophenyl, 2,6-dichlorophenyl, 2-fluoro-6-methylphenyl, 2-chloro-4-methoxyphenyl, 3-methylfuran-2-yl, 1-methylpiperidin-4-yl, (1S,5R)-2-oxo-3,8-diazabicyclo[3.2.1]octan-8-yl, 2-chloro-6-(trifluoromethyl)phenyl, 2,6-dimethylphenyl, 2-cyano-6-fluorophenyl, 2-fluoro-6-methoxyphenyl, 2,3-dimethylphenyl, 4-(hydroxymethyl)-2-methylphenyl, 3-acrylamido-2,6-dichlorophenyl, 3-acrylamidophenyl, 2-acrylamidophenyl, and cyclopropyl.

17. The compound of claim 1, or a pharmaceutically acceptable salt thereof, wherein each $R^{20}$ is independently selected from halo, $C_{1-6}$ alkyl, and $OR^{a2}$.

18. The compound of claim 1, or a pharmaceutically acceptable salt thereof, wherein each $R^{20}$ is independently selected from halo, CN, $C_{1-6}$ alkyl, $C_{1-6}$ haloalkyl, and $NR^{c2}C(O)R^{b2}$, wherein the $C_{1-6}$ alkyl is optionally substituted with $OR^{a4}$.

19. The compound of claim 1, or a pharmaceutically acceptable salt thereof, wherein each $R^{20}$ is independently selected from chloro, fluoro, methyl, and methoxy.

20. The compound of claim 1, or a pharmaceutically acceptable salt thereof, wherein each $R^{20}$ is independently selected from CN, chloro, fluoro, methyl, methoxy, trifluoromethyl, hydroxymethyl, and acrylamido.

21. The compound of claim 1, or a pharmaceutically acceptable salt thereof, wherein $R^1$ is H.

22. The compound of claim 1, or a pharmaceutically acceptable salt thereof, wherein $R^1$ is H, $OR^{a9}$, or $NR^{c9}R^{d9}$.

23. The compound of claim 1, or a pharmaceutically acceptable salt thereof, wherein $R^2$ is H.

24. The compound of claim 1, or a pharmaceutically acceptable salt thereof, wherein $R^3$ is H.

25. The compound of claim 1, or a pharmaceutically acceptable salt thereof, wherein $R^5$ is $C_{1-6}$ alkyl.

26. The compound of claim 1, or a pharmaceutically acceptable salt thereof, wherein $R^5$ is methyl.

27. The compound of claim 1, or a pharmaceutically acceptable salt thereof, wherein the compound has Formula IIIa:

IIIa

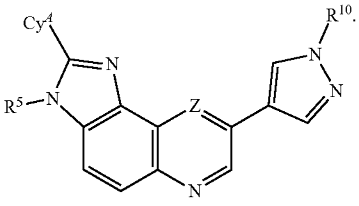

28. The compound of claim 1, or a pharmaceutically acceptable salt thereof, wherein the compound has Formula IIIb:

IIIb

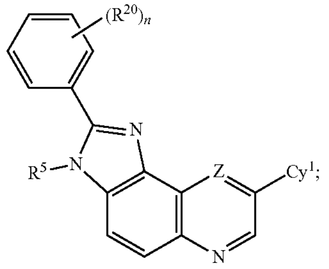

wherein n is 0, 1, 2, or 3.

29. The compound of claim 1, or a pharmaceutically acceptable salt thereof, wherein the compound has Formula IIIc:

IIIc

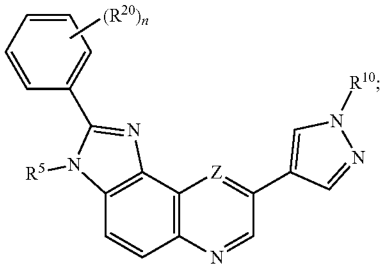

wherein n is 0, 1, 2, or 3.

30. The compound of claim 1, having Formula (IA):

IA

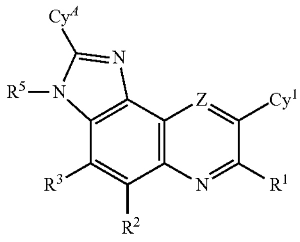

or a pharmaceutically acceptable salt thereof, wherein:

Z is N;

$Cy^1$ is 5-10 membered heteroaryl; wherein each 5-10 membered heteroaryl has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the 5-10 membered heteroaryl is optionally substituted with 1, 2, 3 or 4 substituents independently selected from $R^{10}$, $Cy^A$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{20}$;

$R^1$, $R^2$, and $R^3$ are each independently selected from H, D, $C_{1-6}$ alkyl, $C_{1-6}$ haloalkyl, halo, CN, $OR^{a9}$, and $NR^{c9}R^{d9}$;

$R^5$ is selected from $C_{1-6}$ alkyl, $C_{1-6}$ haloalkyl, $C_{3-10}$ cycloalkyl, and $C_{6-10}$ aryl; wherein said $C_{1-6}$ alkyl, $C_{3-10}$ cycloalkyl, and $C_{6-10}$ aryl are each optionally substituted with 1, 2, 3, or 4 substituents independently selected from $R^{50}$;

each $R^{10}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a1}$, and $NR^{c1}R^{d1}$, wherein said $C_{1-6}$ alkyl, $C_{3-10}$ cycloalkyl, and 4-10 membered heterocycloalkyl are each optionally substituted with 1, 2, 3, or 4 substituents independently selected from $R^{11}$;

each $R^{11}$ is independently selected from $C_{1-6}$ alkyl, $C_{1-6}$ haloalkyl, $C_{3-10}$ cycloalkyl, halo, D, CN, $OR^{a3}$, $C(O)R^{b3}$, $C(O)NR^{c3}R^{d3}$, $C(O)OR^{a3}$, $NR^{c3}R^{d3}$, and $S(O)_2R^{b3}$; wherein said $C_{1-6}$ alkyl, and $C_{3-10}$ cycloalkyl are each optionally substituted with 1, 2, 3, or 4 substituents independently selected from $R^{12}$, each $R^{12}$ is independently selected from $C_{1-6}$ alkyl, halo, D, CN, $OR^{a5}$ and $NR^{c5}R^{d5}$;

each $R^{20}$ is independently selected from $C_{1-6}$ alkyl, $C_{1-6}$ haloalkyl, $C_{3-10}$ cycloalkyl, halo, D, CN, $OR^{a2}$, $C(O)R^{b2}$, $C(O)NR^{c2}R^{d2}$, $C(O)OR^{a2}$, $S(O)NR^{c2}R^{d2}$, and $S(O)_2R^{b2}$; wherein said $C_{1-6}$ alkyl, and $C_{3-10}$ cycloalkyl are each optionally substituted with 1, 2, 3, or 4 substituents independently selected from $R^{21}$, each $R^{21}$ is independently selected from $C_{1-6}$ alkyl, $C_{1-6}$ haloalkyl, halo, D, CN, $OR^{a4}$, and $NR^{c4}R^{a4}$;

each $R^{50}$ is independently selected from $C_{1-6}$ alkyl, $C_{1-6}$ haloalkyl, halo, D, CN, $OR^{a11}$, and $NR^{c11}R^{d11}$;

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, or 6-membered heterocycloalkyl group optionally substituted with 1, 2, 3, or 4 substituents independently selected from $R^{11}$;

each $R^{a2}$, $R^{c2}$ and $R^{d2}$ is independently selected from H, $C_{1-6}$ alkyl, $C_{1-6}$ haloalkyl, and $C_{3-10}$ cycloalkyl; wherein said $C_{1-6}$ alkyl and $C_{3-10}$ cycloalkyl are each optionally substituted with 1, 2, 3, or 4 substituents independently selected from $R^{21}$;

each $R^{b2}$ is independently selected from $C_{1-6}$ alkyl, $C_{1-6}$ haloalkyl, and $C_{3-10}$ cycloalkyl; wherein said $C_{1-6}$ alkyl and $C_{3-10}$ cycloalkyl are each optionally substituted with 1, 2, 3, or 4 substituents independently selected from $R^{21}$;

each $R^{a3}$, $R^{c3}$ and $R^{d3}$ is independently selected from H, $C_{1-6}$ alkyl, $C_{1-6}$ haloalkyl, and $C_{3-6}$ cycloalkyl; wherein said $C_{1-6}$ alkyl and $C_{3-6}$ cycloalkyl are each optionally substituted with 1, 2, 3, or 4 substituents independently selected from $R^{12}$;

each $R^{b3}$ is independently selected from $C_{1-6}$ alkyl, $C_{1-6}$ haloalkyl, and $C_{3-6}$ cycloalkyl; wherein said $C_{1-6}$ alkyl and $C_{3-6}$ cycloalkyl are each optionally substituted with 1, 2, 3, or 4 substituents independently selected from $R^{12}$;

each $R^{a4}$, $R^{c4}$ and $R^{d4}$ is independently selected from H, $C_{1-6}$ alkyl, and $C_{1-6}$ haloalkyl;

each $R^{a5}$, $R^{c5}$ and $R^{d5}$ is independently selected from H, $C_{1-6}$ alkyl, and $C_{1-6}$ haloalkyl;

each $R^{a9}$, $R^{c9}$, and $R^{d9}$ is independently selected from H, $C_{1-6}$ alkyl, and $C_{1-6}$ haloalkyl; and each $R^{a11}$, $R^{c11}$ and $R^{d11}$ is independently selected from H, $C_{1-6}$ alkyl, and $C_{1-6}$ haloalkyl.

31. The compound of claim 1, having Formula (IA):

IA

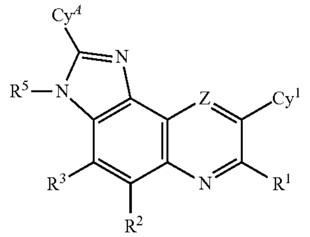

or a pharmaceutically acceptable salt thereof, wherein:

Z is N;

$Cy^1$ is selected from 5-10 membered heteroaryl; wherein each 5-10 membered heteroaryl has at least one ring-forming carbon atom and 1, 2, 3, or 4 ring-forming heteroatoms independently selected from N, O, and S; wherein a ring-forming carbon atom of 5-10 membered heteroaryl is optionally substituted by oxo to form a carbonyl group; and wherein the 5-10 membered heteroaryl is optionally substituted with 1 or 2 substituents independently selected from $R^{10}$;

$Cy^A$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1, 2, or 3 substituents independently selected from $R^{20}$;

$R^1$, $R^2$, and $R^3$ are each independently selected from H, D, $C_{1-6}$ alkyl, $C_{1-6}$ haloalkyl, halo, and CN;

$R^5$ is selected from $C_{1-6}$ alkyl and $C_{1-6}$ haloalkyl;

each $R^{10}$ is independently selected from $C_{1-6}$ alkyl, $C_{1-6}$ haloalkyl, $C_{3-10}$ cycloalkyl, 4-10 membered heterocycloalkyl, halo, D, CN, $OR^{a1}$, and $NR^{c1}R^{d1}$, wherein said $C_{1-6}$ alkyl, $C_{3-10}$ cycloalkyl, and 4-10 membered heterocycloalkyl are each optionally substituted with 1, 2, or 3 substituents independently selected from $R^{11}$;

each $R^{11}$ is independently selected from $C_{1-6}$ alkyl, $C_{1-6}$ haloalkyl, halo, D, CN, $OR^{a3}$, $C(O)R^{b3}$, $C(O)NR^{c3}R^{d3}$, and $NR^{c3}R^{d3}$, each $R^{20}$ is independently selected from $C_{1-6}$ alkyl, $C_{1-6}$ haloalkyl, halo, D, CN, $OR^{a2}$, and $NR^{c2}R^{d2}$;

each $R^{a1}$, $R^{c1}$ and $R^{d1}$ is independently selected from H, $C_{1-6}$ alkyl, $C_{1-6}$ haloalkyl, $C_{3-10}$ cycloalkyl, and 4-10 membered heterocycloalkyl; wherein said $C_{1-6}$ alkyl, $C_{3-10}$ cycloalkyl, and 4-10 membered heterocycloalkyl are each optionally substituted with 1 or 2 substituents independently selected from $R^{11}$;

or any $R^{c1}$ and $R^{d1}$ attached to the same N atom, together with the N atom to which they are attached, form a 4-, 5-, or 6-membered heterocycloalkyl group optionally substituted with 1 or 2 substituents independently selected from $R^{11}$;

each $R^{a2}$, $R^{c2}$ and $R^{d2}$, is independently selected from H, $C_{1-6}$ alkyl, and $C_{1-6}$ haloalkyl;

each $R^{a3}$, $R^{c3}$ and $R^{d3}$, is independently selected from H, $C_{1-6}$ alkyl, and $C_{1-6}$ haloalkyl; and each $R^{b3}$ is independently selected from $C_{1-6}$ alkyl and $C_{1-6}$ haloalkyl.

32. The compound of claim 1, wherein the compound is selected from:

2-(2-Fluoro-6-methylphenyl)-3-methyl-8-(1-methyl-1H-pyrazol-4-yl)-3H-imidazo[4,5-f]quinoxaline;

2-(2-Chloro-4-methoxyphenyl)-3-methyl-8-(1-methyl-1H-pyrazol-4-yl)-3H-imidazo[4,5-f]quinoxaline;

3-Methyl-8-(1-methyl-1H-pyrazol-4-yl)-2-(3-methylfuran-2-yl)-3H-imidazo[4,5-f]quinoxaline;

3-(4-(2-(2-Chloro-6-fluorophenyl)-3-methyl-3H-imidazo[4,5-f]quinoxalin-8-yl)-1H-pyrazol-1-yl)cyclobutan-1-ol; and 1-(4-(5-(2-(2-Chloro-6-fluorophenyl)-3-methyl-3H-imidazo[4,5-f]quinoxalin-8-yl)pyridin-2-yl)piperazin-1-yl)ethan-1-one, or a pharmaceutically acceptable of any of the aforementioned.

33. The compound of claim 1, wherein the compound is selected from:

3-Methyl-8-(1-methyl-1H-pyrazol-4-yl)-2-(1-methylpiperidin-4-yl)-3H-imidazo[4,5-f]quinoxaline; and (1S,5R)-8-(3-Methyl-8-(1-methyl-1H-pyrazol-4-yl)-3H-imidazo[4,5-f]quinoxalin-2-yl)-3,8-diazabicyclo[3.2.1]octan-2-one;

or a pharmaceutically acceptable salt of any of the aforementioned.

34. A pharmaceutical composition comprising a compound of claim 1 or a pharmaceutically acceptable salt thereof, and a pharmaceutically acceptable carrier or excipient.

* * * * *